(12) United States Patent
Zhou et al.

(10) Patent No.: US 9,738,604 B2
(45) Date of Patent: Aug. 22, 2017

(54) ETHYNYLBENZENE DERIVATIVES

(75) Inventors: Pei Zhou, Cary, NC (US); Eric J. Toone, Durham, NC (US)

(73) Assignee: Duke University, Durham, NC (US)

(*) Notice: Subject to any disclaimer, the term of this patent is extended or adjusted under 35 U.S.C. 154(b) by 226 days.

(21) Appl. No.: 13/820,404

(22) PCT Filed: Sep. 6, 2011

(86) PCT No.: PCT/US2011/050548
§ 371 (c)(1),
(2), (4) Date: May 20, 2013

(87) PCT Pub. No.: WO2012/031298
PCT Pub. Date: Mar. 8, 2012

(65) Prior Publication Data
US 2013/0231323 A1 Sep. 5, 2013

Related U.S. Application Data

(60) Provisional application No. 61/379,935, filed on Sep. 3, 2010.

(51) Int. Cl.
| | |
|---|---|
| C07C 237/34 | (2006.01) |
| C07C 259/06 | (2006.01) |
| C07D 207/273 | (2006.01) |
| C07C 275/14 | (2006.01) |
| C07C 275/24 | (2006.01) |
| C07C 275/28 | (2006.01) |
| C07C 311/19 | (2006.01) |
| C07C 311/39 | (2006.01) |
| C07D 205/085 | (2006.01) |
| C07D 231/12 | (2006.01) |

(Continued)

(52) U.S. Cl.
CPC ........ *C07D 207/273* (2013.01); *C07C 237/34* (2013.01); *C07C 259/06* (2013.01); *C07C 275/14* (2013.01); *C07C 275/24* (2013.01); *C07C 275/28* (2013.01); *C07C 311/19* (2013.01); *C07C 311/37* (2013.01); *C07C 311/39* (2013.01); *C07D 205/085* (2013.01); *C07D 209/20* (2013.01); *C07D 213/73* (2013.01); *C07D 231/12* (2013.01); *C07D 233/64* (2013.01); *C07D 249/04* (2013.01); *C07D 257/04* (2013.01); *C07D 261/08* (2013.01); *C07D 263/16* (2013.01); *C07D 265/30* (2013.01); *C07D 275/03* (2013.01); *C07D 277/22* (2013.01); *C07D 295/155* (2013.01); *C07D 307/36* (2013.01); *C07D 333/06* (2013.01)

(58) Field of Classification Search
None
See application file for complete search history.

(56) References Cited

U.S. PATENT DOCUMENTS

| | | |
|---|---|---|
| 7,358,359 B2 | 4/2008 | Andersen et al. |
| 7,691,843 B2 | 4/2010 | Raju et al. |

(Continued)

FOREIGN PATENT DOCUMENTS

| | | |
|---|---|---|
| WO | 9742179 A1 | 11/1997 |
| WO | 2004/062601 A2 | 7/2004 |

(Continued)

OTHER PUBLICATIONS

"Fluorine in medicinal chemistry: Recent therapeutic applications of fluorinated small molecules" by Kirk, J. Fluorine Chem. 127, 1013-29 (2006).*

(Continued)

*Primary Examiner* — Theodore R West
(74) *Attorney, Agent, or Firm* — McDonnell Boehnen Hulbert & Berghoff

(57) ABSTRACT

Disclosed are compounds of formulae (I), (II), and (II)I: and pharmaceutically acceptable salts thereof, wherein the variables, R, $R_1$, $R_2$, $R_3$, $R_{101}$, L, D, Q, Y, X, and Z are defined herein. These compounds are useful for treating Gram-negative bacteria infections.

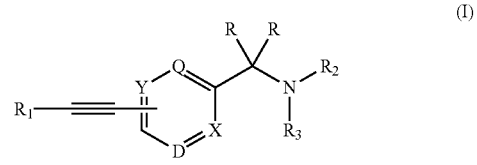

(I)

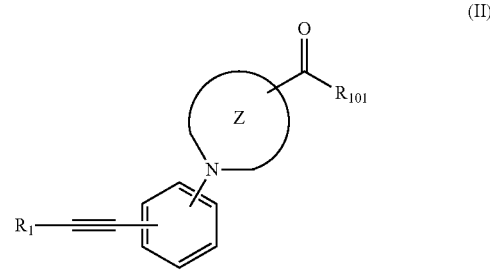

(II)

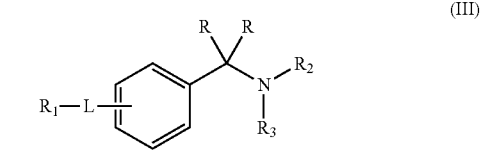

(III)

13 Claims, No Drawings

(51) Int. Cl.

| | |
|---|---|
| *C07D 249/04* | (2006.01) |
| *C07D 257/04* | (2006.01) |
| *C07D 261/08* | (2006.01) |
| *C07D 263/16* | (2006.01) |
| *C07D 265/30* | (2006.01) |
| *C07D 275/03* | (2006.01) |
| *C07D 277/22* | (2006.01) |
| *C07D 295/155* | (2006.01) |
| *C07D 307/36* | (2006.01) |
| *C07D 333/06* | (2006.01) |
| *C07C 311/37* | (2006.01) |
| *C07D 209/20* | (2006.01) |
| *C07D 213/73* | (2006.01) |
| *C07D 233/64* | (2006.01) |

(56) References Cited

U.S. PATENT DOCUMENTS

| | | | |
|---|---|---|---|
| 7,989,660 | B2 | 8/2011 | Andersen et al. |
| 8,084,615 | B2 | 12/2011 | Andersen et al. |
| 2004/0229955 | A1 | 11/2004 | Andersen et al. |
| 2009/0163496 | A1 | 6/2009 | Andersen et al. |
| 2010/0190766 | A1 | 7/2010 | Moser et al. |
| 2013/0072677 | A1 | 3/2013 | Takashima et al. |

FOREIGN PATENT DOCUMENTS

| | | |
|---|---|---|
| WO | 2007/064732 A1 | 6/2007 |
| WO | 2007/064749 A1 | 6/2007 |
| WO | 2008/027466 A1 | 3/2008 |
| WO | 2008/154642 A2 | 12/2008 |
| WO | 2009/158369 A1 | 12/2009 |
| WO | 2010/017060 A1 | 2/2010 |
| WO | 2010/031750 A1 | 3/2010 |
| WO | 2010/100475 A1 | 9/2010 |
| WO | 2011/005355 A1 | 1/2011 |
| WO | 2011/073845 A1 | 3/2011 |
| WO | 2011/045703 A2 | 4/2011 |
| WO | 2011/051201 A1 | 5/2011 |
| WO | 2011/132712 A1 | 10/2011 |

OTHER PUBLICATIONS

"Fluorine in Pharmaceuticals: Looking Beyond Intuition" by Müller et al., Science 317, 1881-86 (2007).*
"Fluorine in medicinal chemistry" by Purser et al., Chem. Soc. Rev. 37, 320-30 (2008).*
"The Trifluoromethyl Group in Medicinal Chemistry" by Yale, J. Med. Pharm. Chem. 1, 121-33 (1959).*
Ritzen et al: "Discovery of a potent and brain penetrant mGluR5 positive allosteric modulator", Biorganic & Medicinal Chemistry Letters, vol. 19, Apr. 24, 2009 (Apr. 24, 2009), pp. 3275-3278 See compounds on table 1, p. 3276.
Rodriguez et al.: "Discovery of novel allosteric modulators of metabotropic glutamate receptor subtype 5 reveals chemical and functional diversity and invivo activity." Molecular Pharmacology, vol. 78, 2010, pp. 1105-1123, XP008145887, See compound on table 1, p. 1111 and tables 3-4, pp. 1117-1118.
Lehrfeld, J.: "Synthesis of 6-Substituted Nicotinic Acid Uerivatives as Analogs of Ergot Alkaloicls" Journal of Medicinal Chemistryvol. 7. No. 2; Jan. 1, 1964 (Jan. 1, 1964). pp. 150-154. XP055013512. Retrieved from the Internet: URL:http://pubs.acs.orgj-journaljjmcmar [retrieved on Nov. 30, 2011] See compounds of table III. pp. 151.
International Search Report and Written Opinion in the International Application No. PCT/US2011/050548 dated Jul. 25, 2012.
International Preliminary Report on Patentability in the International Application No. PCT/US2011/050548.

* cited by examiner

ETHYNYLBENZENE DERIVATIVES

CROSS-REFERENCE TO RELATED APPLICATIONS

This application is a U.S. national phase of International Application No. PCT/US2011/050548, filed Sep. 6, 2011, the disclosure of which is hereby incorporated by reference in its entirety, and which claims benefit of U.S. Provisional Application Ser. No. 61/379,935, filed Sep. 3, 2010, the disclosure of which is incorporated by reference herein in its entirety.

STATEMENT REGARDING FEDERALLY SPONSORED RESEARCH OR DEVELOPMENT

This invention was made with government support under NIH/NIAID R01 AI055588 grant entitled "Structural and Biochemical Studies of LpxC Inhibition." The government has certain rights.

BACKGROUND OF THE INVENTION

Field of the Invention

This invention relates to ethynylbenzene derivatives, and in particular, to such compounds that inhibit UDP-3-O—(R-3-hydroxydecanoyl)-N-acetylglucosamine deacetylase (LpxC), and to methods of using such compounds to treat Gram-negative bacterial infections.

Description of the Related Art

Antimicrobial resistance is increasing and becoming alarmingly common. This problem is compounded when bacterial strains are resistant to multiple antibacterials. There clearly is a need for new antibacterials, particularly antibacterials with novel mechanisms of action.

The gene lpxC encodes the enzyme uridyldiphospho-3-O—(R-hydroxydecanoyl)-N-acetylglucosamine deacetylase (LpxC). This enzyme is involved in the synthesis of lipid A, the lipid moiety of lipopolysaccharide, which is an essential component of all Gram-negative bacteria. Commercially useful LpxC inhibitors would need to both inhibit the enzymatic activity of LpxC from a variety of bacteria and defeat the resistance mechanisms of Gram-negative bacteria.

SUMMARY OF THE INVENTION

In a broad aspect, the disclosure encompasses the compounds of formula I, shown below, pharmaceutical compositions containing those compounds and methods of using such compounds to treat and/or prevent bacterial infections.

Thus, one aspect (embodiment 1) of the disclosure provides compounds of formula I:

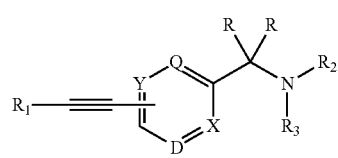

or a pharmaceutically acceptable salt thereof, wherein Q, Y, D, and X independently represent CH or nitrogen, provided that at least two of Q, Y, D, and X are CH;
each R is independently hydrogen, or $C_1$-$C_6$ alkyl, or two R groups form =O;

$R_1$ is —C($R_5$)=C($R_4$)($R_5$), —C≡C—$R_4$, aryl optionally substituted with $R_6$, heteroaryl optionally substituted with $R_6$, or heterocyclyl optionally substituted with $R_6$;

$R_2$ is —CH($R_9$)($R_{10}$), or heterocyclyl optionally substituted with one or more $R_{10}$;

$R_3$ is hydrogen or $C_1$-$C_6$ alkyl;

or $R_2$ and $R_3$ together with the nitrogen to which they are attached form heterocyclyl ring optionally substituted with one or more $R_{10}$;

$R_4$ is $C_1$-$C_6$ alkyl optionally substituted with $R_7$, aryl optionally substituted with $R_8$, heteroaryl optionally substituted with $R_8$, or heterocyclyl optionally substituted with $R_8$;

each $R_5$ is independently hydrogen, or $C_1$-$C_6$ alkyl;

each $R_6$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;

each $R_7$ is independently selected from the group consisting of halogen, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy;

each $R_8$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, —$CONH_2$, —CON($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, —NHCONH($C_1$-$C_6$ alkyl), —NHC(=NH)$NH_2$, —NH—S(O)$_{0-2}$—($C_1$-$C_6$ alkyl), —NH—S(O)$_{0-2}$-aryl, —NH—S(O)$_{0-2}$-heteroaryl, aryl($C_1$-$C_6$ alkyl), heteroaryl($C_1$-$C_6$ alkyl), heterocyclyl($C_1$-$C_6$ alkyl), —$CH_2$—$NHCONH_2$, —$CH_2$—NHCONH($C_1$-$C_6$ alkyl), and —$CH_2$—OCO($C_1$-$C_6$ alkyl);

$R_9$ is hydrogen, $C_1$-$C_6$ alkyl, aryl, aryl($C_1$-$C_6$ alkyl), heteroaryl, heteroaryl($C_1$-$C_6$ alkyl), heterocyclyl, or heterocyclyl($C_1$-$C_6$ alkyl), wherein each alkyl, aryl, heteroaryl, or heterocyclyl moiety is optionally substituted with one or more $R_{11}$;

$R_{10}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, oxo, —$CONH_2$, —CON($C_1$-$C_6$ alkyl), —CON($C_1$-$C_6$ alkyl)$_2$, —CONH—OH, —CONH—$NH_2$, —$CO_2$H, and —$CO_2$($C_1$-$C_6$ alkyl);

each $R_{11}$ is independently selected from the group consisting of halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —$CONH_2$, —CON($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, —NHCONH($C_1$-$C_6$ alkyl), —NHC(=NH)$NH_2$, —NH—S(O)$_{0-2}$—($C_1$-$C_6$ alkyl), —NH—S(O)$_{0-2}$-aryl, and —NH—S(O)$_{0-2}$-heteroaryl;

provided that when $R_1$ is phenylethaynyl, aminophenylethynyl, or pyridinylethynyl, two R groups form oxo, and $R_3$ is hydrogen, then $R_2$ is not 3-hydroxy-1-(hydroxyamino)-1-oxobutan-2-yl, 3-hydroxy-1-(hydroxyamino)-3-methyl-1-oxobutan-2-yl), 3-amino-1-(hydroxyamino)-1-oxopropan-2-yl, 3-amino-1-(hydroxyamino)-3-methyl-1-oxobutan-2-yl).

The disclosure also provides synthetic intermediates that are useful in making the compounds of formula I.

The disclosure also provides methods of preparing compounds of the disclosure and the intermediates used in those methods.

The disclosure also provides pharmaceutical compositions comprising a compound of formula I or a pharmaceutically acceptable salt thereof and at least one pharmaceutically acceptable carrier, solvent, adjuvant or diluent.

The disclosure also provides methods for inhibiting UDP-3-O—(R-3-hydroxydecanoyl)-N-acetylglucosamine deacetylase (LpxC), and methods of treating Gram-negative bacterial infections.

The disclosure further provides a compound or pharmaceutical composition thereof in a kit with instructions for using the compound or composition.

DETAILED DESCRIPTION OF THE INVENTION

In one embodiment, the disclosure provides compounds of formula I wherein R groups form =O, i.e., an oxo group (Embodiment 2).

In another embodiment based on formula I, $R_1$ is —C≡C—$R_4$. (Embodiment 3) Other embodiments are those where $R_1$ is —C≡C—$R_4$, and $R_4$ is aryl optionally substituted with $R_8$, or heteroaryl optionally substituted with $R_8$. (Embodiment 4)

In still other embodiments based on formula I, $R_4$ is aryl optionally substituted with $R_8$, and $R_8$ is selected from the group consisting of halogen, —$NO_2$, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy. (Embodiment 5)

In another embodiments based on formula I, $R_4$ is heteroaryl optionally substituted with $R_8$, and $R_8$ is selected from the group consisting of halogen, —$NO_2$, $C_1$-$C_6$ alkyl, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy. (Embodiment 6) In embodiment 7, $R_4$ is thienyl, imidazolyl, triazolyl, tetrazolyl, pyrazolyl), isoxazolyl, oxazolyl, isothiazolyl, thiazolyl, or furanyl, each substituted with $R_8$, and $R_8$ is selected from the group consisting of halogen, —$NO_2$, $C_1$-$C_6$ alkyl, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, and $C_1$-$C_6$ haloalkoxy.

In another embodiment based on formula I, the compound may be represented by the formula:

(Embodiment 8)

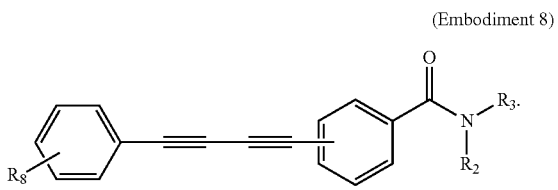

In still other embodiments based on formula I, $R_8$ is selected from the group consisting of is halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, hydroxy($C_1$-$C_6$ alkyl), alkoxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, —$CONH_2$, —$CON(C_1$-$C_6$ alkyl), —CON($C_1$-$C_6$ alkyl)$_2$, —COH, —$CO_2$H, —$CO_2$($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, —NHCONH($C_1$-$C_6$ alkyl), —NH—S(O)$_{0-2}$—($C_1$-$C_6$ alkyl), —NH—S(O)$_{0-2}$-aryl, —NH—S(O)$_{0-2}$-heteroaryl, aryl($C_1$-$C_6$ alkyl), heteroaryl($C_1$-$C_6$ alkyl), heterocyclyl($C_1$-$C_6$ alkyl), —$CH_2$—$NHCONH_2$, —$CH_2$—NHCONH($C_1$-$C_6$ alkyl), and —$CH_2$—OCO($C_1$-$C_6$ alkyl). (Embodiment 9)

In embodiment 10, which is based on formula I, $R_8$ is selected from the group consisting of is halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, hydroxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, —$CONH_2$, —CON($C_1$-$C_6$ alkyl), —CON($C_1$-$C_6$ alkyl)$_2$, —COH, —$CO_2$H, —NHCO($C_1$-$C_6$ alkyl), —$NHCONH_2$, —NHCONH($C_1$-$C_6$ alkyl), —NH—S(O)$_{0-2}$—($C_1$-$C_6$ alkyl), heteroaryl($C_1$-$C_6$ alkyl), heterocyclyl($C_1$-$C_6$ alkyl), —$CH_2$—$NHCONH_2$, and —$CH_2$—NHCONH($C_1$-$C_6$ alkyl).

Embodiment 11, which is based on formula I, provides compounds wherein $R_8$ is selected from the group consisting of is halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, —$CONH_2$, —COH, —$CO_2$H, —NHCO($C_1$-$C_6$ alkyl), —$NHCONH_2$, —NHCONH($C_1$-$C_6$ alkyl), and —NH—S(O)$_{0-2}$—($C_1$-$C_6$ alkyl).

In embodiment 12, which is based on formula I, $R_8$ is selected from the group consisting of is —$NH_2$, —NH($C_1$-$C_6$ alkyl), —N($C_1$-$C_6$ alkyl)$_2$, —NHCO($C_1$-$C_6$ alkyl), —$NHCONH_2$, —NHCONH($C_1$-$C_6$ alkyl), and —NH—S(O)$_{0-2}$—($C_1$-$C_6$ alkyl).

In other embodiment, which is based on formula I, $R_8$ is selected from the group consisting of is hydroxy($C_1$-$C_6$ alkyl), amino($C_1$-$C_6$ alkyl), —$CH_2$—NH($C_1$-$C_6$ alkyl), —$CH_2$—N($C_1$-$C_6$ alkyl)$_2$, heteroaryl($C_1$-$C_6$ alkyl), heterocyclyl($C_1$-$C_6$ alkyl), —$CH_2$—$NHCONH_2$, and —$CH_2$—NHCONH($C_1$-$C_6$ alkyl). (Embodiment 13)

In embodiment 14, which is based on formula I, $R_8$ is selected from the group consisting of is amino($C_1$-$C_6$ alkyl), —$CH_2$—NH($C_1$-$C_6$ alkyl), —$CH_2$—N($C_1$-$C_6$ alkyl)$_2$, —$CH_2$—$NHCONH_2$, and —$CH_2$—NHCONH($C_1$-$C_6$ alkyl). In embodiment 13, $R_8$ is selected from the group consisting of is hydroxy($C_1$-$C_6$ alkyl), heteroaryl($C_1$-$C_6$ alkyl), and heterocyclyl($C_1$-$C_6$ alkyl).

In embodiment 15, which is based on formula I, the compound may be represented by the formula:

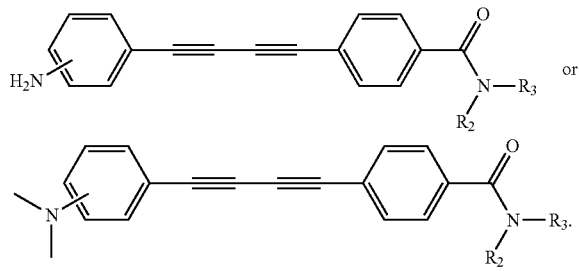

Embodiment 16 based on formula I provides compounds of formula:

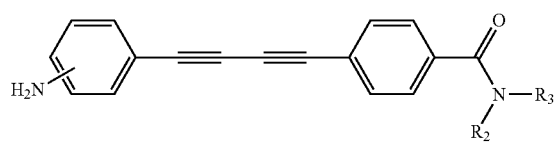

Embodiment 17 which is based on formula I, provides compounds of formula:

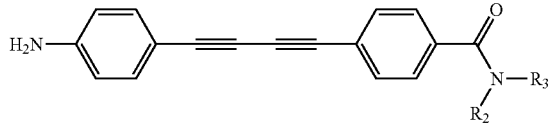

Embodiment 18 which is based on formula I, provides compounds of formula:

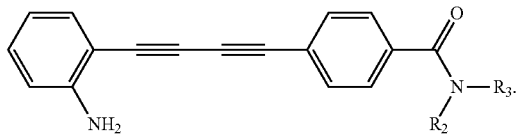

In embodiment 19 which is based on formula I, I, the compound may be represented by the formula:

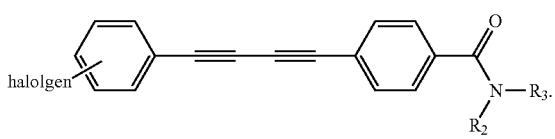

In one embodiment of embodiment 19, halogen is —F, and in other embodiment of embodiment 19, halogen is —Cl.

In embodiment 20 which is based on formula I, the compound may be represented by the formula:

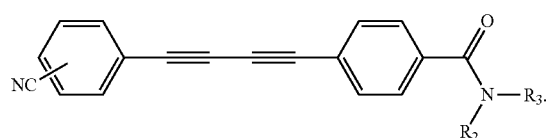

In embodiment 20-a which is based on formula I, the compound may be represented by the formula:

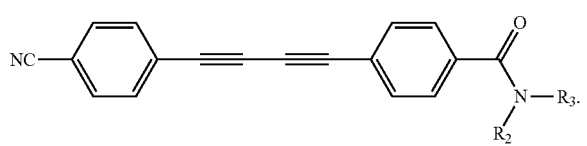

In embodiment 20-b which is based on formula I, the compound may be represented by the formula:

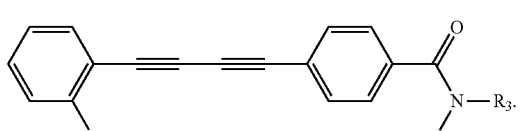

In embodiment 21 based on formula I, the compound may be represented by the formula:

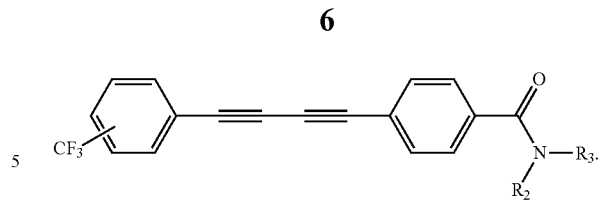

In embodiment 21-a, the trifluoromethyl group is at the para position of the $R_1$ phenyl group, and in embodiment 21-b, the trifluoromethyl group is at the meta position of the $R_1$ phenyl group. Thus, in embodiment 21-a based on formula I, the compound may be represented by the formula:

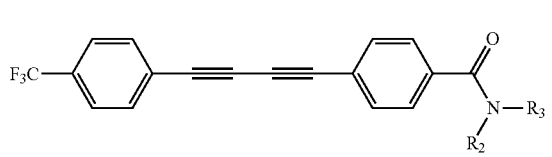

Thus, in embodiment 21-b based on formula I, the compound may be represented by the formula:

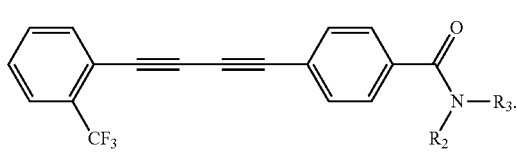

In embodiment 22 based on formula I, the compound may be represented by the formula:

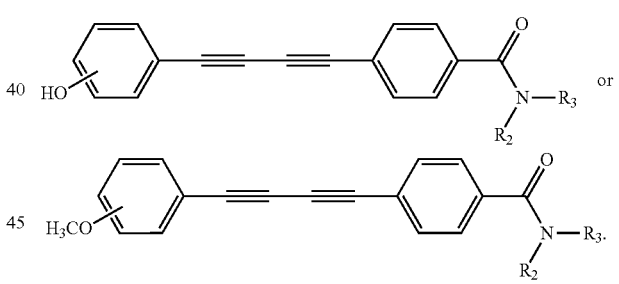

In embodiment 22-a, the hydroxy group is at the para position of the $R_1$ phenyl group, and in embodiment 21-b, the hydroxy group is at the meta position of the $R_1$ phenyl group.

In embodiment 22-c, the methoxy group is at the para position of the $R_1$ phenyl group, and in embodiment 22-d, the methoxy group is at the meta position of the $R_1$ phenyl group.

In embodiment 23 based on formula I, the compound may be represented by the formula:

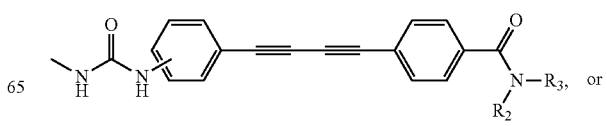

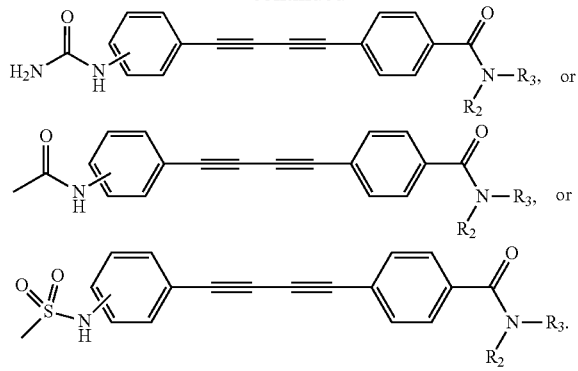

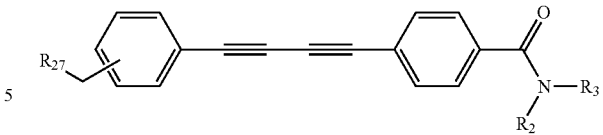

wherein $R_{27}$ is —OH, —NH$_2$, —N(C$_1$-C$_6$ alkyl)$_2$, or —NHCONH$_2$.

In embodiment 25-a, the $R_{27}$-methyl group is at the para position of the $R_1$ phenyl group, and in embodiment 25-b, the $R_{27}$-methyl group is at the meta position of the $R_1$ phenyl group.

In embodiment 26 based on formula I, the compound may be represented by the formula:

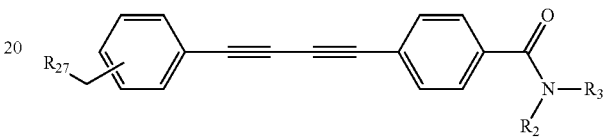

wherein $R_{27}$ is aryl, heteroaryl, or heterocyclyl.

In embodiment 26-a, the $R_{27}$-methyl group is at the para position of the $R_1$ phenyl group, and in embodiment 26-b, the $R_{27}$-methyl group is at the meta position of the $R_1$ phenyl group.

Another embodiment of the invention, i.e., Embodiment A, encompasses compounds of any of embodiments 1-26 where:
$R_2$ is —CH($R_9$)($R_{10}$);
$R_3$ is hydrogen;
$R_9$ is C$_1$-C$_6$ alkyl, aryl(C$_1$-C$_6$ alkyl), or heteroaryl(C$_1$-C$_6$ alkyl), wherein each alkyl, aryl, or heteroaryl moiety is optionally substituted with one or more $R_{11}$;
$R_{10}$ is —CONH$_2$, —CON(C$_1$-C$_6$ alkyl), —CON(C$_1$-C$_6$ alkyl)$_2$, —CONH—OH, —CONH—NH$_2$, —CO$_2$H, or —CO$_2$(C$_1$-C$_6$ alkyl); and
each $R_{11}$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), oxo, hydroxy(C$_1$-C$_6$ alkyl), alkoxy(C$_1$-C$_6$ alkyl), amino(C$_1$-C$_6$ alkyl), —CONH$_2$, —CON(C$_1$-C$_6$ alkyl), —CON(C$_1$-C$_6$ alkyl)$_2$, —CONH—OH, —CONH—NH$_2$, —COH, —CO$_2$H, —CO$_2$(C$_1$-C$_6$ alkyl), —OCO(C$_1$-C$_6$ alkyl), —NHCO(C$_1$-C$_6$ alkoxy), —NHCO(C$_1$-C$_6$ alkyl), —NHCONH$_2$, —NHCONH(C$_1$-C$_6$ alkyl), —NHC(=NH)NH$_2$, —NH—S(O)$_{0-2}$—(C$_1$-C$_6$ alkyl), —NH—S(O)$_{0-2}$-aryl, and —NH—S(O)$_{0-2}$-heteroaryl.

Particular embodiments based on formula I include those of Embodiment A-1, i.e., compounds of Embodiment A wherein
$R_9$ is aryl(C$_1$-C$_6$ alkyl), or heteroaryl(C$_1$-C$_6$ alkyl), wherein each alkyl, aryl, or heteroaryl moiety is optionally substituted with one or more $R_{11}$; and
each $R_{11}$ is independently selected from the group consisting of halogen, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), oxo, hydroxy(C$_1$-C$_6$ alkyl), alkoxy(C$_1$-C$_6$ alkyl), amino(C$_1$-C$_6$ alkyl), —OCO(C$_1$-C$_6$ alkyl), —NHCO(C$_1$-C$_6$ alkoxy), —NHCO(C$_1$-C$_6$ alkyl), —NHCONH$_2$, and —NHCONH(C$_1$-C$_6$ alkyl)

In embodiment 23-a, the urea group is at the para position of the $R_1$ phenyl group, and in embodiment 23-b, the urea group is at the meta position of the $R_1$ phenyl group.

In embodiment 23-c, the methylurea group is at the para position of the $R_1$ phenyl group, and in embodiment 23-d, the methylurea group is at the meta position of the $R_1$ phenyl group.

In embodiment 23-e, the acetamide group is at the para position of the $R_1$ phenyl group, and in embodiment 23-f, the acetamide group is at the meta position of the $R_1$ phenyl group.

In embodiment 23-g, the methylsulfonamide group is at the para position of the $R_1$ phenyl group, and in embodiment 23-h, the methylsulfonamide group is at the meta position of the $R_1$ phenyl group.

In embodiment 24 based on formula I, the compound may be represented by the formula:

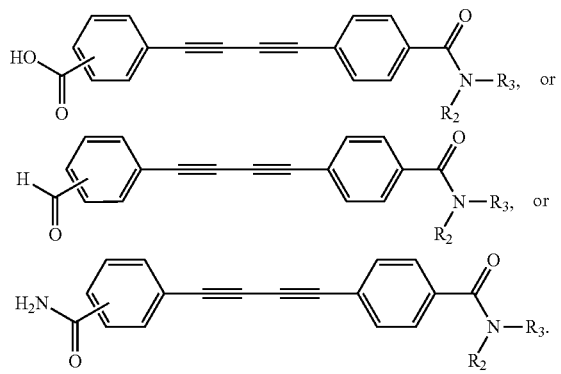

In embodiment 24-a, the carboxylic acid group is at the para position of the $R_1$ phenyl group, and in embodiment 24-b, the carboxylic group is at the meta position of the $R_1$ phenyl group.

In embodiment 24-c, the formyl group is at the para position of the $R_1$ phenyl group, and in embodiment 24-d, the formyl group is at the meta position of the $R_1$ phenyl group.

In embodiment 24-e, the carbamoyl group is at the para position of the $R_1$ phenyl group, and in embodiment 24-f, the carbamoyl group is at the meta position of the $R_1$ phenyl group.

In embodiment 25 based on formula I, the compound may be represented by the formula:

Particular embodiments based on formula I include those of Embodiment A-2, i.e., compounds of Embodiment A-1 wherein $R_9$ is aryl($C_1$-$C_2$ alkyl), or heteroaryl($C_1$-$C_2$ alkyl), wherein each alkyl, aryl, or heteroaryl moiety is optionally substituted with one or more $R_{11}$; and each $R_{11}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —NHCONH$_2$, and —NHCONH($C_1$-$C_6$ alkyl).

Particular embodiments based on formula I include those of Embodiment A-3, i.e., compounds of Embodiment A-2 wherein $R_9$ is benzyl, optionally substituted on either the ring portion or the methylene with one or more $R_{11}$; and each $R_{11}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —NHCONH$_2$, and —NHCONH($C_1$-$C_6$ alkyl).

Particular embodiments based on formula I include those of Embodiment A-4, i.e., compounds of Embodiment A-3 wherein $R_2$ is —CH($R_9$)($R_{10}$);

$R_9$ is benzyl, optionally substituted on either the ring portion or the methylene with one or more $R_{11}$;

$R_{10}$ is —CONH$_2$, —CON($C_1$-$C_6$ alkyl), —CON($C_1$-$C_6$ alkyl)$_2$, —CONH—OH, —CONH—NH$_2$, —CO$_2$H, or —CO$_2$($C_1$-$C_6$ alkyl); and each $R_{11}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —NHCONH$_2$, and —NHCONH($C_1$-$C_6$ alkyl).

Particular embodiments based on formula I include those of Embodiment A-5, i.e., compounds of Embodiment A-4 where $R_2$ is of formula:

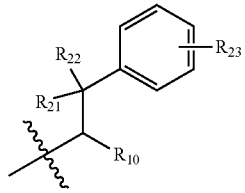

wherein $R_{10}$ is —CONH$_2$, —CON($C_1$-$C_6$ alkyl), —CON($C_1$-$C_6$ alkyl)$_2$, —CONH—OH, —CONH—NH$_2$, —CO$_2$H, or —CO$_2$($C_1$-$C_6$ alkyl);

$R_{21}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —NHCONH$_2$, and —NHCONH($C_1$-$C_6$ alkyl);

$R_{22}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —NHCONH$_2$, and —NHCONH($C_1$-$C_6$ alkyl); and $R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

Particular embodiments based on formula I include those of Embodiment A-6, i.e., compounds of Embodiment A-5 where:

$R_{10}$ is —CONH—OH, —CONH—NH$_2$, or —CO$_2$H; and $R_{21}$ is —$NH_2$ or —OH;

$R_{22}$ is selected from the group consisting of hydrogen, $C_1$-$C_6$ alkyl, $C_1$-$C_6$ haloalkyl, hydroxy($C_1$-$C_6$ alkyl), alkoxy($C_1$-$C_6$ alkyl), and amino($C_1$-$C_6$ alkyl); and $R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

Particular embodiments based on formula I include those of Embodiment A-7, i.e., compounds of Embodiment A-5 where:

$R_{10}$ is —CONH—OH; and $R_{21}$ is —OH;

$R_{22}$ is hydrogen or $C_1$-$C_6$ alkyl; and $R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

Particular embodiments based on formula I include those of Embodiment A-8, i.e., compounds of Embodiment A-1 where $R_9$ is heteroaryl($C_1$-$C_2$ alkyl) optionally substituted with one or more $R_{11}$; and each $R_{11}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —NHCONH$_2$, and —NHCONH($C_1$-$C_6$ alkyl).

Particular embodiments based on formula I include those of Embodiment A-9, i.e., compounds of Embodiment A-8 wherein the heteroaryl is selected from the group consisting of pyrrolyl, imidazolyl, triazolyl, pyrazolyl, tetrazolyl, furyl, oxazolyl, pyridinyl, pyrazinyl, pyrimidinyl, pyridazinyl, triazinyl, benzimidazolyl, indazolyl, indolyl, and quinolinyl, each of which is optionally substituted with one or more $R_{11}$.

Particular embodiments based on formula I include those of Embodiment A-10, i.e., compounds of Embodiment A-9 wherein the heteroaryl is selected from the group consisting of pyrrolyl, imidazolyl, triazolyl, pyridinyl, benzimidazolyl, indazolyl, and indolyl, each of which is optionally substituted with one or more $R_{11}$.

Particular embodiments based on formula I include those of Embodiment A-11, i.e., compounds of Embodiments A-9 or A-10, wherein
$R_2$ is —CH($R_9$)($R_{10}$);
$R_9$ is heteroaryl($C_1$-$C_2$ alkyl) optionally substituted with one or more $R_{11}$;
$R_{10}$ is —$CONH_2$, —CON($C_1$-$C_6$ alkyl), —CON($C_1$-$C_6$ alkyl)$_2$, —CONH—OH, —CONH—$NH_2$, —$CO_2$H, or —$CO_2$($C_1$-$C_6$ alkyl); and
each $R_{11}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, and —NHCONH($C_1$-$C_6$ alkyl).

Particular embodiments based on formula I include those of Embodiment A-12, i.e., compounds of Embodiment A-11, wherein $R_2$ is of formula:

wherein
the heteroaryl is optionally substituted with one or more $R_{23}$;
$R_{10}$ is —$CONH_2$, —CON($C_1$-$C_6$ alkyl), —CON($C_1$-$C_6$ alkyl)$_2$, —CONH—OH, —CONH—$NH_2$, —$CO_2$H, or —$CO_2$($C_1$-$C_6$ alkyl);
$R_{21}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, and —NHCONH($C_1$-$C_6$ alkyl);
$R_{22}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —OCO($C_1$-$C_6$ alkyl), —NHCO($C_1$-$C_6$ alkoxy), —NHCO($C_1$-$C_6$ alkyl), —$NHCONH_2$, and —NHCONH($C_1$-$C_6$ alkyl); and
$R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

Particular embodiments based on formula I include those of Embodiment A-13, i.e., compounds of Embodiment A-12 wherein
$R_{10}$ is —CONH—OH, —CONH—$NH_2$, or —$CO_2$H; and
$R_{21}$ is hydrogen, —$NH_2$, or —OH;
$R_{22}$ is selected from the group consisting of hydrogen, $C_1$-$C_6$ alkyl, $C_1$-$C_6$ haloalkyl, hydroxy($C_1$-$C_6$ alkyl), alkoxy($C_1$-$C_6$ alkyl), and amino($C_1$-$C_6$ alkyl); and
$R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

Particular embodiments based on formula I include those of Embodiment A-14, i.e., compounds of Embodiment A-13 wherein
$R_{10}$ is —CONH—OH; and
$R_{21}$ is —OH;
$R_{22}$ is hydrogen or $C_1$-$C_6$ alkyl; and
$R_{23}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl).

Particular embodiments based on formula I include those of Embodiment A-15, i.e., compounds of Embodiment A wherein
$R_9$ is $C_1$-$C_6$ alkyl, optionally substituted with one or more $R_{11}$; and
each $R_{11}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —$CONH_2$, —CON($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —NHC(=NH)$NH_2$, —OCO($C_1$-$C_6$ alkyl), —NHCO($C_1$-$C_6$ alkoxy), —NHCO($C_1$-$C_6$ alkyl), —$NHCONH_2$, and —NHCONH($C_1$-$C_6$ alkyl).

Particular embodiments based on formula I include those of Embodiment A-16, i.e., compounds of Embodiment A-15 wherein
$R_2$ is —CH($R_9$)($R_{10}$);
$R_9$ is $C_1$-$C_6$ alkyl, optionally substituted with one or more $R_{11}$;
$R_{10}$ is —CONH—OH, —CONH—$NH_2$, or —$CO_2$H; and
each $R_{11}$ is independently selected from the group consisting of halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy($C_1$-$C_6$ alkyl), alkoxy($C_1$-$C_6$ alkyl), amino($C_1$-$C_6$ alkyl), —$CONH_2$, —CON($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —NHC(=NH)$NH_2$, —OCO($C_1$-$C_6$ alkyl), —NHCO($C_1$-$C_6$ alkoxy), —NHCO($C_1$-$C_6$ alkyl), —$NHCONH_2$, and —NHCONH($C_1$-$C_6$ alkyl).

Particular embodiments based on formula I include those of Embodiment A-17, i.e., compounds of Embodiment A-16 wherein
$R_2$ is —CH($R_9$)($R_{10}$);
$R_9$ is $C_1$-$C_4$ alkyl, optionally substituted with one or more $R_{11}$;
$R_{10}$ is —CONH—OH; and
each $R_{11}$ is independently selected from the group consisting of halogen, $C_1$-$C_4$ alkyl, $C_1$-$C_4$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), —$CONH_2$, —CON($C_1$-$C_6$ alkyl), —CON($C_1$-$C_6$ alkyl)$_2$, —CONH—OH, —CONH—$NH_2$, —COH, —$CO_2$H, —$CO_2$($C_1$-$C_6$ alkyl), —NHC(=NH)$NH_2$, —OCO($C_1$-$C_6$ alkyl), —NHCO($C_1$-$C_6$ alkoxy), —NHCO($C_1$-$C_6$ alkyl), —$NHCONH_2$, and —NHCONH($C_1$-$C_6$ alkyl)

Particular embodiments based on formula I include those of Embodiment A-18, i.e., compounds of any of embodiments 1-26 where
$R_2$ is heterocyclyl optionally substituted with one or more $R_{10}$;
$R_3$ is hydrogen; and $R_{10}$ is halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, oxo, —$CONH_2$, —CON($C_1$-$C_6$ alkyl), —CON($C_1$-$C_6$ alkyl)$_2$, —CONH—OH, —CONH—$NH_2$, —$CO_2H$, and —$CO_2$($C_1$-$C_6$ alkyl).

Particular embodiments based on formula I include those of Embodiment A-19, i.e., compounds of Embodiment A-18 wherein the heterocyclyl ring is 4- to 7-member ring containing 1 or 2 hetero atoms selected from nitrogen, oxygen, and sulfur, and the ring may be saturated or partially unsaturated, and optionally substituted with one or more $R_{10}$.

Particular embodiments based on formula I include those of Embodiment A-20, i.e., compounds of Embodiment A-19 wherein, wherein the heterocyclyl ring is selected from the group consisting of azetidinyl, pyrrolidinyl, piperidinyl, piperazinyl, morpholinyl, homopiperazinyl, homopiperidinyl, diazepanyl, imidazolidinyl, 2,3-dihydro-1H-imidazol-4-yl, 1,4,5,6-tetrahydropyrazin-2-yl, 2,3,4,7-tetrahydro-1H-1,4-diazepin-1-yl, 1,4,5,6-tetrahydropyridin-3-yl, 4,5-dihydro-1H-pyrrol-3-yl, and 3,4-dihydro-2H-1,4-oxazin-6-yl, each of which is optionally substituted with one or more $R_{10}$.

Particular embodiments based on formula I include those of Embodiment A-21, i.e., compounds of Embodiment A-20 wherein $R_2$ is heterocyclyl optionally substituted with one or more $R_{10}$, wherein the heterocyclyl ring is selected from the group consisting of azetidinyl, pyrrolidinyl, and piperidinyl;

$R_3$ is hydrogen; and $R_{10}$ is halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, oxo, —$CONH_2$, —CON($C_1$-$C_6$ alkyl), —CON($C_1$-$C_6$ alkyl)$_2$, —CONH—OH, —CONH—$NH_2$, —$CO_2H$, and —$CO_2$($C_1$-$C_6$ alkyl).

Particular embodiments based on formula I include those of Embodiment A-22, i.e., compounds of Embodiment A-21 wherein $R_2$ is heterocyclyl optionally substituted with one or more $R_{10}$, wherein the heterocyclyl ring is selected from the group consisting of azetidinyl, pyrrolidinyl, and piperidinyl; and $R_{10}$ is —$NH_2$, —NH($C_1$-$C_6$ alkyl), —N($C_1$-$C_6$ alkyl)$_2$, —OH, and oxo.

Particular embodiments of Formula I include those of Embodiment A-23, i.e., compounds of any of embodiments 1-26 where $R_2$ and $R_3$ together with the nitrogen to which they are attached form heterocyclyl ring optionally substituted with one or more $R_{10}$;

$R_{10}$ is halogen, —$NO_2$, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, oxo, —$CONH_2$, —CON($C_1$-$C_6$ alkyl), —CON($C_1$-$C_6$ alkyl)$_2$, —CONH—OH, —CONH—$NH_2$, —$CO_2H$, and —$CO_2$($C_1$-$C_6$ alkyl).

Particular embodiments based on formula I include those of Embodiment A-24, i.e., compounds of Embodiment A-23 wherein the heterocyclyl ring is 4- to 7-member ring containing 1 or 2 hetero atoms selected from nitrogen, oxygen, and sulfur, and the ring may be saturated or partially unsaturated, and optionally substituted with one or more $R_{10}$.

Particular embodiments based on formula I include those of Embodiment A-25, i.e., compounds of Embodiment A-24 wherein the heterocyclyl ring is selected from the group consisting of azetidinyl, pyrrolidinyl, piperidinyl, piperazinyl, morpholinyl, homopiperazinyl, homopiperidinyl, diazepanyl, imidazolidinyl, 2,3-dihydro-1H-imidazol-4-yl, 1,4,5,6-tetrahydropyrazin-2-yl, 2,3,4,7-tetrahydro-1H-1,4-diazepin-1-yl, 1,4,5,6-tetrahydropyridin-3-yl, 4,5-dihydro-1H-pyrrol-3-yl, and 3,4-dihydro-2H-1,4-oxazin-6-yl, each of which is optionally substituted with one or more $R_{10}$.

Particular embodiments based on formula I include those of Embodiment A-26, i.e., compounds of Embodiment A-25 wherein the heterocyclyl ring is selected from the group consisting of azetidinyl, pyrrolidinyl, and piperidinyl, each of which is optionally substituted with one or more $R_{10}$.

Other embodiments based on formula I include those of Embodiment A-27, i.e., compounds of any of embodiments 1-26 where $R_2$ is of formula:

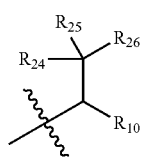

$R_{24}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —NHCO($C_1$-$C_6$ alkyl), —$NHCONH_2$, —NHCONH($C_1$-$C_6$ alkyl), —OCO($C_1$-$C_6$ alkyl), and —NHCO($C_1$-$C_6$ alkoxy);

$R_{25}$ is selected from the group consisting of hydrogen, halogen, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), and amino($C_1$-$C_6$ alkyl);

$R_{26}$ is $C_1$-$C_6$ haloalkyl; and $R_{10}$ is —$CONH_2$, —CON($C_1$-$C_6$ alkyl), —CON($C_1$-$C_6$ alkyl)$_2$, —CONH—OH, —CONH—$NH_2$, —$CO_2H$, or —$CO_2$($C_1$-$C_6$ alkyl).

Embodiment A-28 includes compounds of embodiment A-27, wherein $R_{26}$ is $C_1$ haloalkyl. Embodiment A-29 includes compounds of embodiment A-28 wherein $R_{26}$ is —$CH_2F$, —$CHF_2$, or —$CF_3$. Embodiment A-30 includes compounds of embodiment A-29 where $R_{26}$ is —$CHF_2$. Embodiment A-29-a includes compounds of embodiment A-29 where $R_{26}$ is —$CH_2F$ and Embodiment A-29-b includes compounds of embodiment A-29 where $R_{26}$ is —$CF_3$.

Particular embodiments based on formula I include those of Embodiment A-31, i.e., compounds of embodiment A-27 to A-30 wherein $R_{25}$ is hydrogen, halogen, $C_1$-$C_6$ alkyl, or $C_1$-$C_6$ haloalkyl.

Other embodiments based on formula I include those of Embodiment A-32, i.e., compounds of Embodiment A-31 wherein $R_{25}$ is hydrogen or $C_1$-$C_6$ alkyl. Embodiment A-33 includes compounds of embodiment A-32 where $R_{25}$ is hydrogen. Embodiment A-34 includes compounds of embodiment A-32 where $R_{25}$ is $C_1$-$C_6$ alkyl. Embodiment A-35 includes compounds of embodiment A-34 where $R_{25}$ is methyl.

Particular embodiments based on formula I include those of Embodiment A-36, i.e., compounds of embodiment A-27 where $R_{25}$ is methyl, and $R_{26}$ is —$CHF_2$.

Other particular embodiments based on formula I include those of Embodiment A-37, i.e., compounds of embodiment A-27 where $R_{25}$ is hydrogen, and $R_{26}$ is —$CHF_2$.

Some embodiments based on formula I include those of Embodiment A-38, i.e., compounds of embodiment A-27 to A-37 where $R_{24}$ is selected from the group consisting of —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —SH, —$S(C_1$-$C_6$ alkyl), —$NHCO(C_1$-$C_6$ alkyl), —$NHCONH_2$, —$NHCONH(C_1$-$C_6$ alkyl), —$OCO(C_1$-$C_6$ alkyl), and —$NHCO(C_1$-$C_6$ alkoxy). Embodiment A-39 includes compounds of embodiment A-38 where $R_{24}$ is selected from the group consisting of —$NH_2$, —$NH(C_1$-$C_6$ alkyl), —$N(C_1$-$C_6$ alkyl)$_2$, —NHCO($C_1$-$C_6$ alkyl), —$NHCONH_2$, —$NHCONH(C_1$-$C_6$ alkyl), and —$NHCO(C_1$-$C_6$ alkoxy).

Embodiment A-40 includes compounds of embodiment A-39 where $R_{24}$ is —$NH_2$. Embodiment A-41 includes compounds of embodiment A-39 where $R_{24}$ is —$NHCO(C_1$-$C_6$ alkyl), —$NHCONH_2$, —$NHCONH(C_1$-$C_6$ alkyl), or —$NHCO(C_1$-$C_6$ alkoxy). Embodiment A-42 includes the compounds of embodiment A-39 where $R_{24}$ is —OH or $C_1$-$C_6$ alkoxy. Embodiment A-43 includes compounds of embodiment A-32 where $R_{24}$ is —OH.

Some embodiments based on formula I include those of Embodiment A-44, i.e., compounds of embodiment A-27 to A-43 where $R_{10}$ is —CONH—OH, —CONH—$NH_2$, or —$CO_2H$. Embodiment A-45 includes compounds of embodiment A-44 wherein $R_{10}$ is —CONH—OH.

Particular embodiments of Formula I include those of Embodiment A-44, i.e., compounds of embodiment A-27 to A-45 where $R_3$ is hydrogen.

In another embodiment (Embodiment B), the invention provides compounds of the formula II:

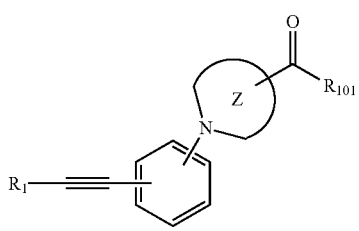

and pharmaceutically acceptable salts thereof, wherein
Z represents a heterocyclyl ring containing 4-8 members, where the ring may contain, in addition to the nitrogen attached to the phenyl group, 1 or 2 additional hetero atoms selected from nitrogen, oxygen, and sulfur, and the ring may be saturated or partially unsaturated;
$R_1$ is —$C(R_5)$=$C(R_4)(R_5)$, —C≡C—$R_4$, aryl optionally substituted with $R_6$, heteroaryl optionally substituted with $R_6$, or heterocyclyl optionally substituted with $R_6$;
  $R_4$ is $C_1$-$C_6$ alkyl optionally substituted with $R_7$, aryl optionally substituted with $R_8$, heteroaryl optionally substituted with $R_8$, or heterocyclyl optionally substituted with $R_8$;
  each $R_5$ is independently hydrogen, or $C_1$-$C_6$ alkyl;
  each $R_6$ is independently selected from the group consisting of halogen, —$NO_2$, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy;
  each $R_7$ is independently selected from the group consisting of halogen, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy;
  each $R_8$ is independently selected from the group consisting of halogen, —$NO_2$, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —SH, —$S(C_1$-$C_6$ alkyl), oxo, hydroxy($C_1$-$C_6$ alkyl), alkoxy ($C_1$-$C_6$ alkyl), amino($C_1$-$C_6$ alkyl), —$CH_2$—$NH(C_1$-$C_6$ alkyl), —$CH_2$—$N(C_1$-$C_6$ alkyl)$_2$, —$CONH_2$, —CON($C_1$-$C_6$ alkyl), —$CON(C_1$-$C_6$ alkyl)$_2$, —CONH—OH, —CONH—$NH_2$, —COH, —$CO_2H$, —$CO_2(C_1$-$C_6$ alkyl), —$OCO(C_1$-$C_6$ alkyl), —$NHCO(C_1$-$C_6$ alkoxy), —$NHCO(C_1$-$C_6$ alkyl), —$NHCONH_2$, —NHCONH ($C_1$-$C_6$ alkyl), —NHC(=NH)$NH_2$, —NH—$S(O)_{0-2}$—($C_1$-$C_6$ alkyl), —NH—$S(O)_{0-2}$-aryl, —NH—$S(O)_{0-2}$-heteroaryl, aryl($C_1$-$C_6$ alkyl), heteroaryl($C_1$-$C_6$ alkyl), heterocyclyl($C_1$-$C_6$ alkyl), —$CH_2$—$NHCONH_2$, —$CH_2$—$NHCONH(C_1$-$C_6$ alkyl), and —$CH_2$—$OCO(C_1$-$C_6$ alkyl);

$R_{101}$ is independently selected from the group consisting of $R_{112}$ and $NR_{112}R_{113}$,
  where $R_{112}$ and $R_{113}$ independently represent hydrogen, halogen, $C_1$-$C_6$ alkyl, —OH, $C_1$-$C_6$ alkoxy, $C_1$-$C_6$ haloalkoxy, or $C_1$-$C_6$ alkyl substituted with up to three groups selected from hydroxyl, —$CONH_2$, —CON ($C_1$-$C_6$ alkyl), —$CON(C_1$-$C_6$ alkyl)$_2$, —CONH—OH, —CONH—$NH_2$, —$CO_2H$, —$CO_2(C_1$-$C_6$ alkyl), and $R_{115}$,
  where $R_{115}$ represents phenyl or naphthyl, or a 5- or 6-membered heteroaryl group optionally fused to benzo, where $R_{115}$ is optionally substituted with up to three groups selected from halogen, hydroxyl, $C_1$-$C_6$ alkyl, $C_1$-$C_6$ alkoxy, $C_1$-$C_3$ haloalkyl, nitro, cyano, —$(CH_2)_m NR_{215}R_{216}$, $C(O)NR_{215}R_{216}$, and $NR_{215}R_{216}$, where m is 1, 2, 3, or 4, and $R_{215}$ and $R_{216}$ independently represent hydrogen, $C_1$-$C_6$ alkyl, hydroxyl($C_1$-$C_6$)alkyl, and amino($C_1$-$C_6$)alkyl.

Particular embodiments based on Formula II include those of Embodiment B-1, i.e., compounds of Embodiment B wherein $R_1$ is —C≡C—$R_4$, and $R_4$ is aryl optionally substituted with up to three of $R_8$, or heteroaryl optionally substituted with up to three of $R_8$,
where each $R_8$ is independently selected from the group consisting of halogen, —$NO_2$, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy.

Particular embodiments based on Formula II include those of Embodiment B-2, i.e., compounds of Embodiment B or B-1 wherein Z is pyrrolidinyl, piperidinyl, piperazinyl, morpholinyl, homopiperazinyl, homopiperidinyl, diazepanyl, imidazolidinyl, 2,3-dihydro-1H-imidazol-4-yl, 1,4,5,6-tetrahydropyrazin-2-yl, 2,3,4,7-tetrahydro-1H-1,4-diazepin-1-yl, 1,4,5,6-tetrahydropyridin-3-yl, 4,5-dihydro-1H-pyrrol-3-yl, or 3,4-dihydro-2H-1,4-oxazin-6-yl.

Particular embodiments based on Formula II include those of Embodiment B-3, i.e., compounds of Embodiment B, B-1, or B-2 where $R_{101}$ is $NR_{112}HR_{113}$, and
  $R_{112}$ represents hydrogen or $C_1$-$C_6$ alkyl;
  $R_{113}$ represents $C_1$-$C_6$ alkyl substituted with up to three groups selected from hydroxyl, —$CONH_2$, —CON ($C_1$-$C_6$ alkyl), —$CON(C_1$-$C_6$ alkyl)$_2$, —CONH—OH, —CONH—$NH_2$, —$CO_2H$, and —$CO_2(C_1$-$C_6$ alkyl).

Particular embodiments based on Formula II include those of Embodiment B-4, i.e., compounds of Embodiment B or B-1 through B-3 where $R_{101}$ represents a group of the formula:

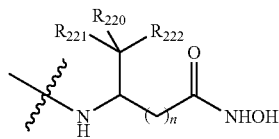

where
R$_{220}$ is hydroxy, sulfhydryl, amino, or C$_1$-C$_2$ alkylamino;
R$_{221}$ is C$_1$-C$_6$ alkyl or C$_1$-C$_6$ haloalkyl;
R$_{222}$ is hydrogen or phenyl optionally substituted with —(CH$_2$)$_m$NR$_{215}$R$_{216}$;
m is 1, 2, 3, or 4; and n is 0 or 1.

Particular embodiments based on Formula II include those of Embodiment B-5, i.e., compounds of Embodiment B or B-1 through B-4 where R$_{220}$ is hydroxyl or amino; R$_{221}$ is methyl or ethyl; and R$_{222}$ is hydrogen or phenyl optionally substituted with —(CH$_2$)$_m$NR$_{215}$R$_{216}$, where R$_{215}$ is hydrogen, m is 1 or 2; and R$_{216}$ is aminomethyl or methylaminomethyl.

Particular embodiments based on Formula II include those of Embodiment B-6, i.e., compounds of Embodiment B or B-1 through B-5 where Z is piperazin-1-yl or piperidin-1-yl, each of which is attached to the phenyl carrying the acetylenyl group in a position para to the acetylenyl group.

Particular embodiments based on Formula II include those of Embodiment B-7, i.e., compounds of Embodiment B or B-1 through B-6 where in the C(O)R$_{101}$ group is attached to Z in the 4-position based on the point of attachment of Z to the phenyl carrying the acetylenyl group.

In another embodiment (Embodiment C), the invention provides compounds of the formula III:

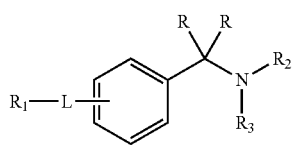

or a pharmaceutically acceptable salt thereof, wherein
each R is independently hydrogen, or C$_1$-C$_6$ alkyl, or two R groups form =O;
L is —O—C(R$_5$)(R$_5$)—C≡C— or —C≡C—C(R$_5$)(R$_5$)—O—;
R$_1$ is C$_1$-C$_6$ alkyl optionally substituted with R$_7$, aryl optionally substituted with R$_8$, heteroaryl optionally substituted with R$_8$, or heterocyclyl optionally substituted with R$_8$;
R$_2$ is —CH(R$_9$)(R$_{10}$), or heterocyclyl optionally substituted with one or more R$_{10}$;
R$_3$ is hydrogen or C$_1$-C$_6$ alkyl;
or R$_2$ and R$_3$ together with the nitrogen to which they are attached form heterocyclyl ring optionally substituted with one or more R$_{10}$;
each R$_5$ is independently hydrogen, or C$_1$-C$_6$ alkyl;
each R$_7$ is independently selected from the group consisting of halogen, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy;
each R$_8$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy;
R$_9$ is hydrogen, C$_1$-C$_6$ alkyl, aryl, aryl(C$_1$-C$_6$ alkyl), heteroaryl, heteroaryl(C$_1$-C$_6$ alkyl), heterocyclyl, or heterocyclyl(C$_1$-C$_6$ alkyl), wherein each alkyl, aryl, heteroaryl, or heterocyclyl moiety is optionally substituted with one or more R$_{11}$;
R$_{10}$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, oxo, —CONH$_2$, —CON(C$_1$-C$_6$ alkyl), —CON(C$_1$-C$_6$ alkyl)$_2$, —CONH—OH, —CONH—NH$_2$, —CO$_2$H, and —CO$_2$(C$_1$-C$_6$ alkyl); and
each R$_{11}$ is independently selected from the group consisting of halogen, —NO$_2$, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, —SH, —S(C$_1$-C$_6$ alkyl), oxo, hydroxy(C$_1$-C$_6$ alkyl), alkoxy(C$_1$-C$_6$ alkyl), amino (C$_1$-C$_6$ alkyl), —CONH$_2$, —CON(C$_1$-C$_6$ alkyl), —CON (C$_1$-C$_6$ alkyl)$_2$, —CONH—OH, —CONH—NH$_2$, —CO$_2$H, —CO$_2$(C$_1$-C$_6$ alkyl), —NHCONH$_2$, —NHC(=NH)NH$_2$, —NH—S(O)$_{0-2}$—(C$_1$-C$_6$ alkyl), —NH—S(O)$_{0-2}$-aryl, and —NH—S(O)$_{0-2}$-heteroaryl.

Particular embodiments based on Formula III include those of Embodiment C-1, i.e., compounds of Embodiment C where two R groups form =O.

Particular embodiments based on Formula III include those of Embodiment C-2, i.e., compounds of Embodiment C or C-1 where
L is —O—C(R$_5$)(R$_5$)—C≡C—;
R$_1$ is C$_1$-C$_6$ alkyl optionally substituted with R$_7$, aryl optionally substituted with R$_8$, heteroaryl optionally substituted with R$_8$, or heterocyclyl optionally substituted with R$_8$;

Other particular embodiments based on Formula III include those of Embodiment C-3, i.e., compounds of Embodiment C-2 which have the formula:

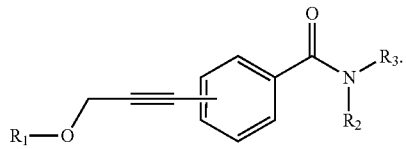

Particular embodiments based on Formula III include those of Embodiment C-4, i.e., compounds of Embodiment C or C-1 through C-3 wherein R$_1$ is aryl optionally substituted with R$_8$, where R$_8$ is selected from the group consisting of halogen, —NO$_2$, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy.

Particular embodiments based on Formula III include those of Embodiment C-5, i.e., compounds of Embodiment C-4 where R$_1$ is phenyl optionally substituted halogen, —NO$_2$, —NH$_2$, —OH, C$_1$-C$_6$ alkoxy, and C$_1$-C$_6$ haloalkoxy.

Particular embodiments based on Formula III include those of Embodiment C-6, i.e., compounds of Embodiments C4 or C5 wherein
L is —C≡C—C(R$_6$)(R$_6$)—O—;
R$_1$ is C$_1$-C$_6$ alkyl optionally substituted with R$_7$, aryl optionally substituted with R$_8$, heteroaryl optionally substituted with R$_8$, or heterocyclyl optionally substituted with R$_8$;

Particular embodiments based on Formula III include those of Embodiment C-7, i.e., compounds of Embodiment C-6 where the compound is of formula:

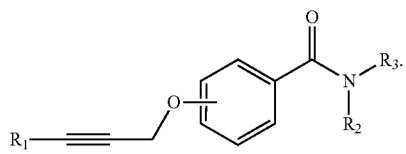

Particular embodiments based on Formula III include those of Embodiment C-8, i.e., compounds of Embodiment C-6 or C-7 wherein R$_1$ is aryl optionally substituted with R$_8$, where $R_8$ is selected from the group consisting of halogen, —$NO_2$, —$NH_2$, —$NH(C_1$-$C_6$ alkyl), —$N(C_1$-$C_6$ alkyl)$_2$, —OH, $C_1$-$C_6$ alkoxy, and $C_1$-$C_6$ haloalkoxy.

Particular embodiments based on Formula III include those of Embodiment C-9, i.e., compounds of Embodiment C-8, wherein $R_1$ is phenyl optionally substituted halogen, —$NO_2$, —$NH_2$, —OH, $C_1$-$C_6$ alkoxy, and $C_1$-$C_6$ haloalkoxy.

Particular embodiments based on Formula III include those of Embodiment C-10, i.e., compounds of any Embodiment C or C-1 through C-9 wherein $R_2$ is —$CH(R_9)(R_{10})$;

$R_3$ is hydrogen;

$R_9$ is $C_1$-$C_6$ alkyl, aryl($C_1$-$C_6$ alkyl), or heteroaryl($C_1$-$C_6$ alkyl), wherein each alkyl, aryl, or heteroaryl moiety is optionally substituted with one or more $R_{11}$;

$R_{10}$ is —$CONH_2$, —$CON(C_1$-$C_6$ alkyl), —$CON(C_1$-$C_6$ alkyl)$_2$, —CONH—OH, —CONH—$NH_2$, —$CO_2H$, or —$CO_2(C_1$-$C_6$ alkyl); and each $R_{11}$ is independently selected from the group consisting of halogen, —$NO_2$, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —SH, —$S(C_1$-$C_6$ alkyl), oxo, hydroxy($C_1$-$C_6$ alkyl), alkoxy($C_1$-$C_6$ alkyl), amino ($C_1$-$C_6$ alkyl), —$CONH_2$, —$CON(C_1$-$C_6$ alkyl), —CON ($C_1$-$C_6$ alkyl)$_2$, —CONH—OH, —CONH—$NH_2$, —$CO_2H$, —$CO_2(C_1$-$C_6$ alkyl), —$NHCONH_2$, —NHC(=NH)$NH_2$, —NH—$S(O)_{0-2}$—($C_1$-$C_6$ alkyl), —NH—S$(O)_{0-2}$-aryl, and —NH—$S(O)_{0-2}$-heteroaryl.

Particular embodiments based on Formula III include those of Embodiment C-10, i.e., compounds of any Embodiment C or C-1 through C-9 wherein $R_2$ is heterocyclyl optionally substituted with one or more $R_{10}$;

$R_3$ is hydrogen; and $R_{10}$ is halogen, —$NO_2$, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, oxo, —$CONH_2$, —CON ($C_1$-$C_6$ alkyl), —$CON(C_1$-$C_6$ alkyl)$_2$, —CONH—OH, —CONH—$NH_2$, —$CO_2H$, and —$CO_2(C_1$-$C_6$ alkyl).

Therapeutics Applications

The invention provides methods of treating Gram-negative bacterial infections, the method comprising administering to a subject in need of such treatment an effective amount of one or more compounds of the invention Particular Gram-negative bacteria are *Pseudomonas aeruginosa, Stenotrophomonas maltophilia, Burkholderia cepacia, Alcaligenes xylosoxidans, Acinetobacter,* Enterobacteriaceae, *Haemophilus, Neisseria* species, *Francisella tularensis, Yersinia pestis, Burkholderia pseudomallei, Burkholderia mallei, Rickettsia prowazekii, Coxiella burnetti, Campylobacter jejuni, Shigella, Moraxella catarrhalis,* and *Chlamydia trachomatis*. In one embodiment, the Gram-negative bacteria is *Neisseria gonorrhoeae*. In another embodiment, the Gram-negative bacteria is *Acinetobacter Baumannii*.

Specific enterobacteriaceae is selected from the group consisting of *Serratia, Proteus, Klebsiella, Enterobacter, Citrobacter, Salmonella, Providencia, Morganella, Cedecea, Edwardsiella, Escherichia coli, Enterobacter cloacae,* and *Enterobacter aerogenes*.

In another aspect, the invention provides methods for inhibiting a deacetylase enzyme in Gram-negative bacteria, the method comprising contacting the bacteria with an effective amount of one or more compounds of the invention. A specific deacetylase enzyme is LpxC.

Pharmaceutical Compositions

In another aspect, the present disclosure provides compositions comprising one or more of compounds as described above with respect to formula I and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect.

For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

Definitions

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC$($CH_3$)—, —$CH_2CH(CH_2CH_3$)$CH_2$—.

The term "alkylene" refers to a bivalent alkyl group. An "alkylene chain" is a polymethylene group, i.e., —($CH_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

An "aralkyl" or "arylalkyl" group comprises an aryl group covalently attached to an alkyl group, either of which independently is optionally substituted. Preferably, the aralkyl group is aryl($C_1$-$C_6$)alkyl, including, without limitation, benzyl, phenethyl, and naphthyl methyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The terms "heterocyclyl" and "heterocycloalkyl" as used herein, mean a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —$NO_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present disclosure can modulate atherosclerosis by stimulating the removal of cholesterol from atherosclerotic lesions in a human.

"Treating" or "treatment" as used herein covers the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, ameliorating, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Methods of Preparation

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below.

General Procedure

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Starting materials can be obtained from commercial sources or prepared by well-established literature methods known to those of ordinary skill in the art. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/I, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

LC/MS analysis is conducted on an Agilent 1200 HPLC with a quadrupole mass analyzer. LC chromatography used an Agilent XDB-C18 column (4.6×50 mm, 1.8 μm) with a water/acetonitrile (each with 0.2% (v/v) formic acid) gradient at a flow rate of 0.5 mL/min. HRMS analyses are performed at the Duke MS Center. Thin-layer chromatography (TLC) is performed on Sigma-Aldrich plates with a fluorescent indicator. Proton ($^1$H) and carbon ($^{13}$C) NMR spectra are recorded at 300 and 75 MHz, respectively, on a Varian Spectrometer. Chemistry shifts (δ) are reported in parts per million (ppm) referenced to $^1$H (TMS at 0.00), $^{13}$C (DMSO at 39.55, CDCl$_3$ at 77.0, and CD$_3$OD at 49.0). Column chromatography is conducted using either silica gel (Silicycle 40-64 μm) or prepacked RediSep columns (Teledyne Isco Inc., Lincoln, Nebr.) on an Isco CombiFlash Rf instrument. All moisture-sensitive reactions are carried out using dry solvents and under a slight pressure of ultra-pure quality argon. Glassware is dried in an oven at 140° C. for at least 12 h prior to use, and then assembled quickly while hot, sealed with rubber septa, and allowed to cool under a stream of argon. Reactions are stirred magnetically using Teflon-coated magnetic stirring bars. Commercially available disposable syringes are used for transferring reagents and solvents.

The disclosures of all articles and references mentioned in this application, including patents, are incorporated herein by reference in their entirety.

EXAMPLES

The preparation of the compounds of the disclosure is illustrated further by the following examples, which are not to be construed as limiting the disclosure in scope or spirit to the specific procedures and compounds described in them. In all cases, unless otherwise specified, the column chromatography is performed using a silica gel solid phase.

Example 1

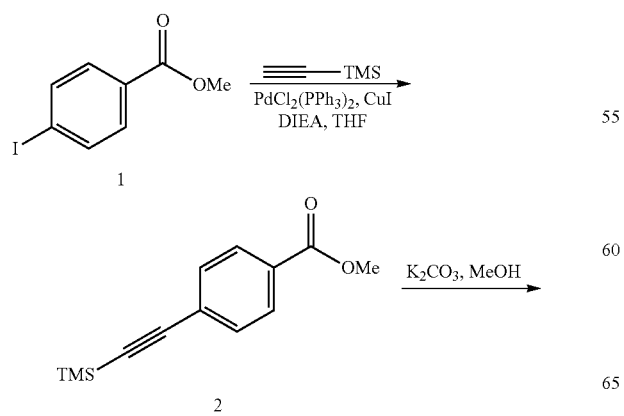

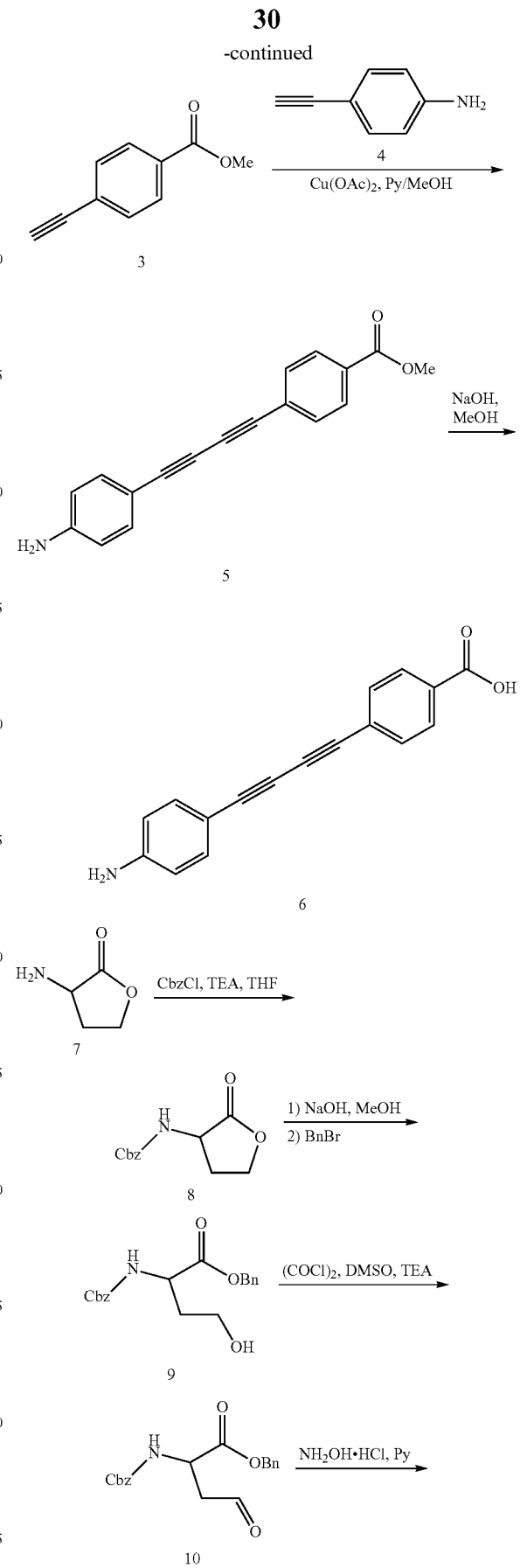

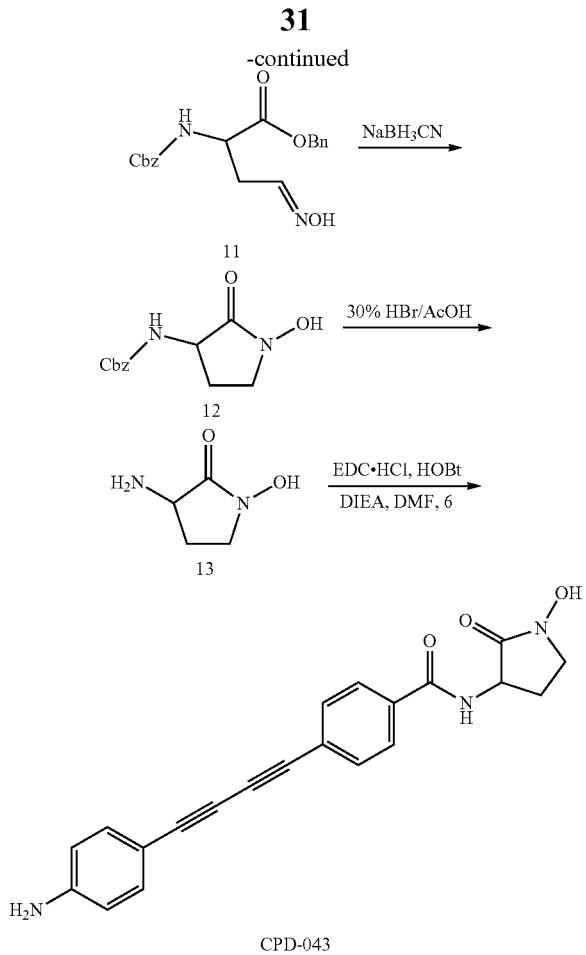

CPD-043

2: To an oven-dried round bottom flask equipped with water cooled west condenser and magnetic stir bar are added Methyl 4-iodobenzoate (10.48 g, 40 mmol), bis triphenylphosphine) palladium (II) dichloride (1.404 g, 2.0 mmol, 0.05 equiv) and copper (I) iodide (0.076 g, 4 mmol, 0.10 equiv.). The vessel is then sealed with a rubber septum under argon and are added anhydrous THF (100 mL) and diisopropylethylamine (28 mL, 160 mmol, 4 equiv). Finally, the (trimethylsily) acetylene (8 mL, 52 mmol, 1.3 equiv) is added and the reaction mixture is heated by oil at 60 C for 22 h. The resulting dark solution is condensed to dryness with a rotavapor, and the residue is treated with water (100 mL), extracted with EtOAc (3×100 mL). The combined extracts are washed with water (50 mL) and brine (anhydrous Na$_2$SO$_4$). The crude products are purified by flash chromatography (eluting with 50-60% DCM in hexane) to afford 2 (7.9 g, 85.1%) yellow solid. $^1$H NMR (300 MHz, CDCl$_3$) δ 0.25 (s, 9H), 3.90 (s, 3H), 7.51 (d, J=8.7 Hz, 2H), 7.96 (d, J=8.7 Hz, 2H); $^{13}$C NMR (75 MHz, CDCl$_3$) δ 0.06, 52.44, 79.90, 104.28, 127.98, 129.60, 129.90, 132.09, 166.71; LC/MS m/s [M+Na]$^+$ 255.1.

3: The silylatealkyne compound starting material (7.9 g, 34 mmol) is dissolved in anhydrous MeOH (150 mL), and then potassium carbonate (23.46 g, 170 mmol, 5 equiv) is added. The mixture is stirred for 3 h under argon at room temperature. The mixture is added to water (150 mL) to quench the reaction. The mixture is extracted with diethyl ether (3×100 mL), and then the combined organic extracts are dried over anhydrous Na$_2$SO$_4$. The solvent is evaporated in vacuum to afford the crude product, which is purified by chromatography (eluting with 25-30% DCM in hexane) to afford 3 (4.4 g, 80% yield) as brown solid. $^1$H NMR (300 MHz, CDCl$_3$) δ 3.23 (s, 1H), 3.91 (s, 3H), 7.54 (d, J=8.7 Hz, 2H), 7.98 (d, J=8.7 Hz, 2H); $^{13}$C NMR (75 MHz, CDCl$_3$) δ 52.20, 80.31, 83.01, 126.96, 129.68, 130.34, 132.30, 166.63; LC/MS m/s [M+H]$^+$ 161.2.

5: Copper (II) acetate (1.13 g, 6.2 mmol, 2 equiv) is added at room temperature and under stream of argon to a stirred solution of 3 (0.50 g, 3.1 mmol) and 4-ethynylbenzenamin (2.64 g, 15.5 mmol, 5 equiv) dissolved in anhydrous pyridine (5 mL), and MeOH (5 mL), and the mixture are stirred at room temperature for 24 h. The resulting blue solution is condensed to dryness with a rotavapor, and the residue is treated with water (50 mL), extracted with EtOAc (3×70 mL), and dried over anhydrous Na$_2$SO$_4$. The crude products are purified by flash chromatography (eluting with 20-30% EtOAc in hexane) to afford 5 (0.30 g, 35% yield) as yellow solid. $^1$H NMR (300 MHz, DMSO-$_{d6}$) δ 3.83 (s, 3H), 5.85 (s, 2H), 6.54 (d, J=8.1 Hz, 2H), 7.25 (d, J=8.4 Hz, 2H), 7.64 (d, J=8.1 Hz, 2H), 7.92 (d, J=8.1 Hz, 2H); $^{13}$C NMR (75 Hz, DMSO-$_{d6}$) δ 53.04, 71.77, 78.29, 80.49, 86.98, 105.73, 114.28, 126.74, 130.06, 130.32, 132.98, 134.76, 151.64, 166.19; LC/MS m/s [M+H]$^+$ 276.1.

6: A 3N solution of NaOH (10 mL) is added to stir solution of methyl ester (0.50 g, 1.82 mmol) in MeOH (100 mL) at room temperature. The reaction solution is heated to reflux for 1 h. Then the reaction turned clear. All of the starting material is gone by TLC. The reaction is cooled to room temperature and some MeOH is removed by evaporation under reduced pressure (50 mL). Water (20 mL) is added to the mixture. Conc. HCl is added dropwise to the stirred solution until acidic by pH paper (pH=2). The yellow precipitate that formed is collected by suction filtration. The solid is washed with water (2×20 mL) to give 6 (0.45 g, 90% yield). $^1$H NMR (300 MHz, DMSO-$_{d6}$) δ 6.95 (d, J=8.4 Hz, 2H), 7.45 (d, J=8.4 Hz, 2H), 7.66 (d, J=8.4 Hz, 2H), 7.93 (d, J=8.4 Hz, 2H); $^{13}$C NMR (75 MHz, DMSO-$_{d6}$) δ 72.99, 77.22, 81.23, 85.02, 112.00, 118.79, 125.80, 130.24, 131.93, 133.07, 134.64, 144.23, 167.19; LC/MS m/s [M+H]$^+$ 262.1.

8: Benzl chloroformate (2.42 g, 14.2 mmol, 1.10 equiv) is added dropwise to a stirred mixture of α-Amino-γ-butyrolactone hydroxybromide (2.35 g, 12.9 mmol) in anhydrous THF (20 mL) under argon. The mixture is cooled to 0° C., triethylamino (2.61 g, 25.8 mmol, 2.00 equiv) is added dropwise. The whole reaction mixture is stirred at 0° C. for 1 h, then allowed to warm to room temperature with the stirring is continued for 16 h. The resulting suspension solution is concentrated to dryness and the residue is treated with water (50 mL). The mixture is acidified to pH=3 with 3N HCl, and extracted with EtOAc (3×70 mL). The combined organic layers are washed with brine (50 mL), and dried (anhydrous Na$_2$SO$_4$). Evaporation of the solvent affords viscous oil, which is purified by CombiFlash (eluting with EtOAc in hexane 0-40%) to give 8 (2.638 g, 87% yield) as white solid. $^1$H (300 MHz, CDCl$_3$) δ 2.12-2.21 (m, 1H), 2.64-2.73 (m, 1H), 4.15-4.24 (m, 1H), 4.39 (t, J=17.4 Hz, 2H), 5.10 (s, 2H), 5.51 (d, J=5.1 Hz, 1H), 7.26-7.73 (m, 5H); $^{13}$C (75 MHz, CDCl$_3$) δ 30.26, 50.66, 66.00, 67.53, 128.40, 128.55, 128.82, 136.17, 156.38, 175.40; LC/MS m/s [M+H]$^+$ 236.1.

9: A solution of sodium hydroxide (0.44 g, 11.1 mmol, 1.00 equiv) in anhydrous methanol (15 mL) is added to a stirred suspension of the 8 (2.60 g, 11.1 mmol) in anhydrous methanol (10 mL). The whole mixture is stirred at room temperature under argon for 3 h. The resulting solution is concentrated to dryness as a white solid. The carboxylate salt is dissolved in anhydrous dimethylformamide (20 mL)

and benzyl bromide (1.90 g, 11.1 mmol, 1.00 equiv) is added. The mixture is stirred at room temperature under argon for 36 h, and then concentrated to dryness. The residue is treated with water (50 mL), extracted with ether (3×80 mL). The ether layers are washed with 1N HCl (50 mL), water (50 mL), brine (50 mL), and dried (anhydrous $Na_2SO_4$). Evaporation of the solvent affords a solid, which is purified by CombiFlash (eluting with EtOAc in hexane 0-40%) to give 9 (3.23 g, 85% yield) as white solid. $^1$H (300 MHz, $CDCl_3$) δ 1.67-1.78 (m, 1H), 2.10-2.21 (m, 1H), 2.93 (t, J=12.0 Hz, 1H), 3.58-3.75 (m, 2H), 4.55-4.62 (m, 1H), 5.11 (s, 2H), 5.18 (s, 2H), 5.79 (d, J=7.8 Hz, 1H), 7.29-7.35 (m, 5H); $^{13}$C (75 MHz, $CDCl_3$) δ 35.75, 51.61, 58.58, 67.52, 67.62, 128.41, 128.82, 128.89, 135.38, 136.28, 157.04, 172.63; LC/MS m/s $[M+H]^+$ 344.3.

10: Anhydrous dimethylsulphoxide (DMSO) (1.45 ml, 20.38 mmol, 2.20 equiv) in dichloromethane (10 mL) is added dropwise to a stirred solution of oxalylchloride (5.10 mL, 10.19 mmol, 1.10 equiv) at −78° C. under argon. The solution is stirred for 20 min, and then the alcohol (3.18 g, 9.26 mmol) in dichloromethane (15 mL) is added over 3 min. The resulting slurry is stirred for 15 min and anhydrous triethylamine (6.45 mL, 46.3 mmol, 5.00 equiv) is added. The mixture is stirred for an additional 5 min at −78° C., then is allowed to warm to room temperature for 10 min. The whole mixture is concentrated to dryness, and the residue is treated with water (50 mL), extracted with EtOAc (3×80 mL). The organic layers are washed with brine (50 mL), dried (anhydrous $Na_2SO_4$). Evaporation of the solvent affords the crude product, which is purified by CombiFlash (eluting with EtOAc in hexane 0-30%) to give 10 (2.76 g, 87%) as a white solid. $^1$H (300 MHz, $CDCl_3$) δ 3.08 (q, J=54.9 Hz, 2H), 4.67-4.73 (m, 1H), 5.10 (s, 2H), 5.21 (s, 2H), 5.78 (d, J=8.4 Hz, 1H), 7.29-7.38 (m, 10H), 9.67 (s, 1H); $^{13}$C (75 MHz, $CDCl_3$) δ 45.99, 49.38, 67.40, 67.91, 128.35, 128.54, 128.80, 128.88, 135.28, 136.28, 156.19, 170.81, 199.43; LC/MS m/s $[M+H]^+$ 342.3.

11: To a solution of 10 (2.74 g, 8.0 mmol) in anhydrous pyridine (10 mL) and methanol (10 mL) is added hydroxylamine hydrochloride (0.97 g, 14.0 mmol, 1.75 equiv). The reaction mixture is stirred at room temperature under argon for 3 h, and then concentrated to dryness. The residue is purified by CombiFlash (elution with EtOAc in hexane 0-30%) to give 11 (2.78 g, 98% yield) as white solid. $^1$H (300 MHz, $CDCl_3$) δ 2.69 (t, J=12.0 Hz, 1H), 2.87 (t, J=12.9 Hz, 1H), 4.62 (t, J=14.1 Hz, 1H), 5.10 (d, J=2.4 Hz, 2H), 5.18 (d, J=3.6 Hz, 2H), 5.81 (d, J=8.1 Hz, 1H), 5.97 (d, J=8.7 Hz, 1H), 6.76 (t, J=10.5 Hz, 1H), 7.27-7.34 (m, 10H); $^{13}$C (75 MHz, $CDCl_3$) δ 28.42, 32.53, 51.950, 67.40, 67.82, 128.39, 128.61, 128.79, 128.89, 135.30, 136.29, 147.24, 156.31, 171.56; LC/MS m/s $[M+H]^+$ 357.4.

12: To a solution of a mixture of oximes 11 (1.81 g, 5.08 mmol) in anhydrous methanol (30 mL) is added $NaBH_3CN$ (321 mg, 5.1 mmol, 1.00 equiv) and the reaction mixture is stirred at room temperature under argon for 1.5 h. The pH of the solution during the period of the reaction is kept at 2-3 by addition of methanolic HCl (1N) solution during the period of the reaction. The reaction mixture is neutralized with 1N NaOH and concentrated to dryness. The residue is dilute by water (50 mL), extracted with $CHCl_3$ (3×80 mL), and dried (anhydrous $Na_2SO_4$). Evaporation of the solvent affords the crude product, which is purified by CombiFlash (eluting with MeOH in DCM 0-7%) to give 12 (440 mg, 35% yield) as white solid. $^1$H (300 MHz, $CD_3OD$) δ 1.90-2.03 (m, 1H), 2.36-2.47 (m, 1H), 3.47-3.58 (m, 2H), 4.258 (t, J=18.3 Hz, 1H), 5.08 (s, 2H), 7.28-7.35 (m, 5H); $^{13}$C (75 MHz, $CD_3OD$) δ 23.97, 46.20, 50.19, 66.51, 127.72, 127.85, 128.30, 136.95, 157.22, 168.18; LC/MS m/s $[M+H]^+$ 251.1.

13: To a mixture of 30% HBr in acetic acid (0.78 mL) and trifluoroacetic acid (0.32 mL) is added pyrrolidone 12 (200 mg, 0.80 mmol), and the mixture is stirred at room temperature for 70 min. Ether (50 mL) is added to the reaction and the resulting precipitate is filtered off. The precipitate is dissolved in milliQ water (2 mL) and passed through a columnfilled with Dowex 50W×4 ($H^+$) (sigma) (10 g), eluting with milliQ water (200 mL), then 1N $NH_3$ solution (200 mL). The eluent is concentrated in vacuum to give 13 (83 mg, 89% yield) as white solid. $^1$H (300 MHz, $D_2O$) δ 1.71-1.81 (m, 1H), 2.28-2.32 (m, 1H), 3.37-3.41 (m, 2H), 3.74 (t, J=16.5 Hz, 1H); $^{13}$C (75 MHz, $D_2O$) δ 22.32, 48.09, 49.91, 163.03; LC/MS m/s $[M+H]^+$ 117.1.

CPD-043: To a stirred of amine 13 (40 mg, 0.345 mmol) and acid (108 mg, 0.414 mmol, 1.20 equiv) in anhydrous DMF (1.5 mL) is added EDC.HCl (79.1 mg, 0.414 mmol, 1.20 equiv), and HOBt (55.9 mg, 0.414 mmol, 1.20 equiv) at room temperature. The mixture is cooled with an ice-bath to 0° C., and the DIPEA (0.24 mL, 1.38 mmol, 4.0 equiv). The whole mixture is stirred under argon at 0° C. for 1 h, then allowed to warm to ambient temperature with the stirring is continued for additional 36 h. The resulting yellow solution is concentrated to dryness. The residue is treated with water (10 mL), extracted with EtOAc (3×50 mL). The organic layers are washed with 1N NaOH (10 mL), brine (50 mL), and dried (anhydrous $Na_2SO_4$). Evaporation of the solvent affords the crude product, which is purified by CombiFlash (eluting with MeOH in DCM 0-10%) to give CPD-043, 4-((4-aminophenyl)buta-1,3-diynyl)-N-(1-hydroxy-2-oxopyrrolidin-3-yl)benzamide (43 mg, 35%) as yellow solid. $^1$H (300 MHz, DMSO-$_{d6}$) δ 1.91-2.01 (m, 1H), 2.27-2.36 (m, 1H), 3.42-3.47 (m, 2H), 4.53 (q, J=26.7 Hz, 2H), 5.84 (s, 2H), 6.52 (d, J=8.7 Hz, 2H), 7.24 (d, J=8.4 Hz, 2H), 7.63 (d, J=8.4 Hz, 2H), 7.85 (d, J=8.4 Hz, 2H), 8.92 (d, J=8.4 Hz, 1H), 9.81 (s, 1H); $^{13}$C (75 MHz, DMSO-$_{d6}$) δ 24.18, 46.59, 48.97, 71.79, 77.36, 80.79, 86.40, 105.78, 114.25, 124.84, 128.33, 130.19, 132.73, 134.72, 151.57, 165.80, 167.33; LC/MS m/s $[M+H]^+$ 360.2.

Example 2

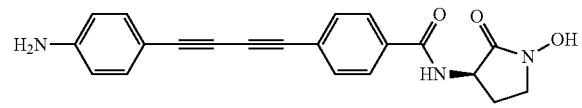

CPD-044, (R)-4-((4-aminophenyl)buta-1,3-diynyl)-N-(1-hydroxy-2-oxopyrrolidin-3-yl)benzamide CPD-044: Following the procedure of CPD-043: $^1$H (300 MHz, DMSO-$_{d6}$) δ 1.91-2.01 (m, 1H), 2.27-2.36 (m, 1H), 3.42-3.47 (m, 2H), 4.53 (q, J=26.7 Hz, 2H), 5.84 (s, 2H), 6.52 (d, J=8.7 Hz, 2H), 7.24 (d, J=8.4 Hz, 2H), 7.63 (d, J=8.4 Hz, 2H), 7.85 (d, J=8.4 Hz, 2H), 8.92 (d, J=8.4 Hz, 1H), 9.81 (s, 1H); $^{13}$C (75 MHz, DMSO-$_{d6}$) δ 24.18, 46.59, 48.97, 71.79, 77.36, 80.79, 86.40, 105.78, 114.25, 124.84, 128.33, 130.19, 132.73, 134.72, 151.57, 165.80, 167.33; LC/MS m/s $[M+H]^+$ 360.2.

Example 3

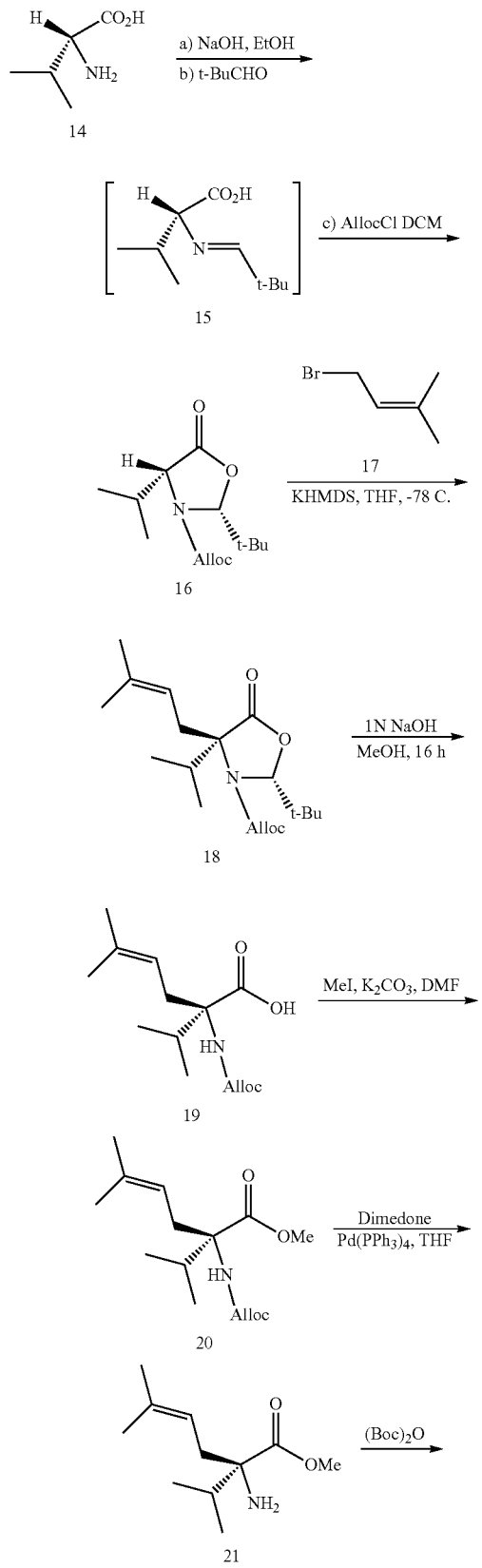

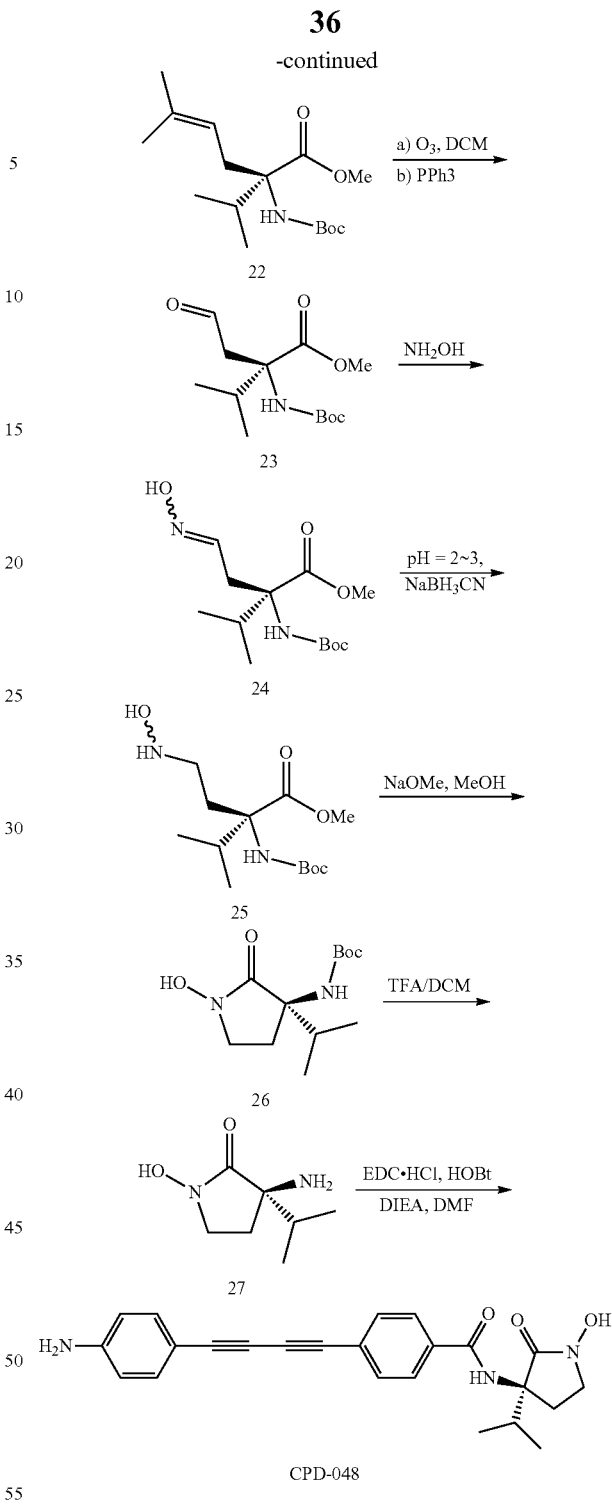

Oxazolidinone 16. A suspension of L-Valine (7.0 g, 59.8 mmol) in anhydrous ethanol (400 mL) is treated with a solution of NaOH (2.5 g, 59.8 mmol, 1.00 equiv) in H₂O (8 mL). The resultant mixture homogenized while stirring at room temperature for 30 min. After evaporation of most of the solvent in vacuo, the oily concentrate is diluted with pentane (300 mL). t-But CHO (8.61 mL, 74.34 mmol, 1.50 equiv) is then added and the mixture heated at reflux under a Dean-Stark trap until H₂O generation ceased (ca. 48 h). The mixture is cooled to room temperature and concentrated in vacuo, affording a white powder, which is dried azeotropically with toluene (3×200 mL) and stored under vacuum overnight. A suspension of the dried salt in DCM (200 mL) is cooled to 0° C., allyl chloroformate (9.40 mL, 89.7 mmol, 1.50 equiv) is added, and the slurry is stirred at 5 OC for 14 days. After dilution with $H_2O$ (200 mL), DMAP (50 mg) is introduced to catalyze the hydrolysis of excess chloroformate. The mixture is stirred for 24 h and then extracted with EtOAc (1 L). The organic layer is washed with 10% aqueousNaHSO$_4$ (100 m mL), saturated aqueous NaHCO$_3$ (100 mL), and brine (200 mL each), dried over MgS04, and concentrated in vacuo. The crude product is purified by CombiFlash (eluting with EtOAc in hexane 0-10%) to obtain 16 as solid. 12.5 g (2 steps 78% yield).

Prenyloxazolidinone 18. A solution of oxazolidinone 16 (12.0 g, 44.6 mmol) in anhydrous THF (150 mL) is cooled to −78° C., and 0.5 M KHMDS in toluene (107.0 mL, 53.52 mmol, 1.20 equiv) is added via a dropping syringe at a rate that maintained an internal temperature of −70° C. The resultant yellow solution is stirred for 15 min and then treated dropwise with I-bromo-3-methyl-2-butene (13.3 mL, 89.2 mmol, 2.00 equiv), again maintaining an internal temperature no higher than −70° C. The reaction is stirred 30 min future at −78° C. and quenched at low temperature (−78° C.) with 10% aqueous NaHSO$_4$ (300 mL). Following extraction with EtOAc (2×100 mL), the combined organic layers are washed with 10% aqueous NaHSO$_4$ (2×200 mL), saturated aqueous NaHCO$_3$ (200 mL), and brine (200 mL), dried over Na$_2$SO$_4$, and concentrated in vacuo. The crude product is purified by CombiFlash (eluting with EtOAc in hexane 0-10%) affords 18 (8.77 g, 58% yield) as colorless oil:

Alloc-Protected Amino Ester 20. A solution of oxazolidinone 18 (8.5 g, 25.2 mmol) in a mixture of methanol (50 mL) and 1 N aqueous NaOH (50 mL) is heated at reflux for 18 h. The mixture is cooled to room temperature and concentrated in vacuo, and the resultant mixture is acidified with 10% aqueous NaHSO$_4$ to pH=1 and then extracted with EtOAc (3×50 mL). The combined organic phases are washed with H$_2$O (50 mL) and brine (50 mL), dried over Na$_2$SO$_4$, and concentrated in vacuo. A solution of the crude residue in DMF (30.0 mL) is treated with anhydrous K$_2$CO$_3$ (6.88 g) and cooled to 0° C. Iodomethane (10.80 mL, 75.6 mmol, 3.00 equiv) is slowly added and the resultant yellow mixture stirred at 0° C. for 30 min and at room temperature for 30 min. The reaction mixture is quenched with H$_2$O (30 mL) and extracted with ether (2×100 mL). The combined extracts are washed with H$_2$O (4×50 mL), saturated aqueous NaHCO$_3$ (50 mL), and brine (50 mL), dried over Na$_2$SO$_4$, and concentrated in vacuo. The crude product is purified by CombiFlash (eluting with EtOAc in hexane 0-10%) to give 20 as a colorless oil. (4.96 g, 70% yield).

Primary Amine 21. A mixture of alloc derivative 20 (4.90 g, 17.3 mmol), dimedone (12.13 g, 86.5 mmol, 5.00 equiv), and Pd(PPh$_3$)$_4$ (100 mg, 0.087 mmol, 0.05 equiv) in THF (50 mL) is stirred at room temperature for 16 h. Following dilution with ether (200 mL) and extraction with 1 N HCl (5×75 mL), the combined aqueous layers are made basic by addition of solid K$_2$CO$_3$, and additional base is added to facilitate extraction of the product. The resultant mixture is extracted with EtOAc (3×100 mL), and the combined organic layers are washed with saturated aqueous NaHCO$_3$ (100 mL) and brine (100 mL), dried over Na$_2$SO$_4$, and concentrated in vacuo. The crude product is purified by CombiFlash (eluting with EtOAc in hexane 0-20%) to obtain 21 as a colorless oil (3.30 g, 97% yield).

Boc Derivative 22. A solution of amine 21 (3.00 g, 15.0 mmol) and di-tert-butyl dicarbonate (3.95 g, 18.1 mmol, 1.20 equiv) in THF (20 mL) is heated at reflux for 16 h and then allowed to cooled H$_2$O (30 mL) and DMAP (50 mg) are added to hydrolyze excess dicarbonate. After 30 min the mixture is extracted with EtOAc (2×50 mL), and the combined organic layers are washed with 10% aqueous NaHSO$_4$, saturated aqueous NaHCO$_3$ (50 mL), and brine (2×25 mL), dried over MgSO$_4$, and concentrated in vacuo. The crude product is purified by CombiFlash (eluting with EtOAc in DCM 0-10%) to give 22 (2.40 g, 53% yield) as clear colorless oil.

Aldehyde 23. A solution of 22 (1.00 g, 3.30 mmol) and sudan II (10 mg) in DCM (20 mL) is cooled to −78° C., and ozone is bubbled into the reaction until a red color disappeared (5 min). After excess ozone is purged with argon, Dimethyl sulfide (1.0 mL, 1.33 mmol) is added and the solution is allowed to warm to room temperature. After 2 h, the yellow solution is concentrated in vacuo to give 23 as yellow oil. The product is going to next step without future purification.

Oxime 24: To a solution of 23 (0.90 g, 8.0 mmol) in anhydrous pyridine (10 mL) and ethanol (0.10 mL) is added hydroxylamine hydrochloride (0.80 g, 9.9 mmol, 3.5 equiv). The reaction mixture is stirred at room temperature under argon for 3 h, and then concentrated to dryness. The residue is purified by CombiFlash (elution with MeOH in DCM 0-2%) to give 24 as yellow oil (0.90 g, 95.0% yield).

25: To a solution of a mixture of oximes 24 (0.300 g, 1.04 mmol) in anhydrous methanol (10 mL) is added NaBH$_3$CN (66 mg, 1.04 mmol, 1.00 equiv) and the reaction mixture is stirred at room temperature under argon for 40 min. The pH of the solution during the period of the reaction is keep at 2-3 by addition of methanolic HCl (1N) solution during the period of the reaction. The reaction mixture is neutralized with 1N NaOH and concentrated to dryness. The residue is dilute by water (20 mL), extracted with CHCl$_3$ (3×80 mL), and dried (anhydrous Na$_2$SO$_4$). Evaporation of the solvent affords the crude product, which is purified by CombiFlash (eluting with MeOH in DCM 0-5%) to give 25 (245 mg, 91% yield) as colorless oil.

26: A solution of 25 (100 mg, 0.34 mg) in anhydrous Methanol (10 mL) is added sodium methoxide in MeOH (0.11 mL, 0.41 mmol, 1.20 equiv, 25% in methanol). The reaction mixture is stirred at reflux for 3 h under argon. Then the reaction mixture is condensed to dryness and diluted with water (20 mL). The residue is treated with 0.1 N HCl to pH 7, extracted with DCM (3×50 mL). The combined organic layers are washed brine (30 mL), dried (anhydrous Na$_2$SO$_4$). The crude product is purified by CombiFlash (eluting with MeOH in DCM 0-5%) to give the 26 as whit solid (90 mg, 93% yield).

27: To a solution of 26 in anhydrous DCM (4 mL) is added trifluoroacetic acid (1 mL) under argon at room temperature. The reaction mixture is stirred for 80 min. Then the solution is concentrated to dryness. The residue is dissolved in milliQ water (2 mL) and passed through a columnfilled with Dowex 50W×4 (H$^+$) (sigma) (10 g), eluting with milliQ water (200 mL), then 1N NH$_3$ solution (200 mL). The eluent is concentrated in vacuum to give 27 (53.0 mg, 96% yield) as white solid.

CPD-048: To a stirred of 27 (40.0 mg, 0.25 mmol) and 6 (91.2 mg, 0.35 mmol, 1.40 equiv, prepared as in Example 1) in anhydrous DMF (1.0 mL) is added EDC.HCl (67.0 mg, 0.35 mmol, 1.40 equiv), HOBt (47.0 mg, 0.35 mmol, 1.40 equiv) at room temperature. The mixture is cooled with an ice-bath to 0° C., and the DIPEA (0.24 mL, 1.25 mmol, 5.0 equiv). The whole mixture is stirred under argon at 0° C. for 1 h, then allowed to warm to ambient temperature with the stirring is continued for additional 20 h. The resulting yellow solution is concentrated to dryness. The residue is treated with water (10 mL), extracted with EtOAc (3×50 mL). The organic layers are washed with 1N NaOH (10 mL), brine (50 mL), and dried (anhydrous Na$_2$SO$_4$). Evaporation of the solvent affords the crude product, which is purified by CombiFlash (eluting with MeOH in DCM 0-10%) to give CPD-048 (48.1 mg, 40%) as yellow solid. $^1$H NMR (300 MHz, CDCl$_3$) δ 0.98 (d, J=6.6 Hz, 3H), 1.04 (d, J=6.9 Hz, 3H), 1.25 (s, 1H), 1.81-1.95 (m, 1H), 1.95-2.04 (m, 1H), 2.26-2.35 (m, 1H), 3.61-3.68 (m, 1H), 3.70-3.77 (m, 1H), 3.95 (br, s, 2H), 6.59 (d, J=8.7 Hz, 2H), 7.33 (d, J=8.7 Hz, 2H), 758 (d, J=9.0 Hz, 2H), 8.03 (d, J=8.7 Hz, 2H); $^{13}$C NMR (75 MHz, CDCl$_3$) δ 16.12, 17.86, 34.33, 44.99, 59.94, 71.93, 78.81, 79.65, 85.41, 110.23, 114.82, 126.40, 128.80, 130.28, 132.65, 134.49, 148.17, 163.36, 173.35; LC/MS m/s [M+H]$^+$ 402.6.

Example 4

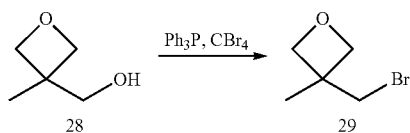

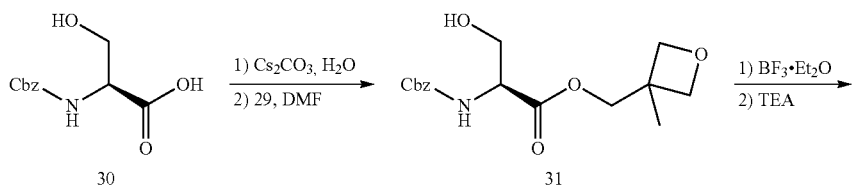

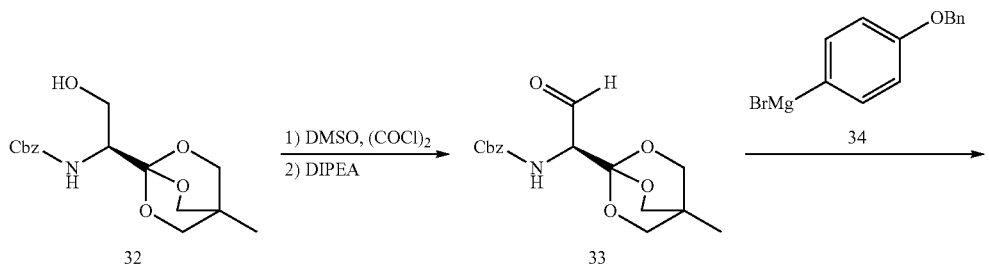

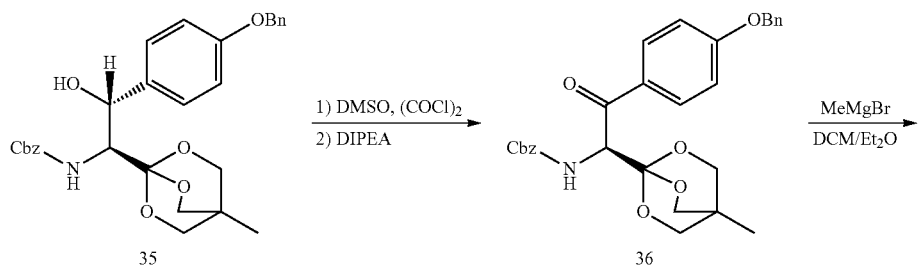

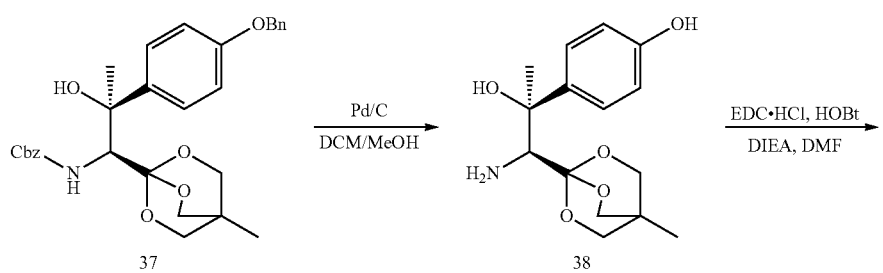

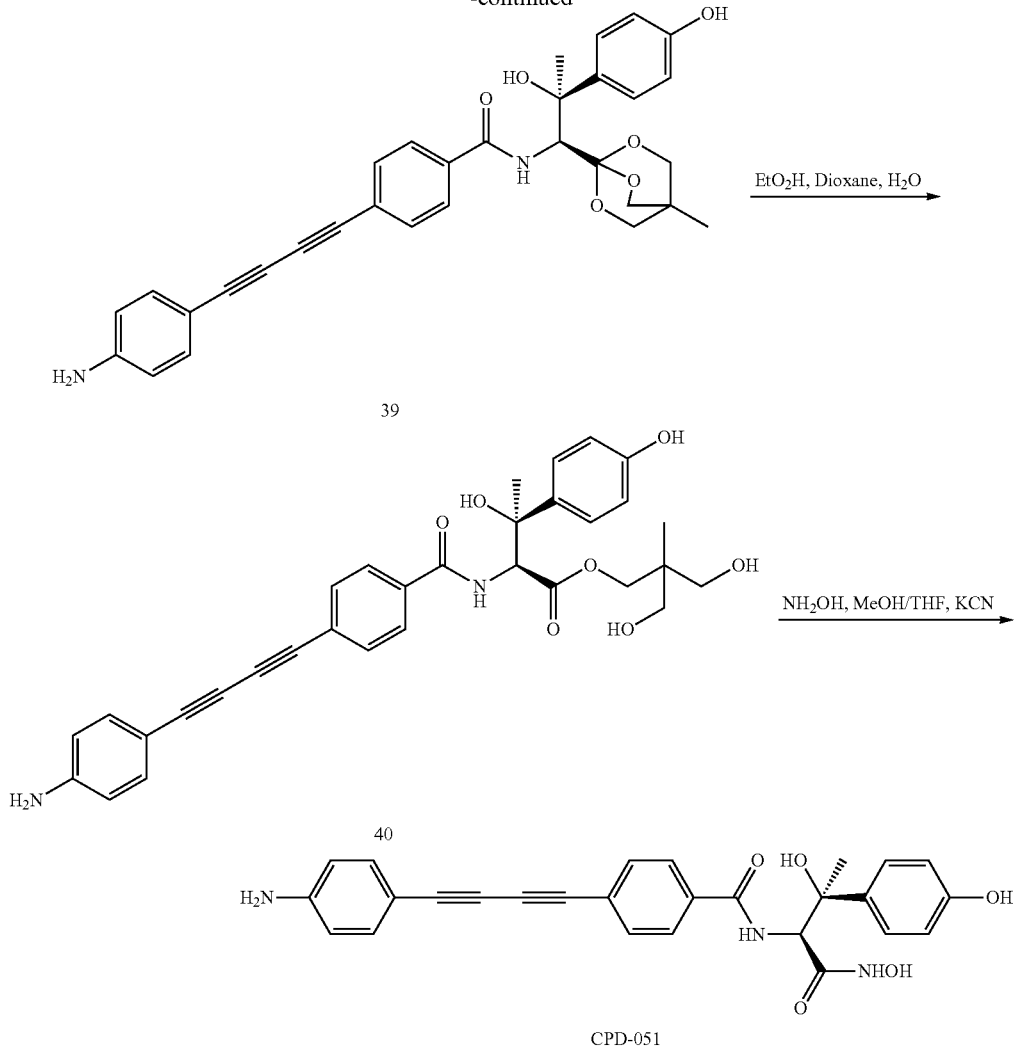

29: A solution of p-toluenesulfonyl chloride (74.36 g, 0.39 mol, 1.5 equiv) in anhydrous pyridine (300 mL) is dropwise added 3-methyl-3-oxetane-methanol (26.52 g, 0.26 mol) over 10 min at 0° C. under argon. After 5 min, the reaction mixture is allowed to warm to room temperature with the stirring is continued for an additional 1.5 h. The mixture is then slowly added to a vigorously stirring mixture of milliQ water 800 mL and crushed ice 800 g for 30 min. Then the white precipitate is collected on whatman filter #1 and washed with cold water (300 mL). The product is dried under high vacuum to obtain a white power of oxetane tosylate 29 (47.88 g 72% yield). $^1$H NMR (300 MHz, CDCl$_3$) δ 1.28 (s, 3H), 2.43 (s, 3H), 4.08 (s, 2H), 4.29-4.35 (m, 2H), 7.34 (d, J=7.8 Hz, 2H), 7.78 (d, J=7.5 Hz, 2H); $^{13}$C NMR (75 MHz, CDCl$_3$) δ 20.85, 21.86, 39.45, 74.50, 79.13, 128.15, 130.22, 132.81, 145.34; LC/MS m/s [M+H]$^+$ 164.9.

31: Cbz-L-Ser (29.60 g, 0.167 mol), 3-methyl-(3-tosyl-methyl oxetane) 29 (29.95 g, 0.125 mol), tetrabutylammonium iodide (2.30 g, 0.06 mol, 0.05 equiv), TEA (14.04 g, 0.138 mol, 1.1 equiv) and anhydrous DMF (100 mL) are combined in an oil bath and slowly heated to 70° C. for 36 h under argon. The reaction mixture is allowed to cool to room temperature, and the DMF is removed under reduced pressure. The remaining residue is dissolved in 1.00 L of EtOAc, washed with 1.0 N HCl (2×250 mL), saturated NaHCO$_3$ (2×250 mL), brine (250 mL), and dried (anhydrous Na$_2$SO$_4$). The solvent is removed under reduced pressure, and the remaining residue is purified by CombiFlash (eluting with 0-50% EtOAc in hexane) to give 31 (25.20 g, 64% yield) as pale yellow oil. $^1$H NMR (300 MHz, CDCl$_3$) δ 1.26 (s, 3H), 3.34 (br, s, 1H), 3.84-3.87 (m, 1H), 4.02-4.07 (m, 2H), 4.35-4.52 (m, 6H), 5.11 (s, 2H), 5.94 (d, J=7.5 Hz, 1H), 7.26-7.33 (m, 5H); $^{13}$C NMR (75 MHz, CDCl$_3$) δ 20.98, 39.70, 56.57, 63.39, 67.34, 69.18, 79.66, 128.33, 128.44, 128.75, 136.38, 156.51, 170.98; LC/MS m/s [M+H]$^+$ 324.1.

32: Cbz-L-Ser-oxetane ester 31 (11.00 g, 34.00 mmol) is dissolved in anhydrous DCM (100 mL) and is cooled to 0° C. under argon. BF$_3$.Et$_2$O (0.13 mL, 0.92 mmol, 0.03 equiv) is diluted in DCM (5.0 mL) and added to the reaction flask. The reaction mixture is allowed to warm to room temperature. After 5 h, Et$_3$N (1.40 mL, 9.86 mmol, 0.3 equiv) is added with the sitting is continued for an additional 30 min. Then the result solution is concentrated to dryness to thick oil. The crude product is purified by CombiFlash (eluting with 0-5% MeOH in DCM) to afford 32 (6.90 g, 62.7% yield) as whit foam. $^1$H NMR (300 MHz, CDCl$_3$) δ 0.78 (s, 3H), 2.64 (q, J=12.6 Hz, 1H), 3.62-3.95 (m, 9H), 5.03-5.14

(m, 2H), 5.37 (d, J=9.0 Hz, 1H), 7.26-7.34 (m, 5H); $^{13}$C NMR (75 MHz, CDCl$_3$) δ 14.48, 30.76, 55.60, 62.14, 67.12, 72.90, 108.68, 128.28, 128.36, 128.69, 136.69, 156.67; LC/MS m/s [M+H]$^+$ 324.1.

33: Cbz-L-Ser OBO ester 32 (6.87 g, 21.27 mmol) is dissolved in anhydrous DCM (100 mL) under argon and cooled to −78° C. in flask I. Oxalyl chloride (17.00 mL, 2.0 M in DCM, 70.19 mmol, 1.6 equiv) is added to anhydrous DCM (100 mL) in a separate flask II under argon and cooled to −78° C. Anhydrous DMSO (5.36 mL, 70.19 mmol, 3.30 equiv) is added to the oxalyl chloride solution (flask II), and the mixture stirred at −78° C. for 15 min. The alcohol solution is transferred by syringe at −78° C. to the flask II over a period of 20 min. The resulting cloudy white mixture is stirred for 1.5 h at −78° C. DIPEA (18.44 mL, 106.35 mmol, 5.0 equiv) is added and the solution is stirred for 30 min at −78° C. and 10 min at 0° C. Ice-cold DCM (200 mL) is added, and the solution is washed with ice-cold 3% NH$_4$Cl (3×200 mL), brine (200 mL), dried (anhydrous Na$_2$SO$_4$). The crude product is crystallized from DCM/Hexane to obtain 33 (4.3 g, 63% yield) as yellow solid. $^1$H NMR (300 MHz, CDCl$_3$) δ 0.81 (s, 3H), 3.93 (s, 6H), 4.60 (d, J=8.7 Hz, 1H), 5.12 (s, 2H), 5.36 (d, J=8.7 Hz, 1H), 7.26-7.40 (m, 5H), 9.68 (s, 1H); $^{13}$C NMR (75 MHz, CDCl$_3$) δ 14.47, 31.09, 63.50, 67.43, 73.12, 107.40, 128.36, 128.70, 136.40, 156.42, 159.90; LC/MS m/s [M+H]$^+$ 307.4.

35: Cbz-L-Ser(ald)-OBO ester 33 (1.60 g, 5.00 mmol) is dissolved in anhydrous DCM (20 mL) under argon. A solution of 4-Benzyloxyphenyl magnesium bromide in THF (20 mL, 20 mmol, 4.00 equiv) is added quickly by syringe at ice-bath and stirred vigorously. After 3 min, the reaction mixture is allowed to warm to room temperature with stirring is continued for 70 min. Then the reaction mixture is quenched by sat. NH$_4$Cl 300 mL (pH=7) and is stirred for an additional 15 min. The mixture is extracted with DCM (3×80 mL). The combined organic layers are washed with brine (50 mL), dried (anhydrous Na$_2$SO$_4$). The crude product is purified by CombiFlash (eluting with 0-7% EtOAc in DCM) to give 35 (0.272 g, 54.0% yield) as foam solid. $^1$H NMR (300 MHz, CDCl$_3$) δ 0.83 (s, 3H), 3.36 (s, 1H), 3.98 (s, 6H), 4.07 (d, J=10.5 Hz, 1H), 4.88-5.08 (m, 5H), 5.48 (d, J=10.5 Hz, 1H), 6.91 (d, J=9.0 Hz, 2H), 7.22-7.46 (m, 12H); $^{13}$C NMR (75 MHz, CDCl$_3$) δ 14.56, 30.93, 58.87, 66.76, 70.16, 70.65, 73.06, 109.04, 114.72, 127.36, 127.77, 127.99, 128.14, 128.63, 128.80, 132.84, 136.99, 137.414, 156.61, 158.33; LC/MS m/s [M+H]$^+$ 506.2

36: 35 (0.74 g, 1.47 mmol) is dissolved in anhydrous DCM (10 mL) under argon and cooled to −78° C. in flask I. Oxalyl chloride (1.20 mL, 2.0 M in DCM, 2.40 mmol, 1.6 equiv) is added to anhydrous DCM (10 mL) in a separate flask II under argon and cooled to −78° C. Anhydrous DMSO (0.34 mL, 4.85 mmol, 3.30 equiv) is added to the oxalyl chloride solution (flask II), and the mixture stirred at −78° C. for 15 min. The alcohol solution is transferred by syringe at −78° C. to the flask II over a period of 20 min. The resulting cloudy white mixture is stirred for 2 h at −78° C. DIPEA (1.28 mL, 7.35 mmol, 5.0 equiv) is added and the solution is stirred for 30 min at −78° C. and 10 min at 0° C. Ice-cold DCM (100 mL) is added, and the solution is washed with ice-cold 3% NH$_4$Cl (3×50 mL), brine (100 mL), dried (anhydrous Na$_2$SO$_4$). The crude product is purified by CombiFlash (eluting with 0-40% EtOAc in hexane) to give 36 (0.62 g, 84% yield) as white foam. $^1$H NMR (300 MHz, CDCl$_3$) δ 0.75 (s, 3H), 3.86 (s, 6H), 5.10 (s, 2H), 5.13 (s, 2H), 5.55 (d, J=9.3 Hz, 1H), 5.95 (d, J=9.3 Hz, 1H), 7.00 (d, J=9.0 Hz, 2H), 7.27-7.45 (m, 10H), 8.06 (d, J=9.0 Hz, 2H); $^{13}$C NMR (75 MHz, CDCl$_3$) δ 14.48, 30.90, 57.35, 67.23, 70.37, 73.17, 107.60, 114.60, 127.76, 128.30, 128.48, 128.67, 128.93, 129.91, 132.120, 136.43, 136.60, 156.16, 163.22, 193.49; LC/MS m/s [M+H]$^+$ 504.1.

37: 36 (0.80 g, 1.60 mmol) is dissolved in anhydrous DCM (4 mL) under argon. A solution of methyl magnesium bromide in Et$_3$O (3.0 M, 3.10 mL, 9.26 mmol, 5.8 equiv) is added quickly by syringe at ice-bath and stirred vigorously. After 3 min, the reaction mixture is allowed to warm to room temperature with stirring is continued for 10 h. Then the reaction mixture is quenched by sat. NH$_4$Cl 100 mL (pH=7) and is stirred for an additional 15 min. The mixture is extracted with DCM (3×50 mL). The combined organic layers are washed with brine (50 mL), dried (anhydrous Na$_2$SO$_4$). The crude product is purified by CombiFlash (eluting with 0-50% EtOAc in hexane) to give 37 (0.81 g, 98% yield) as white solid. $^1$H NMR (300 MHz, CDCl$_3$) δ 0.73 (s, 3H), 1.50 (s, 3H), 3.73 (s, 3H), 3.71-3.80 (m, 6H), 4.22 (d, J=10.2 Hz, 1H), 4.98-5.14 (m, 4H), 5.33 (d, J=10.5 Hz, 1H), 6.90 (d, J=8.7 Hz, 2H), 7.28-7.43 (m, 12H); $^{13}$C NMR (75 MHz, CDCl$_3$) δ 14.45, 27.17, 30.62, 61.09, 66.96, 70.13, 72.60, 76.04, 109.50, 113.93, 126.76, 127.11, 127.76, 128.12, 128.68, 128.75, 136.90, 137.51, 138.83, 156.60, 157.49; LC/MS m/s [M+H]$^+$ 520.2.

38: To a solution of 37 (0.62 g, 1.2 mmol) in anhydrous MeOH (10 mL) is added 10% Pd/C (62.0 mg, 10%) at room temperature under a balloon of hydrogen. The reaction mixture is stirred for 14 h. Then the catalyst is removed by filtration through a celite pad and washed with MeOH (50 mL). The filtrate is evaporated under reduced vacuo to obtain the 37 (0.343 g, 97% yield) as white solid, which is going to next step without future purification. $^1$H NMR (300 MHz, CD$_3$OD) δ 0.77 (s, 3H), 1.60 (s, 3H), 2.96 (s, 1H), 3.86 (s, 6H), 6.73 (d, J=8.7 Hz, 2H), 7.26 (d, J=8.7 Hz, 2H); $^{13}$C NMR (75 MHz, CD$_3$OD) δ 12.98, 24.07, 30.11, 62.99, 72.29, 75.52, 109.59, 114.24, 127.21, 136.78, 16.25; LC/MS m/s [M+H]$^+$ 296.1.

39: To a stirred mixture of 38 (218 mg, 0.83 mmol) and 6 (295 mg, 1.00 mmol, 1.20 equiv, prepared as in Example 1) in anhydrous DMF (5 mL) is added N-ethyl-N'-(3-dimethylaminopropyl)carbodiimide hydrochloride (EDC hydrochloride) (192 mg 1.00 mmol, 1.20 equiv), 1-hydroxybenzotriazole (HOBt) (135 mg, 1.00 mmol, 1.20 equiv) at room temperature. The mixture is cooled with an ice-bath, and diisopropylethylamine (DIEA) (0.58 mL, 3.33 mmol, 5.0 equiv) is added. The whole reaction mixture is stirred under argon and at 0° C. for 1 h, then allowed to warm to temperature with the stirring is continued for additional 24 h. The resulting yellow solution is condensed to dryness with a rotavapor, and the residue is treated with water (20 mL), extracted with DCM (3×50 mL). The combined extracts are washed with brine (20 mL), and dried over anhydrous Na$_2$SO$_4$. Evaporation of the solvent affords the crude products, which is purified by CombiFlash (eluting with 0-10% MeOH in DCM) to afford 39 (350 mg, 78% yield) as yellow solid. $^1$H NMR (300 MHz, DMSO-$_{d6}$) δ 0.70 (s, 3H), 1.50 (s, 3H), 3.78 (s, 6H), 4.42 (d, J=8.7 Hz, 1H), 4.53 (s, 1H), 5.82 (s, 1H), 6.53 (d, J=8.4 Hz, 4H), 7.18 (d, J=8.7 Hz, 2H), 7.24 (d, J=8.4 Hz, 2H), 7.56 (d, J=8.4 Hz, 2H), 7.68-7.73 (m, 3H), 9.00 (s, 1H); $^{13}$C NMR (75 MHz, DMSO-$_{d6}$) δ 14.29, 27.15, 30.57, 49.29, 60.06, 71.80, 72.32, 75.56, 77.08, 80.89, 86.26, 105.86, 109.45, 114.27, 124.39, 127.54, 132.44, 134.68, 135.48, 137.60, 151.54, 155.96, 165.50; LC/MS m/s [M+H]$^+$ 539.4.

40: 39 (60.0 mg, 0.10 mmol) is dissolved in dioxane (2.0 mL). The mixture is diluted with acetic acid (2.0 mL) and water (2.0 mL) at room temperature under argon. The suspension mixture is stirred for 1 h. Then the yellow clear solution is concentrated to dryness. The residue is treated with saturated NaHCO$_3$ (20 mL) to pH=10, extracted with EtOAc (3×40 mL). The combined organic layers are washed with water (2×30 mL), brined (30 mL), and dried (anhydrous Na$_2$SO$_4$). The solvent is removed by rotavapor to give the 40 (61.4 mg, 99% yield) as yellow solid, which is going to next step without future purification. $^1$H NMR (300 MHz, CD$_3$OD) δ 0.65 (s, 3H), 1.57 (s, 3H), 3.17-3.26 (m, 4H), 3.70 (d, J=10.8 Hz, 1H), 3.93 (d, J=11.1 Hz, 1H), 5.06 (s, 1H), 6.62 (d, J=8.7 Hz, 2H), 6.79 (d, J=8.7 Hz, 2H), 7.25 (d, J=9.0 Hz, 2H), 7.36 (d, J=8.7 Hz, 2H), 7.59 (d, J=8.7 Hz, 2H), 7.83 (d, J=8.7 Hz, 2H); $^{13}$C NMR (75 MHz, CD$_3$OD) δ 15.52, 27.12, 40.38, 61.79, 64.47, 67.39, 70.80, 75.32, 76.80, 78.98, 84.68, 108.33, 114.24, 114.82, 126.20, 126.35, 127.51, 132.19, 133.84, 135.88, 150.20, 156.50, 168.00, 170.56; LC/MS m/s [M+H]$^+$ 557.2.

CPD-051: 40 (55.6 mg, 0.10 mmol) is taken into a mixture of THF/MeOH (1:1 volume) 2.0 mL. 50% aq hydroxylamine (0.20 mL, 3.0 mmol, 30 equiv) is added and followed by potassium cyanide (6.5 mg, 0.10 mmol, 1.0 equiv) at room temperature under argon. The reaction mixture is stirred room temperature for 14 h. Then the yellow solution is concentrated to dryness. The residue is treated water (30 mL), extracted with EtOAc (3×50 mL). The combined organic layers are washed with water (5×30 mL), brine (30 mL), and dried (anhydrous Na$_2$SO$_4$). The crude product is purified by CombiFlash (eluting with 0-7% MeOH in DCM) to give CPD-051 (28.0 mg, 59.7% yield) as yellow solid. $^1$H NMR (300 MHz, CD$_3$OD) δ 1.50 (s, 3H), 4.86 (s, 1H), 6.62 (d, J=8.7 Hz, 2H), 6.76 (d, J=8.7 Hz, 2H), 7.24 (d, J=8.1 Hz, 2H), 7.34 (d, J=8.4 Hz, 2H), 7.57 (d, J=8.1 Hz, 2H), 7.82 (d, J=8.4 Hz, 2H); $^{13}$C NMR (75 MHz, CD$_3$OD) δ 25.86, 57.98, 70.73, 75.68, 76.64, 78.96, 84.58, 108.30, 114.21, 114.73, 126.06, 126.45, 127.57, 132.08, 133.81, 133.94, 135.69, 150.24, 156.48, 167.89; LC/MS m/s [M+H]$^+$ 470.8.

Example 5

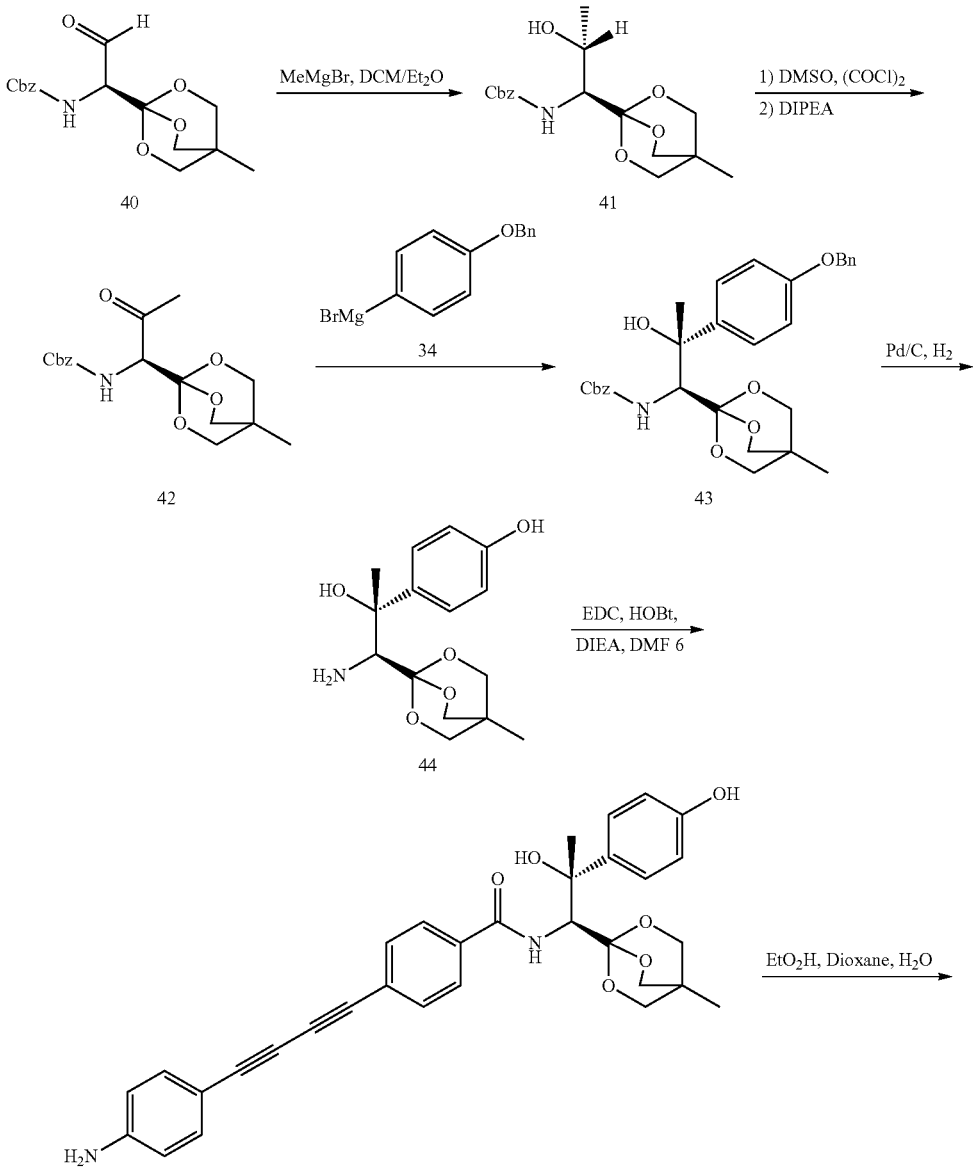

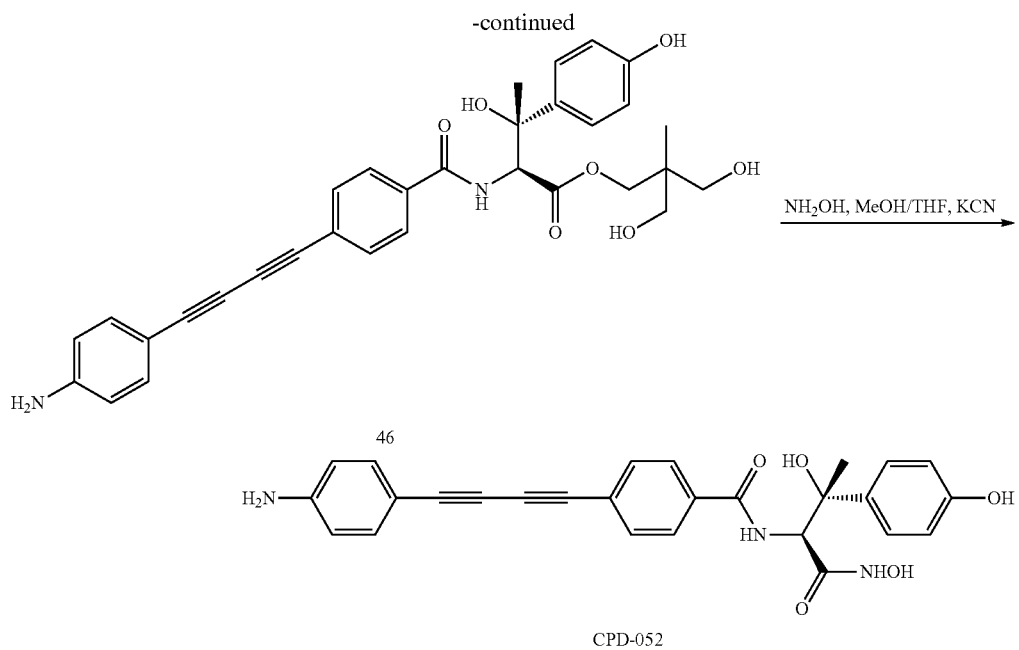

CPD-052

41: Cbz-L-ser(ald)-OBO ester 40 (2.90 g, 9. Mmol) is dissolved in anhydrous DCM (11.0 mL) under argon. A solution of MeMgBr in Et$_2$O (11.7 mL, 36.0 mmol, 4.00 equiv) is added quickly by syringe at −78° C. and stirred vigorously for 1.5 h. Then the reaction is quenched by saturated NH$_4$Cl (300 mL) with the stirring is continued for an additional 15 min. The mixture is extracted with DCM (3×80 mL). The combined organic layers are washed with brine (50 mL), and dried (anhydrous Na$_2$SO$_4$). The crude product is purified by CombiFlash (eluting with 0-50% EtOAc in hexane) to afford the 41 (1.52 g, 50% yield) as white solid. $^1$H NMR (300 MHz, CDCl$_3$) δ 0.80 (s, 3H), 1.11 (d, J=6.3 Hz, 3H), 2.87 (s, 3H), 3.75 (d, J=10.5 Hz, 1H), 3.92 (s, 6H), 4.35 (q, J=19.5 Hz, 1H), 5.08-5.18 (m, 2H), 5.34 (d, J=10.5 Hz, 1H), 7.26-7.36 (m, 5H); $^{13}$C NMR (75 MHz, CDCl$_3$) δ 14.53, 19.22, 30.84, 57.95, 65.43, 67.06, 72.93, 108.99, 127.77, 128.19, 128.67, 136.85, 157.19; LC/MS m/s [M+H]$^+$ 378.1.

42: Cbz-L-Threonine OBO ester 41 (1.30 g, 3.86 mmol) is dissolved in anhydrous DCM (10 mL) under argon and cooled to −78° C. in flask I. Oxalyl chloride (6.20 mL, 2.0 M in DCM, 6.17 mmol, 1.6 equiv) is added to anhydrous DCM (10 mL) in a separate flask II under argon and cooled to −78° C. Anhydrous DMSO (0.55 mL, 12.74 mmol, 3.30 equiv) is added to the oxalyl chloride solution (flask II), and the mixture stirred at −78° C. for 15 min. The alcohol solution is transferred by syringe at −78° C. to the flask II over a period of 20 min. The resulting cloudy white mixture is stirred for 4 h at −78° C. DIPEA (3.85 mL, 19.3 mmol, 5.0 equiv) is added and the solution is stirred for 30 min at −78° C. and 10 min at 0° C. Ice-cold DCM (100 mL) is added, and the solution is washed with ice-cold 3% NH$_4$Cl (3×100 mL), brine (100 mL), dried (anhydrous Na$_2$SO$_4$). The crude product is crystallized from DCM/Hexane to obtain 42 (1.06 g, 82% yield) as white solid. $^1$H NMR (300 Hz, CDCl$_3$) δ 0.791 (s, 3H), 2.303 (s, 3H), 3.900 (s, 6H), 4.581 (d, J=8.4 Hz, 1H), 5.087 (s, 2H), 5.624 (d, J=8.1 Hz, 1H), 7.255-7.342 (m, 5H); $^{13}$C NMR (300 Hz, CDCl$_3$) δ 14.441, 29.937, 30.874, 63.375, 67.259, 73.170, 107.131, 128.295, 128.678, 136.500, 156.210, 202.864; LC/MS m/s [M+H]$^+$ 356.2.

43: Cbz-L-Thre(keto)-OBO ester 42 (1.03 g, 3.07 mmol) is dissolved in a solution of 4-Benzyloxyphenyl magnesium bromide in THF (21.90 mL, 21.90 mmol, 7.00 equiv) ice-bath and stirred vigorously under argon. After 3 min, the reaction mixture is allowed to warm to room temperature with stirring is continued for 90 min. Then the reaction mixture is quenched by sat. NH$_4$Cl 300 mL (pH=7) and is stirred for an additional 15 min. The mixture is extracted with DCM (3×80 mL). The combined organic layers are washed with brine (50 mL), dried (anhydrous Na$_2$SO$_4$). The crude product is purified by CombiFlash (eluting with 0-50% EtOAc in hexane) to give 43 (0.94 g, 55% yield) as white foam, which is crystallized from MeOH to afford 0.62 g (40.0% yield) as white solid. $^1$H NMR (300 MHz, CDCl$_3$) δ 0.82 (s, 3H), 1.66 (s, 3H), 3.48 (s, 1H), 3.87-3.99 (m, 6H), 4.19 (d, J=10.2 Hz, 1H), 4.87-5.06 (m, 4H), 5.31-5.33 (m, 2H), 7.26-7.46 (m, 12H); $^{13}$C NMR (75 MHz, CDCl$_3$) δ 14.56, 29.71, 30.74, 60.71, 66.50, 70.11, 72.72, 76.03, 109.78, 114.27, 126.23, 127.64, 127.77, 127.92, 128.12, 128.55, 128.78, 137.08, 137.45, 138.45, 156.52, 157.60; LC/MS m/s [M+H]$^+$ 520.2.

44: To a solution of 43 (0.60 g, 1.2 mmol) in anhydrous MeOH (10 mL) is added 10% Pd/C (60.0 mg, 10% w/w) at room temperature under a balloon of hydrogen. The reaction mixture is stirred for 14 h. Then the catalyst is removed by filtration through a celite pad and washed with MeOH (50 mL). The filtrate is evaporated under reduced vacuo to obtain the 43 (0.339 g, 99.0% yield) as white solid, which is going to next step without future purification. $^1$H NMR (300 MHz, CDCl$_3$) δ 0.82 (s, 3H), 1.57 (s, 3H), 3.93 (s, 6H), 4.06 (br, s, 2H), 5.29 (s, 1H), 6.54 (d, J=8.1 Hz, 2H), 7.13 (d, J=7.8 Hz, 2H); $^{13}$C NMR (75 MHz, CDCl$_3$) δ 14.51, 29.91, 30.67, 61.76, 72.74, 74.88, 109.85, 115.72, 125.63, 137.17, 155.57; LC/MS m/s [M+H]$^+$ 296.1.

45: To a stirred mixture of 44 (218 mg, 0.83 mmol) and 6 (295 mg, 1.00 mmol, 1.20 equiv, prepared as in Example 1) in anhydrous DMF (5 mL) is added N-ethyl-N'-(3-dimethylaminopropyl)carbodiimide hydrochloride (EDC hydrochloride) (192 mg 1.00 mmol, 1.20 equiv), 1-hydroxybenzotriazole (HOBt) (135 mg, 1.00 mmol, 1.20 equiv) at room temperature. The mixture is cooled with an ice-bath, and diisopropylethylamine (DIEA) (0.58 mL, 3.33 mmol, 5.0 equiv) is added. The whole reaction mixture is stirred under argon and at 0° C. for 1 h, then allowed to warm to temperature with the stirring is continued for additional 24 h. The resulting yellow solution is condensed to dryness with a rotavapor, and the residue is treated with water (20 mL), extracted with DCM (3×50 mL). The combined extracts are washed with brine (20 mL), and dried over anhydrous $Na_2SO_4$. Evaporation of the solvent affords the crude product, which is purified by CombiFlash (eluting with 0-3% MeOH in DCM) to afford 45 (353 mg, 79.1% yield) as yellow solid. $^1$H NMR (300 MHz, DMSO-$_{d6}$) δ 0.74 (s, 3H), 1.56 (s, 3H), 3.84 (s, 6H), 4.38 (m 1H), 4.47 (s, 1H), 5.82 (s, 2H), 6.51 (d, J=2.7 Hz, 2H), 6.54 (d, J=2.7 Hz, 2H), 7.16 (d, J=8.7 Hz, 2H), 7.23 (d, J=8.4 Hz, 2H), 7.49-7.57 (m, 5H), 9.00 (s, 1H); $^{13}$C NMR (75 MHz, DMSO-$_{d6}$) δ 14.38, 29.55, 30.62, 59.47, 71.79, 72.33, 75.58, 77.08, 80.81, 86.25, 105.85, 109.40, 114.26, 114.65, 124.35, 126.62, 128.19, 132.53, 134.68, 135.42, 138.53, 151.53, 155.90, 165.04; LC/MS m/s [M+H]$^+$ 539.2.

46: 45 (320 mg, 0.595 mmol) is dissolved in dioxane (2.0 mL). The mixture is diluted with acetic acid (2.0 mL) and water (2.0 mL) at room temperature under argon. The suspension mixture is stirred for 0.5 h. Then the yellow clear solution is concentrated to dryness. The residue is treated with saturated $NaHCO_3$ (20 mL) to pH=10, extracted with EtOAc (3×40 mL). The combined organic layers are washed with water (2×30 mL), brined (30 mL), and dried (anhydrous $Na_2SO_4$). The crude product is purified by CombiFlash to give 46 (320 mg, 97% yield) as yellow solid. $^1$H NMR (300 MHz, CD$_3$OD) δ 0.91 (s, 3H), 1.69 (s, 3H), 3.42-3.51 (m, 4H), 4.11 (q, J=31.8 Hz, 2H), 4.95 (s, 1H), 6.61 (d, J=6.9 Hz, 2H), 6.74 (d, J=9.0 Hz, 2H), 7.32 (d, J=8.7 Hz, 2H), 7.34 (d, J=8.7 Hz, 2H), 7.49 (d, J=8.7 Hz, 2H), 7.54 (d, J=8.7 Hz, 2H); $^{13}$C NMR (75 MHz, CD$_3$OD) δ 15.83, 27.46, 40.77, 62.13, 64.47, 64.61, 67.39, 70.78, 75.10, 76.67, 78.95, 84.60, 108.33, 114.23, 114.77, 125.98, 126.13, 127.21, 132.05, 133.81, 136.31, 150.18, 156.36, 167.65, 170.50; LC/MS m/s [M+H]$^+$ 557.2.

CPD-052: 46 (55.6 mg, 0.10 mmol) is taken into a mixture of THF/MeOH (1:1 volume) 2.0 mL. 50% aq hydroxylamine (0.40 mL, 6.0 mmol, 60 equiv) is added and followed by potassium cyanide (13.0 mg, 0.20 mmol, 2.0 equiv) at room temperature under argon. The reaction mixture is stirred room temperature for 24 h. Then the yellow solution is concentrated to dryness. The residue is treated water (30 mL), extracted with EtOAc (3×50 mL). The combined organic layers are washed with water (5×30 mL), brine (30 mL), and dried (anhydrous $Na_2SO_4$). The crude product is purified by CombiFlash (eluting with 0-7% MeOH in DCM) to give CPD-052 (22.0 mg, 46.9% yield) as yellow solid, which is washed Et$_2$O (3×20 mL). The filtrate is concentrated to dryness to obtain pure CPD-052 (11.0 mg, yield 23.5%). $^1$H NMR (300 MHz, CD$_3$OD) δ 1.63 (s, 3H), 4.75 (s, 1H), 6.61 (d, J=8.4 Hz, 2H), 6.71 (d, J=8.7 Hz, 2H), 7.23 (d, J=8.4 Hz, 2H), 7.33 (d, J=8.7 Hz, 2H), 7.49 (d, J=8.4 Hz, 2H); $^{13}$C NMR (75 MHz, CD$_3$OD) δ 26.93, 59.36, 70.71, 74.83, 76.57, 78.92, 84.53, 108.29, 114.20, 114.60, 125.89, 126.21, 127.24, 131.98, 133.78, 136.00, 150.22, 156.28, 167.28, 168.09, LC/MS m/s [M+H]$^+$ 470.5.

Example 6

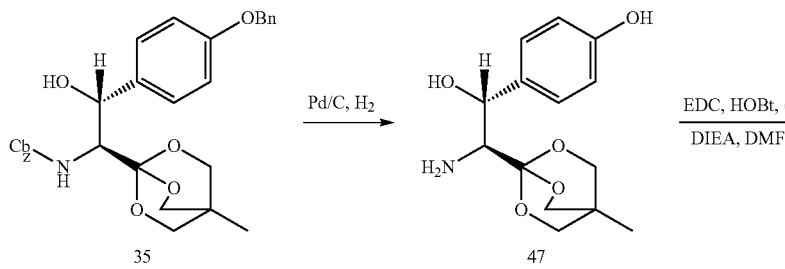

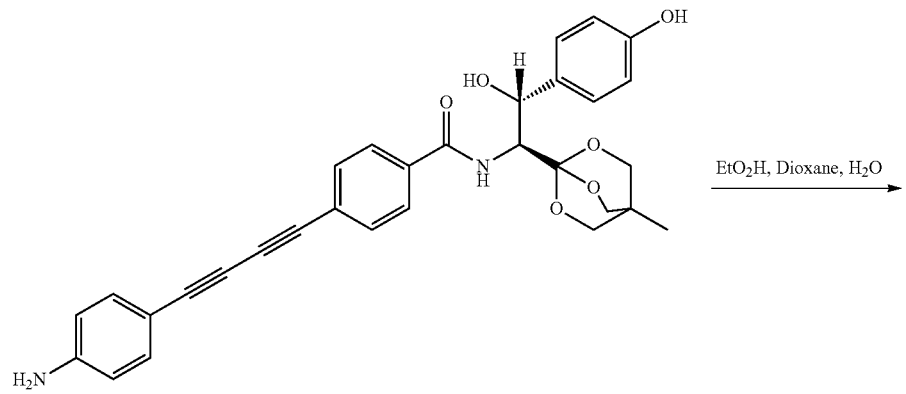

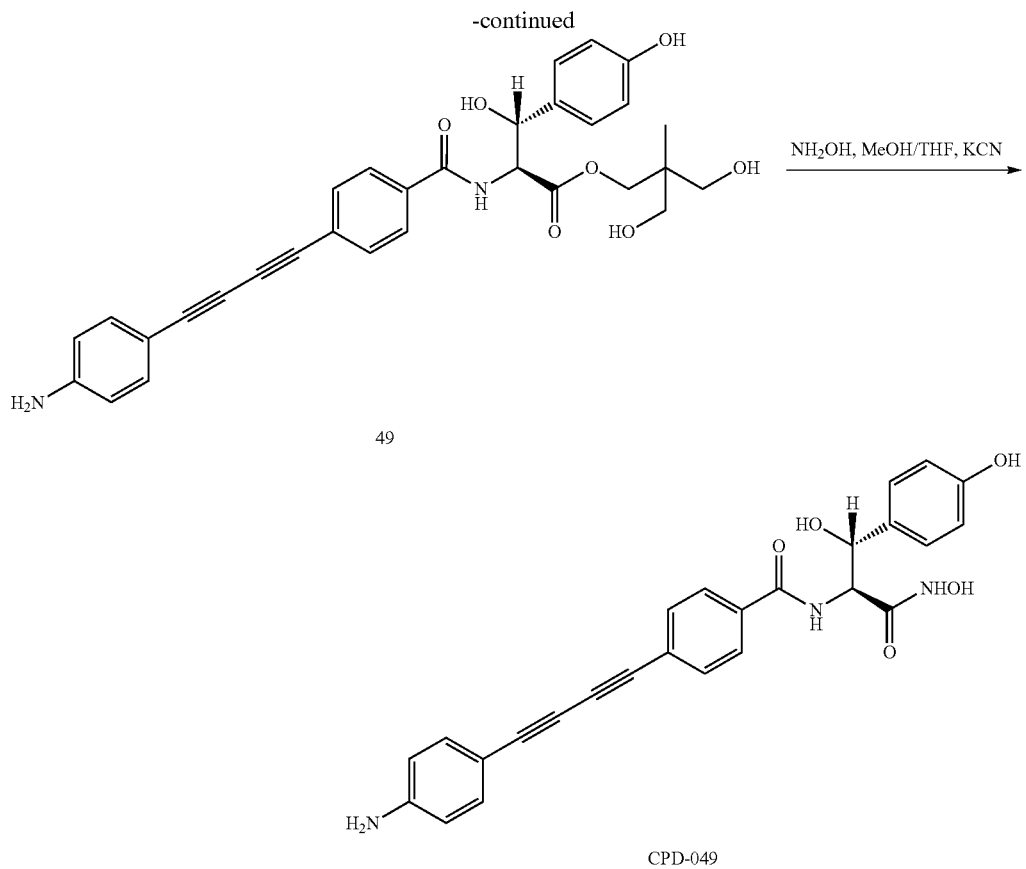

CPD-049

47: To a solution of 35 (0.50 g, 1.0 mmol) in anhydrous MeOH (10 mL) is added 10% Pd/C (50.0 mg, 10% w/w) at room temperature under a balloon of hydrogen. The reaction mixture is stirred for 14 h. Then the catalyst is removed by filtration through a celite pad and washed with MeOH (50 mL). The filtrate is evaporated under reduced vacuo to obtain the 47 (0.277 g, 99% yield) as white solid, which is going to next step without future purification. $^1$H NMR (300 MHz, CD$_3$OD) δ 0.81 (s, 3H), 3.94 (s, 6H), 5.02 (d, J=2.4 Hz, 1H), 6.73 (d, J=8.7 Hz, 2H), 7.17 (d, J=8.7 Hz, 2H); $^{13}$C NMR (75 MHz, CD$_3$OD) δ 13.05, 30.36, 60.33, 70.65, 72.57, 108.90, 114.70, 127.11, 133.26, 156.48; LC/MS m/s [M+H]$^+$ 282.2.

48: To a stirred mixture of 47 (218 mg, 0.83 mmol) and 6 (295 mg, 1.00 mmol, 1.20 equiv, prepared as in Example 1) in anhydrous DMF (5 mL) is added N-ethyl-N'-(3-dimethylaminopropyl)carbodiimide hydrochloride (EDC hydrochloride) (192 mg 1.00 mmol, 1.20 equiv), 1-hydroxybenzotriazole (HOBt) (135 mg, 1.00 mmol, 1.20 equiv) at room temperature. The mixture is cooled with an ice-bath, and diisopropylethylamine (DIEA) (0.58 mL, 3.33 mmol, 5.0 equiv) is added. The whole reaction mixture is stirred under argon and at 0° C. for 1 h, then allowed to warm to temperature with the stirring is continued for additional 24 h. The resulting yellow solution is condensed to dryness with a rotavapor, and the residue is treated with water (20 mL), extracted with DCM (3×50 mL). The combined extracts are washed with brine (20 mL), and dried over anhydrous Na$_2$SO$_4$. Evaporation of the solvent affords the crude product, which is purified by CombiFlash (eluting with 0-3% MeOH in DCM) to afford 48 (337 mg, 98.3% yield) as yellow solid. $^1$H NMR (300 MHz, CD$_3$OD) δ 0.79 (s, 3H), 3.96 (s, 6H), 4.41 (d, J=1.5 Hz, 1H), 5.27 (s, 1H), 6.61 (d, J=9.0 Hz, 2H), 6.67 (d, J=8.7 Hz, 2H), 7.17 (d, J=8.4 Hz, 2H), 7.25 (d, J=8.7 HZ, 2H), 7.52 (d, J=8.7 Hz, 2H), 7.70 (d, J=8.7 Hz, 2H); $^{13}$C NMR (75 MHz, CD$_3$OD) δ 13.08, 30.46, 58.04, 70.50, 7.91, 72.68, 76.58, 79.16, 84.58, 108.38, 108.51, 114.28, 114.68, 125.72, 127.08, 127.36, 132.07, 132.68, 133.87, 134.41, 150.159, 156.47, 167.73; LC/MS m/s [M+H]$^+$ 525.2.

49: 48 (130 mg, 0.248 mmol) is dissolved in dioxane (1.0 mL). The mixture is diluted with acetic acid (1.0 mL) and water (1.0 mL) at room temperature under argon. The suspension mixture is stirred for 0.5 h. Then the yellow clear solution is concentrated to dryness. The residue is treated with saturated NaHCO$_3$ (20 mL) to pH=10, extracted with EtOAc (3×40 mL). The combined organic layers are washed with water (2×30 mL), brined (30 mL), and dried (anhydrous Na$_2$SO$_4$). The crude product is purified by CombiFlash to give the 49 (120 mg, 90% yield) as yellow solid. $^1$H NMR (300 MHz, CD$_3$OD) δ 0.87 (s, 3H), 3.43-3.44 (m, 4H), 4.07 (d, J=1.2 Hz, 2H), 4.91 (d, J=4.2 Hz, 1H), 5.28 (d, J=3.9 Hz, 1H), 6.60 (d, J=8.7 Hz, 2H), 6.75 (d, J=8.7 Hz, 2H), 7.24 (d, J=5.4 Hz, 2H) 7.27 (d, J=5.4 Hz, 2H), 7.53 (d, J=8.4 Hz, 2H), 7.72 (d, J=8.7 Hz, 2H); $^1$H NMR (75 MHz, CD$_3$OD) δ 15.68, 40.87, 59.83, 64.44, 67.43, 70.84, 72.84, 76.68, 79.05, 84.60, 108.39, 114.26, 114.94, 126.00, 127.29, 127.46, 131.73, 132.09, 133.84, 150.16, 157.03, 168.300, 170.73; LC/MS m/s [M+Na]$^+$ 565.1.

CPD-049: 49 (54.2 mg, 0.10 mmol) is taken into a mixture of THF/MeOH (1:1 volume) 2.0 mL. 50% aq hydroxylamine (0.20 mL, 3.0 mmol, 30 equiv) is added and followed by potassium cyanide (6.5 mg, 0.10 mmol, 1.0 equiv) at room temperature under argon. The reaction mixture is stirred room temperature for 3.5 h. Then the yellow solution is concentrated to dryness. The residue is treated water (30 mL), extracted with EtOAc (30% 1-butanol) (3×50 mL). The combined organic layers are washed with milliQ water (5×30 mL), brine (30 mL), and dried (anhydrous $Na_2SO_4$). The solvent is removed by reduced pressure to give CPD-049 (36.0 mg, 79.1% yield) as yellow solid. $^1$H NMR (300 MHz, DMSO-$_{d6}$) δ 4.55 (q, J=13.5 Hz, 1H), 4.97 (t, J=9.9 Hz, 1H), 5.54 (d, J=6.0 Hz, 1H), 5.83 (s, 2H), 6.54 (d, J=0.7 Hz, 2H), 6.64 (d, J=8.7 HZ, 2H), 7.14 (d, J=8.7 Hz, 2H), 7.25 (d, J=8.4 HZ, 2H), 7.60 (d, J=8.4 Hz, 2H), 7.80 (d, J=8.7 Hz, 2H), 8.12 (d, J=8.7 Hz, 1H), 8.79 (s, 1H), 9.22 (s, 1H), 10.60 (s, 1H); $^{13}$C NMR (75 MHz, DMSO-$_{d6}$) δ 58.86, 71.81, 72.90, 77.29, 80.83, 86.37, 105.85, 114.28, 115.30, 124.72, 128.01, 128.47, 132.60, 133.06, 134.71, 134.98, 151.56, 157.03, 165.99, 167.23; LC/MS [M+Na]$^+$ 478.0.

Example 7

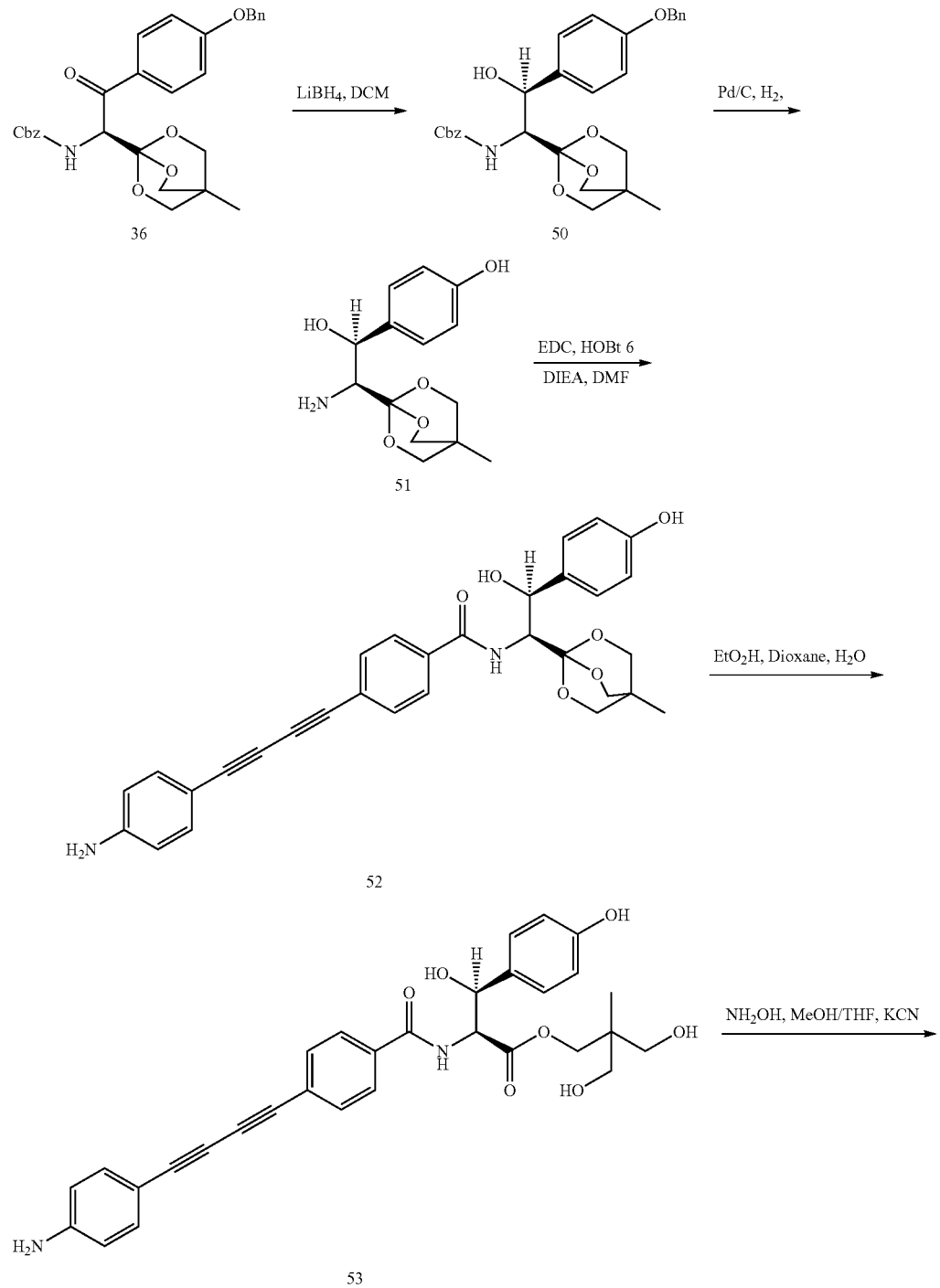

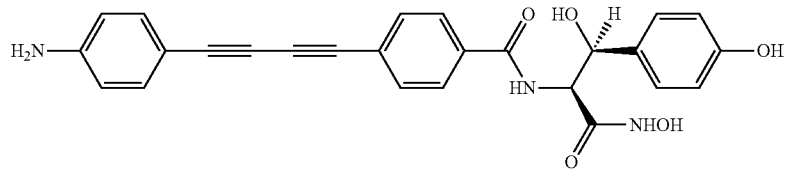

CPD-050

50: 36 (0.50 g, 1.00 mmol) is dissolved in anhydrous DCM (15 mL) and MeOH (15 mL) under argon, and then cooled to −78° C. Then a solution of 2.0 M LiBH$_4$ in THF (4.80 mL, 8.00 mmol, 8.0 equiv) is added dropwise. The reaction mixture is stirred at −78° C. for 10 h, and then slowly warm to room temperature. The mixture is diluted with DCM (100 mL) and then quenched with saturated NH$_4$Cl (50 mL). The organic layer is separated. And the aqueous layer is extracted with DCM (2×50 mL). The organic layers are combined, washed with saturated NH$_4$Cl (50 mL), brine (50 mL), and dried (anhydrous Na$_2$SO$_4$). The solvent is reduced in vacuum to dryness. The crude product is purified by CombiFlash (eluting with 0-60% EtOAc in hexane) to obtain 50 (0.44 g, 88% yield) as white solid. $^1$H NMR (300 MHz, CD$_3$Cl) δ 0.83 (s, 3H), 3.96 (s, 6H), 4.11 (d, J=1.5 Hz, 1H), 4.14-4.21 (m, 1H), 4.78-4.87 (m, 3H), 5.00 (s, 1H), 5.02 (s, 2H), 6.91 (d, J=8.4 Hz, 2H), 7.11 (d, J=6.6 Hz, 2H), 7.25-7.45 (m, 10H); $^{13}$C NMR (75 MHz, CD$_3$Cl) δ 14.51, 30.92, 58.94, 66.72, 70.10, 73.03, 74.02, 108.96, 114.51, 127.71, 127.83, 128.11, 128.60, 128.78, 129.12, 132.95, 136.83, 137.38, 156.04, 158.62; LC/MS m/s [M+H]$^+$ 505.2.

51: To a solution of 50 (0.40 g, 0.80 mmol) in anhydrous MeOH (20 mL) is added 10% Pd/C (40.0 mg, 10% w/w) at room temperature under a balloon of hydrogen. The reaction mixture is stirred for 14 h. Then the catalyst is removed by filtration through a celite pad and washed with MeOH (50 mL). The filtrate is evaporated under reduced vacuo to obtain the 51 (0.280 g, 96% yield) as white solid, which is going to next step without future purification. $^1$H NMR (300 MHz, CD$_3$OD) δ 0.82 (s, 3H), 3.02 (d, J=7.2 Hz, 1H), 3.95 (s, 6H), 4.72 (d, J=7.2 Hz, 1H), 6.75 (d, J=8.4 Hz, 2H), 7.19 (d, J=8.7 HZ, 2H); $^{13}$C NMR (75 MHz, CD$_3$OD) δ 12.97, 30.32, 59.78, 72.52, 73.42, 108.66, 114.71, 128.85, 157.18; LC/MS m/s [M+H]+ 282.2.

52: To a stirred mixture of 51 (93 mg, 0.36 mmol) and 6 (120 mg, 0.43 mmol, 1.20 equiv, prepared as in Example 1) in anhydrous DMF (5 mL) is added N-ethyl-N'-(3-dimethylaminopropyl)carbodiimide hydrochloride (EDC hydrochloride) (82 mg 0.43 mmol, 1.20 equiv), 1-hydroxybenzotriazole (HOBt) (58 mg, 0.43 mmol, 1.20 equiv) at room temperature. The mixture is cooled with an ice-bath, and diisopropylethylamine (DIEA) (0.25 mL, 1.44 mmol, 4.0 equiv) is added. The whole reaction mixture is stirred under argon and at 0° C. for 1 h, then allowed to warm to temperature with the stirring is continued for additional 36 h. The resulting yellow solution is condensed to dryness with a rotavapor, and the residue is treated with water (20 mL), extracted with DCM (3×50 mL). The combined extracts are washed with brine (20 mL), and dried over anhydrous Na$_2$SO$_4$. Evaporation of the solvent affords the crude product, which is purified by CombiFlash (eluting with 0-4% MeOH in DCM) to afford 52 (165 mg, 87% yield) as yellow solid. $^1$H NMR (300 MHz, CD$_3$OD) δ 0.82 (s, 3H), 3.98 (s, 6H), 4.54 (d, J=8.4 Hz, 1H), 4.95 (d, J=8.4 Hz, 1H), 6.61 (d, J=8.7 Hz, 2H), 6.68 (d, J=8.7 Hz, 2H), 7.21 (d, J=6.6 Hz, 2H), 7.23 (d, J=6.6 Hz, 2H), 7.43 (s, 4H); $^{13}$C NMR (75 MHz, CD$_3$OD) δ 12.99, 30.460, 57.49, 70.77, 72.67, 73.07, 76.29, 79.06, 84.38, 108.35, 108.66, 114.21, 114.47, 125.41, 127.26, 128.85, 131.68, 131.79, 133.79, 134.74, 150.19, 156.97, 167.68; LC/MS m/s [M+H]$^+$ 525.1.

53: 52 (150 mg, 0.286 mmol) is dissolved in dioxane (1.0 mL). The mixture is diluted with acetic acid (1.0 mL) and water (1.0 mL) at room temperature under argon. The suspension mixture is stirred for 70 min. Then the yellow clear solution is concentrated to dryness. The residue is treated with saturated NaHCO$_3$ (20 mL) to pH=10, extracted with EtOAc (3×40 mL). The combined organic layers are washed with water (2×30 mL), brined (30 mL), and dried (anhydrous Na$_2$SO$_4$). The crude product is purified by CombiFlash (eluting with 0-10% MeOH in DCM) to give 53 (126 mg, 88% yield) as yellow solid. $^1$H NMR (300 MHz, CD$_3$OD) δ 0.86 (s, 3H), 3.45-3.43 (m, 4H), 4.09 (q, J=32.4 Hz, 2H), 4.89 (d, J=7.5 Hz, 1H), 5.05 (d, J=7.5 Hz, 1H), 6.60 (d, J=8.7 Hz, 2H), 6.78 (d, J=8.4 Hz, 2H), 7.24 (d, J=8.7 Hz, 2H), 7.26 (d, J=8.7 Hz, 2H), 7.48 (d, J=8.4 Hz, 2H), 7.60 (d, J=8.7 Hz, 2H); $^{13}$C NMR (75 MHz, CD$_3$OD) δ 15.75, 40.83, 59.21, 64.58, 67.31, 70.92, 73.33, 76.75, 79.10, 84.65, 108.44, 114.32, 115.03, 125.98, 127.42, 127.96, 131.62, 132.07, 133.76, 133.88, 150.10, 157.23, 167.84, 171.21; LC/MS m/s [M+H]$^+$ 543.2.

CPD-050: 53 (54.2 mg, 0.10 mmol) is taken into a mixture of THF/MeOH (1:1 volume) 2.0 mL. 50% aq hydroxylamine (0.20 mL, 3.0 mmol, 30 equiv) is added and followed by potassium cyanide (10.0 mg, 0.10 mmol, 1.5 equiv) at room temperature under argon. The reaction mixture is stirred room temperature for 3.5 h. Then the yellow solution is concentrated to dryness. The residue is treated water (5 mL), washed with EtOAc (10 mL). The precipitate is then washed with milliQ water (3×30 mL), dried under high vacuum to give CPD-050 (35.0 mg, 77% yield) as yellow solid. $^1$H NMR (300 MHz, CD$_3$OD) δ 4.69 (d, J=8.7 Hz, 1H), 4.91 (d, J=9.0 Hz, 1H), 6.61 (d, J=8.4 Hz, 2H), 6.72 (d, J=8.4 Hz, 2H), 7.23 (d, J=9.0 Hz, 2H), 7.27 (d, J=8.4 Hz, 2H), 7.48 (d, J=8.1 Hz, 2H), 7.56 (d, J=8.1 Hz, 2H); $^{13}$C NMR (75 MHz, CD$_3$OD) δ 56.73, 70.72, 73.14, 76.49, 78.96, 84.48, 108.32, 114.20, 114.81, 125.80, 127.34, 128.26, 131.91, 132.01, 133.78, 134.04, 150.21, 157.21, 167.37, 168.52; LC/MS m/s [M+H]$^+$ 456.2.

Example 8
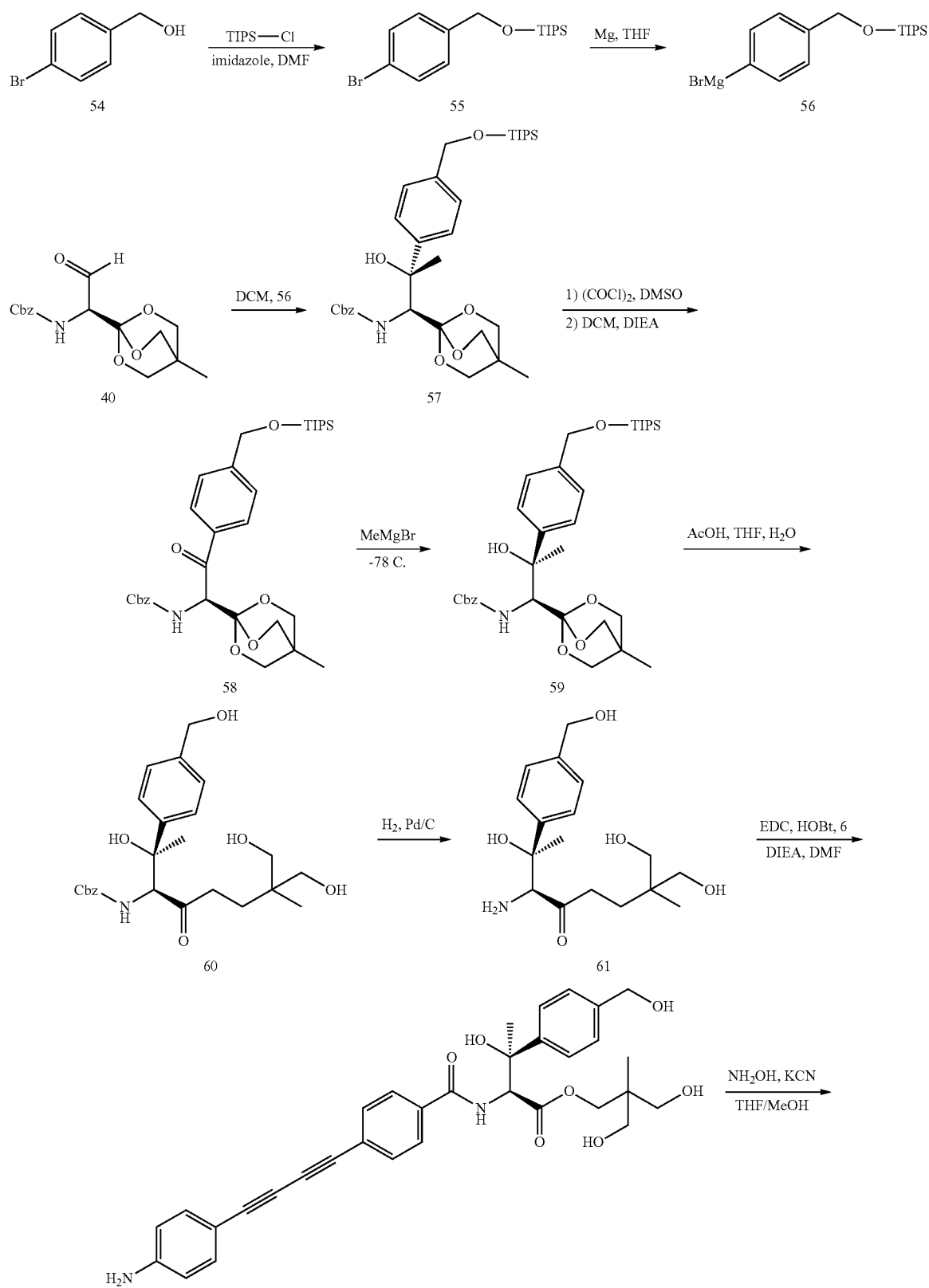

lp;1p

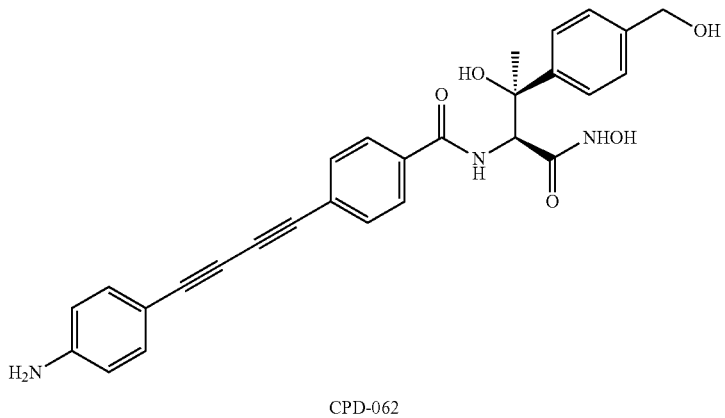

CPD-062

55: ¹H (300 MHz, CDCl₃) δ 1.07-1.22 (m, 21H), 4.79 (s, 2H), 7.24 (d, J=9.6 Hz, 2H), 7.46 (d, J=8.4 Hz, 2H); ¹³C (75 MHz, CDCl₃) δ 12.25, 18.26, 64.65, 120.66, 127.65, 131.47, 140.92; LC/MS m/s [M+H]⁺ 342.2.

57: ¹H (300 MHz, CDCl₃) δ 0.83 (s, 3H), 1.09-1.16 (m, 21H), 3.37 (s, 1H), 3.89-3.98 (m, 6H), 4.09 (d, J=10.2 Hz, 1H), 4.82 (s, 2H), 4.97 (q, J=39.3 Hz, 2H), 5.34 (s, 1H), 5.48 (d, J=10.2 Hz, 1H), 7.20-7.35 (m, 9H); ¹³C 75 MHz, CDCl₃) δ 12.29, 14.56, 18.32, 30.94, 58.80, 65.09, 66.75, 70.91, 73.06, 109.09, 125.44, 125.72, 125.99, 127.96, 128.04, 128.60, 136.96, 138.77, 140.88, 156.56; LC/MS m/s [M+H]⁺ 586.3.

58: ¹H (300 MHz, CDCl₃) δ 0.75 (s, 3H), 1.09-1.19 (m, 21H), 3.85 (s, 6H), 4.89 (s, 2H), 5.10 (s, 2H), 5.59 (d, J=9.6 Hz, 1H), 5.95 (d, J=9.6 Hz, 1H), 7.26-7.35 (m, 5H), 7.44 (d, J=8.1 Hz, 2H), 8.04 (d, J=8.1 Hz, 2H); ¹³C 75 MHz, CDCl₃) δ 12.24, 14.47, 18.27, 30.91, 57.61, 64.90, 67.29, 73.17, 107.55, 125.51, 128.31, 128.68, 129.80, 135.37, 136.53, 147.80, 156.18, 194.99; LC/MS m/s [M+H]⁺ 584.0.

59: ¹H (300 MHz, CDCl₃) δ 0.70 (s, 3H), 1.08-1.16 (m, 21H), 1.50 (s, 3H), 3.66-3.76 (m, 6H), 4.19 (s, 1H), 4.27 (d, J=10.5 Hz, 1H), 4.82 (s, 2H), 5.08 (q, J=38.1 Hz, 2H), 5.39 (d, J=10.8 Hz, 1H), 7.25-7.38 (m, 9H); ¹³C 75 MHz, CDCl₃) δ 12.29, 14.42, 18.31, 27.63, 30.57, 60.99, 65.16, 67.01, 72.53, 76.33, 109.49, 125.01, 125.25, 128.14, 128.20, 128.46, 128.69, 136.89, 139.71, 144.86, 156.75; LC/MS m/s [M+H]⁺ 600.1

60: ¹H (300 MHz, CDCl₃) δ 0.61 (s, 3H), 1.54 (s, 3H), 2.97 (br, s, 3H), 3.09 (br, s, 3H), 3.67 (d, J=10.5 Hz, 2H), 3.81 (d, J=10.8 Hz, 2H), 4.60 (s, 2H), 4.71 (d, J=9.0 Hz, 1H), 5.12 (q, J=31.2 Hz, 2H), 6.11 (d, J=9.3 Hz, 1H), 7.29-7.43 (m, 9H); ¹³C 75 MHz, CDCl₃) δ 16.61, 27.54, 40.06, 61.87, 64.95, 65.92, 67.67, 68.13, 76.24, 125.29, 128.12, 128.38, 128.58, 128.83, 136.18, 140.30, 143.72, 156.79, 172.03; LC/MS m/s [M+H]⁺ 560.4.

61: ¹H (300 MHz, CD₃OD) δ 0.72 (s, 3H), 1.63 (s, 3H), 3.23 (br, s, 3H), 3.69 (s, 1H), 3.74 (d, J=11.1 Hz, 1H), 3.84 (d, J=11.1 Hz, 1H), 4.58 (s, 2H), 7.32 (d, J=8.4 Hz, 2H), 7.42 (d, J=8.1 Hz, 2H); ¹³C 75 MHz, CD₃OD) δ 15.67, 26.09, 40.30, 63.63, 63.75, 64.42, 67.14, 75.06, 125.47, 126.68, 140.34, 144.08, 173.01; LC/MS m/s [M+H]⁺ 326.1

62: ¹H NMR (300 MHz, DMSO-d₆) δ 0.49 (s, 3H), 1.50 (s, 3H), 2.99 (br, s, 4H), 3.56 (d, J=10.8 Hz, 1H), 3.74 (d, J=10.8 Hz, 1H), 4.27 (br, s, 2H), 4.96 (s, 1H), 5.12 (br, s, 1H), 5.52 (s, 1H), 5.84 (br, s, 1H), 6.54 (d, J=8.7 Hz, 2H), 7.26 (d, J=8.7 Hz, 4H), 7.43 (d, J=8.4 Hz, 2H), 7.68 (d, J=8.4 Hz, 2H), 7.87 (d, J=8.4 Hz, 2H); ¹³C NMR (300 MHz, DMSO-d₆) δ 16.73, 28.63, 62.50, 63.41, 63, 94, 67.76, 71.80, 75.37, 77.49, 80.75, 86.50, 105.83, 110.42, 114.27, 119.70, 125.10, 125.52, 126.64, 128.48, 132.82, 134.72, 141.31, 144.77, 151.55, 166.35, 170.17; LC/MS m/s [M+H]+.

CPD-062: (20 mg, 47% yield), ¹H NMR (300 MHz, DMSO-d₆) δ 1.42 (s, 3H), 3.78 (d, J=5.7 Hz, 1H), 4.45 (d, J=5.4 Hz, 1H), 4.82 (d, J=9.6 Hz, 1H), 5.12 (t, J=11.1 Hz, 1H), 5.83 (s, 2H), 6.54 (d, J=8.4 Hz, 2H), 7.21-7.26 (m, 4H), 7.42 (d, J=8.4 Hz, 2H), 7.83-7.89 (m, 2H), 8.43 (d, J=9.6 Hz, 1H), 8.84 (s, 1H), 10.58 (s, 1H); ¹³C NMR (75 MHz, DMSO-d₆); δ 27.29, 58.35, 63.36, 71.81, 75.64, 77.31, 80.83, 86.39, 105.84, 114.29, 124.79, 125.86, 126.48, 128.45, 128.70, 132.57, 134.71, 14.95, 141.38, 145.04, 151.56, 166.25, 166.98; LC/MS m/s [M+H]⁺ 484.5.

Example 9

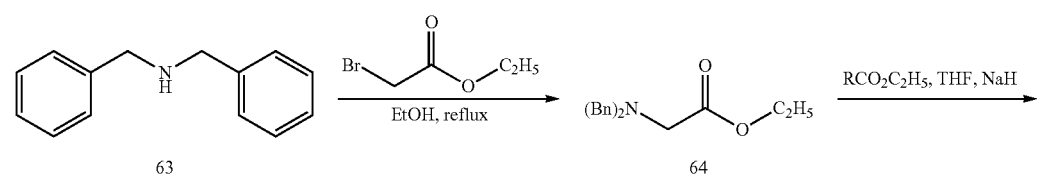

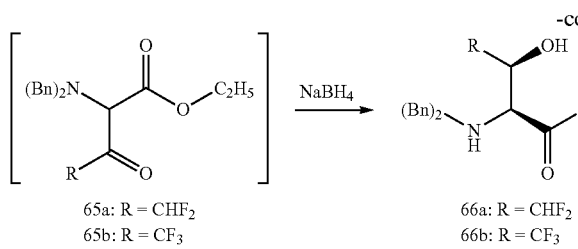
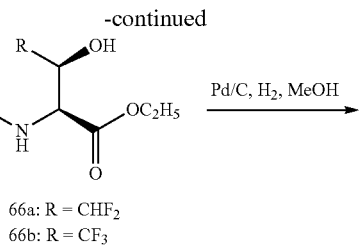
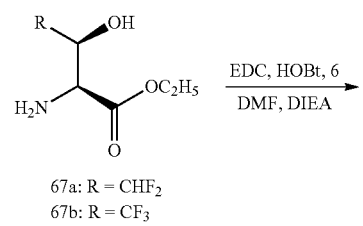
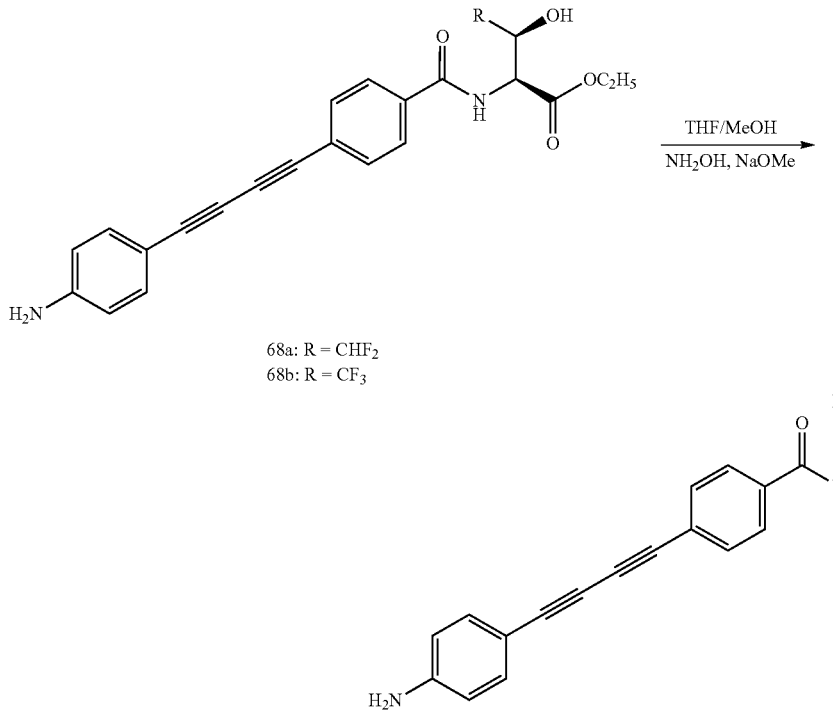

To a solution of dibenzylamine 63 (13.8 mL, 71.9 mmol, 1.1 equiv) in absolute ethanol (50 mL), ethyl bromoacetate (7.25 mL, 65.4 mmol) is added. The reaction mixture is refluxed for 12 h under argon. After evaporation under vacuum of most of the ethanol, 1N sodium hydroxide (100 mL) and dichloromethane (700 mL) are added, and the phases separated. The organic layer is washed with water (100 mL), brine (100 mL) and dried (anhydrous $Na_2SO_4$). The crude product is crystallized from ethanol/water to give 64 (12.50 g, 67% yield) as white needle solid.

To a solution of 64 (2.00 g, 0.71 mmol) and ethyl fluoroacetate (15.53 mmol) in anhydrous tetrahydrofuran (15 mL), sodium hydride (50% suspension in mineral oil) (1.02 g, 25.42 mmol) is added. The reaction mixture is refluxed for 5 h under argon and then cooled to 0° C. and treated with acetic acid (1.42 mL, 26.10 mmol). Sodium borohydride (668 mg, 17.66 mmol) is then added and the suspension is stirred overnight (14 h) at room temperature. The result deep red solution is treated with 1N hydrochloride acid to pH=5, stirred for 10 min, and then treated with sat. $NaHCO_3$ (100 mL) to pH=9-10. The mixture is extracted with EtOAc (3×80 mL). The combined organic layers are washed with water (30 mL), brine (30 mL), and dried (anhydrous $Na_2SO_4$). The crude product is purified by CombiFlash (eluting with 0-10% EtOAc in hexane) to obtain the 66 as a white solid.

A solution of 66 (4.68 mmol) in absolute ethanol (20 mL) is added 10% Pd/C (0.34 g, 20% w % w). The reaction mixture is stirred at room temperature under a balloon of hydrogen for overnight (14 h). Filtration of the catalyst and evaporation of the filtrate to dryness give a white solid 67, which is going to next step without the future purification.

To a stirred mixture of 6 (120 mg, 0.46 mmol, prepared as in Example 1) and 67 (0.55 mmol, 1.20 equiv) in anhydrous DMF (5 mL) is added N-ethyl-N'-(3-dimethylaminopropyl) carbodiimide hydrochloride (EDC hydrochloride) (105.8 mg 0.55 mmol, 1.20 equiv), 1-hydroxybenzotriazole (HOBt) (74.6 mg, 0.55 mmol, 1.20 equiv) at room temperature. The mixture is cooled with an ice-bath, and diisopropylethylamine (DIEA) (0.32 mL, 1.84 mmol, 4.00 equiv) is added. The whole reaction mixture is stirred under argon and at 0° C. for 1 h, then allowed to warm to temperature with the stirring is continued for additional 16 h. The resulting yellow solution is condensed to dryness with a rotavapor, and the residue is treated with water (20 mL), extracted with EtOAc (3×50 mL). The combined extracts are washed with water (20 mL), brine (20 mL), and dried over anhydrous $Na_2SO_4$. Evaporation of the solvent affords the crude product, which is purified by flash chromatography (eluting with 0-1.5% MeOH in DCM) to give 68 as yellow solid.

To an ice-cold solution of 68 (0.229 mmol) dissolved in anhydrous MeOH (1 mL) and THF (1 mL) is added hydroxylamine hydrochloride (79.7 mg, 1.147 mmol, 5.0 equiv) followed by 25% sodium methoxide in methanol solution (0.40 mL, 1.72 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated NH$_4$Cl (2 mL), extracted with EtOAc (3×50 mL). The combined extracts are washed with water (30 mL), brine (30 mL), and dried over anhydrous Na$_2$SO$_4$. Evaporation of the solvent affords the crude product, which is purified by CombiFlash (eluting with 0-5% MeOH in DCM) to afford title compound as a yellow solid.

64 $^1$H (300 MHz, CDCl$_3$) δ 1.29 (t, J=15.0 Hz, 3H), 3.32 (s, 2H), 3.84 (s, 4H), 4.18 (q, J=21.9 Hz, 2H), 7.24-7.44 (m, 10H); $^{13}$C (75 MHz, CDCl$_3$) δ 14.547, 53.793, 57.981, 60.409, 127.354, 128.541, 129.156, 139.295, 171.653; LC/MS m/s [M+H]$^+$ 284.5.

65a: (2.00 g, 78% yield), $^1$H (300 MHz, CDCl$_3$) δ 1.41 (t, J=15.3 Hz, 3H), 3.47 (d, J=9.9 Hz, 1H), 3.54 (d, J=12.9 Hz, 2H), 3.82 (s, 1H), 4.02 (d, J=13.2 Hz, 2H), 4.15-4.26 (m, 1H), 4.27-4.41 (m, 2H), 5.47-5.85 (m, 1H), 7.26-7.38 (m, 10H); $^{13}$C (75 MHz, CDCl$_3$) δ 14.72, 55.21, 59.65, 61.45, 66.94, 67.25, 67.56, 112.47, 115.70, 118.94, 128.04, 128.96, 129.47, 137.66, 169.34; LC/MS m/s [M+H]$^+$ 379.2.

66a: (0.81 g, 95% yield), $^1$H (300 MHz, CDCl$_3$) δ 1.27 (t, J=14.4 Hz, 3H), 3.74 (d, J=1.5 Hz, 1H), 4.04-4.13 (m, 1H), 4.22 (q, J=22.2 Hz, 2H), 5.62-6.01 (m, 1H); $^{13}$C (75 MHz, CDCl$_3$) δ 14.27, 53.29, 62.16, 170.50, 70.84, 71.17, 112.59, 115.82, 119.05, 172.81; LC/MS m/s [M+H]$^+$ 184.0.

68a: (0.176 g, 90% yield), $^1$H (300 MHz, CD$_3$OD) δ 1.30 (t, J=14.4 Hz, 3H), 4.25 (q, J=21.3 Hz, 2H), 4.31-4.40 (m, 1H), 5.01 (d, J=1.8 Hz, 1H), 5.62-5.01 (m, 1H), 6.60 (d, J=8.7 Hz, 2H), 7.25 (d, J=9.0 Hz, 2H), 7.58 (d, J=8.4 Hz, 2H), 7.84 (d, J=8.7 Hz, 2H); $^{13}$C (75 MHz, CD$_3$OD) δ 13.27, 53.57, 61.95, 70.11, 70.44, 70.78, 76.74, 79.00, 84.63, 108.34, 112.09, 114.24, 115.31, 118.53, 126.20, 127.65, 132.13, 133.66, 133.84, 150.20, 168.46, 169.62; LC/MS m/s [M+H$^+$] 427.1.

CPD-056: (70.0 mg, 72% yield) $^1$H (300 MHz, CD$_3$OD) δ 4.21-4.31 (m, 1H), 4.87-4.86 (m, 1H), 5.63-6.01 (m, 1H), 6.62 (d, J=8.7 Hz, 2H), 7.24 (d, J=8.7 Hz, 2H), 7.57 (d, J=8.7 Hz, 2H), 7.86 (d, J=8.7 Hz, 2H); $^{13}$C (75 MHz, CD$_3$OD) δ 52.38, (69.91, 70.23, 70.56), 70.74, 76.74, 78.97, 84.64, 108.31, (112.12, 115.34, 118.57), 114.22, 126.21, 127.67, 132.08, 133.53, 133.82, 150.22, 167.26, 167.95; LC/MS m/s [M+H$^+$] 414.2.

66b: (2.00 g, 30% yield) as a white solid. $^1$H (300 MHz, CDCl$_3$) δ $^1$1.42 t, J=15.3 Hz, 3H), 3.45 (d, J=13.2 Hz, 2H), 3.54 (d, J=9.6 Hz, 1H), 3.99 (d, J=13.2 Hz, 2H), 4.19-4.49 (m, 4H), 7.27-7.40 (m, 10H); $^3$C (75 MHz, CDCl$_3$) δ 14.70, 54.95, 59.07, 61.72, (65.25, 65.66, 66.07, 66.48), (119.23, 122.96, 126.69, 130.41), 127.44, 128.24, 128.55, 129.06, 129.50, 137.02, 168.41; LC/MS m/s [M+H]$^+$ 397.1.

67b: (0.81 g, 88% yield) $^1$H (300 MHz, CDCl$_3$) δ 1.29 (t, J=14.1 Hz, 3H), 3.90 (s, 1H), 4.21-4.29 (m, 4H); $^{13}$C (75M Hz, CDCl$_3$) δ 14.19, 52.314, 62.67, (68.56, 68.97, 69.37, 69.77), (119.26, 123.01, 126.77, 130.53), 171.17; LC/MS m/s [M+H]$^+$ 201.0.

68b: (0.176 g, 69% yield) as a yellow solid. $^1$H (300 MHz, CD$_3$OD) δ 1.30 (t, J=14.7 Hz, 3H), 4.27 (q, J=21.3 Hz, 2H), 4.67-4.78 (m, 1H), 5.18 (d, J=1.5 Hz, 1H), 6.62 (d, J=8.1 Hz, 2H), 7.25 (d, J=8.1 Hz, 2H), 7.59 (d, J=8.1 Hz, 2H), 7.83 (d, J=8.1 Hz, 2H); $^{13}$C (75 MHz, CD$_3$OD) δ 13.21, 52.80, 62.16, (68.79, 69.20), 70.71, 76.68, 78.95, 84.60, 108.29, 114.20, 122.81, 126.20, 126.56, 127.61, 132.11, 133.81, 150.24, 168.24, 169.01; LC/MS m/s [M+H]$^+$ 445.1.

CPD-057: (70.0 mg, 82% yield) as a yellow solid. $^1$H (300 MHz, CD$_3$OD) δ 4.58-4.66 (m, 1H), 5.03 (d, J=2.7 Hz, 1H), 6.62 (d, J=8.1 Hz, 2H), 7.25 (d, J=8.1 Hz, 2H), 7.59 (d, J=7.8 Hz, 2H), 7.84 (d, J=8.1 Hz, 2H); $^{13}$C (75 MHz, CD$_3$OD) δ 51.87, (68.11, 68.52, 68.93, 69.33), 70.72, 76.75, 78.94, 84.65, 108.28, 114.21, (119.25, 122.99, 126.74, 130.49), 126.25, 127.64, 132.10, 133.56, 133.81, 150.24, 166.66, 167.85; LC/MS m/s [M+H]$^+$ 432.3

Example 10

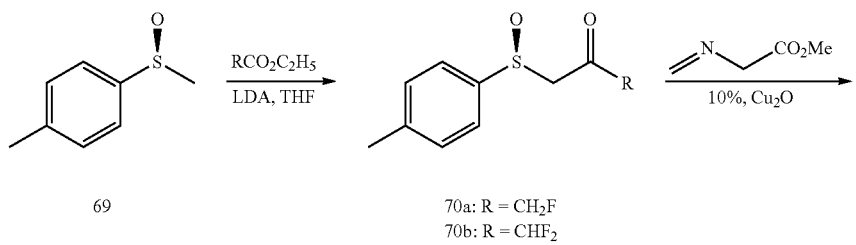

69

70a: R = CH$_2$F
70b: R = CHF$_2$

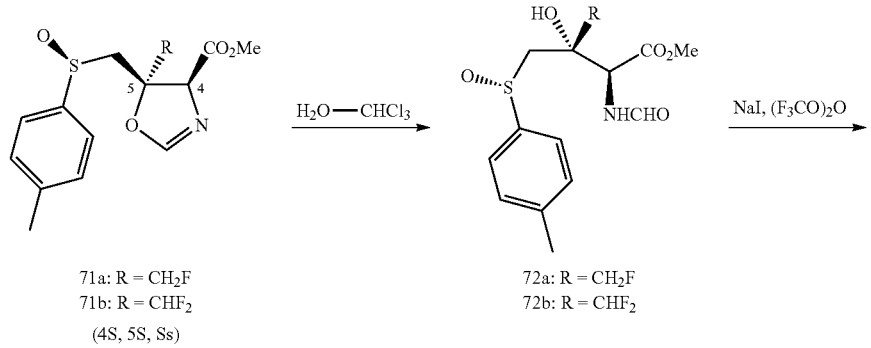

71a: R = CH$_2$F
71b: R = CHF$_2$
(4S, 5S, Ss)

72a: R = CH$_2$F
72b: R = CHF$_2$

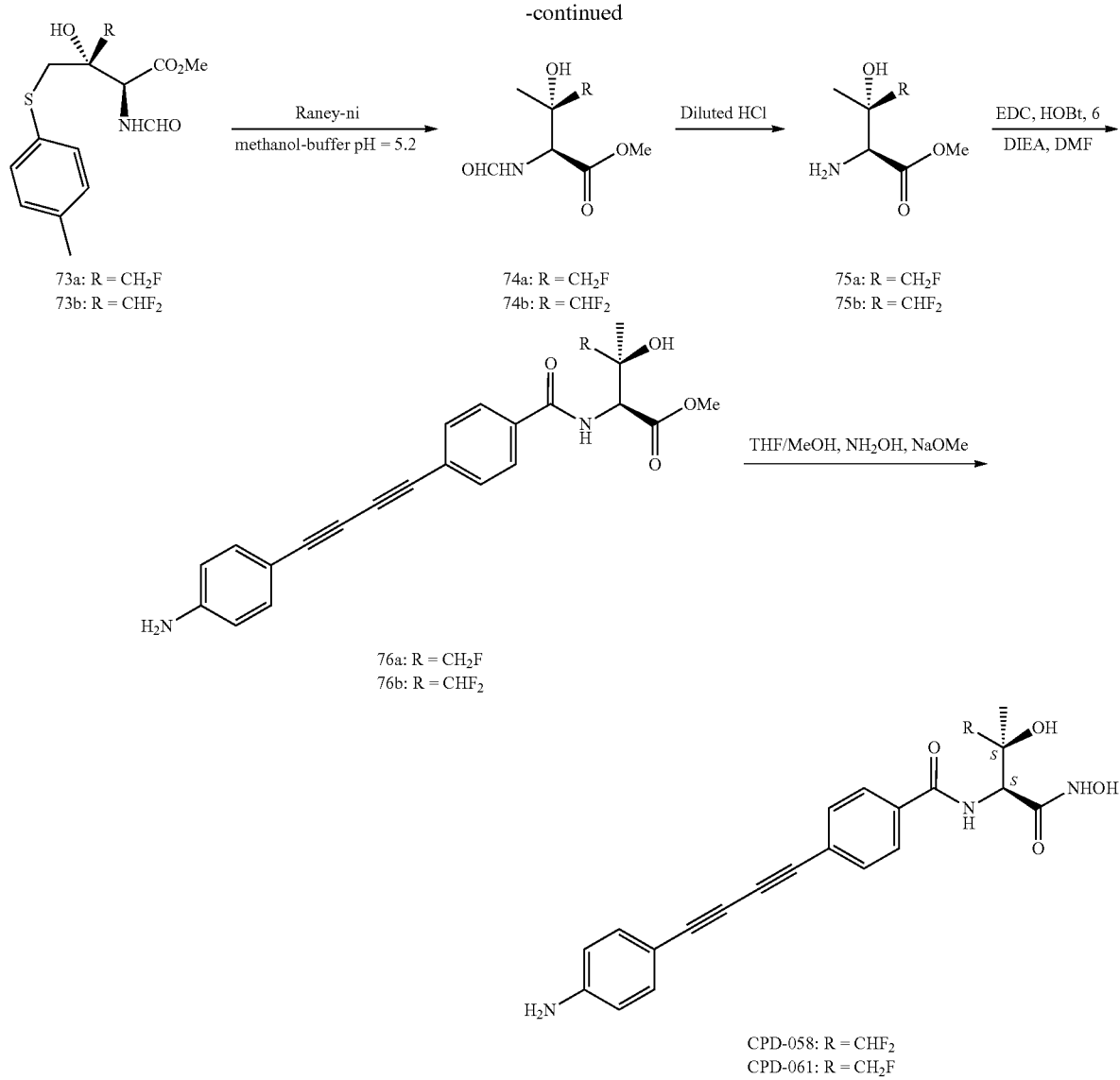

73a: R = CH$_2$F
73b: R = CHF$_2$

74a: R = CH$_2$F
74b: R = CHF$_2$

75a: R = CH$_2$F
75b: R = CHF$_2$

76a: R = CH$_2$F
76b: R = CHF$_2$

CPD-058: R = CHF$_2$
CPD-061: R = CH$_2$F

To a solution of diisopropylamine (16.21 mmol) in anhydrous THF (30 mL) is added BuLi (1.70 in hexane, 9.15 mL, 15.56 mmol, 1.20 equiv) at −78° C. After 30 min, a solution of S(−)-methyl p-Tol sulfoxide in anhydrous THF (10 mL) is added dropwise. Then the reaction mixture is stirred at −78° C. for 30 min. Ethyl fluoroacetate (15.56 mmol, 1.20 equiv) is added dropwise. The reaction mixture is stirred at −78° C. for 2 h under argon. Then the mixture is quenched with saturated NH$_4$Cl (100 mL), extracted with EtOAc (3×100 mL). The combined extracts are washed with water (100 mL), brine (100 mL) and dried (anhydrous Na$_2$SO$_4$). The crude product is purified by CombiFlash (eluting with EtOAc in hexane 0-50%) to give the 70 as a white solid.

To a solution of 70 (11.2 mmol) in anhydrous Diethyl ether (50 mL) is added Cu$_2$O (0.16 g, 1.12 mmol, 0.10 equiv) at 0° C. under argon. The reaction mixture is added dropwise methyl isocyanoacetate (2.210 g, 2.00 equiv). The reaction mixture is stirred at 0° C. for 2 hours, then is allowed to warm to room temperature for 14 hours. The mixture is concentrated to dryness. The crude product is purified by CombiFlash (eluting with EtOAc in hexane 0-60%) to give the 71 as yellow oil.

To a solution of 71 (1.20 g, 3.78 mmol) in CHCl$_3$ (1 mL) is added milliQ water (30 mL). The reaction mixture is stirred at room temperature under argon for 24 hours. Then the mixture is diluted with DCM (100 mL), washed with water (40 mL), brine (40 mL) and dried (anhydrous Na$_2$SO$_4$). The crude product is purified by CombiFlash (eluting with MeOH in DCM 0-5%) to give 72 as white solid.

To a solution of 72 (3.4 mmol) in acetone (20 mL) is added Sodium iodide (1.18 g, 7.84 mmol, 2.4 equiv) at −10° C. under argon. A solution of trifluoroacetatic anhydride (0.75 mL in 2 mL acetone) is added dropwise in 8 min. The reaction mixture is stirred at −10° C. for 9 min, then is concentrated to dryness. The residue is diluted with water (30 mL), extracted with EtOAc (3×50 mL). The combined organic layers are washed with water (30 mL), brine (30 mL) and dried (anhydrous Na$_2$SO$_4$). The crude product is purified by CombiFlash (eluting with MeOH in DCM 0-3%) to give 73 as yellow oil.

To a solution of 73 (2.82 mmol) in acetate buffer (pH 5.2) and MeOH (1:2, 90 mL) is added Raney Ni (suspension in methanol, 54 mL) followed by addition of sodium hypophite monohydrate (3.18 g in milliQ water 12 mL) immediately. The reaction mixture is stirred at room temperature for 14 hours under argon. The mixture is filtered through a celite pad and washed with MeOH (200 ml). The filtrate is concentrated to dryness. The residue is treated with water (50 mL), extracted with EtOAc (3×50 mL). The combine organic layers are washed with water (30 mL), 10% NaHCO$_3$ (2×30 mL), brine (30 mL), and dried (anhydrous Na$_2$SO$_4$). The crude product is purified by CombiFlash (eluting with MeOH in DCM 0-5%) to give 74 as white solid.

Hydrochloride acid (0.188 mL, 2.26 mmol, 1.0 equiv) in methanol (1 mL) is added to a solution of 74 (2.26 mmol) in methanol (5 mL). The reaction mixture is stirred at room temperature for 14 hours. Then the mixture is concentrated to dryness. The residue is treated with water (30 mL), adjusted pH to 10 with 10% NaHCO$_3$, extracted with EtOAC (3×50 mL). The combined extracts are washed with water (30 mL), brine (30 mL) and dried (anhydrous Na$_2$SO$_4$). Evaporation of the solvent is affords 75 as white solid, which is going to next step without future purification.

To a solution of 6 (100 mg, 0.383 mmol, prepared as in Example 1) in anhydrous DMF (5 mL) is added 75 (0.402 mmol, 1.05 equiv), EDC.HCl (88.1 mg, 0.460 mmol, 1.2 equiv), HOBt (62.2 mg, 0.46 mmol, 1.2 equiv) at room temperature under argon. The mixture is cooled to 0° C., DIEA (0.27 mL, 1.53 mmol, 4.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×30 mL). The combined extracts are washed with water (30 mL), brine (30 mL), and dried (anhydrous Na$_2$SO$_4$). The crude product is purified by CombiFlash (eluting with MeOH in DCM 0-2.5%) to give 76 as a yellow solid.

To an ice-cold solution of 76 (0.235 mmol) dissolved in anhydrous MeOH (1 mL) and THF (1 mL) is added hydroxylamine hydrochloride (81 mg, 1.173 mmol, 5.0 equiv) followed by 25% sodium methoxide in methanol solution (0.401 mL, 1.762 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated NH$_4$Cl (2 mL), extracted with EtOAc (3×50 mL). The combined extracts are washed with water (30 mL), brine (30 mL), and dried over anhydrous Na$_2$SO$_4$. Evaporation of the solvent affords the crude product, which is purified by CombiFlash (eluting with 0-5% MeOH in DCM) to afford the title compound as a yellow solid.

70a: $^1$H (300 MHz, CDCl$_3$) δ 2.40 (s, 3H), 3.87 (dd, J=3.3, 13.2 Hz, 1H), 3.94 (dd, J=2.7, 13.8 Hz, 1H), 4.70 (s, 1H), 4.86 (s, 1H), 7.33 (d, J=7.8 Hz, 2H), 7.51 (d, J=8.4 Hz, 2H); $^{13}$C (75 MHz, CDCl$_3$) δ 21.69, 63.86, (84.72, 87.19), 124.21, 130.51, 139.24, 142.83, (197.25, 197.52); LC/MS m/s [M+H]$^+$ 215.0.

71a: $^1$H (300 MHz, CDCl$_3$) δ 2.37 (s, 3H), 2.84-2.90 (m, 1H), 3.03 (d, J=13.5 Hz, 1H), 3.68 (s, 3H), 4.60 (dd, J=10.8, 45.6 Hz, 1H), 4.91 (s, 1H), 5.11 (ddd, J=1.2, 10.8, 48.3 Hz, 1H), 7.02 (s, 1H), 7.29 (d, J=7.5 Hz, 2H), 7.46 (d, J=8.1 Hz, 2H); $^{13}$C (75 MHz, CDCl$_3$) δ 21.61, 52.96, 60.47, (71.41, 71.49), 82.24, 84.62, (85.33, 85.57), 124.11, 130.48, 140.38, 142.52, 155.80, 169.20; LC/MS m/s [M+H]$^+$ 314.1.

72a: $^1$H (300 MHz, CDCl$_3$) δ 2.37 (s, 3H), 3.12 (s, 2H), 3.73 (s, 3H), 4.50 (s, 1H), 4.66 (s, 1H), 5.01 (d, J=9.0 Hz, 1H), 5.40 (s, 1H), 7.28 (d, J=8.1 Hz, 2H), 7.40 (d, J=9.3 Hz, 1H), 7.51 (d, J=7.8 Hz, 2H), 8.20 (s, 1H); $^{13}$C (75 MHz, CDCl$_3$) δ 21.61, 53.25, 55.48, 62.04, (74.40, 74.64), (83.53, 85.87), 124.37, 130.41, 140.08, 142.27, 162.19, 169.92; LC/MS m/s [M+H]$^+$ 331.1.

73a: $^1$H (300 MHz, CDCl$_3$) δ 2.29 (s, 3H), 3.27-3.28 (m, 2H), 3.74 (s, 3H), 3.77 (d, J=4.5 Hz, 1H), 4.33 (s, 1H), 4.48 (s, 1H), 5.01 (d, J=9.3 Hz, 1H), 6.89 (d, J=8.4 Hz, 1H), 7.08 (d, J=7.8 Hz, 2H), 7.30 (d, J=7.2 Hz, 2H), 8.20 (s, 1H); $^{13}$C (75 MHz, CDCl$_3$) δ 21.24, 40.08, 53.16, 54.40, (75.01, 75.25), (82.64, 84.97), 130.18, 130.97, 132.14, 137.45, 161.73, 170.12; LC/MS m/s [M+H]$^+$ 316.1.

74a: $^1$H (300 MHz, CDCl$_3$) δ 1.24 (d, J=2.1 Hz, 3H), 3.73 (s, 3H), 4.17 (s, 1H), 4.32 (s, 1H), 4.41 (br, s, 1H), 4.74 (d, J=8.7 Hz, 1H), 7.23 (d, J=8.4 Hz, 1H), 8.17 (s, 1H); $^{13}$C (75 MHz, CDCl$_3$) δ 21.04, 52.87, 55.38, (72.79, 73.04), (85.37, 87.70), 162.35, 170.63; LC/MS m/s [M+H]$^+$ 194.2.

75a: $^1$H (300 MHz, CDCl$_3$) δ 1.06 (d, J=2.4 Hz, 3H), 3.57 (s, 1H), 3.72 (s, 3H), 4.26 (dd, J=9.3, 13.8 Hz, 1H), 4.52 (dd, J=4.44 (dd, J=9.3, 14.1 Hz, 1H); $^{13}$C (75 MHz, CDCl$_3$) δ 19.78, 19.84, 52.46, 57.49, (72.25, 72.48), (85.34, 87.66), 147.05; LC/MS m/s [M+H]$^+$ 166.0.

76a: $^1$H (300 MHz, CD$_3$OD) δ 1.37 (d, J=2.1 Hz, 3H), 3.76 (s, 3H), 4.267 (dd, J=9.3, 19.5 Hz, 1H), 4.42 (dd, J=9.3, 19.8 Hz, 1H), 4.81 (s, 1H), 6.61 (d, J=8.4 Hz, 2H), 7.24 (d, J=8.4 Hz, 2H), 7.56 (d, J=8.1 Hz, 2H), 7.82 (d, J=8.1 Hz, 2H); $^{13}$C (75 MHz, CD$_3$OD) δ 20.51, 51.69, 70.91, (71.94, 72.19), 76.86, 79.08, 84.73, (85.50, 87.83), 108.34, 114.27, 126.19, 127.20, 127.57, 132.18, 133.60, 133.89, 150.16, 168.18, 170.60; LC/MS m/s [M+H]$^+$ 437.1.

70b: (2.64 g, 88% yield). $^1$H (300 MHz, CDCl$_3$) δ 2.40 (s, 3H), 3.08 (q, J=39.9 Hz, 2H), 5.44 (t, J=111.0 Hz, 1H), 7.33 (d, J=8.4 Hz, 2H), 7.56 (d, J=7.8 Hz, 2H); $^{13}$C (75 MHz, CDCl$_3$) δ 21.67, 58.08, 62.48, (93.80, 94.13, 94.47), (110.57, 113.87, 117.18), 124.45, 130.59, 139.13, 142.91; LC/MS m/s [M+H]$^+$ 233.0.

71b: (1.38 g, yield 38%). (Less polar one is product). $^1$H (300 MHz, CDCl$_3$) δ 2.38 (s, 3H), 2.83 (dd, J=3, 13.8 Hz, 1H), 3.20 (d, J=14.1 Hz, 1H), 3.68 (s, 3H), 5.08 (d, J=2.4 Hz, 1H), 6.58 (q, J=110.7 H2, 1H), 7.05 (s, 1H), 7.30 (d, J=8.7 Hz, 2H), 7.49 (s, J=8.1 Hz, 2H); $^{13}$C (75 MHz, CDCl$_3$) δ 21.62, 53.12, 58.78, 70.40, (84.01, 84.31, 84.70), (109.33, 112.64, 115.92), 124.18, 130.54, 140.13, 142.71, 155.26, 168.72; LC/MS m/s [M+H]$^+$ 331.0

72b: (1.20 g, 94% yield). $^1$H (300 MHz, CDCl$_3$) δ 2.39 (s, 3H), 3.09 (dd, J=2.1, 14.4 Hz, 1H), 3.21 (d, J=14.1 Hz, 1H), 3.79 (s, 3H), 5.16 (d, J=9.6 Hz, 1H), 5.59 (s, 1H), 6.04 (d, J=110.7 Hz, 1H), 7.22 (d, J=9.6 Hz, 1H), 7.30 (d, J=7.8 Hz, 2H), 7.55 (d, J=8.4 Hz, 2H), 8.22 (s, 1H); $^{13}$C (75 MHz, CDCl$_3$) δ 21.64, 53.49, 54.07, 58.98, (74.91, 75.20, 75.50), (111.77, 115.07, 118.38), 124.39, 130.48, 139.69, 142.56, 161.95, 169.46; LC/MS m/s [M+H]$^+$ 350.1.

73b: (1.0 g, 88% yield). $^1$H (300 MHz, CDCl$_3$) δ 2.30 (s, 3H), 3.35 (s, 2H), 3.76 (s, 3H), 4.20 (s, 1H), 5.10 (d, J=9.6 Hz, 1H), 5.92 (t, J=110.4 Hz, 1H), 6.76 (d, J=9.6 Hz, 1H), 7.09 (d, J=8.1 Hz, 2H), 7.31 (d, J=8.4 Hz, 2H), 8.21 (s, 1H); $^{13}$C (75 MHz, CDCl$_3$) δ 21.24, 38.43, 53.27, 53.48, (75.06, 75.34, 75.63), (112.44, 115.75, 119.06), 130.23, 130.37, 131.15, 131.39, 132.00, 137.72, 161.62, 169.69; LC/MS m/s [M+H]$^+$ 334.0.

74b: (0.519 g, 87% yield). $^1$H (300 MHz, CD$_3$OD) δ 3.75 (s, 3H), 4.68 (s, 1H), 5.75 (t, J=112.2 Hz, 1H), 8.13 (s, 1H); $^{13}$C (75 MHz, CD$_3$OD) δ 16.18, 51.68, 55.05, (72.24, 72.53, 72.82), (112.58, 115.85, 119.13), 162.60, 169.54; LC/MS m/s [M+H]$^+$ 212.1.

75b: (0.412 g, 99% yield) $^1$H (300 MHz, CD$_3$OD) δ 1.31 (s, 3H), 3.87 (s, 3H), 4.18 (s, 1H), 5.99 (t, J=110.1 Hz, 1H);

$^{13}$C (75 MHz, CD$_3$OD) δ 20.02, 56.75, 60.09, 75.37, (116.33, 119.60, 122.87), 170.87; LC/MS m/s [M+H]$^+$ 184.0.

76b: (120 mg, 74% yield). $^1$H (300 MHz, CD$_3$OD) δ 1.38 (s, 3H), 3.77 (s, 3H), 4.85 (s, 1H), 5.87 (t, J=111.9 Hz, 1H), 6.61 (d, J=8.7 Hz, 2H), 7.25 (d, J=8.7 Hz, 2H), 7.57 (d, J=8.7 Hz, 2H), 7.82 (d, J=8.7 Hz, 2H); $^{13}$C (75 MHz, CD$_3$OD) δ 16.78, 51.78, 57.12, 70.83, 72.88, 76.83, 79.01, 84.69, 108.35, 114.25, 116.05, 126.27, 127.60, 13216, 133.48, 133.86, 150.17, 168.16, 169.91; LC/MS m/s [M+H]$^+$ 455.1.

CPD-058: (70.0 mg, 82% yield), $^1$H (300 MHz, CD$_3$OD) δ 1.36 (s, 3H), 4.73 (s, 1H), 5.80 (t, J=112.2 Hz, 1H), 6.61 (d, J=8.7 Hz, 2H), 7.24 (d, J=8.7 Hz, 2H), 7.57 (d, J=8.1 Hz, 2H), 7.82 (d, J=8.4 Hz, 2H); $^{13}$C (75 MHz, CD$_3$OD) δ 16.54, 54.87, 70.81, (72.60, 72.90, 73.19), 76.83, 78.97, 84.68, 108.36, (112.72, 115.96, 119.23), 114.26, 126.27, 127.53, 132.16, 133.47, 133.84, 150.16, 166.52, 167.51; LC/MS m/s [M+NH]$^+$ 428.2.

CPD-061: (30 mg, 40% yield), $^1$H NMR (300 MHz, CD$_3$OD) δ 1.32 (s, 3H), 3.62 (d, J=5.7 Hz, 2H), 4.61 (s, 1H), 6.62 (d, J=8.1 Hz, 2H), 7.24 (d, J=8.1 Hz, 2H), 7.58 (d, J=8.1 Hz, 2H), 7.85 (d, J=7.5 Hz, 2H); $^{13}$C NMR (75 MHz, CD$_3$OD); δ 21.53, 29.58, 55.07, (60.86, 61.35), (70.72, 72.30), 76.66, 78.96, 84.59, 108.29, 114.20, 126.10, 127.63, 132.06, 133.81, 150.24, 166.52, 168.69; LC/MS m/s [M+H]$^+$ 410.3.

Example 11

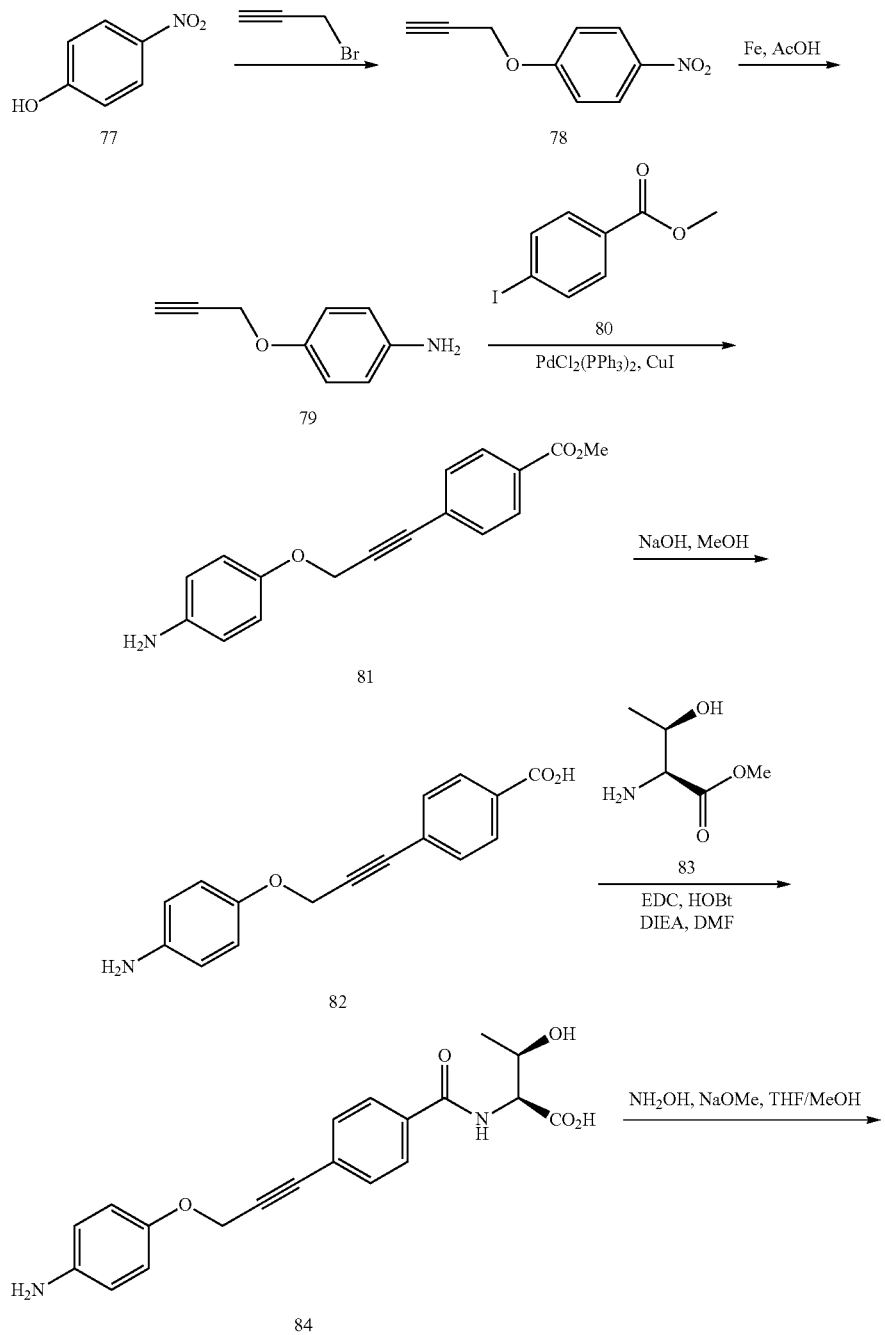

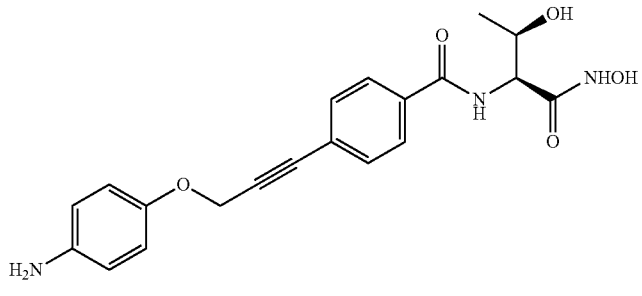

CPD-059

A mixture of 4-nitrophenol 77 (10.0 g, 71.8 mmol) and $K_2CO_3$ (14.90 g, 71.8 mmol, 1.0 equiv) in anhydrous acetone (60 mL) is stirred for 2 h, at room temperature. Propargyl bromide (9.56 mL, 86.16 mmol, 1.2 equiv) is then added. The reaction mixture is heated under reflux for 20 h under argon. Acetone is removed from the mixture, and the residue is poured in water (200 mL). The mixture is extracted with chloroform (3×100 mL). The combined organic layers are washed with water (100 mL), brine (100 mL), and dried (anhydrous $Na_2SO_4$). Evaporation of the solvent the crude product is purified by CombinFlash (eluting with DCM in Hexane 0-50%) to give 78 (10.90 g, 85% yield) as yellow solid.

To 78 (10.80 g, 61.1 mmol) in anhydrous THF (20 mL) and acetic acid (140 mL) along with activated powdered molecular sieves 4 Å (18.53 g) is stirred mildly for 2 h at room temperature under argon. The flask is then immersed in 0° C. bath and stirred well for 20 min. To the cooled reaction mixture is then added the Fe powder (30 g), then is allowed to warm to room temperature with stirring continued for 48 h. The mixture is then diluted with THF (300 mL) and filtered through a celite pad with washing THF (100 mL). The solution is rotary evaporated under full vacuum to dryness. The residue is treated with $H_2O$ (300 mL). And the mixture is added 4N NaOH to tune the pH to 10. Then the mixture is extracted with DCM (3×300 mL). The combined organic layers are washed with water (300 mL), brine (300 mL), and dried (anhydrous $Na_2SO_4$). The crude product is purified by CombinFlash (eluting with MeOH in DCM 0-5%) to obtain 79 (4.28 g, 47% yield) as red oil.

To an oven-dried round bottom flask equipped with water cooled west condenser and magnetic stir bar are added the Methyl 4-iodobenzoate (6.14 g, 23.46 mmol), bis(triphenylphosphine) palladium (II) dichloride (0.487 g, 0.69 mmol, 0.02 equiv) and copper (I) iodide (0.220 g, 1.16 mmol, 0.04 equiv.). The vessel is then sealed with a rubber septum under argon triethylamine (100 mL). Finally, 79 (4.15 g, 28.2 mmol, 1.2 equiv) in triethylamin (30 mL) is added. The reaction mixture is stirred at room temperature for 36 h. The resulting dark solution is filtered. The filtrate is concentrated to dryness with a rotavapor, and the residue is treated with water (100 mL), extracted with EtOAc (3×200 mL). The combined extracts are washed with water (50 mL) and brine (anhydrous $Na_2SO_4$). The crude products are purified by flash chromatography (eluting with 0-30% EtOAc in hexane) to afford 81 (6.0 g, 76%) as yellow solid.

A 1N solution of NaOH (22 mL, 21.3 mmol, 2.00 equiv) is added to stir solution of 81 (3.00 g, 10.6 mmol) in MeOH (100 mL) at room temperature. The reaction solution is heated to reflux for 1 h. Then the reaction turned clear. All of the starting material is gone by TLC. The reaction is cooled to room temperature and some MeOH (50 mL) is removed by evaporation under reduced pressure (50 mL). Water (20 mL) is added to the mixture. Conc. HCl is added dropwise to the stirred solution until acidic by pH paper (pH=2). The yellow precipitate that formed is collected by suction filtration. The solid is washed with water (2×30 mL) to give 82 (2.8 g, 99% yield).

To a solution of 82 (300 mg, 1.12 mmol) in anhydrous DMF (8 mL) is added L-threonine methyl ester 83 (0.229 g, 1.35 mmol, 1.2 equiv), EDC.HCl (0.259 mg, 1.35 mmol, 1.2 equiv), HOBt (0.182 mg, 1.35 mmol, 1.2 equiv) at room temperature under argon. The mixture is cooled to 0° C., DIEA (00.98 mL, 5.60 mmol, 5.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×50 mL). The combined extracts are washed with water (30 mL), brine (30 mL), and dried (anhydrous $Na_2SO_4$). The crude product is purified by CombiFlash (eluting with MeOH in DCM 0-5%) to give 84 (170 mg, 40% yield) as yellow solid.

To an ice-cold solution of 84 (120 mg, 0.29 mmol) dissolved in anhydrous MeOH (1 mL) and THF (1 mL) is added hydroxylamine hydrochloride (102 mg, 1.47 mmol, 5.0 equiv) followed by 25% sodium methoxide in methanol solution (0.51 mL, 2.18 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated $NH_4Cl$ (2 mL), extracted with EtOAc (3×50 mL). The combined extracts are washed with water (30 mL), brine (30 mL), and dried over anhydrous $Na_2SO_4$. Evaporation of the solvent affords the crude product, which is purified by CombiFlash (eluting with 0-5% MeOH in DCM) to afford CPD-059 (64 mg, 57% yield) as yellow solid. $^1$H NMR (300 MHz, DMSO-$d_6$) δ 1.07 (d, J=6.3 Hz, 3H), 3.99-4.03 (m, 1H), 4.23 (q, J=13.5 Hz, 1H), 4.67 (s, 2H), 4.86 (s, 2H), 6.52 (d, J=9.0 Hz, 2H), 6.76 (d, J=8.7 Hz, 2H), 7.52 (d, J=8.4 Hz, 2H), 7.89 (d, J=8.1 Hz, 2H), 8.11 (d, J=8.4 Hz, 1H), 8.84 (br, s, 1H), 10.66 (br, s, 1H); $^{13}$C NMR (75 MHz, DMSO-$d_6$): δ 21.02, 57.57, 58.80, 67.11, 86.05, 88.60, 115.46, 116.88, 125.26, 128.55, 131.93, 134.78, 143.95, 149.31, 166.36, 167.65; LC/MS m/s [M+H]$^+$ 384.2.

Example 12
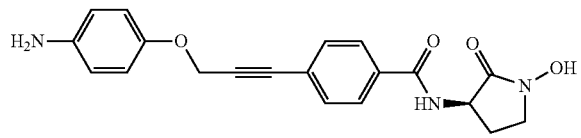 [SMILES: Nc1ccc(OCC#Cc2ccc(C(=O)N[C@@H]3CCN(O)C3=O)cc2)cc1]
(R)-4-(3-(4-aminophenoxy)prop-1-ynyl)-N-(1-hydroxy-2-oxopyrrolidin-3-yl)benzamide
CPD-060: Following the procedure of CPD-059, (30 mg, 45% yield), $^1$H NMR (300 MHz, DMSO-$_{d6}$) δ 1.88-2.01 (m, 1H), 2.27-2.36 (m, 1H), 3.42-3.47 (m, 2H), 4.52 (q, J=26.7 Hz, 1H), 4.86 (s, 2H), 6.51 (d, J=8.7 Hz, 2H), 6.75 (d, J=9.0 Hz, 2H), 7.52 (d, J=8.4 Hz, 2H), 7.84 (d, J=8.4 Hz, 2H), 8.88 (d, J=8.4 Hz, 1H), 9.77 (s, 1H); $^{13}$C NMR (75 MHz, DMSO-$_{d6}$); δ 24.18, 46.59, 48.96, 57.55, 86.00, 88.68, 115.47, 116.87, 125.34, 128.29, 132.06, 134.54, 143.90, 149.32, 165.91, 167.35; LC/MS m/s [M+H]$^+$ 366.3.
Example 13
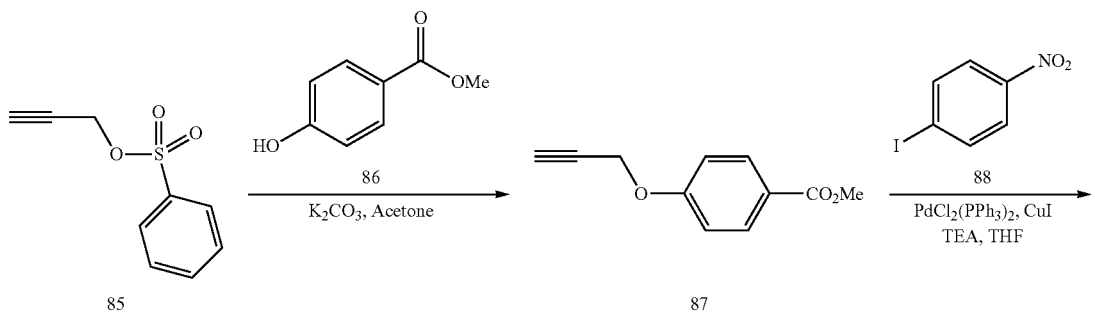
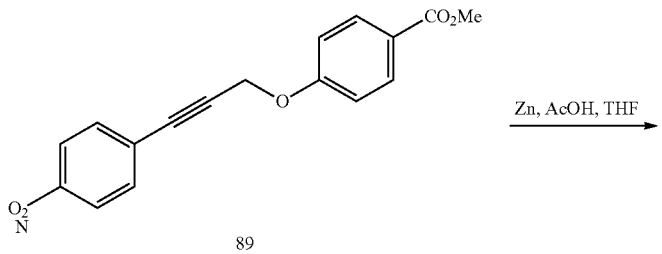
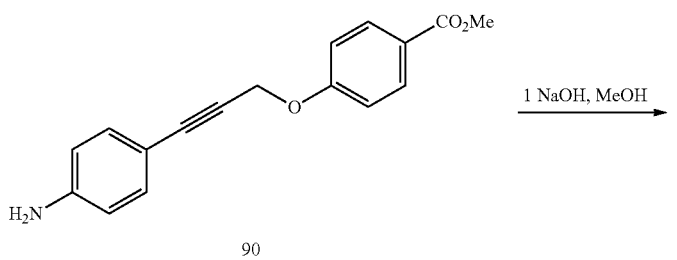
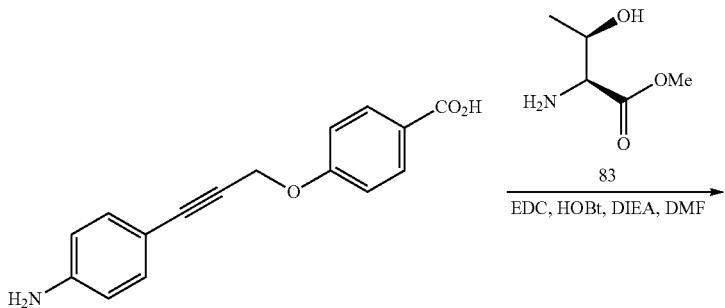

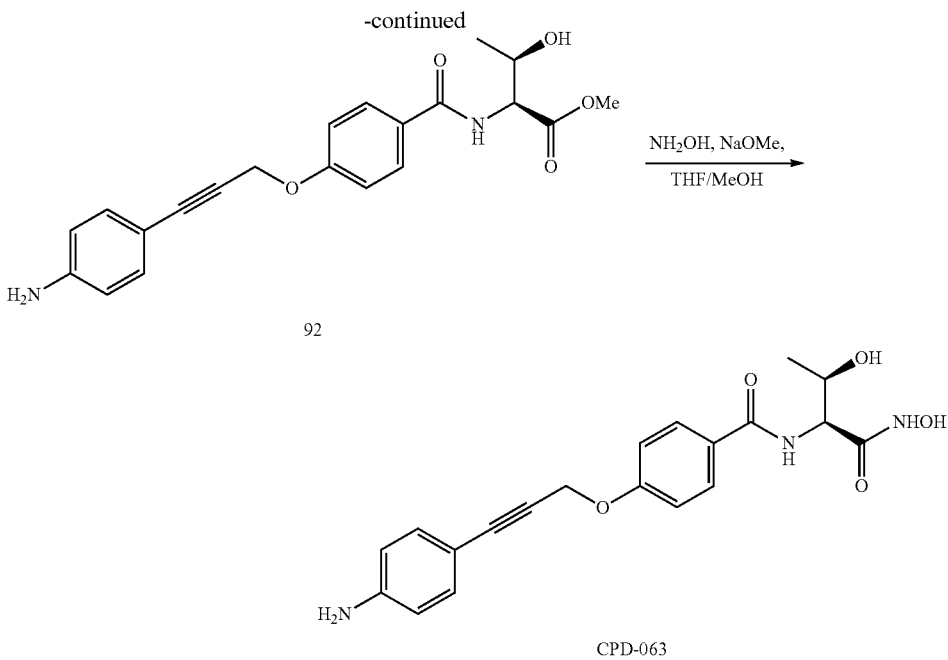

A mixture of Methyl 4-hydroxybenzoate 86 (5.0 g, 32.8 mmol) in anhydrous acetone (60 mL) is added $K_2CO_3$ (4.54 g, 32.8 mmol, 1.0 equiv) and propargyl benzesulfonate (7.8 mL, 49.2 mmol, 1.5 equiv). The reaction mixture is heated under reflux for 2.5 h under argon. TLC shows that the starting material is consumed. Acetone is then removed from the mixture, and the residue is poured in water (100 mL). The mixture is extracted with EtOAc (3×100 mL). The combined organic layers are washed with water (100 mL), brine (100 mL), and dried (anhydrous $Na_2SO_4$). Evaporation of the solvent the crude product is purified by CombinFlash (eluting with EtOAc in Hexane 0-16%) to give 87 (6.0 g, 96% yield) as white solid.

To an oven-dried round bottom flask equipped with water cooled west condenser and magnetic stir bar are added the 1-iodo-4-nitrobenol (0.79 g, 3.2 mmol, 1.2 equiv), bis(triphenylphosphine) palladium (II) dichloride (0.046 g, 0.065 mmol, 0.025 equiv) and copper (I) iodide (0.046 g, 0.015 mmol, 0.04 equiv.). The vessel is then sealed with a rubber septum under argon triethylamine (20 mL). Then 87 (0.50 g, 2.60 mmol) is added. The reaction mixture is stirred at room temperature for 18 h. The resulting suspension dark solution is filtered. The filtrate is concentrated to dryness with a rotavapor, and the residue is treated with water (50 mL), extracted with EtOAc (3×50 mL). The combined extracts are washed with water (30 mL) and brine (30 mL), and dried (anhydrous $Na_2SO_4$). The crude products are purified by flash chromatography (eluting with 0-20% EtOAc in hexane) to afford 89 (0.52 g, 64%) as yellow solid.

To a solution of 89 (480 mg, 1.54 mmol) in anhydrous THF (5 mL) is added AcOH (5 mL). The mixture is cooled to 0° C. under argon with stirring continued for 30 min. Then zinc dust (1.25 g, 19.2 mmol, 30 equiv) is added. The reaction mixture is stirred at 0° C. for 2 h, then is allowed to warm to room temperature for 18 h. The zinc dust is filtered through a celite pad and washed with THF (50 mL). The filtrate is concentrated to dryness. The residue is treated with 0.25 mM EDTA (20 mL), and is adjusted pH to 12 with 1 N NaOH. The mixture is extracted with EtOAc (3×50 mL). The combined organic layers are washed with water (50 mL), brine (50 mL), and dried (anhydrous $Na_2SO_4$). The crude product is purified by CombinFlsh (eluting with EtOAc in Hexane 0-40%) to obtain 90 (148 mg, 34% yield) as white solid.

A 1N solution of NaOH (10 mL, 10 mmol, 4.0 equiv) is added to stir solution of 90 (0.70 g, 2.5 mmol) in MeOH (30 mL) at room temperature. The reaction solution is heated to reflux for 1 h. Then the reaction turned clear. All of the starting material is gone by TLC. The reaction is cooled to room temperature and some MeOH (20 mL) is removed by evaporation under reduced pressure. Water (20 mL) is added to the mixture. Conc. HCl is added dropwise to the stirred solution until acidic by pH paper (pH=2). The yellow precipitate that formed is collected by suction filtration. The solid is washed with water (2×30 mL) to give 91 (0.6 g, 91% yield).

To a solution of 91 (200 mg, 0.75 mmol) in anhydrous DMF (8 mL) is added L-threonine methyl ester 83 (152 mg, 0.90 mmol, 1.2 equiv), EDC.HCl (173 mg, 0.90 mmol, 1.2 equiv), HOBt (122 mg, 0.90 mmol, 1.2 equiv) at room temperature under argon. The mixture is cooled to 0° C., DIEA (0.65 mL, 3.75 mmol, 5.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×50 mL). The combined extracts are washed with water (30 mL), brine (30 mL), and dried (anhydrous $Na_2SO_4$). The crude product is purified by CombiFlash (eluting with MeOH in DCM 0-5%) to give 92 (191 mg, 50% yield) as yellow solid.

To an ice-cold solution of 92 (100 mg, 0.26 mmol) dissolved in anhydrous MeOH (1 mL) and THF (1 mL) is added hydroxylamine hydrochloride (91 mg, 1.30 mmol, 5.0 equiv) followed by 25% sodium methoxide in methanol solution (0.46 mL, 1.95 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated NH₄Cl (2 mL), extracted with EtOAc (3×50 mL). The combined extracts are washed with water (30 mL), brine (30 mL), and dried over anhydrous Na₂SO₄. Evaporation of the solvent affords the crude product, which is purified by CombiFlash (eluting with 0-8% MeOH in DCM) to afford CPD-063 (55 mg, 55% yield) as yellow solid. $^1$H NMR (300 MHz, DMSO-$_{d6}$) δ 1.07 (d, J=6.3 Hz, 3H), 3.99-4.03 (m, 1H), 4.25 (q, J=13.8 Hz, 1H), 4.87 (br, s, 1H), 5.03 (s, 2H), 5.52 (s, 2H), 6.49 (d, J=8.7 Hz, 2H), 7.08 (d, J=9.9 Hz, 2H), 7.83 (s, 1H), 7.88 (d, J=9.0 Hz, 2H); $^{13}$C NMR (75 MHz, DMSO-$_{d6}$) δ 21.04, 57.21, 58.56, 67.20, 81.98, 89.21, 107.89, 114.21, 115.02, 127.54, 129.95, 133.49, 150.43, 160.50, 166.55, 167.92; LC/MS m/s [M+H]$^+$ 384.2.

Example 14

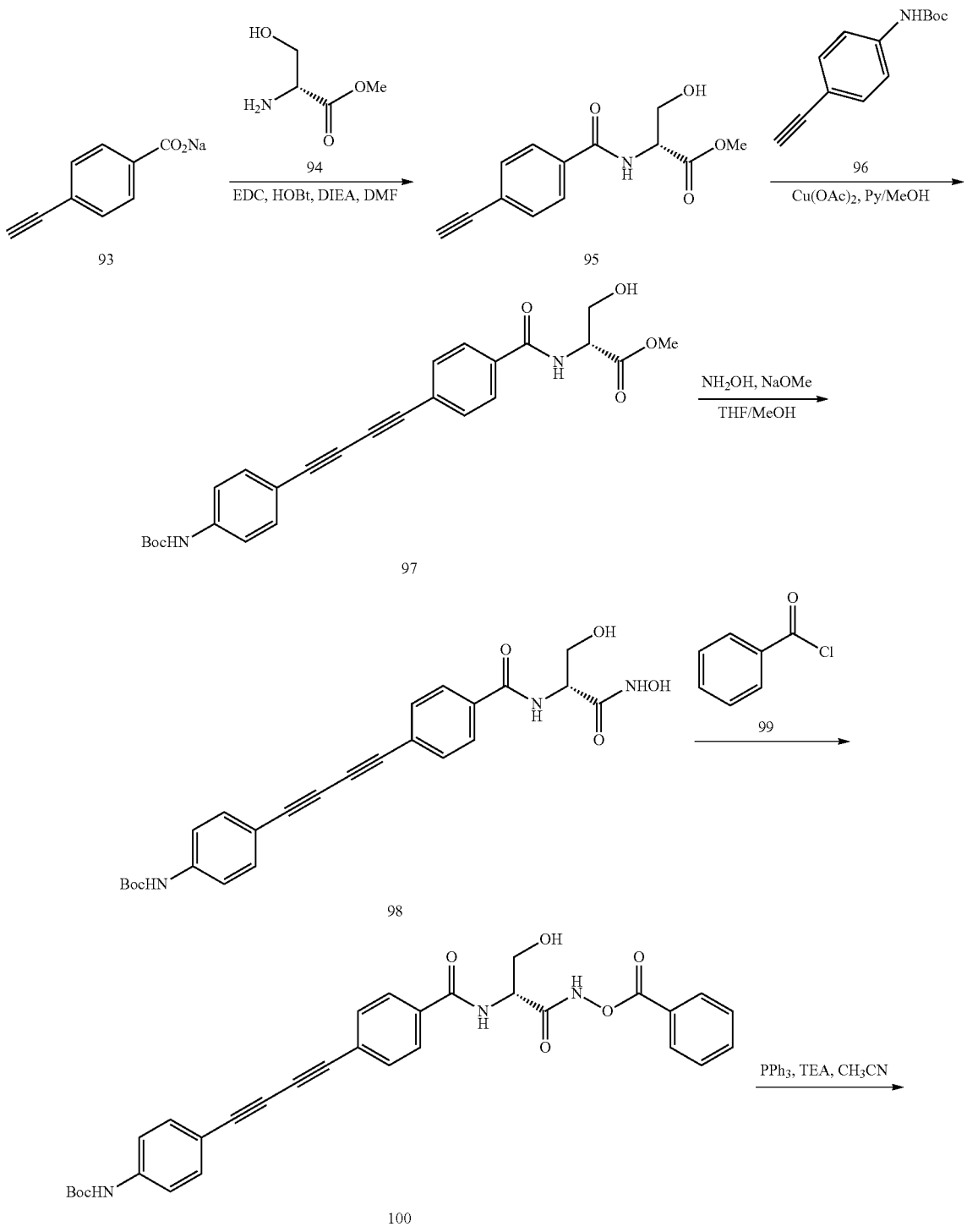

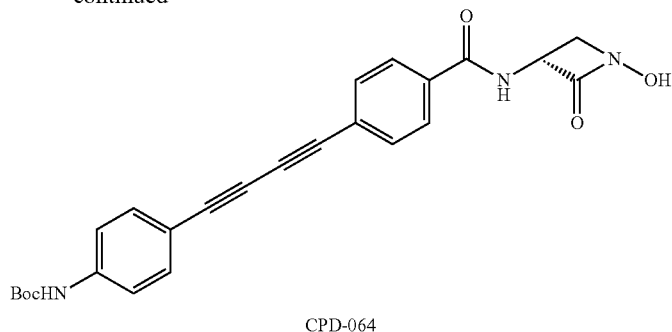

CPD-064

To a solution of sodium 4-ethynylbenzoate 93 (3.70 g, 22 mmol) in anhydrous DMF (100 mL) is added D-serine methyl ester 94 (4.80 g, 30.8 mmol, 1.4 equiv), EDC.HCl (5.90 mg, 30.8 mmol, 1.4 equiv), HOBt (4.16 g, 30.8 mmol, 1.4 equiv) at room temperature under argon. The mixture is cooled to 0° C., DIEA (9.58 mL, 110 mmol, 5.00 equiv) is added. The reaction mixture is stirred at 0° C. for 2 hours, then is allowed to warm to room temperature for 14 hours. The yellow solution is then concentrated to dryness. The residue is treated with water (100 mL), extracted with EtOAc (3×100 mL). The combined extracts are washed with water (100 mL), brine (100 mL), and dried (anhydrous $Na_2SO_4$). The crude product is purified by CombiFlash (eluting with MeOH in DCM 0-5%) to give 95 (4.20 g, 77% yield) as white solid.

Copper (II) acetate (3.67 g, 20.2 mmol, 2.0 equiv) is added at room temperature and under stream of argon to a stirred solution of 95 (2.50 g, 10.1 mmol) and 96 (5.50 g, 25.3 mmol, 2.5 equiv) dissolved in anhydrous pyridine (30 mL), and MeOH (30 mL), and the mixture are stirred at room temperature for 24 h. The resulting blue solution is condensed to dryness with a rotavapor, and the residue is treated with water (100 mL), extracted with EtOAc (3×100 mL). The combined organic layers are washed water (80 mL), brine (80 mL), and dried over anhydrous $Na_2SO_4$. The crude products are purified by flash chromatography (eluting with 0-70% EtOAc in hexane) to afford 97 (1.80 g, 38% yield) as yellow solid.

To an ice-cold solution of 97 (1.70 g, 3.68 mmol) dissolved in anhydrous MeOH (10 mL) and THF (10 mL) is added hydroxylamine hydrochloride (1.28 g, 18.40 mmol, 5.0 equiv) followed by 25% sodium methoxide in methanol solution (6.5 mL, 27.6 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (100 mL) and saturated $NH_4Cl$ (50 mL). The yellow suspension solution is filtered. The solid is washed with water (2×30 mL), EtOAc (3×30 mL). Then the pad is dried on high vacuum to obtain 98 (1.30 g, 76% yield).

To a solution of 98 (1.10 g, 2.38 mmol) in anhydrous MeOH (30 mL) and THF (30 mL) is added triethylamine (0.36 mL, 2.62 mmol, 1.10 equiv). The mixture solution is cooled to 0° C., then benzylchloride 99 (0.28 mL, 2.38 mmol, 1.00 equiv) is added dropwise. The reaction mixture is stirred at 0° C. for 20 min, then is concentrated to dryness. The residue is treated with water (80 mL), extracted with EtOAc (3×80 mL). The combined organic layers are washed with water (80 mL), brine (80 mL), and dried (anhydrous $Na_2SO_4$). The crude product is purified by CombinFlash (eluting with MeOH in DCM 0-3%) to obtain 100 (1.04 g, 77% yield) as yellow solid.

To a solution of 100 (100 mg, 0.176 mmol) in anhydrous MeCN (5 mL) and THF (5 mL) is added TPP (49 mg, 0.185 mmol, 1.05 equiv), $CCl_4$ (0.044 mL), and triethylamine (0.027 mL, 0.194 mmol, 1.1 equiv). The reaction mixture is stirred at room temperature for 48 h under argon. Then the yellow suspension solution is concentrated to dryness. The residue is diluted with water (30 mL), extracted with EtOAc (3×50 mL). The combined organic layers are washed with water (30 mL), brine (30 mL), and dried (anhydrous $Na_2SO_4$). The crude product is purified by CominFlash (eluting with MeOH in DCM 0-2.5%) to give CPD-064 (30 mg, 38% yield) as yellow solid. $^1H$ NMR (300 MHz, DMSO-$d_6$) δ 1.46 (s, 9H), 4.17-4.21 (m, 1H), 4.55 (t, J=17.4 Hz, 1H), 5.73-5.77 (m, 1H), 5.51 (br, s, 4H), 7.69 (d, J=8.1 Hz, 2H), 7.91 (d, J=8.4 Hz, 2H), 8.33 (s, 1H), 9.37 (d, J=8.1 Hz, 1H), 9.68 (s, 1H); $^{13}C$ NMR (75 MHz, DMSO-$d_6$) δ 28.72, 59.27, 69.98, 73.04, 76.58, 80.39, 81.26, 84.25, 113.61, 118.62, 124.60, 128.53, 133.00, 134.06, 134.75, 142.10, 153.15, 158.79, 165.88; LC/MS m/s $[M+H]^+$ 445.5.

Example 15

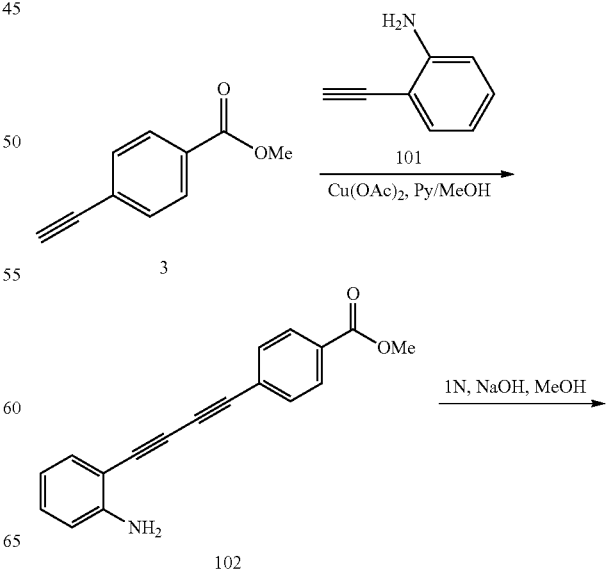

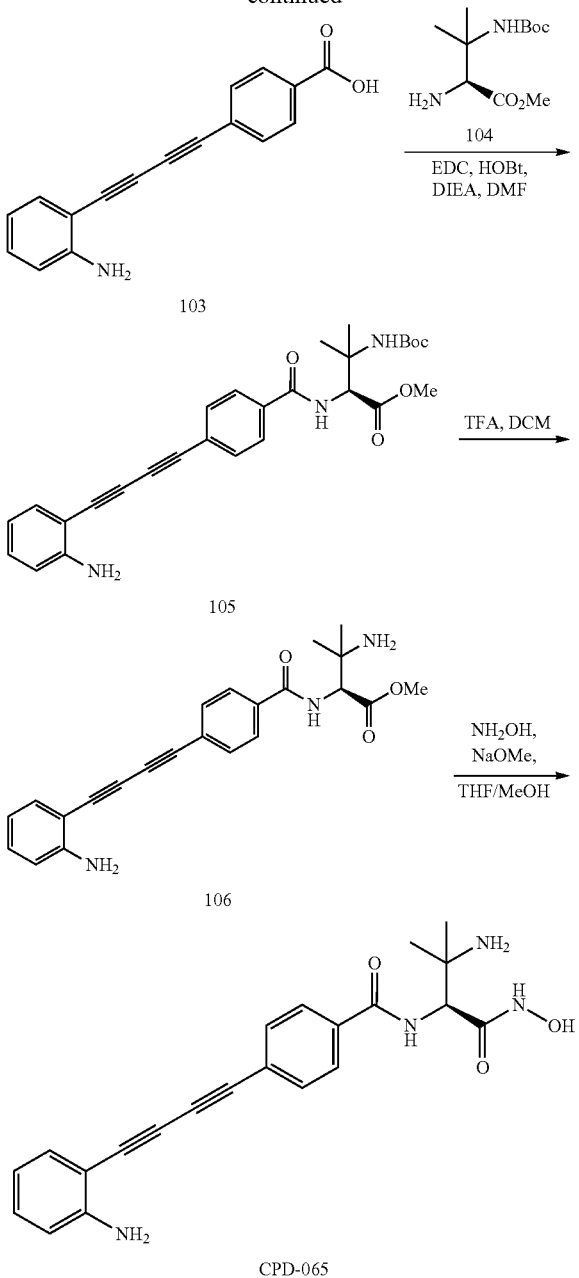

NMR (75 MHz, CDCl₃), δ 52.57, 77.03, 78.97, 80.50, 81.95, 110.99, 114.70, 118.21, 126.80, 128.59, 129.79, 131.21, 132.49, 133.40, 145.00, 166.57; LC/MS m/s [M+H]⁺ 276.3.

A 1N solution of NaOH (20 mL) is added to stir solution of 102 (1.0 g, 3.6 mmol) in MeOH (50 mL) at room temperature. The reaction solution is heated to reflux for 1 h. Then the reaction turned clear. All of the starting material is gone by TLC. The reaction is cooled to room temperature and some MeOH is removed by evaporation under reduced pressure (30 mL). Water (30 mL) is added to the mixture. Conc. HCl is added dropwise to the stirred solution until acidic by pH paper (pH=2). The yellow precipitate that formed is collected by suction filtration. The solid is washed with water (2×30 mL), methanol (2×30 mL) to give 103 (0.72 g, 75% yield). ¹H NMR (300 MHz, DMSO-$d_6$) δ 5.69 (br, s, 2H), 6.47-6.53 (m, 1H), 6.70 (d, J=7.8 Hz, 1H), 7.08-7.14 (m, 1H), 7.23-7.26 (m, 1H), 7.67 (d, J=6.9 Hz, 2H), 7.95 (d, J=8.7 Hz, 2H); ¹³C NMR (75 MHz, DMSO-$d_6$) δ 77.61, 78.40, 82.15, 82.43, 103.43, 114.99, 116.58, 125.98, 130.29, 131.90, 132.98, 133.71, 152.52, 167.23; LC/MS m/s [M+H]⁺ 262.3.

To a solution of 103 (180 mg, 0.69 mmol) in anhydrous DMF (5 mL) is added 104 (237 mg, 0.97 mmol, 1.4 equiv), EDC.HCl (185 mg, 0.97 mmol, 1.2 equiv), HOBt (131 mg, 0.97 mmol, 1.4 equiv) at room temperature under argon. The mixture is cooled to 0° C., DIEA (0.5 mL, 2.76 mmol, 5.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×50 mL). The combined extracts are washed with water (30 mL), brine (30 mL), and dried (anhydrous Na₂SO₄). The crude product is purified by CombiFlash (eluting with MeOH in DCM 0-1.5%) to give 105 (230 mg, 68% yield) as yellow solid. ¹H NMR (300 MHz, CDCl₃) δ 1.45 (s, 9H), 1.47 (s, 3H), 1.51 (s, 3H), 4.35 (s, 1H), 4.73 (t, J=8.1 Hz, 2H), 6.64-6.70 (m, 2H), 7.12-7.18 (m, 1H), 7.33 (d, J=8.1 Hz, 1H), 7.59 (d, J=8.1 Hz, 2H), 7.91 (d, J=8.4 Hz, 2H), 9.14 (br, s, 1H); ¹³C NMR (75 MHz, CDCl₃); δ 24.87, 28.22, 28.54, 52.44, 54.54, 62.47, 76.28, 79.04, 80.03, 80.70, 82.13, 106.12, 114.67, 118.15, 125.38, 127.65, 131.09, 132.67, 133.36, 134.20, 145.00, 156.65, 166.34, 170.77; LC/MS m/s [M+H]⁺ 490.3.

To an ice-cold solution of 105 (190 mg, 0.39 mmol) dissolved in anhydrous DCM (6 mL) is added TFA (1 mL). The reaction mixture is stirred at 0° C. for 2 h under argon, then is allowed to warm to room temperature for 12 h. The mixture is quenched with saturated Na₂CO₃. The mixture is concentrated to dryness. The residue is diluted with water (30 mL), extracted with EtOAc (3×50 mL). The combined extracts are washed with water (30 mL), brine (30 mL), and dried (anhydrous Na₂SO₄). The crude product was purified by CombinFlash (eluting with MeOH in DCM 0-5%) to obtain 106 (135 mg, 88% yield) as yellow solid.

To an ice-cold solution of 106 (100 mg, 0.256 mmol) dissolved in anhydrous THF (1 mL) and MeOH (1 mL) is added hydroxylamine hydrochloride (89 mg, 1.28 mmol, 5.0 equiv) followed by 25% sodium methoxide in methanol solution (0.46 mL, 1.95 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated NH₄Cl (2 mL), extracted with EtOAc (3×80 mL). The combined extracts are washed with water (30 mL), brine (30 mL), and dried over Copper (II) acetate (11.33 g, 62.6 mmol, 2.0 equiv) is added at room temperature and under stream of argon to a stirred solution of 3 (5.0 g, 31 mmol) and 3-ethynylbenzenamin 101 (10.99 g, 93.9 mmol, 3.0 equiv) dissolved in anhydrous pyridine (5 mL), and MeOH (5 mL), and the mixture are stirred at room temperature for 48 h. The resulting blue solution is condensed to dryness with a rotavapor, and the residue is treated with water (100 mL), extracted with EtOAc (3×150 mL). The combined organic layers are washed with water (100 mL), brine (100 mL), and dried over anhydrous Na₂SO₄. The crude product is purified by flash chromatography (eluting with 0-20% EtOAc in hexane) to afford 102 (2.10 g, 25% yield) as yellow solid. ¹H NMR (300 MHz, CDCl₃) δ 3.92 (s, 3H), 4.34 (s, 2H), 6.66-6.71 (m, 2H), 7.14-7.19 (m, 1H), 7.35 (d, J=8.1 Hz, 1H), 7.57 (d, J=6.9 Hz, 2H), 8.01 (d, J=8.4 Hz, 2H); ¹³C anhydrous Na₂SO₄. Evaporation of the solvent affords the crude product, which is purified by CombiFlash (eluting with 0-15% MeOH in DCM) to afford CPD-065 (71 mg, 71% yield) as yellow solid. ¹H NMR (300 MHz, CD₃OD) δ 1.17 (s, 3H), 1.25 (s, 3H), 4.46 (s, 1H), 6.57-6.62 (m, 1H), 6.74 (d, J=8.1 Hz, 1H), 7.10-7.15 (m, 1H), 7.24-7.27 (m, 1H), 7.60 (d, J=8.4 Hz, 2H), 7.86 (d, J=8.4 Hz, 2H); ¹³C NMR (75 MHz, CD₃OD); δ 25.87, 26.76, 52.58, 75.91, 77.77, 80.24, 80.98, 105.00, 114.53, 117.03, 125.63, 127.69, 130.88, 132.19, 132.82, 134.17, 151.16, 167.81, 167.98; LC/MS m/s [M+H]+ 391.5.

Example 16

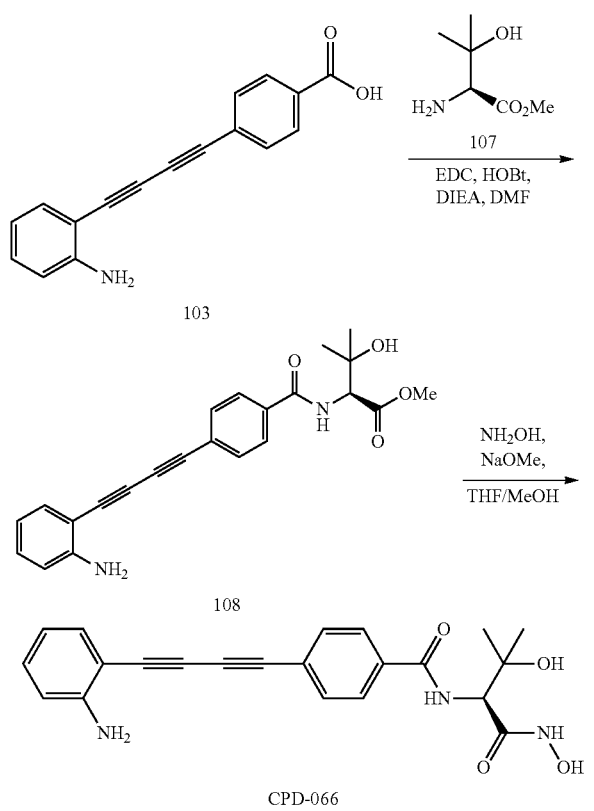

CPD-066

To a solution of 103 (180 mg, 0.69 mmol, prepared as in Example 15) in anhydrous DMF (5 mL) is added 107 (237 mg, 0.97 mmol, 1.4 equiv), EDC.HCl (185 mg, 0.97 mmol, 1.2 equiv), HOBt (131 mg, 0.97 mmol, 1.4 equiv) at room temperature under argon. The mixture is cooled to 0° C., DIEA (0.5 mL, 2.76 mmol, 5.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×50 mL). The combined extracts are washed with water (30 mL), brine (30 mL), and dried (anhydrous Na₂SO₄). The crude product is purified by CombiFlash (eluting with MeOH in DCM 0-3%) to give 108 (150 mg, 56% yield) as yellow solid. ¹H NMR (300 MHz, CD₃OD) δ; ¹³C NMR (75 MHz, CD₃OD); LC/MS m/s [M+H]⁺ 391.1

To an ice-cold solution of 108 (100 mg, 0.256 mmol) dissolved in anhydrous THF (1 mL) and MeOH (1 mL) is added hydroxylamine hydrochloride (89 mg, 1.28 mmol, 5.0 equiv) followed by 25% sodium methoxide in methanol solution (0.46 mL, 1.95 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated NH₄Cl (2 mL), extracted with EtOAc (3×80 mL). The combined extracts are washed with water (30 mL), brine (30 mL), and dried over anhydrous Na₂SO₄. Evaporation of the solvent affords the crude product, which is purified by CombiFlash (eluting with 0-15% MeOH in DCM) to afford CPD-066 (50 mg, 50% yield) as yellow solid. ¹H NMR (300 MHz, CD₃OD) δ 1.27 (s, 3H), 1.34 (s, 3H), 4.50 (s, 1H), 6.57-6.62 (m, 1H), 6.73-6.76 (m, 1H), 7.10-7.15 (m, 1H), 7.24-7.68 (m, 1H), 7.61 (d, J=8.7 Hz, 2H), 7.86 (d, J=8.4 Hz); ¹³C NMR (75 MHz, CD₃OD); δ 25.79, 26.10, 58.79, 71.57, 75.90, 77.75, 80.23, 80.96, 104.98, 114.52, 117.02, 125.64, 127.59, 130.88 132.22, 132.80, 134.19, 151.16, 167.77, 168.04; LC/MS m/s [M+H]⁺ 392.2.

Example 17

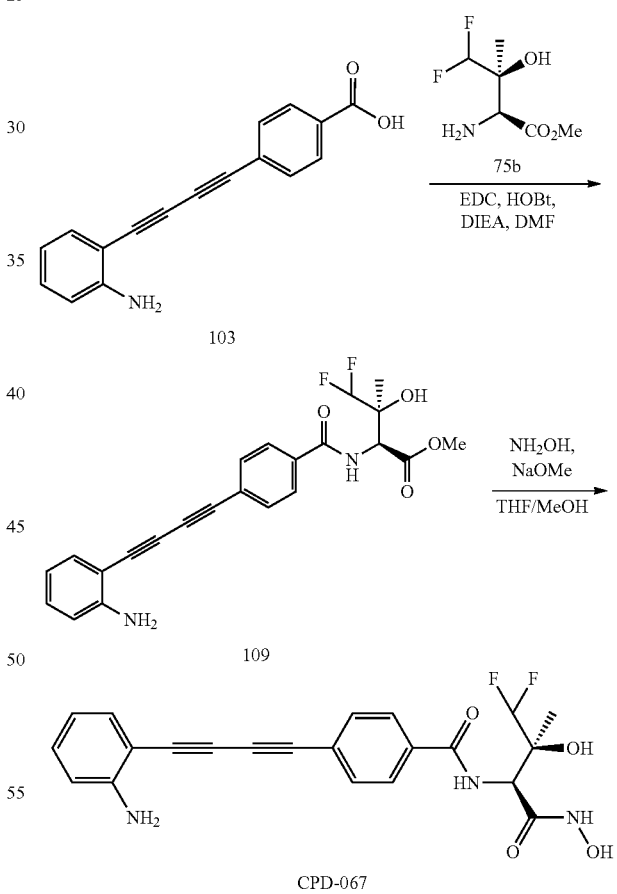

CPD-067

To a solution of 103 (180 mg, 0.69 mmol, prepared as in Example 15) in anhydrous DMF (5 mL) is added 75b (237 mg, 0.97 mmol, 1.4 equiv), EDC.HCl (185 mg, 0.97 mmol, 1.2 equiv), HOBt (131 mg, 0.97 mmol, 1.4 equiv) at room temperature under argon. The mixture is cooled to 0° C., DIEA (0.5 mL, 2.76 mmol, 5.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×50 mL). The combined extracts are washed with water (30 mL), brine (30 mL), and dried (anhydrous $Na_2SO_4$). The crude product is purified by CombiFlash (eluting with MeOH in DCM 0-1.5%) to give 109 (150 mg, 80% yield) as yellow solid. $^1$H NMR (300 MHz, $CD_3OD$) δ 1.38 (s, 3H), 3.78 (s, 3H), 4.85 (s, 1H), 5.88 (t, J=112.2 Hz, 1H), 6.57-6.63 (m, 1H), 6.74 (d, J=8.7 Hz, 1H), 7.01-7.16 (m, 1H), 7.24-7.27 (m, 1H), 7.62 (d, J=8.7 Hz, 2H), 7.84 (d, J=8.7 Hz, 2H); $^{13}$C NMR (75 MHz, $CD_3OD$) δ 16.77, 51.76, 57.15, (72.59, 72.88, 73.18), 75.97, 77.73, 80.27, 80.93, 104.97, 114.52, (112.76, 116.05, 119.33), 117.02, 125.81, 127.65, 130.89, 132.24, 132.81, 133.86, 151.17, 152.36, 168.10, 169.89; LC/MS m/s $[M+H]^+$ 427.1.

To an ice-cold solution of 109 (100 mg, 0.256 mmol) dissolved in anhydrous THF (1 mL) and MeOH (1 mL) is added hydroxylamine hydrochloride (89 mg, 1.28 mmol, 5.0 equiv) followed by 25% sodium methoxide in methanol solution (0.46 mL, 1.95 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated $NH_4Cl$ (2 mL), extracted with EtOAc (3×80 mL). The combined extracts are washed with water (30 mL), brine (30 mL), and dried over anhydrous $Na_2SO_4$. Evaporation of the solvent affords the crude product, which is purified by CombiFlash (eluting with 0-15% MeOH in DCM) to afford CPD-067 (71 mg, 71% yield) as yellow solid. $^1$H NMR (300 MHz, $CD_3OD$) δ 1.35 (s, 3H), 4.73 (s, 1H), 5.80 (t, J=112.2 Hz, 1H), 6.57-6.62 (m, 1H), 6.74 (d, J=9.0 Hz, 1H), 7.10-7.16 (m, 1H), 7.24-7.27 (m, 1H), 7.62 (d, J=8.7 Hz, 2H), 7.85 (d, J=8.4 Hz, 2H); $^{13}$C NMR (75 MHz, $CD_3OD$) δ 16.55, 54.89, (72.64, 72.90, 73.24), 75.98, 77.73, 80.28, 80.92, 104.97, 114.53, (112.73, 115.99, 119.25), 117.02, 125.81, 127.59, 130.89, 132.26, 132.81, 133.86, 151.17, 166.51, 167.45; LC/MS m/s $[M+H]^+$ 428.3.

Example 18

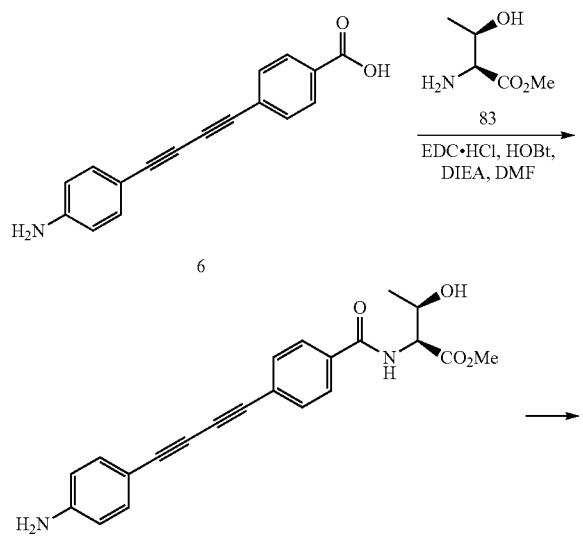

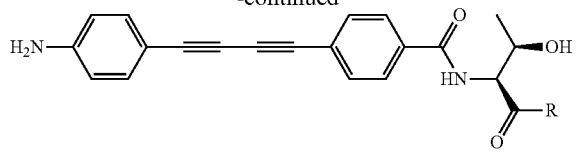

CPD-045: R = $NHNH_2$
CPD-046: R = OH
CPD-047: R = $NH_2$

To a solution of 6 (180 mg, 0.69 mmol, prepared as in Example 1) in anhydrous DMF (5 mL) is added L-threonine methyl ester hydrochloride 83 (164 mg, 0.97 mmol, 1.4 equiv), EDC.HCl (185 mg, 0.97 mmol, 1.2 equiv), HOBt (131 mg, 0.97 mmol, 1.4 equiv) at room temperature under argon. The mixture is cooled to 0° C., DIEA (0.5 mL, 2.76 mmol, 5.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×50 mL). The combined extracts are washed with water (30 mL), brine (30 mL), and dried (anhydrous $Na_2SO_4$). The crude product is purified by CombiFlash (eluting with MeOH in DCM 0-3%) to give 110 (228 mg, 88% yield) as yellow solid. $^1$H NMR (300 MHz, $CDCl_3$) δ 1.28 (d, J=6.3 Hz, 3H), 3.80 (s, 3H), 3.94 (br, s, 1H), 4.47-4.44 (m, 1H), 4.79-4.83 (m, 1H), 6.60 (d, J=8.7 Hz, 2H), 6.94 (d, J=8.4 Hz, 2H), 7.34 (d, J=8.7 Hz, 2H), 7.57 (d, J=8.4 Hz, 2H), 7.80 (d, J=8.4 Hz, 2H); $^{13}$C NMR (75 MHz, $CDCl_3$) δ 20.36, 52.97, 57.79, 68.45, 72.02, 79.90, 84.54, 110.51, 114.84, 126.33, 127.45, 132.73, 133.63, 134.43, 148.01, 167.21, 171.73; LC/MS, m/s $[M+H]^+$ 377.3.

CPD-045: To a stirred mixture of 110 (100 mg, 0.266 mg) in anhydrous methanol (2 mL) is added $N_2H_4 \cdot H_2O$ (0.27 mL, 2.660 mmol, 10.0 equiv) under argon. The reaction mixture is stirred at room temperature for 16 h. The precipitate is filtered and washed with EtOAc (2×20 mL), and then dried by full vacuum overnight to give CPD-045 (77.5 mg, 77% yield) a white solid. $^1$H (300 Hz, DMSO-$d_6$) δ 1.061 (d, 2H, J=6.3 Hz), 4.021 (q, 1H, J=18.0 Hz), 4.214 (d, 2H, J=3.3 Hz), 4.318 (d, 2H, J=13.5 Hz), 4.865 (d, 1H, J=6.3 Hz), 5.832 (s, 2H), 6.532 (d, 2H, J=8.7 HZ), 7.244 (d, 2H, J=8.4 Hz), 7.637 (d, 2H, J=8.7 Hz), 7.906 (d, 2H, J=8.4 Hz), 8.091 (d, 2H, J=8.7 Hz), 9.161 (s, 1H); $^{13}$C (300 Hz, DMSO-$d_6$) δ 21.01, 59.41, 67.24, 71.77, 77.27, 80.83, 86.34, 105.82, 114.25, 124.72, 128.58, 132.57, 134.68, 135.01, 151.52, 166.27, 170.11; LC/MS m/s $[M+H]^+$ 377.1.

CPD-046: To a stirred mixture of 110 (100 mg, 0.266 mmol) in methanol (2 mL) is added NaOH (11.0 mg, 0.266 mmol, 1.0 equiv) in milliQ water (0.50 mL) under argon. The reaction mixture is stirred at room temperature for 16 h, and then concentrated to dryness. The residue is treated with water (20 mL) and tuned the pH to 6 with 0.1 N HCl. The yellow solution is then concentrated to dryness. The crude product is treated with methanol (20 mL) and filtered to give CPD-046 (95 mg, 99% yield) as yellow solid. $^1$H (300 MHz, $CD_3OD$) δ 1.21 (d, J=6.6 Hz, 3H), 4.28-4.33 (m, 1H), 4.48 (d, J=3.3 Hz, 1H), 6.62 (d, J=9.0 Hz, 2H), 7.24 (d, J=8.7 Hz, 2H), 7.57 (d, J=8.4 Hz, 2H), 7.89 (d, J=8.7 Hz, 2H); $^{13}$C (75 MHz, $CD_3OD$) δ 19.32, 60.23, 68.33, 70.77, 76.46, 79.05, 84.44, 108.35, 114.21, 125.73, 127.37, 132.07, 133.79, 134.51, 150.19, 167.42, 176.00; LC/MS m/s $[M+H]^+$ 363.5.

CPD-047: To a stirred mixture of 110 (100 mg, 0.266 mmol) in anhydrous methanol (1 mL) is added 7 N $NH_3$ in methanol (10 mL) at pressure flask. The reaction mixture is stirred at 5° C. for 90 h. LC/MS monitoring showed it is completed. Then the yellow suspension is concentrated to dryness. The crude product is washed with EtOAc (3×5 mL) to give CPD-047 (98.0 mg, 98% yield) as yellow solid. $^1$H (300 MHz, CD$_3$OD) δ 1.24 (d, J=6.6 Hz, 2H), 4.32 (q, J=10.2 Hz, 1H), 4.55 (d, J=3.6 Hz, 1H), 6.64 (d, J=8.4 Hz, 2H), 7.24 (d, J=8.4 Hz, 2H), 7.58 (d, J=8.4 Hz, 2H), 7.88 (d, J=8.4 Hz, 2H); $^{13}$C (75 MHz, CD$_3$OD) δ 19.23, 59.27, 67.42, 70.79, 76.70, 79.02, 84.61, 108.33, 114.24, 126.08, 127.56, 132.12, 133.83, 150.20, 168.11, 174.09; LC/MS m/s [M+H]$^+$ 362.1.

Example 19

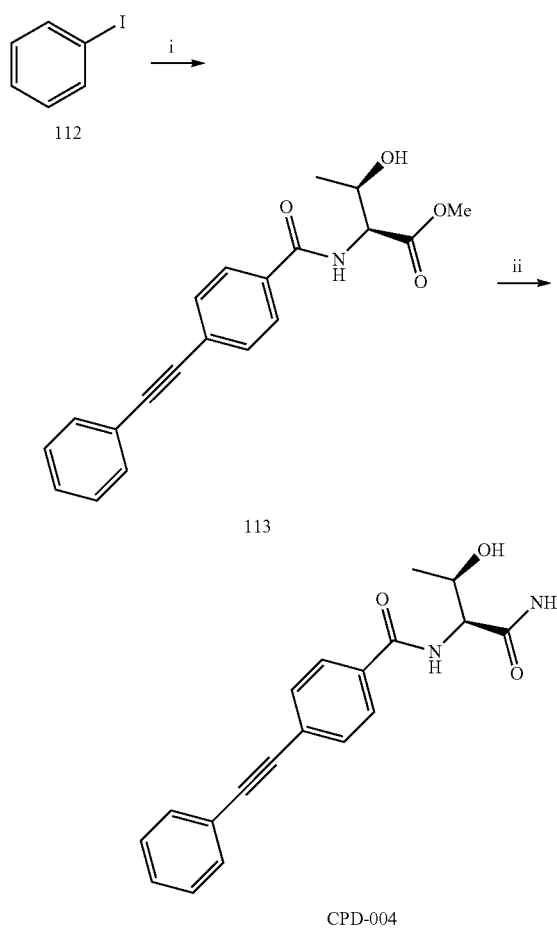

(i) 111, PdCl$_2$(PPh$_3$)$_2$, CuI, TEA, THF room temperature, 24 h; (ii) NH$_2$OH.HCl, NaOMe, MeOH/THF, 0° C., 2 h, then, room temperature, 16 h.

111: To a stirred mixture of sodium 4-ethynylbenzoate (2.52 g, 15 mmol) and L-threonine methyl ester hydrochloride (3.05 g, 18 mmol, 1.2 equiv) in anhydrous DMF (100 mL) is added N-ethyl-N'-(3-dimethylaminopropyl)carbodiimide hydrochloride (EDC.HCl) (3.45 g 18 mmol, 1.2 equiv) and 1-hydroxybenzotriazole hydrate (HOBt) (2.45 g 18 mmol, 1.2 equiv) at room temperature. The mixture is chilled with an ice-bath, and diisopropylethylamine (DIEA) (10.45 mL, 60 mmol, 4.0 equiv) is added. The whole reaction mixture is stirred under argon at 0° C. for 1 h, and then allowed to warm to ambient temperature, and with the stirring continued for additional 20 h. The resulting yellow solution is condensed to dryness with a rotavapor, and the residue is treated with water (100 mL), extracted with EtOAc (3×100 mL). The combined extracts are washed with 1N HCl (2×70 mL) and brine (100 mL), and dried (anhydrous Na$_2$SO$_4$). Evaporation of the solvents affords the crude product (3.5 g), which is crystallized from EtOAc/hexane to give 111 (1.9 g, 48% yield) as light yellow crystal. $^1$H NMR (300 MHz, CDCl$_3$): δ 1.28 (d, J=6.3 Hz, 3H), 3.21 (s, 2H), 3.79 (s, 3H), 4.41-4.49 (m, 1H), 4.80 (dd, J=2.4, 8.7 Hz, 1H), 6.94 (d, J=9.0 Hz, 1H), 7.55 (d, J=8.4 Hz, 2H), 7.79 (d, J=8.7 Hz, 2H); $^{13}$C NMR (75 MHz, CDCl$_3$): δ 20.34, 52.95, 57.81, 68.42, 79.94, 82.89, 126.06, 127.39, 132.55, 133.86, 167.28, 171.74; MS (ESI, positive): m/z 284 [M+Na]$^+$.

113: To an ice-cold solution of methyl ester 111 (1.1 mmol) dissolved in anhydrous MeOH (5 mL) and THF (5 mL) is added hydroxylamine hydrochloride (3.3 mmol, 3 equiv) followed by 25% sodium methoxide in methanol solution (5 mmol, 4.5 equiv). The reaction mixture is stirred under argon and at 0° C. for 2 h, then allowed to warm to ambient temperature with the stirring is continued overnight (16 h). The resulting yellow suspension is condensed to dryness with a rotavapor, and the residue is treated with 1N HCl aqueous solution (10 mL). The mixture is extracted with EtOAc (100 mL), washed with brine (30 mL), and dried (anhydrous Na$_2$SO$_4$). Evaporation of the solvent affords the crude product, which is purified by flash chromatography (eluting with 4-10% MeOH in DCM) to afford hydroxamic acid as yellow solid.

Example 20

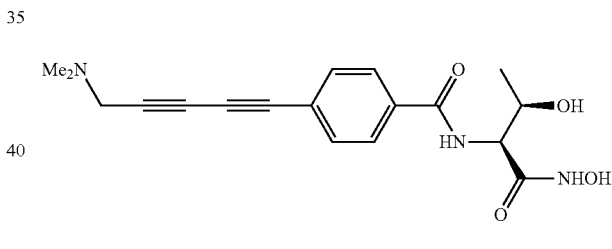

CPD-007, 4-(5-(dimethylamino)penta-1,3-diynyl)-N-((2S,3R)-3-hydroxy-1-(hydroxyamino)-1-oxobutan-2-yl)benzamide CPD-007: 32% yield; $^1$H NMR (300 MHz, CD$_3$OD): δ 1.22 (d, J=5.7 Hz, 3H), 2.36 (s, 6H), 3.50 (s, 2H), 4.20 (m, 1H), 4.40 (d, 1H), 7.58 (d, J=7.8 Hz, 2H), 7.86 (d, J=7.8 Hz, 2H); MS (ESI, negative): 342 (M−1).

Example 21

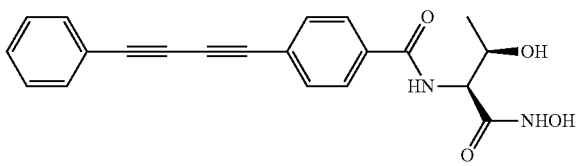

CPD-009, N-((2S,3R)-3-hydroxy-1-(hydroxyamino)-1-oxobutan-2-yl)-4-(phenylbuta-1,3-diynyl)benzamide CPD-009: 57% yield; $^1$H NMR (300 MHz, CD$_3$OD): δ 1.20 (d, J=4.8 Hz, 3H), 4.19 (m, 1H), 4.40 (d, J=3.9 Hz, 1H), 7.35-7.51 (m, 5H), 7.59 (d, J=6 Hz, 2H), 7.86 (d, J=6 Hz, 2H); MS (ESI, negative): 361 (M−1).

Example 22

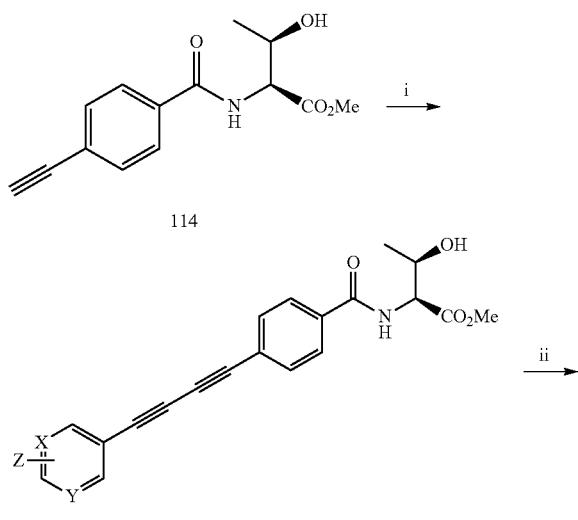

115a: x = y = CH, z = 4-NH$_2$
115b: x = y = CH, z = 3-NH$_2$
115c: x = y = CH, z = 2-NH$_2$
115d: x = CH, y = N, z = 4-NH$_2$
115e: x = y = N, z = 4-NH$_2$
115f: x = CH, y = N, z = H

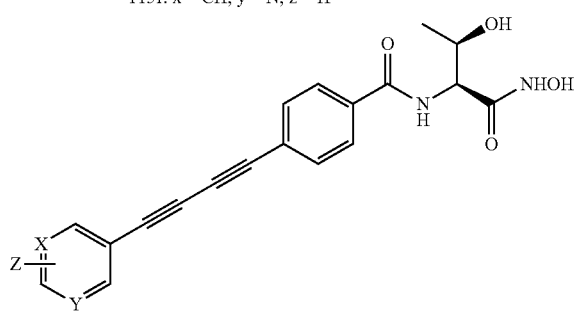

CPD-011: x = y = CH, z = 4-NH$_2$
CPD-012: x = y = CH, z = 3-NH$_2$
CPD-013: x = y = CH, z = 2-NH$_2$
CPD-035: x = CH, y = N, z = 4-NH$_2$
CPD-036: x = y = N, z = 4-NH$_2$
CPD-038: x = CH, y = N, z = H (i) substituted acetylene, Cu(OAc)$_2$, pyridine, MeOH, room temperature. (ii) hydroxylamine hydrochloride, 25% NaOMe/MeOH, THF, 0° C., 2 h, then room temperature, 16 h.

General procedure for Glaser coupling with 114: Copper (II) acetate (0.36 g, 2 mmol, 2.0 equiv) is added at room temperature to a stirred solution of 114 (0.26 g, 1 mmol) and substituted acetylene (5 mmol, 5 equiv) dissolved in anhydrous pyridine (4 mL) and MeOH (4 mL), and the reaction mixture is stirred at room temperature for 18 h (80 h for 3-ethynybenzenamine and 2-ethynybenzenamine). The resulting blue solution is condensed to dryness with a rotavapor, and the residue is treated with water (50 mL) and extracted with EtOAc (3×50 mL). The combined organic layers are washed with water (50 mL) and brine (50 mL), and dried (Na$_2$SO$_4$). The crude product is purified by CombiFlash (eluting with 50-75% EtOAc in hexane) to afford diacetylene methyl ester 115a-f as yellow solid.

115a: 67% yield; $^1$H NMR (300 MHz, CDCl$_3$): δ 1.28 (d, J=6.3 Hz, 3H), 3.79 (s, 3H), 3.94 (br, s, 1H), 4.47-4.44 (m, 1H), 4.80 (dd, J=2.4, 8.7 Hz, 1H), 6.59 (d, J=8.7 Hz, 2H), 6.93 (d, J=8.4 Hz, 2H), 7.33 (d, J=8.7 Hz, 2H), 7.57 (d, J=8.4 Hz, 2H), 7.79 (d, J=8.4 Hz, 2H); $^{13}$C NMR (75 MHz, CDCl$_3$): δ 20.35, 52.96, 57.79, 68.44, 72.01, 79.89, 84.53, 110.51, 114.84, 126.32, 127.44, 132.72, 133.62, 134.43, 148.01, 167.21, 171.72; MS (ESI, positive): m/z 399 [M+Na]$^+$.

115b: 62% yield; $^1$H NMR (300 MHz, CDCl$_3$): δ 1.26 (d, J=6.3 Hz, 3H), 3.76 (s, 3H), 4.42-4.44 (m, 1H), 4.78 (dd, J=2.4, 9.0 Hz, 1H), 6.68 (d, J=8.1 Hz, 1H), 6.80 (s, 1H), 6.92 (d, J=7.5 Hz, 1H), 7.09 (t, J=15.6 Hz, 1H), 7.54 (d, J=8.7 Hz), 7.77 (d, J=8.4 Hz, 2H); $^{13}$C NMR (75 MHz, CDCl$_3$): δ 20.35, 52.94, 58.00, 68.35, 73.19, 80.33, 83.54, 116.79, 118.66, 122.28, 123.24, 125.88, 127.51, 129.64, 132.84, 133.89, 146.60, 167.34, 171.73; MS (ESI, positive): m/z 399 [M+Na]$^+$.

115c: 26% yield; $^1$H NMR (300 MHz, CDCl$_3$): δ 1.27 (d, J=6.3 Hz, 3H), 3.77 (s, 3H), 4.35 (br, 1H), 4.41-4.46 (m, 1H), 4.79 (dd, J=2.4, 8.7 Hz, 1H), 6.64-6.69 (m, 2H), 7.06 (d, J=8.7 Hz, 1H), 7.12-7.18 (m, 1H), 7.77 (dd, J=1.5, 8.1 Hz, 2H), 7.55 (d, J=8.7 Hz, 2H), 7.79 (d, J=8.4 Hz, 2H); $^{13}$C NMR (75 MHz, CDCl$_3$): δ 20.35, 52.95, 57.98, 68.37, 76.70, 98.95, 80.33, 81.81, 105.95, 114.70, 118.20, 125.87, 127.54, 131.16, 132.72, 133.38, 133.90, 149.98, 167.29, 171.73; MS (ESI, positive): m/z 399 [M+Na]$^+$.

115d: 23% yield; $^1$H NMR (300 MHz, DMSO-d$_6$): δ 1.12 (d, J=6.3 Hz, 3H), 3.63 (s, 3H), 4.14-4.17 (m, 1H), 4.47 (q, J=12.3 Hz, 1H), 4.95 (d, J=7.5 Hz, 1H), 6.42 (d, J=6.0 Hz, 1H), 6.68 (s, 2H), 7.54 (d, J=10.8 Hz, 1H), 7.66 (d, J=8.4 Hz, 2H), 7.90 (d, J=8.7 Hz, 2H), 8.17 (s, 1H), 8.40 (d, J=8.4 Hz, 1H); $^{13}$C NMR (75 MHz, DMSO-d$_6$): δ 20.93, 52.63, 59.77, 67.07, 74.21, 76.88, 81.47, 83.40, 104.28, 108.40, 124.67, 128.59, 132.81, 134.79, 140.91, 153.94, 160.49, 166.71, 171.69; MS (ESI, positive): m/z 378 [M+H]$^+$.

115e: 27% yield; $^1$H NMR (300 MHz, DMSO-d$_6$): δ 1.12 (d, J=6.3 Hz, 3H), 3.63 (s, 3H), 4.13-4.19 (m, 1H), 4.45-4.49 (m, 1H), 4.95 (d, J=7.5 Hz, 1H), 7.39 (s, 1H), 7.681 (d, J=8.4 Hz, 2H), 7.91 (d, J=8.4 Hz, 2H), 8.48 (s, 2H); $^{13}$C NMR (75 MHz, DMSO-d$_6$): δ 20.92, 52.63, 59.78, 67.06, 76.37, 76.86, 80.09, 82.35, 104.37, 124.36, 128.62, 132.91, 135.00, 162.47, 162.65, 166.69, 177.68; MS (ESI, positive): m/z 397 [M+H]$^+$.

115f: 30% yield; $^1$H NMR (300 MHz, CD$_3$OD): δ 1.24 (d, J=6.6 Hz, 3H), 3.77 (s, 3H), 4.36-4.42 (m, 1H), 4.69 (d, J=3.3 Hz, 1H), 7.46 (q, J=13.8 Hz, 1H), 7.66 (d, J=8.7 Hz, 2H), 7.91 (d, J=8.4 Hz, 2H), 7.99 (d, J=8.1 Hz, 1H), 8.56 (d, J=6.3 Hz, 1H), 8.71 (s, 1H); $^{13}$C NMR (75 MHz, CD$_3$OD): δ 19.30, 51.74, 58.85, 67.30, 76.38, 78.36, 81.44, 119.42, 123.91, 124.73, 127.70, 132.56, 134.77, 140.30, 149.07, 152.28, 168.22, 171.30; MS (ESI, positive): m/z 363 [M+H]$^+$.

General procedure for converting 115a-f into the corresponding hydroxamic acids: To an ice-cold solution of 115 (120 mg, 0.32 mmol) dissolved in anhydrous MeOH (1.5 mL) and THF (1.5 mL) is added hydroxylamine hydrochloride (110 mg, 1.60 mmol, 5 equiv) followed by 25% sodium methoxide in methanol solution (0.53 mL, 2.20 mmol, 7 equiv). The reaction mixture is stirred under argon and at 0° C. for 2 h, then allowed to warm to ambient temperature with the stirring continued overnight (16 h). The resulting yellow suspension is condensed to dryness with a rotavapor, and the residue is treated water (50 mL). The mixture is extracted with EtOAc (3×50 mL). The combined organic layers are washed with brine (30 mL) and dried. Evaporation of the solvent affords the crude product, which is purified by CombiFlash (eluting with MeOH in DCM 7-10%) to afford hydroxamic acid as yellow solid.

CPD-011, (2S,3R)-2-{4'-[(4''-aminophenyl)buta-1',3'-diynyl]benzamido}-1,3-dihydroxybutanamide: 61% yield; $^1$H (300 MHz, CD$_3$OD): δ 1.23 (d, J=6.6 Hz, 3H), 4.21-4.17 (m, 1H), 4.43 (d, J=5.1 Hz, 1H), 6.62 (d, J=6.9 Hz, 1H), 7.24 (d, J=8.7 Hz, 1H), 7.58 (d, J=8.7 Hz, 2H), 7.63 (d, J=8.4 Hz), 7.87 (d, J=8.4 Hz, 2H), 7.72 (d, J=8.7 Hz, 2H); $^{13}$C NMR (75 MHz, CD$_3$OD): δ 19.14, 57.90, 67.23, 70.73, 76.63, 78.97, 84.57, 108.32, 114.22, 126.06, 127.56, 132.07, 133.81, 150.22, 168.08, 168.41; HRMS: calculated for C$_{21}$H$_{19}$N$_3$O$_4$ 377.1376. found 377.1376 (M$^+$).

CPD-012, (2S,3R)-2-{4'-[(3''-aminophenyl)buta-1',3'-diynyl]benzamido}-1,3-dihydroxybutanamide: 66% yield; $^1$H NMR (300 MHz, CD$_3$OD): δ 1.23 (d, J=6.3 Hz, 3H), 4.18-4.21 (m, 1H), 4.43 (d, J=5.1 Hz, 1H), 6.73-6.77 (m, 1H), 6.80-6.84 (m, 2H), 7.05-7.10 (m, 1H), 7.60 (d, J=8.4 Hz, 2H), 7.88 (d, J=8.4 Hz, 2H); $^{13}$C NMR (75 MHz, CD$_3$OD): δ 19.16, 57.91, 67.24, 71.82, 75.76, 79.52, 83.29, 116.72, 118.17, 121.69, 121.76, 125.47, 127.61, 129.18, 132.30, 134.22, 148.19, 168.02, 168.41; HRMS: calculated for C$_{21}$H$_{19}$N$_3$O$_4$ 377.1376. found 377.1369 (M$^+$).

CPD-013, (2S,3R)-2-{4'-[(2''-aminophenyl)buta-1',3'-diynyl]benzamido}-1,3-dihydroxybutanamide: 74% yield; $^1$H NMR (300 MHz, CD$_3$OD): δ 1.23 (d, J=6.3 Hz, 3H), 4.18-4.22 (m, 1H), 4.44 (d, J=5.1 Hz, 1H), 6.57-6.62 (m, 1H), 6.74 (dd, J=0.6, 8.1 Hz, 1H), 7.09-7.15 (m, 1H), 7.26 (dd, J=1.2, 7.5 Hz, 1H), 7.60 (d, J=8.4 Hz, 2H), 7.88 (d, J=6.9 Hz, 2H); $^{13}$C NMR (75 MHz, CD$_3$OD): δ 19.16, 57.92, 67.26, 75.86, 77.75, 80.21, 80.99, 105.01, 114.53, 117.03, 125.61, 127.38, 127.63, 130.87, 132.03, 132.19, 132.80, 134.14, 151.15, 168.03, 168.39; HRMS: calculated for C$_{21}$H$_{19}$N$_3$O$_4$ 377.1376. found 377.1374 (M$^+$).

CPD-035, (2S,3R)-2-{4'-[[(2''-amino)pyridin-5''-yl]buta-1',3'-diynyl]benzamido}-1,3-dihydroxybutanamide: 35% yield; $^1$H NMR (300 MHz, DMSO-d$_6$): δ 1.06 (d, J=6.3 Hz, 3H), 4.10 (q, J=12.0 Hz, 1H), 4.23 (q, J=14.1 Hz, 1H), 4.90 (d, J=5.7 Hz, 1H), 6.42 (d, J=8.7 Hz, 1H), 6.68 (s, 2H), 7.52 (d, J=8.7 Hz, 1H), 7.65 (d, J=8.1 Hz, 2H), 7.91 (d, J=8.4 Hz, 2H), 8.18 (t, J=9.6 Hz, 2H), 7.91 (d, J=8.4 Hz, 2H), 8.85 (s, 1H), 10.68 (s, 1H); $^{13}$C NMR (75 MHz, DMSO-d$_6$): δ 21.00, 58.86, 67.07, 74.22, 76.76, 81.54, 83.31, 104.30, 108.42, 124.41, 128.64, 132.68, 135.22, 140.91, 153.91, 160.48, 166.25, 167.61; HRMS: calculated for C$_{20}$H$_{18}$N$_4$O$_4$ 378.1328. found 378.1318 (M$^+$).

CPD-036, (2S,3R)-2-{4'-[[(2''-amino)pyrimidin-5''-yl]buta-1',3'-diynyl]benzamido}-1,3-dihydroxybutanamide: 30% yield; $^1$H NMR (300 MHz, DMSO-d$_6$): δ 1.10 (d, J=6.0 Hz, 3H), 4.01-4.04 (m, 1H), 4.24-4.28 (m, 1H), 4.90 (d, J=6.0 Hz, 1H), 7.41 (s, 2H), 7.70 (d, J=8.0 Hz, 2H), 7.92-7.96 (m, 2H), 8.19 (d, J=9.0 Hz, 1H), 8.56 (s, 2H), 8.87 (s, 1H); $^{13}$C NMR (75 MHz, DMSO-d$_6$): δ 20.79, 59.65, 66.939, 76.05, 76.67, 79.80, 82.21, 104.18, 110.00, 123.89, 128.45, 132.57, 135.23, 162.21, 162.44, 128.46, 132.57, 135.23, 162.21, 162.439, 166.02, 167.37; HRMS: calculated for C$_{19}$H$_{17}$N$_5$O$_4$ 379.1281. found 379.1292 (M$^+$).

CPD-038, (2S,3R)-2-{4'-[(pyridin-3''-yl)buta-1',3'-diynyl]benzamido}-1,3-dihydroxybutanamide: 52% yield; $^1$H NMR (300 MHz, DMSO-d$_6$): δ 1.08 (d, J=6.0 Hz, 3H), 4.01-4.05 (m, 1H), 4.22-4.27 (m, 1H), 4.89 (d, J=6.0 Hz, 1H), 7.48 (q, J=12.6 Hz, 1H), 7.73 (d, J=8.1 Hz, 2H), 7.95 (d, J=7.8 Hz, 2H), 8.05 (d, J=7.5 Hz, 1H), 8.22 (d, J=8.4 Hz, 1H), 8.65 (s, 1H), (8.81 (s, 1H), 8.87 (s, 1H), 10.69 (s, 1H); $^{13}$C NMR (75 MHz, DMSO-d$_6$): δ 21.02, 58.86, 67.09, 75.47, 76.80, 80.32, 82.77, 118.38, 123.52, 124.40, 128.72, 133.09, 135.88, 140.48, 149.74, 150.70, 153.41, 166.21, 167.58; HRMS: calculated for C$_{20}$H$_{17}$N$_3$O$_4$H$^+$ 364.1297. found 364.1301 (MH$^+$).

Example 23

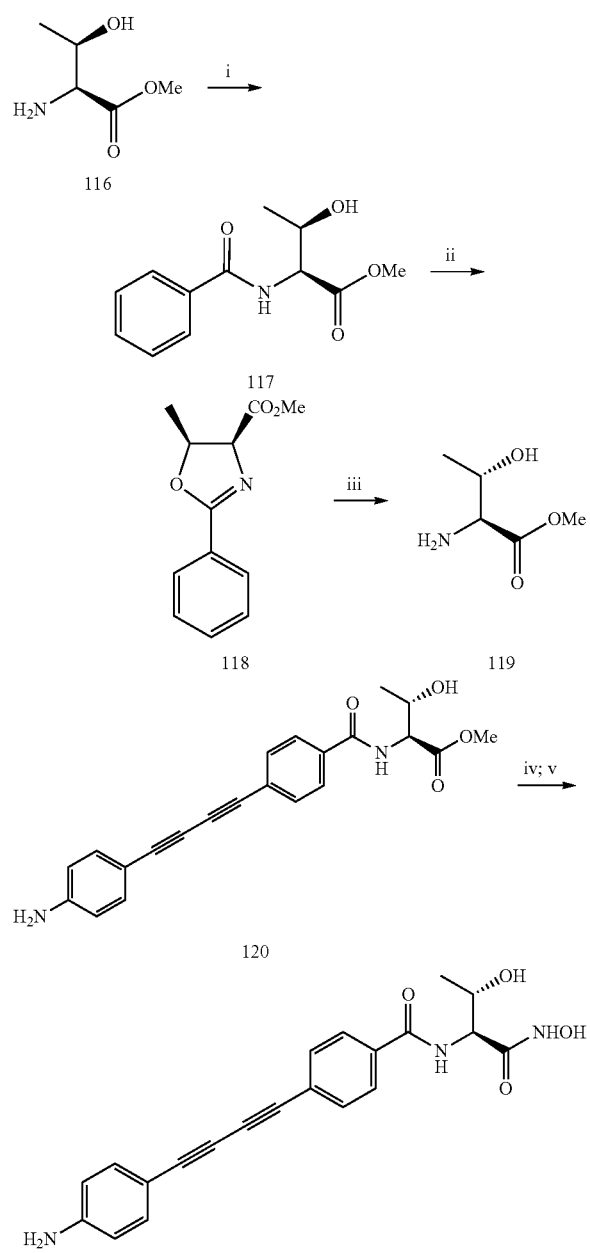

(i) benzoyl chloride, Et$_3$N, MeOH, 0° C., 2 h, 92%. (ii) SOCl$_2$, 0° C., 5 days, 94%. (iii) (1) 5N HCl, reflux, 5 h; (2) SOCl$_2$, MeOH, reflux, 1 h, 98%. (iv) 6, EDC.HCl, HOBt, DIEA, DMF, 0° C., 1 h, then room temperature, 18 h, 92%.

(v) hydroxylamine hydrochloride, 25% NaOMe/MeOH, THF, 0° C., 2 h, then room temperature, 14 h, 70%.

117: L-Threonine methyl ester hydrochloride 116 (5.0 g, 29.5 mmol) is dissolved in anhydrous MeOH (25 mL), and Et$_3$N (12.4 mL, 81 mmol) is added at room temperature. After being stirred at room temperature for 15 min, the reaction mixture is cooled to 0° C., and benzoyl chloride (3.76 mL, 32.4 mmol, 1.1 equiv) is added dropwise (over 10 min). The reaction mixture is stirred for 2 h at 0° C. The MeOH and the excess Et$_3$N are evaporated by a rotaevaporator (water bath 40° C.). Water (300 mL) is added to the residue, and the mixture is extracted with EtOAc (3×80 mL). The combined organic layers are washed with water (50 mL), brine (50 mL) and dried. The solvent is evaporated, and the resulting residue is mixed with anhydrous diethyl ether (50 mL), and refluxed for 1 h with stirring. After cooling, a white precipitate resulted, and the white solid is collected by filtration to give methyl (2S,3R)-3-hydroxy-2-(phenylformamido)butanoate 117 (6.45 g, 92% yield) as white solid. $^1$H NMR (300 MHz, CDCl$_3$): δ 1.24 (d, J=6.3 Hz, 3H), 3.26 (d, J=5.1 Hz, 1H), 3.73 (s, 3H), 4.37-4.46 (m, 1H), 4.78 (dd, J=1.8, 9.0 Hz, 1H), 7.13 (d, J=8.7 Hz, 1H), 7.35-7.50 (m, 3H), 7.79-7.82 (m, 2H); $^{13}$C NMR (75 MHz, CDCl$_3$): δ 20.25, 52.82, 58.06, 68.30, 127.47, 128.81, 132.14, 133.86, 168.36, 171.81; MS (ESI, positive): m/z 238 [M+H]$^+$.

118: 117 (6.5 g, 26.5 mmol) is added in portions to an ice-cold stirred solution of thionyl chloride (20 mL), keeping the inner temperature below 3° C. during the addition. After the completion of the addition, the reaction flask is kept in a 5° C. refrigerator for 5 days. Excess thionyl chloride is then removed under 100 torr at 33° C. (bath temperature). The residue is dissolved in anhydrous chloroform (40 mL), and immediately, the chloroform solution is poured slowly into saturated Na$_2$CO$_3$ solution with efficient stirring. If necessary, solid Na$_2$CO$_3$ is added to prevent the solution from becoming acidic. The chloroform layer is separated. The aqueous layer is extracted with chloroform (3×50 mL). The combined organic layers are washed with water (50 mL), brine (50 mL), and dried. The solvent is removed under reduced pressure to give methyl (4S,5S)-5-methyl-2-phenyl-4,5-dihydro-1,3-oxazole-4-carboxylate 118 (5.48 g, 94% yield) as white solid. $^1$H NMR (300 MHz, CDCl$_3$): δ 1.37 (d, J=6.0 Hz, 3H), 3.76 (s, 3H), 4.96-5.08 (m, 2H), 7.37-7.51 (m, 3H), 7.96-7.98 (m, 1H); $^{13}$C NMR (75 MHz, CDCl$_3$): δ 16.46, 52.30, 71.99, 127.47, 128.53, 128.76, 132.02, 166.37, 170.64; MS (ESI, positive): m/z 220 [MαH]$^+$.

119: A mixture of 118 (5.4 g, 24.6 mmol) and 6N HCl (60 mL) is refluxed for 5 h, and after cooling to ambient temperature, the reaction mixture is extracted with diethyl ether (3×70 mL) to remove benzoic acid. The aqueous layer is evaporated to dryness under reduced pressure, and the residue is further dried under high vacuum overnight to afford crude allo-L-threonine. MeOH (25 mL) is cooled to 0° C., and thionyl chloride (1.80 mL, 25.2 mmol) is added dropwise. To the resulting HCl methanol solution is added the crude allo-L-threonine, and the reaction mixture is heated under reflux for 1 h. The solvent is removed in vacuo, and another batch of HCl methanol solution (prepared in the same manner) is added, and then the reaction mixture is heated under reflux for another 1 h. The solvent is removed in vacuo to obtain allo-L-threonine methyl ester hydrochloride 119 (4.15 g, 98% overall yield for the two steps) as tiny red solid. $^1$H NMR (300 MHz, CD$_3$OD): δ 1.27 (d, J=6.6 Hz, 3H), 4.03 (d, J=3.3 Hz, 1H), 4.27-4.33 (m, 1H); $^{13}$C NMR (75 MHz, CD$_3$OD): δ 17.13, 58.17, 65.11, 162.67; MS (ESI, positive): m/z 134 [M+H]$^+$.

120: To a stirred mixture of acid 6 (120 mg, 0.46 mmol, prepared as in Example 1) and allo-L-threonine methyl ester hydrochloride 119 (94 mg, 0.55 mmol, 1.2 equiv) in anhydrous DMF (5 mL) is added EDC.HCl (106 mg 0.55 mmol, 1.2 equiv), HOBt (75 mg, 0.55 mmol, 1.2 equiv) at room temperature. The mixture is chilled to 0° C. with an ice-bath, and diisopropylethylamine (0.32 mL, 1.84 mmol, 4 equiv) is added. The reaction mixture is stirred under argon and at 0° C. for 1 h, then allowed to warm to ambient temperature with the stirring is continued for additional 18 h. The resulting yellow solution is condensed to dryness with a rotavapor, and the residue is treated with water (20 mL), extracted with EtOAc (3×50 mL). The combined extracts are washed with brine (40 mL), and dried. Evaporation of the solvent affords the crude product, which is purified by CombiFlash (eluting with 1-3% MeOH in DCM) to afford methyl (2S,3S)-2-{4'-[(4"-aminophenyl)buta-1',3'-diynyl]benzamido}-3-hydroxybutanoate 120 (159 mg, 92% yield) as yellow solid. $^1$H NMR (300 MHz, DMSO-d$_6$): δ 1.16 (d, J=6.3 Hz, 3H), 3.62 (s, 3H), 3.98-4.08 (m, 1H), 4.37 (t, J=14.4 Hz, 1H), 5.06 (d, J=6.0 Hz, 1H), 5.83 (br s, 2H), 6.53 (d, J=8.7 Hz, 2H), 7.24 (d, J=8.4 Hz, 2H), 7.63 (d, J=8.4 Hz, 2H), 7.87 (d, J=8.7 Hz, 2H), 8.64 (d, J=7.8 Hz, 1H); $^{13}$C NMR (75 MHz, DMSO-d$_6$): δ 21.06, 52.34, 60.14, 67.08, 71.78, 77.41, 80.78, 86.43, 105.83, 114.27, 124.96, 128.63, 132.64, 134.55, 134.70, 151.56, 166.39, 171.94; MS (ESI, positive): m/z 377 [M+H]$^+$.

CPD-053: To an ice-cold solution of 120 (100 mg, 0.26 mmol) dissolved in anhydrous MeOH (1 mL) and THF (1 mL) is added hydroxylamine hydrochloride (92 mg, 1.33 mmol, 5 equiv) followed by 25% sodium methoxide in methanol solution (0.47 mL, 2.0 mmol, 7.5 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated with water (20 mL), extracted with EtOAc (3×50 mL). The combined extracts are washed with brine (20 mL), and dried. Evaporation of the solvent affords the crude product, which is purified by CombiFlash (eluting with 1-8% MeOH in DCM) to afford (2S,3S)-2-{4'-[(4"-aminophenyl)buta-1',3'-diynyl]benzamido}-1,3-dihydroxybutanamide (CPD-053) (70 mg, 70% yield) as yellow solid. $^1$H NMR (300 MHz, DMSO-d$_6$): δ 1.09 (d, J=6.3 Hz, 3H), 3.97 (br s, 1H), 4.23 (t, J=16.5 Hz, 1H), 4.94 (br s, 1H), 5.82 (s, 2H), 6.54 (d, J=8.4 Hz, 2H), 7.24 (d, J=8.7 Hz, 2H), 7.60 (d, J=8.1 Hz, 2H), 7.87 (d, J=8.7 Hz, 2H), 8.42 (d, J=8.7 Hz, 1H), 8.81 (br s, 1H), 10.58 (br s, 1H); $^{13}$C NMR (75 MHz, DMSO-d$_6$) δ 21.09, 57.95, 66.84, 71.79, 77.26, 80.83, 86.34, 105.83, 114.27, 124.70, 128.62, 132.55, 134.69, 135.02, 151.54, 165.93, 167.69; HRMS: calculated for C$_{21}$H$_{19}$N$_3$O$_4$H$^+$ 378.1454. found 378.1454 [M+H]$^+$.

Example 24

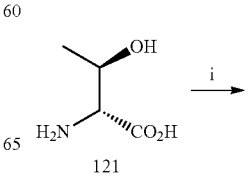

121

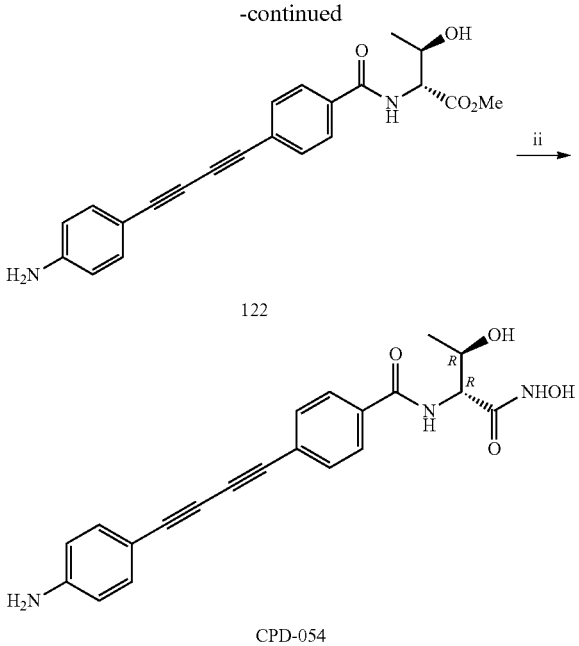

(i) (1) SOCl₂, MeOH, reflux, 1 h, 99%; (2) 6, EDC.HCl, HOBt, DIEA, DMF, 0° C., 1 h, then room temperature, 18 h, 92%. (ii) hydroxylamine hydrochloride, 25% NaOMe/MeOH, THF, 0° C., 2 h, then room temperature, 14 h, 93%.

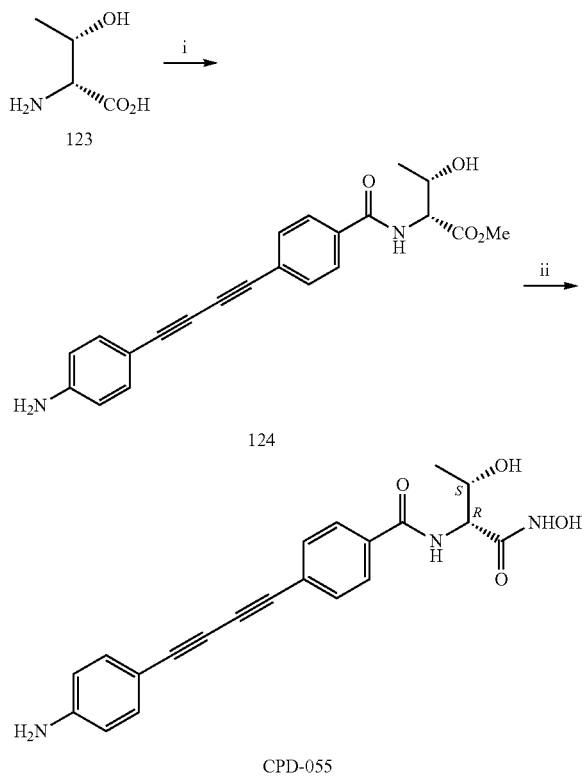

(i) (1) SOCl₂, MeOH, reflux, 1 h, 99%; (2) 6, EDC.HCl, HOBt, DIEA, DMF, 0° C., 1 h, then room temperature, 18 h, 69%. (ii) hydroxylamine hydrochloride, 25% NaOMe/MeOH, THF, 0° C., 2 h, then room temperature, 14 h, 69%.

Anhydrous MeOH (10 mL) is cooled to 0° C., and thionyl chloride (1.22 mL, 16.8 mmol) is added dropwise. To the resultant solution of HCl in methanol is added D-threonine 121 (2.0 g, 16.8 mmol), and the reaction mixture is heated under reflux for 1 h. After the solvent is removed in vacuo, another batch of HCl in methanol solution (10 mL), prepared in the same manner, is added, and the reaction mixture is heated under reflux for another 1 h. The solvent is removed in vacuo to obtain D-threonine methyl ester hydrochloride (2.8 g, 99% yield) as white solid, which is used for next step without further purification. $^1$H NMR (300 MHz, CD$_3$OD): δ 1.33 (d, J=6.9 HZ, 3H), 3.85 (s, 3H), 3.95 (d, J=4.2 Hz, 1H), 4.24-4.31 (m, 1H); $^{13}$C NMR (75 MHz, CD$_3$OD): δ 19.40, 52.60, 58.69, 65.24, 168.49; MS (ESI, positive): m/z 134 [M+H]$^+$.

By following the similar procedure, allo-D-threonine (0.228 g, 1.9 mmol) is converted into allo-D-threonine methyl ester hydrochloride (0.320 g, 99% yield). $^1$H NMR (300 MHz, CD$_3$OD): δ 1.26 (d, J=6.0 Hz, 3H), 3.84 (s, 3H), 4.08 (br s, 1H), 4.26 (br s, 1H); $^{13}$C NMR (75 MHz, CD$_3$OD): δ 17.69, 52.55, 58.30, 65.41, 167.61; MS (ESI, positive): m/z 134 [M+H]$^+$.

By following the similar procedure as in Example 22, methyl (2R,3R)-2-{4'-[(4"-aminophenyl)buta-1',3'-diynyl]benzamido}-3-hydroxybutanoate (122) and methyl (2R,3S)-2-{4'-[(4"-aminophenyl)buta-1',3'-diynyl]benzamido}-3-hydroxybutanoate (124) are obtained.

122: 92% yield; $^1$H NMR (300 MHz, DMSO-d$_6$): δ 1.13 (d, J=6.0 Hz, 3H), 3.64 (s, 3H), 4.14-4.19 (m, 1H), 4.46-4.50 (m, 1H), 4.94 (d, J=7.5 Hz, 1H), 5.83 (br s, 2H), 6.53 (d, J=8.1 Hz, 2H), 7.24 (d, J=7.2 Hz, 2H), 7.65 (d, J=6.9 Hz, 2H), 7.90 (d, J=7.2 Hz, 2H), 8.37 (d, J=7.5 Hz, 1H); $^{13}$C NMR (75 MHz, DMSO-d$_6$): δ 20.92, 52.59, 59.76, 67.08, 71.77, 77.42, 80.77, 86.44, 105.82, 114.27, 125.00, 128.56, 132.71, 134.70, 151.56, 166.74, 171.69; MS (ESI, positive): m/z 377 [M+H]$^+$.

124: 69% yield: $^1$H NMR (300 MHz, DMSO-d$_6$): δ 1.15 (d, J=6.3 Hz, 3H), 3.63 (s, 3H), 4.00-4.06 (m, 1H), 4.36 (t, J=13.2 Hz, 1H), 5.06 (d, J=4.2 Hz, 1H), 5.83 (br s, 2H), 6.53 (d, J=6.9 Hz, 2H), 7.24 (d, J=6.9 Hz, 2H), 7.63 (d, J=6.6 Hz, 2H), 7.87 (d, J=8.1 Hz, 2H), 8.64 (d, J=6.9 Hz, 1H); $^{13}$C NMR (75 MHz, DMSO-d$_6$): δ 21.07, 52.33, 60.14, 67.06, 71.76, 77.40, 80.79, 86.43, 105.81, 114.26, 124.95, 128.63, 132.64, 134.54, 134.70, 151.56, 166.38, 171.94; MS (ESI, positive): m/z 377 [M+H]$^+$.

By following the similar procedure as in Example 22, (2R,3R)-2-{4'-[(4"-aminophenyl)buta-1',3'-diynyl]benzamido}-1,3-dihydroxybutanamide (CPD-054) and (2R,3S)-2-{4'-[(4"-aminophenyl)buta-1',3'-diynyl]benzamido}-1,3-dihydroxybutanamide (CPD-055) have been synthesized.

CPD-054: 93% yield; $^1$H NMR (300 MHz, DMSO-d6): δ 1.07 (d, J=5.4 Hz, 3H), 3.98-4.04 (m, 1H), 4.24 (t, J=12.9 Hz, 1H), 4.87 (d, J=5.7 Hz, 1H), 5.82 (br s, 2H), 6.53 (d, J=8.4 Hz, 2H), 7.24 (d, J=8.4 Hz, 2H), 7.63 (d, J=8.1 Hz, 2H), 7.90 (d, J=6.6 Hz, 2H), 8.13 (d, J=7.8 Hz, 1H), 8.84 (br s, 1H), 10.65 (br s, 1H); $^{13}$C NMR (75 MHz, DMSO-d$_6$): δ 21.00, 58.80, 67.09, 71.79, 77.29, 80.84, 86.36, 105.84, 114.27, 124.74, 128.59, 132.58, 134.69, 135.02, 151.54, 166.28, 167.62; HRMS: calculated for C$_{21}$H$_{19}$N$_3$O$_4$H$^+$ 378.1454. found 378.1453 [M+H]$^+$.

CPD-055: 69% yield: $^1$H NMR (300 MHz, DMSO-d$_6$): δ 1.09 (d, J=6.0 Hz, 3H), 3.95-3.98 (m, 1H), 4.23 (t, J=16.2 Hz, 1H), 4.94 (d, J=3.9 Hz, 1H), 5.82 (br s, 2H), 6.53 (d, J=7.8 Hz, 2H), 7.24 (d, J=7.2 Hz, 2H), 7.61 (d, J=8.1 Hz, 2H), 7.87 (d, J=7.5 Hz, 2H), 8.42 (d, J=8.7 Hz, 1H), 8.81 (br s, 1H), 10.58 (br s, 1H); $^{13}$C NMR (75 MHz, DMSO-d$_6$): δ

21.09, 57.95, 66.84, 71.79, 77.26, 80.83, 86.34, 105.84, 114.27, 124.70, 128.62, 132.55, 134.69, 135.03, 151.55, 165.93, 167.70; HRMS: calculated for $C_{21}H_{19}N_3O_4H^+$ 378.1454. found 378.1460 $[M+H]^+$.

Example 25

(i) amino acid methyl ester, EDC.HCl, HOBt, DIEA, DMF, 0° C., then room temperature, overnight. (ii) hydroxyamine hydrochloride, 25% NaOMe/MeOH, THF, 0° C., 2 h, and then room temperature.

The following compounds are prepared essentially according to the procedures set forth above.

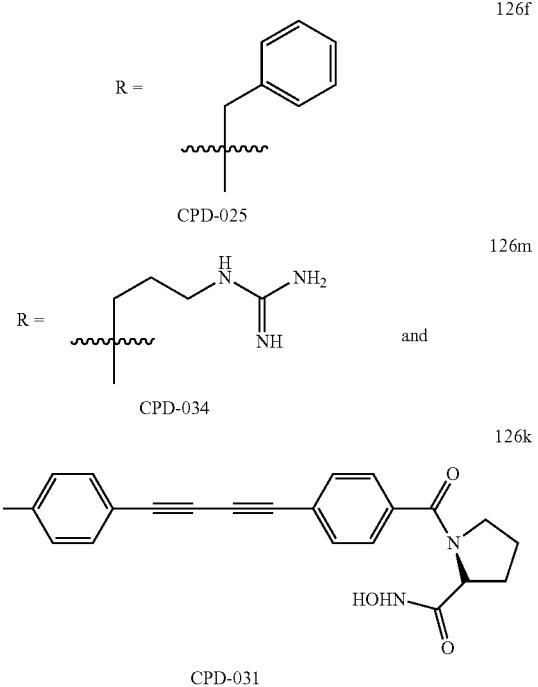

R = [CPD-025 benzyl]

R = [CPD-034 guanidinopropyl]

[126k structure with CPD-031]

To a stirred mixture of diacetylene acid 6 (100 mg, 0.38 mmol, prepared as in Example 1) and amino acid methyl ester hydrochloride (0.54 mmol, 1.40 equiv) in anhydrous DMF (5 mL) is added N-ethyl-N'-(3-dimethylaminopropyl) carbodiimide (EDC.HCl) (103 mg 0.54 mmol, 1.40 equiv), 1-hydroxybenzotriazole (HOBt) (73 mg, 0.54 mmol, 1.40 equiv) at room temperature. The mixture is cooled with an ice-bath, and diisopropylethylamine (DIEA) (0.27 mL, 1.53 mmol, 4.0 equiv) is added. The whole reaction mixture is stirred under argon at 0° C. for 1 h, then is allowed to warm to room temperature with the stirring is continued for additional 18 h. The resulting yellow solution is condensed to dryness with a rotavapor, and the residue is treated with water (20 mL). The mixture is extracted with EtOAc (3×50 mL). The combined extracts are washed with water (50 mL), brine (20 mL) and dried over anhydrous $Na_2SO_4$. Evaporation of the solvent affords the crude product, which is purified by flash chromatography (eluting with 1-2% MeOH in DCM) to afford amid methyl ester 125 a-q as yellow solid.

Methyl (2S)-2-({4'-[4'-(4'-aminophenyl)buta-1',3'-diyn-1'-yl]phenyl}formamido)-3-(1'H-imidazol-4'-yl)propanoate (125a); $^1$H NMR (300 MHz, CDCl$_3$): δ 3.20 (br s, 2H), 3.67 (s, 3H), 4.93 (br s, 1H), 6.59 (d, J=8.7 Hz, 2H), 7.32 (d, J=11.1 Hz, 2H), 7.54 (d, J=8.4 Hz, 3H), 7.80-7.83 (m, 3H), 8.348 (br s, 1H); $^{13}$C NMR (75 MHz, CDCl$_3$): δ 29.24, 52.65, 53.38, 72.07, 79.784, 80.10, 83.07, 84.44, 110.45, 114.84, 115.08, 125.99, 127.52, 132.49, 132.65, 134.41, 135.47, 148.06, 166.70, 172.17; MS (ESI, positive): m/z 413 [M+H$^+$].

5-tert-butyl 1-methyl (2S)-2-({4'-[4'-(4'-aminophenyl)buta-1'-3'-diyn-1'-yl]phenyl}formamido)pentanedioate (125b); $^1$H NMR (300 MHz, CDCl$_3$): δ 1.39 (s, 9H), 2.02-2.22 (m, 2H), 2.24-2.35 (m, 2H), 3.71 (s, 3H), 3.96 (br s, 2H), 4.69 (q, J=20.1 Hz, 1H), 6.54 (d, J=8.4 Hz, 2H), 7.27 (d, J=8.4 Hz, 2H), 7.39 (d, J=7.2 Hz, 1H), 7.48 (d, J=8.1 Hz, 2H), 7.73 (d, J=8.1 Hz, 2H); $^{13}$C NMR (75 MHz, CDCl$_3$): δ 26.87, 28.25. 31.89, 52.79, 52.93, 72.01, 79.99, 81.46, 84.69, 110.00, 114.78, 126.06, 127.43, 132.57, 133.47, 134.36, 148.37, 166.62, 172.66, 173.06; MS (ESI, positive): m/z 416 [M+H$^+$].

4-tert-butyl 1-methyl (2S)-2-({4'-[4'-(4'-aminophenyl)buta-1',3'-diyn-1'-yl]phenyl}formamido)butanedioate (125c); $^1$H NMR (300 MHz, CDCl$_3$): δ 1.43 (s, 9H), 2.84 (dd, J=4.5, 17.1 Hz, 1H), 3.02 (dd, J=4.5, 17.1 Hz, 1H), 3.77 (s, 3H), 4.00 (br s, 2H), 5.00 (m, 1H), 6.58 (d, J=8.7 Hz, 2H), 7.27 (d, J=6.9 Hz, 1H), 7.31 (d, J=8.7 Hz, 2H), 7.54 (d, J=8.7 Hz, 2H), 7.74 (d, J=8.1 Hz, 2H); $^{13}$C NMR (75 MHz CDCl$_3$) 28.24, 37.63, 49.38, 53.02, 72.01, 79.92, 82.21, 84.58, 110.31, 114.82, 126.21, 127.36, 132.700, 133.66, 134.41, 148.15, 166.28, 170.62, 171.60; MS (ESI, positive): m/z 447 [M+H$^+$].

Methyl (2S)-2-({4'-[4'-(4'-aminophenyl)buta-1',3'-diyn-1'-yl]phenyl}formamido)propanoate (125d); $^1$H NMR (300 MHz, DMSO-d$_6$) δ 1.39 (d, J=7.5 Hz, 3H), 3.63 (s, 3H), 4.47 (q, J=28.8 Hz, 1H), 5.83 (br s, 2H), 6.54 (d, J=8.4 Hz, 2H), 7.25 (d, J=8.7 Hz, 2H), 7.64 (d, J=8.1 Hz, 2H), 7.89 (d, J=8.4 Hz, 2H), 8.88 (d, J=6.9 Hz, 2H); $^{13}$C NMR (75 MHz, DMSO-d$_6$) δ 17.37, 49.04, 52.59, 71.80, 77.40, 80.79, 86.42, 105.85, 114.28, 124.94, 128.51, 132.67, 134.46, 134.71, 151.56, 166.05, 173.73; MS (ESI, positive): m/z 347 [M+H]$^+$.

(2S)-3-amino-2-({4'-[4'-(4'-aminophenyl)buta-1',3'-diyn-1'-yl]phenyl}formamido)-N-hydroxypropanamide (125e). 90% yield; $^1$H NMR (300 MHz, DMSO-d$_6$) δ 0.91 (d, J=6.9 Hz, 3H), 0.96 (d, J=6.6 Hz, 3H), 2.13-2.20 (m, 1H), 3.64 (s, 3H), 4.27 (t, J=15.3 Hz, 1H), 5.84 (s, 2H), 6.53 (d, J=8.4 Hz, 2H), 7.25 (d, J=7.2 Hz, 2H), 7.63 (d, J=7.5 Hz, 2H), 7.88 (d, J=7.2 Hz, 2H), 8.71 (d, J=7.8 Hz, 1H); $^{13}$C NMR (75 MHz, DMSO-d$_6$) δ 19.73, 19.81, 30.18, 52.24, 59.40, 71.78, 77.34, 80.82, 86.40, 105.80, 114.26, 124.87, 128.75, 132.59, 134.71, 151.57, 166.83, 172.82; MS (ESI, positive): m/z 375 [M+H$^+$].

Methyl (2S,3R)-2-({4'-[4'-(4'-aminophenyl)buta-1',3'-diyn-1'-yl]phenyl}formamido)-3'-methylpentanoate (125f). 91.3% yield; $^1$H NMR (300 MHz, DMSO-d$_6$) δ 0.82-0.89 (m, 6H), 1.19-1.27 (m, 1H), 1.46-1.49 (m, 1H), 1.92-1.95 (m, 1H), 3.63 (s, 3H), 4.32 (t, J=15.3 Hz, 1H), 5.84 (s, 2H), 6.53 (d, J=8.7 Hz, 2H), 7.24 (d, J=8.7 Hz, 2H), 7.63 (d, J=8.4 Hz, 2H), 7.88 (d, J=8.4 Hz, 2H), 8.72 (d, J=7.5 Hz, 1H); $^{13}$C NMR (75 MHz, DMSO-d$_6$) δ 11.55, 16.19, 25.91, 36.28, 52.34, 58.12, 71.77, 77.35, 80.82, 86.40, 105.80, 114.26, 124.87, 128.74, 132.59, 134.71, 151.57, 166.73, 172.87; MS (ESI, positive): m/z 389 [M+H$^+$].

Methyl 2-({4'-[4'-(4'-aminophenyl)buta-1',3'-diyn-1'-yl]phenyl}formamido)acetate (125 g). 83.3% yield; $^1$H NMR (300 MHz, DMSO-d$_6$) δ 3.64 (s, 3H), 4.01 (d, J=5.7 Hz, 2H), 5.85 (s, 2H), 6.53 (d, J=8.7 Hz, 2H), 7.25 (d, J=8.4 Hz, 2H), 7.65 (d, J=8.4 Hz, 2H), 7.87 (d, J=8.1 Hz, 2H), 9.07 (t, J=7.5 Hz, 1H); $^{13}$C NMR (75 MHz, DMSO-d$_6$) δ 41.95, 52.49, 71.80, 77.42, 80.76, 86.45, 105.78, 114.27, 125.00, 128.34, 132.81, 134.38, 134.73, 151.59, 166.42, 170.97; MS (ESI, positive): m/z 333 [M+H$^+$].

Methyl (2S)-2-({4'-[4'-(4'-aminophenyl)buta-1',3'-diyn-1'-yl]phenyl}formamido)-3-phenylpropanoate (125 h). 89.3% yield; $^1$H NMR (300 MHz, DMSO-d$_6$) δ 3.06-3.19 (m, 2H), 3.62 (s, 3H), 4.60-4.68 (m, 1H), 5.85 (s, 2H), 6.53 (d, J=8.7 Hz, 2H), 7.16-7.27 (m, 7H), 7.62 (d, J=8.1 Hz, 2H), 7.78 (d, J=8.4 Hz, 2H), 8.96 (d, J=7.8 Hz, 1H); $^{13}$C NMR (75 MHz, DMSO-d$_6$) δ 36.86, 52.71, 55.05, 71.774, 77.40, 80.75, 86.45, 105.77, 114.26, 124.96, 127.21, 128.43, 128.95, 129.74, 132.70, 134.38, 134.71, 138.30, 144.23, 151.57, 166.23, 172.75; MS (ESI, positive): m/z 424 [M+H$^+$].

Methyl (2S)-2-({4'-[4'-(4'-aminophenyl)buta-1',3'-diyn-1'-yl]phenyl}formamido)-4-methylpentanoate (125i). 83% yield; $^1$H NMR (300 MHz, CD$_3$OD) δ 0.95-0.100 (m, 6H), 1.68-1.80 (m, 3H), 3.73 (s, 3H), 4.64-4.69 (m, 1H), 6.62 (d, J=8.7 Hz, 2H), 7.24 (d, J=8.7 Hz, 2H), 7.57 (d, J=8.4 Hz, 2H), 7.83 (d, J=8.4 Hz, 2H); $^{13}$C NMR (75 MHz, CD$_3$OD) δ 20.58, 22.14, 25.03, 39.93, 51.65, 70.73, 76.60, 78.99, 84.55, 108.27, 114.20, 125.97, 127.56, 132.04, 133.81, 150.24, 168.32, 173.52; MS (ESI, positive): m/z 389 [M+H$^+$].

Methyl (2S)-2-({4'-[4'-(4'-aminophenyl)buta-1',3'-diyn-1'-yl]phenyl}formamido)-3-hydroxypropanoate (125j). 87.6% yield; $^1$H NMR (300 MHz, CD$_3$OD) δ 3.77 (s, 3H), 3.94-3.99 (m, 2H), 4.73 (t, J=9.3 Hz, 1H), 6.62 (d, J=9.3 Hz, 2H), 7.25 (d, J=9.0 Hz, 2H), 7.58 (d, J=8.4 Hz, 2H), 7.86 (d, J=8.4 Hz, 2H); $^{13}$C NMR (75 MHz, CD$_3$OD) δ 51.76, 55.80, 61.55, 70.77, 76.66, 79.00, 84.60, 108.29, 114.21, 126.06, 127.58, 132.08, 133.83, 150.22, 168.12, 171.09; MS (ESI, positive): m/z 363 [M+H$^+$].

Methyl (2S)-2-({4'-[4'-(4'-aminophenyl)buta-1',3'-diyn-1'-yl]phenyl}formamido)-4-(methylsulfanyl)butanoate (125k). 73.6% yield; $^1$H NMR (300 MHz, DMSO-d$_6$) δ 2.03 (s, 3H), 2.48-2.58 (m, 4H), 3.63 (s, 3H), 4.56 (q, J=14.4 Hz, 1H), 5.84 (s, 2H), 6.53 (d, J=8.4 Hz, 2H), 7.24 (d, J=8.4 Hz, 2H), 7.64 (d, J=8.4 Hz, 2H), 7.88 (d, J=8.4 Hz, 2H), 8.87 (d, J=7.5 Hz, 1H); $^{13}$C NMR (75 MHz, DMSO-d$_6$) δ 15.24, 30.55, 30.71, 52.43, 52.74, 71.77, 77.42, 80.79, 86.45, 105.78, 114.26, 124.98, 128.58, 132.69, 134.44, 134.72, 151.57, 166.56, 173.04; MS (ESI, positive): m/z 407 [M+H$^+$].

Methyl (2S)-2-({4'-[4'-(4'-aminophenyl)buta-1',3'-diyn-1'-yl]phenyl}formamido)-3-(1'H-indol-3'-yl)propanoate (125l). 98.0% yield; $^1$H NMR (300 MHz, CD$_3$OD) δ 3.29-3.40 (m, 2H), 3.41 (d, J=5.4 Hz, 1H), 3.70 (s, 3H), 6.60 (d, J=8.4 Hz, 2H), 6.99 (t, J=14.4 Hz, 1H), 7.06-7.12 (m, 2H), 7.23 (d, J=8.1 Hz, 2H), 7.32 (d, J=7.8 Hz, 1H), 7.499 (d, J=8.4 Hz, 2H), 7.55 (d, J=7.8 Hz, 1H), 7.69 (d, J=8.1 Hz, 2H); $^{13}$C NMR (75 MHz, CD$_3$OD) δ 27.05, 51.63, 54.44, 70.81, 76.61, 79.03, 84.55, 108.33, 109.78, 111.22, 114.23, 117.98, 118.73, 121.36, 123.23, 125.89, 127.49, 132.00, 133.83, 136.88, 150.19, 168.07, 172.86; MS (ESI, positive): m/z 462 [M+H$^+$].

Methyl (2S)-2-({4'-[4'-(4'-aminophenyl)buta-1',3'-diyn-1'-yl]phenyl}formamido)-6-{([tert-butoxy)carbonyl]amino}hexanoate (125m). 87.3% yield; $^1$H NMR (300 MHz, DMSO-d$_6$) δ 1.32 (br s, 13H), 1.76 (d, J=5.7 Hz, 2H), 2.87 (d, J=5.4 Hz, 2H), 3.61 (s, 3H), 4.36 (q, J=13.8 Hz, 1H), 5.84 (s, 2H), 6.52 (d, J=8.4 Hz, 2H), 6.76 (m, 1H), 7.24 (d, J=8.7 Hz, 2H), 7.63 (d, J=8.1 Hz, 2H), 7.88 (d, J=8.1 Hz, 2H), 8.79 (d, J=7.2 Hz, 1H); $^{13}$C NMR (75 MHz, DMSO-d$_6$) δ 23.77, 28.93, 29.79, 30.82, 52.56, 53.50, 71.77, 77.38, 78.01, 80.79, 86.42, 105.79, 114.26, 124.91, 128.57, 132.65, 134.52, 134.70, 151.57, 156.25, 166.46, 173.35; MS (ESI, positive): m/z 526 [M+H$^+$].

Methyl (2S)-2-({4'-[4'-(4'-aminophenyl)buta-1',3'-diyn-1-yl]phenyl}formamido)-5-carbamimidamidopentanoate (125n). 79.8% yield; $^1$H NMR (300 MHz, CD$_3$OD) δ 1.65-1.74 (m, 2H), 1.85-1.91 (m, 2H), 1.99-2.06 (m, 2H), 3.23 (t, J=12.0 Hz, 2H), 3.75 (s, 3H), 4.69 (q, J=14.4 Hz, 1H), 6.62 (d, J=8.7 Hz, 2H), 7.24 (d, J=8.7 Hz, 2H), 7.57 (d, J=8.7 Hz, 2H), 7.85 (d, J=8.7 Hz, 2H); $^{13}$C NMR (75 MHz, CD$_3$OD) δ 25.36, 28.25, 40.69, 51.77, 52.75, 70.77, 76.74, 78.98, 84.67, 108.25, 114.23, 126.11, 127.60, 132.09, 133.67, 133.84, 150.25, 157.50, 168.34, 172.61.

General procedure for deprotecting of 125b, 125c, 125m, 125p: A flask containing 125 (0.44 mmol) is treated with TFA/DCM (⅓ mL) and stirred at 0° C. under argon for 1 h, then is allowed to warm to ambient temperature with the stirring is continued for additional 14 h. The reaction mixture is then concentrated by rotary evaporation to give a yellow solid. The residue is treated with water (10 mL), adjusted pH (125b, 125c pH (5); 125m, 125p (11)). The mixture is then extracted with EtOAc (3×50 mL). The combined extracts are washed with water (30 mL), brine (30 mL) and dried over anhydrous Na$_2$SO$_4$. Evaporation of the solvent affords crude product, which is purified by flash chromatography (eluting with 1-3% MeOH in DCM) to afford 126 a-d as yellow solid.

(4S)-4-({4'-[4'-(4'-aminophenyl)buta-1',3'-diyn-1-yl]phenyl}formamido)-5-methoxy-5-oxopentanoic acid (126a). 98.8% yield; $^1$H NMR (300 MHz, DMSO-d$_6$) δ 1.92-2.14 (m, 2H), 2.36 (t, J=14.1 Hz, 2H), 3.38 (br s, 1H), 3.63 (s, 3H), 4.46 (m, 1H), 5.84 (br s, 2H), 6.54 (d, J=8.4 Hz, 2H), 7.25 (d, J=8.7 Hz, 2H), 7.64 (d, J=8.1 Hz, 2H), 7.89 (d, J=8.4 Hz, 2H), 8.86 (d, J=7.2 Hz, 1H); $^{13}$C (75 MHz, DMSO-d$_6$) δ 26.43, 30.85, 52.63, 52.81, 71.81, 77.44, 80.79, 86.43, 105.89, 113.16, 114.29, 125.00, 128.55, 131.24, 132.68, 134.44, 134.71, 151.54, 166.51, 172.94, 174.46; MS (ESI, positive): m/z 405 [M+H$^+$].

(3S)-3-({4'-[4'-(4'-aminophenyl)buta-1',3'-diyn-1'-yl]phenyl}formamido)-4-methoxy-4-oxobutanoic acid (126b). 97% yield; $^1$H NMR (300 MHz, CD$_3$OD) 6.89 (dd, J=7.5, 16.8 Hz, 1H), 3.04 (dd, J=5.7, 8.4 Hz, 1H), 3.75 (s, 3H), 4.96-4.98 (m, 1H), 6.62 (d, J=8.7 Hz, 2H) 7.24 (d, J=8.7 Hz, 2H), 7.56 (d, J=8.7 Hz, 2H), 7.81 (d, J=9.0 Hz, 2H); $^{13}$C NMR (75 MHz, CD$_3$OD) δ 35.45, 49.91, 51.92, 70.78, 76.68, 79.00, 84.59, 108.36, 114.26, 126.09, 127.51, 132.10, 133.69, 133.83, 150.16, 167.86, 171.67, 172.76; MS (ESI, positive): m/z 391 [M+H$^+$].

Methyl (2S)-6-amino-2-({4'-[4'-(4'-aminophenyl)buta-1',3'-diyn-1-yl]phenyl}formamido)hexanoate (126c). 97% yield; $^1$H NMR (300 MHz, CD$_3$OD) δ 1.43-1.57 (m, 4H), 1.83-1.94 (m, 2H), 2.67 (t, J=13.5 Hz, 2H), 3.74 (s, 3H), 4.59 (q, J=14.4 Hz, 1H), 6.61 (d, J=8.7 Hz, 2H), 7.24 (d, J=8.7 Hz, 2H), 7.57 (d, J=8.4 Hz, 2H), 7.84 (d, J=8.4 Hz, 2H); $^{13}$C NMR (75 MHz, CD$_3$OD) δ 23.30, 30.84, 31.24, 40.76, 51.63, 53.28, 70.78, 76.66, 79.02, 84.61, 108.25, 114.210 125.99, 127.60, 132.07, 133.84, 150.25, 168.35, 173.07; MS (ESI, positive): m/z 406 [M+H$^+$].

Methyl (2S)-3-amino-2-({4'-[4'-(4'-aminophenyl)buta-1',3'-diyn-1'-yl]phenyl}formamido)propanoate (126d). 82% yield; $^1$H NMR (300 MHz, DMSO-d$_6$) δ 2.95 (br s, 2H), 3.63 (s, 3H), 4.42 (m, 1H), 5.85 (s, 2H), 6.54 (d, J=8.7 Hz, 2H), 7.25 (d, J=8.4 Hz, 2H), 7.65 (d, J=8.4 Hz, 2H), 7.91 (d, J=8.1 Hz, 2H), 8.73 (d, J=5.4 Hz, 1H); $^{13}$C NMR (75 MHz, DMSO-d$_6$) δ 43.48, 52.54, 57.16, 71.79, 77.40, 80.82, 86.43, 105.80, 114.27, 124.92, 128.61, 132.67, 134.73, 151.58, 166.65, 172.30; MS (ESI, positive): m/z 362 [M+H$^+$].

CPD-014, (2S)-2-({4'-[4'-(4'-aminophenyl)buta-1',3'-diyn-1'-yl]phenyl}formamido)-N-hydroxy-3-(1'H-imidazol-4'-yl)propanamide: 48% yield; $^1$H NMR (300 MHz, DMSO-d$_6$) δ 3.12 (q, 2H, J=20.7 Hz), 4.74 (q, J=14.4 Hz, 1H), 6.62 (d, J=9.0 Hz, 2H), 6.93 (s, 1H), 7.22 (d, J=8.7 Hz, 2H), 7.51-7.56 (m, 3H), 7.68 (d, J=1.5 Hz, 1H), 7.76-7.80 (m, 3H); $^{13}$C NMR (75 MHz, DMSO-d$_6$) δ 29.24, 52.06, 70.70, 76.59, 78.96, 80.00, 84.56, 108.28, 114.20, 116.74, 125.96, 127.54, 131.85, 131.99, 133.79, 135.09, 150.24, 167.80, 169.17; HRMS: calculated for C$_{23}$H$_{18}$N$_5$O$_3^+$ 414.1566. found 414.1564 [M+H]$^+$.

CPD-017, Tert-butyl (4S)-4-({4'-[4'-(4'-aminophenyl)buta-1',3'-diyn-1'-yl]phenyl}formamido)-4-(hydroxycarbamoyl)butanoate: 55% yield; $^1$H NMR (300 MHz, CD$_3$OD) δ 1.43 (s, 9H), 1.97-2.16 (m, 2H), 2.37 (t, J=14.7

Hz, 3H), 4.49 (q, J=5.4 Hz, 1H), 6.61 (d, J=8.7 Hz, 2H), 7.24 (d, J=8.7 Hz, 2H), 7.56 (d, J=8.4 Hz, 2H), 7.84 (d, J=8.4 Hz, 2H); $^{13}$C NMR (75 MHz, CD$_3$OD) δ 27.16, 31.52, 51.31, 70.79, 76.65, 79.03, 80.82, 84.58, 108.33, 114.24, 114.62, 126.01, 127.62, 132.04, 133.82, 150.21, 167.96, 169.53, 172.76; HRMS: calculated for $C_{26}H_{27}N_3O_5H^+$ 462.2029. found 462.2016 $[M+H]^+$.

CPD-020, (2S)-2-({4'-[4'-(4'-aminophenyl)buta-1',3'-diyn-1'-yl]phenyl}formamido)-N-hydroxypropanamide: 65% yield; $^1$H NMR (300 MHz, DMSO-d$_6$) δ 1.31 (d, J=7.2 Hz, 3H), 4.38 (m, 1H), 5.83 (s, 2H), 6.54 (d, J=8.7 Hz, 2H), 7.25 (d, J=8.7 Hz, 2H), 7.62 (d, J=8.7 Hz, 2H), 7.90 (d, J=8.7 Hz, 2H), 8.61 (d, J=7.2 Hz, 1H), 8.81 (br s, 1H), 10.65 (br s, 1H); $^{13}$C NMR (75 MHz, DMSO-d$_6$) δ 18.71, 47.73, 71.82, 77.26, 80.87, 86.33, 105.87, 114.29, 124.67, 128.65, 132.51, 134.70, 134.93, 151.55, 165.85, 169.83; HRMS: calculated for $C_{20}H_{17}N_3O_3$ 347.1270. found 347.1280.

CPD-022, (2S)-2-({4'-[4'-(4'-aminophenyl)buta-1',3'-diyn-1'-yl]phenyl}formamido)-N-hydroxy-3-methylbutanamide: 78% yield; $^1$H NMR (300 MHz, DMSO-d$_6$) δ 0.88 (m, 6H), 2.07-2.11 (m, 1H), 4.06 (t, J=17.4 Hz, 1H), 5.83 (s, 2H), 6.52 (d, J=8.7 Hz, 2H), 7.24 (d, J=8.4 Hz, 2H), 7.60 (d, J=8.1 Hz 2H), 7.88 (d, J=8.1 Hz, 2H), 8.52 (d, J=8.4 Hz, 1H), 8.88 (s, 1H), 10.73 (s, 1H); $^{13}$C NMR (75 MHz, DMSO-d$_6$) δ 19.90, 30.35, 57.81, 71.79, 77.21, 80.85, 86.31, 105.81, 114.26, 124.63, 128.65, 132.54, 134.69, 135.05, 151.55, 166.15, 168.29; HRMS: calculated for $C_{22}H_{21}N_3O_3$ 375.1583. found 375.1576 $M^+$.

CPD-023, (2S,3R)-2-({4'-[4'-(4'-aminophenyl)buta-1',3'-diyn-1'-yl]phenyl}formamido)-N-hydroxy-3-methylpentanamide: 60% yield; $^1$H NMR (300 MHz, DMSO-d$_6$) δ 0.78-0.85 (m, 6H), 1.12-1.16 (m, 1H), 1.46-1.53 (m, 1H), 1.88-1.93 (m, 1H), 4.14 (t, J=18.3 Hz, 1H), 5.84 (s 2H), 6.53 (d, J=8.7 Hz, 2H), 7.24 (d, J=8.4 Hz, 2H), 7.60 (d, J=8.4 Hz, 2H), 7.88 (d, J=8.4 Hz, 2H), 8.55 (d, J=8.7 Hz, 1H), 8.88 (s, 1H), 10.74 (s, 1H); $^{13}$C NMR (75 MHz, DMSO-d$_6$) δ 11.17, 16.00, 25.56, 35.97, 56.13, 71.80, 77.22, 80.86, 86.32, 105.82, 114.26, 124.63, 128.64, 132.54, 134.70, 135.04, 151.55, 166.03, 168.36; HRMS: calculated for $C_{23}H_{23}N_3O_3$ 389.1739. found 389.1731 $M^+$.

CPD-024, 2-({4'-[4'-(4'-aminophenyl)buta-1',3'-diyn-1'-yl]phenyl}formamido)-N-hydroxyacetamide: 95% yield; $^1$H NMR (300 Hz, DMSO-d$_6$) δ 3.72 (s, 2H), 5.84 (s, 2H), 6.53 (d, J=8.7 Hz, 2H), 7.24 (d, J=8.4 Hz, 2H), 7.60 (d, J=8.1 Hz, 2H), 7.86 (d, J=7.8 Hz, 2H), 8.59 (br s, 1H); $^{13}$C NMR (75 MHz, DMSO-d$_6$) δ 42.15, 71.83, 77.14, 80.88, 86.27, 105.84, 114.26, 124.49, 128.33, 132.62, 134.70, 135.29, 151.55, 165.23, 165.85; HRMS: calculated for $C_{19}H_{15}N_3O_3$ 333.1113. found 333.1109 $M^+$.

CPD-025, (2S)-2-({4'-[4'-(4'-aminophenyl)buta-1',3'-diyn-1'-yl]phenyl}formamido)-N-hydroxy-3-phenylpropanamide: 77% yield; $^1$H NMR (300 MHz, DMSO-d$_6$) δ 3.00 (d, J=6.6 Hz 2H), 4.57 (m, 1H), 5.84 (s, 2H), 6.53 (d, J=8.7 Hz, 2H), 7.15 (d, J=7.2 Hz, 2H), 7.20-7.31 (m, 5H), 7.58 (d, J=8.1 Hz, 2H), 7.80 (d, J=7.8 Hz, 2H), 8.76 (d, J=6.6 Hz, 2H); $^{13}$C NMR (75 MHz, DMSO-d$_6$) δ 38.13, 53.66, 71.80, 77.23, 80.84, 86.33, 105.82, 114.26, 124.63, 126.94, 128.50, 129.77, 132.52, 134.70, 138.94, 151.54, 165.91, 168.46; HRMS: calculated for $C_{26}H_{21}N_3O_3$ 423.1583; found 423.1581 $M^+$.

CPD-026, (2S)-2-({4'-[4'-(4'-aminophenyl)buta-1',3'-diyn-1'-yl]phenyl}formamido)-N-hydroxy-4-methylpentanamide: 50% yield; $^1$H NMR (300 MHz, CD$_3$OD) δ 0.94-0.99 (m, 6H), 1.62-1.77 (m, 3H), 4.54-4.59 (m, 1H), 6.61 (d, J=8.4 Hz, 2H), 7.24 (d, J=8.4 Hz, 2H), 7.55 (d, J=8.4 Hz, 2H), 7.82 (d, J=8.1 Hz, 2H); $^{13}$C NMR (75 MHz, CD$_3$OD) δ 21.06, 22.05, 24.87, 40.75, 50.26, 70.81, 76.62, 79.05, 84.55, 108.33, 114.24, 125.91, 127.59, 132.02, 133.82, 150.18, 167.95, 170.37; HRMS: calculated for $C_{23}H_{23}N_3O_3$ 389.1739. found 389.1733 $[M+H]^+$.

CPD-027, (2S)-2-({4'-[4'-(4'-aminophenyl)buta-1',3'-diyn-1'-yl]phenyl}formamido)-N,3-dihydroxypropanamide: 66% yield; $^1$H NMR (300 MHz, DMSO-d$_6$) δ 3.65 (s, 2H), 4.36-4.42 (m, 1H), 4.95 (s, 1H), 5.84 (s, 2H), 6.53 (d, J=8.4 Hz, 2H), 7.24 (d, J=8.7 Hz, 2H), 7.62 (d, J=8.1 Hz, 2H), 7.90 (d, J=8.4 Hz, 2H), 8.40 (d, J=8.1 Hz, 1H), 8.83 (s, 1H), 10.67 (s, 1H); $^{13}$C NMR (75 MHz, DMSO-d$_6$) δ 55.01, 62.13, 71.80, 77.27, 80.86, 86.35, 105.81, 114.27, 124.70, 128.66, 132.54, 134.72, 134.97, 151.56, 166.15, 167.43; HRMS: calculated for $C_{20}H_{17}N_3O_4H^+$ 364.1297. found 364.1295 $[M+H]^+$.

CPD-028, (2S)-2-({4'-[4'-(4'-aminophenyl)buta-1',3'-diyn-1-yl]phenyl}formamido)-N-hydroxy-4-(methylsulfanyl)butanamide: 45% yield; $^1$H NMR (300 MHz, DMSO-d$_6$) δ 1.94-2.00 (m, Hz, 2H), 2.10 (s, 3H), 2.37-2.48 (m, 2H), 4.42 (q, J=16.2 Hz, 1H), 5.84 (s, 2H), 6.52 (d, J=8.7 Hz, 2H), 7.24 (d, J=8.7 Hz, 2H), 7.61 (d, J=8.1 Hz, 2H), 7.89 (d, J=8.4 Hz, 2H), 8.62 (d, J=7.8 Hz, 1H), 8.84 (s, 1H), 10.73 (s, 1H); $^{13}$C NMR (75 MHz, DMSO-d$_6$) δ 15.30, 30.57, 31.92, 51.39, 71.79, 77.27, 80.87, 86.35, 105.80, 114.26, 124.70, 128.69, 132.52, 134.70, 134.89, 151.56, 166.26, 168.75; HRMS: calculated for $C_{22}H_{20}N_3O_3SH^+$ 408.1382. found 408.1390 $[M+H]^+$.

CPD-029, (2S)-2-({4'-[4'-(4'-aminophenyl)buta-1',3'-diyn-1-yl]phenyl}formamido)-N-hydroxy-3-(1'H-indol-3'-yl)propanamide: 70% yield; $^1$H NMR (300 MHz, DMSO-d$_6$) δ 3.13 (d, J=6.9 Hz, 2H), 4.63 (m, 1H), 5.84 (s, 2H), 6.52 (d, J=8.4 Hz, 2H), 6.93-7.05 (m, 2H), 7.18 (s, 1H), 7.22-7.29 (m, 3H), 7.58 (d, J=8.1 Hz, 2H), 7.65 (d, J=7.8 Hz, 1H), 7.82 (d, J=8.4 Hz, 2H), 8.7 (d, J=8.1 Hz, 1H), 8.88 (s, 1H), 10.76 (s, 1H), 10.86 (s, 1H); $^{13}$C NMR (75 MHz, DMSO-d$_6$) δ 28.31, 52.74, 71.80, 77.25, 80.84, 86.34, 105.81, 110.94, 112.00, 114.26, 118.94, 119.18, 121.58, 124.41, 124.64, 127.83, 128.55, 132.51, 134.71, 134.88, 136.72, 151.55, 165.92, 169.04; HRMS: calculated for $C_{28}H_{22}N_4O_3H^+$ 463.1770. found 463.1764 $[M+H]^+$.

CPD-030, Tert-butyl N-[(5S)-5-({4-[4-(4-aminophenyl)buta-1,3-diyn-1-yl]phenyl}formamido)-5-(hydroxycarbamoyl)phenyl]carbamate: yield; $^1$H NMR (300 MHz, DMSO-d$_6$) δ 1.32 (br s, 13H), 1.63-1.67 (m, 2H), 2.8-2.86 (m, 2H), 4.25-4.28 (m, 1H), 5.83 (s, 2H), 6.52 (d, J=8.4 Hz, 2H), 6.74 (t, J=6.9 Hz, 1H), 7.23 (d, J=8.4 Hz, 2H), 7.60 (d, J=8.4 Hz, 2H), 7.88 (d, J=8.4 Hz, 2H), 8.81 (s, 1H), 10.67 (s, 1H); $^{13}$C NMR (75 MHz, DMSO-d$_6$) δ 23.74, 28.94, 29.79, 32.04, 52.04, 71.80, 77.23, 78.00, 80.87, 86.32, 105.82, 114.26, 124.63, 128.66, 132.51, 134.70, 135.00, 151.55, 156.24, 166.13, 169.17; HRMS: calculated for $C_{28}H_{32}N_4O_5$ 504.2373. found 504.2376 $[M+H]^+$.

CPD-031, (2S)-1-({4'-[4'-(4'-aminophenyl)buta-1',3'-diyn-1-yl]phenyl}carbonyl)-N-hydroxypyrrolidine-2-carboxamide: 81% yield; $^1$H NMR (300 MHz, CD$_3$OD) δ 1.84-1.90 (m, 1H), 1.97-2.07 (m, 1H), 2.23-2.30 (m, 1H), 3.47-3.55 (m, 1H), 3.61-3.67 (m, 1H), 4.43 (q, J=13.8 Hz, 1H), 6.61 (d, J=8.7 Hz, 2H), 7.24 (d, J=8.7 Hz, 2H), 7.55 (d, J=6.3 Hz, 2H), 7.60 (d, J=7.8 Hz, 2H); $^{13}$C NMR (75 MHz, CD$_3$OD) δ 25.23, 29.96, 50.47, 58.68, 70.75, 76.02, 79.02, 84.26, 108.31, 114.21, 124.71, 126.76, 127.50, 131.99, 132.19, 133.80, 136.15, 150.21, 169.97, 170.53; HRMS: calculated for $C_{22}H_{19}N_3O_3H^+$ 374.1505. found 374.1499 $[M+H]^+$.

CPD-033, (2S)-2-({4'-[4'-(4'-aminophenyl)buta-1',3'-diyn-1-yl]phenyl}formamido)-N-hydroxy-3'-(4'-hydroxyphenyl)propanamide: 67% yield; $^1$H NMR (300 MHz, DMSO-d$_6$) δ 2.87 (d, J=7.2 Hz, 1H), 4.47 (m, 1H), 5.83 (s, 2H), 6.53 (d, J=8.7 Hz, 2H), 6.60 (d, J=8.4 Hz, 2H), 7.08 (d, J=8.4 Hz, 2H), 7.24 (d, J=8.4 Hz, 2H), 7.59 (d, J=8.1 Hz, 2H), 7.80 (d, J=8.4 Hz, 2H), 8.68 (d, J=8.4 Hz, 1H), 8.86 (s, 1H), 9.14 (s, 1H), 10.75 (s, 1H); $^{13}$C NMR (75 MHz, DMSO-$d_6$) δ 53.96, 71.81, 77.23, 80.85, 86.33, 105.82, 114.26, 115.59, 124.63, 128.53, 128.86, 130.74, 132.53, 134.70, 134.93, 151.55, 156.42, 165.96. 168.75; HRMS: calculated for $C_{26}H_{21}N_3O_4H^+$ 440.1610. found 440.1605 [M+H]$^+$.

CPD-034, (2S)-2-({4'-[4'-(4'-aminophenyl)buta-1',3'-diyn-1-yl]phenyl}formamido)-5'-carbamimidamido-N-hydroxypentanamide: 70% yield; $^1$H NMR (300 MHz, DMSO-$d_6$) δ 1.50-1.54 (m, 2H), 1.71-1.74 (m s, 2H), 3.08-3.11 (m, 2H), 4.28 (m, 2H), 5.84 (s, 2H), 6.53 (d, J=8.7 Hz, 2H), 7.24 (d, J=8.7 Hz, 2H), 7.55 (d, J=7.8 Hz, 2H), 7.83 (d, J=6.6 Hz, 2H); $^{13}$C NMR (75 MHz, DMSO-$d_6$) δ 26.00, 30.12, 49.29, 52.19, 71.85, 77.07, 80.92, 86.22, 105.87, 114.26, 124.32, 128.27, 132.56, 134.69, 135.47, 151.53, 157.67, 165.10, 166.73; HRMS: calculated for $C_{23}H_{24}N_6O_3H^+$ 433.1988. found 433.1990 [M+H]$^+$.

Example 26

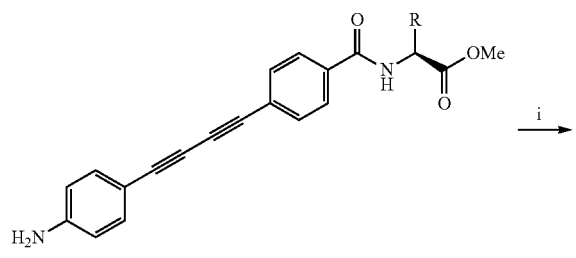

125o: R = (CH$_2$)$_2$CO$_2$t-Bu
125p: R = CH$_2$CO$_2$t-Bu
125r: R = (CH$_2$)$_4$NHBoc
125s: R = CH$_2$NHBoc

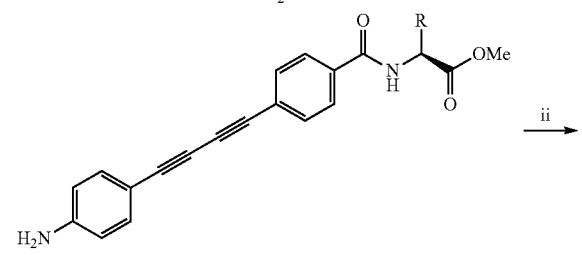

127a: R = (CH$_2$)$_2$CO$_2$t-Bu
127b: R = CH$_2$CO$_2$t-Bu
127c: R = (CH$_2$)$_4$NHBoc
127d: R = CH$_2$NHBoc

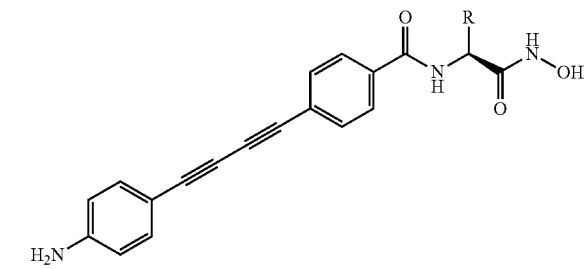

CPD-018: R = (CH$_2$)$_2$CO$_2$t-Bu
CPD-019: R = CH$_2$CO$_2$t-Bu
CPD-021: R = (CH$_2$)$_4$NHBoc
CPD-032: R = CH$_2$NHBoc (i) TFA, DCM, 0° C. to room temperature. (ii) hydroxylamine hydrochloride, 25% NaOMe/MeOH, THF, 0° C., 2 h, then room temperature.

Amid methyl ester 125 o-q are prepared as noted in Example 24.

Methyl (2S)-2-({4'-[4'-(4'-aminophenyl)buta-1',3'-diyn-1'-yl]phenyl}formamido)-3-(4'-hydroxyphenyl)propanoate (125o). 90.8% yield; $^1$H NMR (300 MHz, CD$_3$OD) δ 3.00 (dd, J=9.3, 23.1 Hz, 1H), 3.18 (dd, J=5.4, 13.8 Hz, 1H), 3.70 (s, 3H), 4.81 (m, 1H), 6.61 (d, J=8.7 Hz, 2H), 6.70 (d, J=8.7 Hz, 2H), 7.06 (d, J=8.7 Hz, 2H), 7.24 (d, J=8.7 Hz, 2H), 7.52 (d, J=8.7 Hz, 2H), 7.71 (d, J=8.7 Hz, 2H); $^{13}$C NMR (75 MHz, CD$_3$OD) δ 36.23, 51.61, 55.07, 70.81, 76.62, 79.05, 84.57, 108.32, 114.23, 115.12, 125.92, 127.48, 127.84, 130.06, 132.04, 133.84, 150.20, 156.22, 168.10, 172.56; MS (ESI, positive): m/z 439 [M+H$^+$].

Methyl (2S)-2-({4'-[4'-(4'-aminophenyl)buta-1',3'-diyn-1'-yl]phenyl}formamido)-3-{[(tert-butoxy)carbonyl]amino}propanoate (125p). 88% yield; $^1$H NMR (300 MHz, CD$_3$OD) δ 1.42 (s, 9H), 3.57 (t, J=11.4 Hz, 2H), 3.75 (s, 3H), 4.66 (t, J=11.4 Hz, 1H), 6.62 (d, J=8.7 Hz, 2H), 7.24 (d, J=8.4 Hz, 2H), 7.57 (d, J=7.8 Hz, 2H), 7.84 (d, J=8.1 Hz, 2H); $^{13}$C NMR (75 MHz, CD$_3$OD) δ 27.52, 41.10, 51.52, 54.52, 70.80, 76.74, 79.00, 79.49, 84.65, 108.28, 114.22, 126.12, 127.54, 132.09, 133.57, 133.84, 150.24, 157.86, 167.87, 171.01; MS (ESI, positive): m/z 462 [M+H$^+$].

Methyl (2S)-1-({4'-[4'-(4'-aminophenyl)buta-1',3'-diyn-1'-yl]phenyl}carbonyl)pyrrolidine-2-carboxylate (125q). 79% yield; $^1$H NMR (300 MHz, DMSO-$d_6$); δ 1.85 (t, J=3.3 Hz, 3H), 2.22-2.26 (m, 1H), 3.47-3.58 (m, 2H), 3.64 (s, 3H), 4.43-4.48 (m, 1H), 5.83 (s, 2H), 6.52 (d, J=8.4 Hz, 2H), 7.24 (d, J=8.7 Hz, 2H), 7.34 (d, J=7.8 Hz, 2H), 7.60 (d, J=8.1 Hz, 2H), 7.60 (d, J=8.4 Hz, 2H); $^{13}$C NMR (75 MHz, DMSO-$d_6$) δ 25.69, 29.54, 50.114, 52.59, 59.62, 71.81, 76.79, 80.75, 86.14, 105.82, 114.25, 123.69, 127.60, 128.27, 132.70, 134.690, 137.01, 151.54, 168.03, 172.90; MS (ESI, positive): m/z 373 [M+H$^+$].

General procedure for hydroxamic acid of amid methyl ester 125a-q, 127a-d: To an ice-cold solution of amide methyl ester 125 (0.26 mmol) dissolved in anhydrous MeOH (1 mL) and THF (1 mL) is added hydroxylamine hydrochloride (93 mg, 1.34 mmol, 5.0 equiv), followed by adding 25% sodium methoxide in methanol solution (0.49 mL, 2.03 mmol, 7.5 equiv). The reaction mixture is stirred under argon at 0° C. for 2 h, then is allowed to warm to ambient temperature with the stirring is continued overnight (16 h). The resulting yellow suspension is condensed to dryness with a rotavapor, and the residue is treated water (30 mL), saturated NH$_4$Cl (20 mL). The mixture is extracted with EtOAc (3×50 mL). And the combined extracts are washed with water (30 mL), brine (30 mL) and dried over anhydrous Na$_2$SO$_4$. Evaporation of the solvent affords the crude product, which is purified by combine flash (eluting with 2-5% MeOH in DCM) to afford 127 as yellow solid.

CPD-018, (4S)-4-({4'-[4'-(4'-aminophenyl)buta-1',3'-diyn-1'-yl]phenyl}formamido)-4-(hydroxycarbamoyl)butanoic acid: 99% yield; $^1$H NMR (300 MHz, CD$_3$OD) δ 2.11-2.18 (m, 2H), 2.45 (m, 2H), 4.51 (t, J=14.1 Hz, 1H), 6.62 (d, J=8.7 Hz, 2H), 7.24 (d, J=8.7 Hz, 2H), 7.55 (d, J=8.4 Hz, 2H), 7.84 (d, J=8.1 Hz, 2H); $^{13}$C (75 MHz, CD$_3$OD) δ 27.05, 30.10, 41.30, 51.46, 70.77, 76.61, 79.03, 84.55, 108.34, 114.24, 125.78, 127.60, 132.03, 133.81, 150.18, 168.01, 169.53, 175.36; HRMS: calculated for $C_{22}H_{19}N_3O_5H^+$ 406.1403. found 406.1398 [M+H]$^+$.

CPD-019, (3S)-3-({4'-[4'-(4'-aminophenyl)buta-1',3'-diyn-1'-yl]phenyl}formamido)-3-(hydroxycarbamoyl)propane acid: 46.0% yield; $^1$H NMR (300 MHz, CD$_3$OD) δ

2.83 (dd, J=7.8, 16.5 Hz, 1H), 2.94 (dd, J=6.3, 16.5 Hz, 1H), 6.61 (d, J=8.7 Hz, 2H), 7.24 (d, J=8.7 Hz, 2H), 7.55 (d, J=8.4 Hz, 2H), 7.83 (d, J=8.7 Hz, 2H); $^{13}$C (75 MHz, CD$_3$OD) δ 35.56, 70.76, 76.62, 79.01, 84.55, 108.35, 114.24, 126.00, 127.62, 132.00, 133.80, 150.18, 167.83, 168.84, 172.60; HRMS: calculated for C$_{21}$H$_{17}$N$_3$O$_5$H$^+$ 392.1246. found 392.1242 [M+H]$^+$.

CPD-021, (2S)-3-amino-2-({4'-[4'-(4'-aminophenyl)buta-1',3'-diyn-1-yl]phenyl}formamido)-N-hydroxypropanamide: 75% yield; $^1$H NMR (300 MHz, DMSO-d$_6$) δ 2.83 (d, J=6.6 Hz, 2H), 4.26 (m, 1H), 5.84 (s, 2H), 6.53 (d, J=8.4 Hz, 2H), 7.24 (d, J=8.4 Hz, 2H), 7.62 (d, J=8.1 Hz, 2H), 7.91 (d, J=8.1 Hz, 2H), 8.47 (br s, 1H); $^{13}$C NMR (75 MHz, DMSO-d$_6$) δ 44.25, 55.72, 71.80, 77.24, 80.88, 86.33, 105.82, 114.27, 124.65, 128.68, 132.51, 134.70, 135.07, 151.55, 166.44, 168.30; HRMS: calculated for C$_{20}$H$_{18}$N$_4$O$_3$H$^+$ 363.1457. found 363.1457 [M+H]$^+$.

CPD-032, (2S)-6-amino-2-({4'-[4'-(4'-aminophenyl)buta-1',3'-diyn-1-yl]phenyl}formamido)-N-hydroxyhexanamide: 84% yield; $^1$H NMR (300 MHz, DMSO-d$_6$) δ 1.32 (br s, 6H), 1.67 (m, 2H), 4.28 (m, 1H), 5.84 (s, 2H), 6.52 (d, J=8.4 Hz, 2H), 7.24 (d, J=8.4 Hz, 2H), 7.60 (d, J=8.1 Hz, 1H), 7.88 (d, J=8.4 Hz, 2H), 8.57 (d, J=7.5 Hz, 1H); $^{13}$C NMR (75 MHz, DMSO-d$_6$) δ 23.74, 32.22, 33.46, 42.07, 52.14, 71.80, 77.21, 80.87, 86.31, 105.81, 114.25, 124.60, 128.64, 132.51, 134.69, 135.02, 151.54, 166.08, 169.13; HRMS: calculated for C$_{23}$H$_{24}$N$_4$O$_3$ 404.1848. found 404.1843 M$^+$.

Example 27

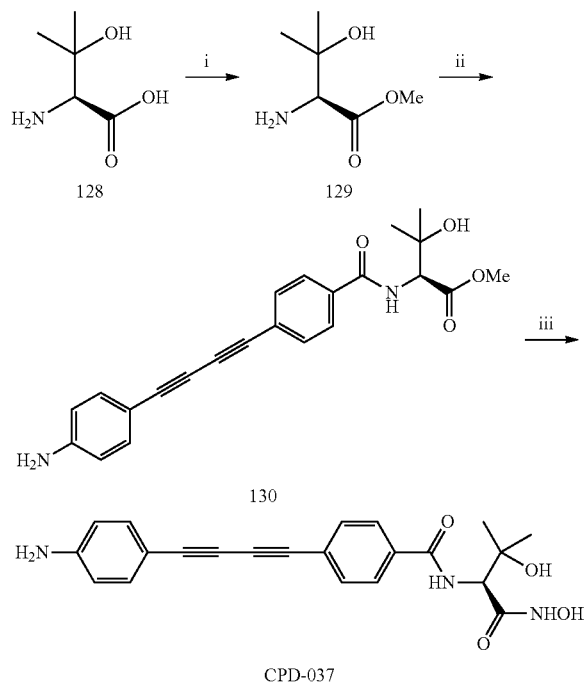

(i) SOCl$_2$, MeOH, reflux 70 h. (ii) EDC.HCl, HOBt, DIEA, DMF, 6, 0° C., 1 h, then room temperature 14 h, 79% (two steps). (iii) Hydroxylamine hydrochloride, 25% NaOMe/MeOH, THF, 0° C., 2 h, then room temperature, 18 h, 72%.

129: To an ice-cold anhydrous MeOH (8 mL) is added dropwise thionyl chloride (0.54 mL, 7.51 mmol, 2.0 equiv), and the solution is stirred at room temperature for 5 min. (S)-(+)-2-amino-3-methylbutanic acid 128 (500 mg, 3.76 mmol) is then added to the solution in one portion, and the reaction mixture is heated at 70° C. for 48 hours. LC/MS analysis showed the completion of the reaction. After cooled to ambient temperature, the solvents are evaporated to dryness and then pumped under high vacuum for 4 h, obtaining the crude (S)-(+)-2-amino-3-hydroxy-3-methylbutanic acid ester hydrochloride 129 (619 mg, 90% yield) as white semi-solid.

130: To a stirred mixture of diacetylene acid 6 (200 mg, 0.76 mmol, prepared as in Example 1) and 129 (300 mg, 0.91 mmol, 1.20 equiv) in anhydrous DMF (5 mL) is added EDC.HCl (204 mg 1.07 mmol, 1.20 equiv), HOBt (145 mg, 1.87 mmol, 1.20 equiv) at room temperature. The mixture is cooled with an ice-bath, and diisopropylethylamine (1.06 mL, 7.12 mmol, 8.0 equiv) is added. The whole reaction mixture is stirred under argon at 0° C. for 1 h, then allowed to warm to ambient temperature with the stirring is continued for additional 20 hours. The resulting yellow solution is condensed to dryness with a rotavapor, and the residue is treated with water (50 mL). The mixture is extracted with EtOAc (3×50 mL). The combined extracts are washed with water (30 mL), brine (30 mL) and dried over anhydrous Na$_2$SO$_4$. Evaporation of the solvent affords the crude product, which is purified by flash chromatography (eluting with 0-6% MeOH in DCM) to afford 130 (240 mg, 80% yield) as red solid. $^1$H NMR (300 MHz, CD$_3$OD) δ 1.32 (s, 3H), 1.36 (s, 3H), 3.76 (s, 3H), 4.64 (s, 1H), 6.61 (d, J=8.7 Hz, 2H), 7.24 (d, J=8.7 Hz, 2H), 7.58 (d, J=8.7 Hz, 2H), 7.83 (d, J=8.7 Hz, 2H); $^{13}$C NMR (75 MHz, CD$_3$OD) δ 26.11, 26.41, 51.48, 61.60, 70.83, 71.38, 76.78, 79.01, 84.67, 108.30, 114.24, 126.14, 127.54, 132.16, 133.86, 150.21, 168.08, 177.11; MS (ESI, positive): m/z 391 [M+H$^+$].

CPD-037, (2S)-2-({4'-[4'-(4'-aminophenyl)buta-1',3'-diyn-1-yl]phenyl}formamido)-N,3'-dihydroxy-3'-methylbutanamide: 72.0% yield; $^1$H NMR (300 MHz, CD$_3$OD) δ 1.27 (s, 3H), 1.33 (s, 3H), 4.50 (s, 1H), 6.61 (d, J=8.7 Hz, 2H), 7.24 (d, J=8.7 Hz, 2H), 7.58 (d, J=8.4 Hz, 2H), 7.85 (d, J=8.4 Hz, 2H); $^{13}$C NMR (75 MHz, CD$_3$OD) δ 25.78, 26.07, 58.80, 70.74, 71.54, 76.68, 78.95, 84.60, 108.28, 114.21, 126.09, 127.55, 132.12, 133.82, 150.24, 167.83, 168.07; HRMS: calculated for C$_{22}$H$_{21}$N$_3$O$_4$H$^+$ 392.1610. found 392.1607 [M+H]$^+$.

Example 28

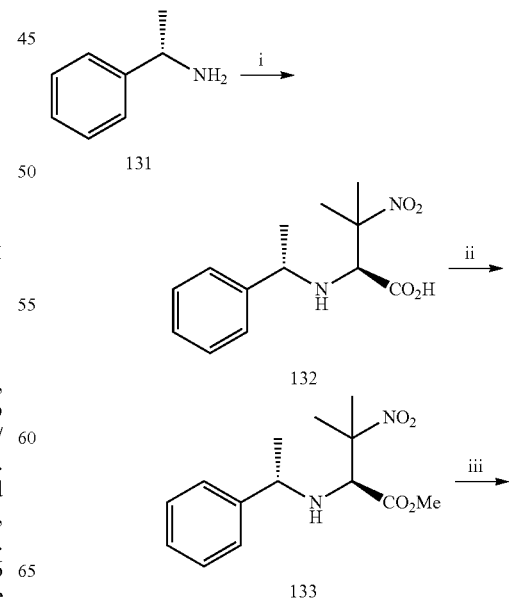

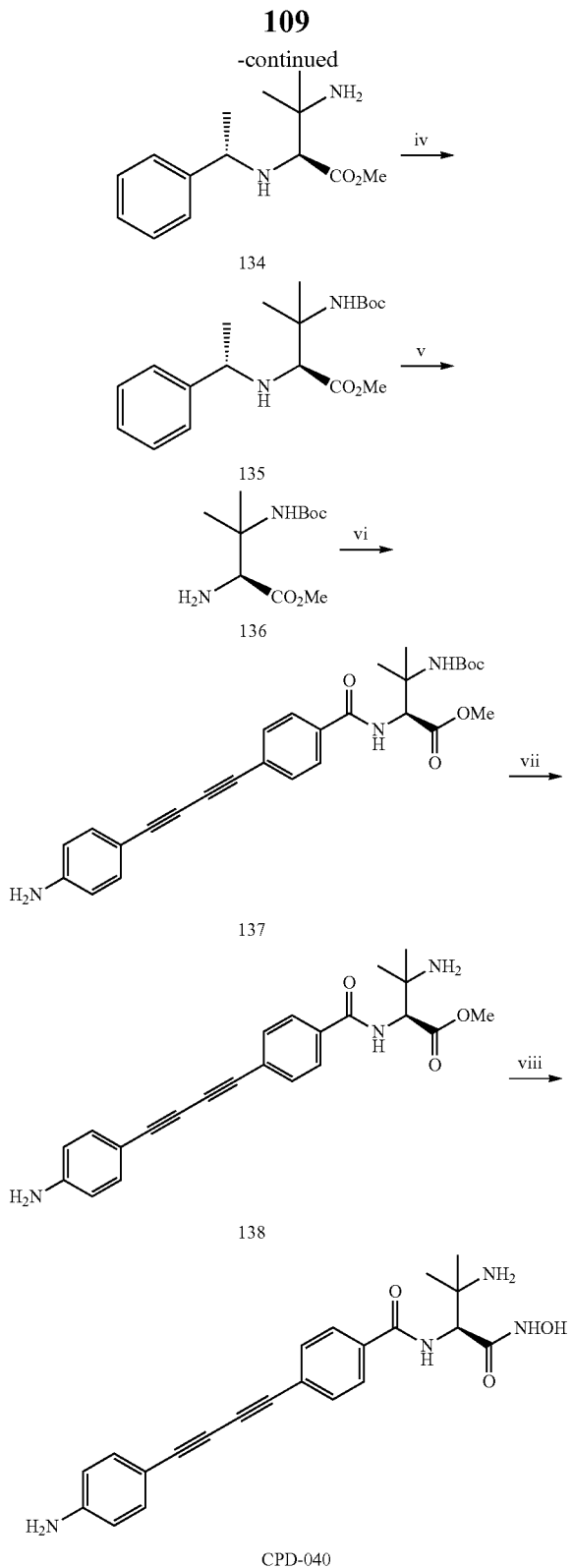

(i) 2-nitropropane, glyoxylic acid, KOH, 35-45° C., 3 h, 50%. (ii) MeI, C$_{s2}$CO$_3$, 0° C., 1 h, then room temperature 12 h, 92%. (iii) Zn, AcOH, 0° C., 2 h then room temperature, 16 h, 68%. (iv) (Boc)$_2$O, DIEA, THF, room temperature 16 h, 88%. (v) H$_2$, Pd/C, room temperature, 2 h, 90%. (vi) EDC.HCl, HOBt, DIEA, DMF, 6, 0° C., 1 h, then room temperature 14 h, 79%. (vii) TFA, DCM, 0° C., 2 h, then room temperature, 10 h, 90%. (viii) Hydroxylamine hydrochloride, 25% NaOMe/MeOH, THF, 0° C., 2 h, then room temperature, 68%.

(2S)-3-methyl-3-nitro-2-{[(1'S)-1'-phenylethyl]amino}butanoic acid (132): The 2-nitropropane (18.5 mL, 0.206 mmol, 1.02 equiv) and water (200 mL) are placed under argon in a 500 mL flask with a stir bar with good stirring, the potassium hydroxide (13.60 g, 0.24 mmol, and 1.20 equiv) is added all at once. The flask is placed in a regulated oil bath heated to 45° C. The (S)-(−)-α-methybenzylamine 131 (25 g, 0.206 mmol, 1.02 equiv) is added very quickly (very fast CO$_2$ absorption). The reaction mixture is maintained at 44-46° C. and stirred swiftly as the glyoxylic acid (50% aq, 18.60 g, 0.202 mmol) is added slowly dropwise (60 min, slowest for the last one-third) via a syringe. The reaction mixture became cloudy, then clear, and when the solid began forming again the addition is slowed down. After completion of the addition, the reaction is stirred for an additional 3 h under argon at 35° C., and stirred swiftly as 3M aq hydrochloric acid (152 mL, 0.46 mmol) is added dropwise (over 30 min). The resulting thick off-white suspension is stirred for overnight (12 h) at room temperature. The cooled suspension is filtered with suction filtration, and the filter cake is rinsed with diluted aqueous HCl (0.2M, 0.5 L), water (0.5 L) and diethyl ether (0.125 L). The solid in the filter cake is dried by suction, and then dried under high vacuum for 3 h at 50° C. to get a slightly off-white power (27 g, 50% yield).

Purification of 3-methyl-3-nitro-(2(S)-(1(S)-phenylethylamino))-butyric acid 132. 3M HCl (63 mL), water (0.72 L) and acetic acid (88 ml) is placed in an Erlenmyer flask and stirred well as it as immersed in a 60° C. bath and warmed to 40-50° C. (internal). When the solution is up to the temperature, dissolved 3-methyl-3-nitro-(2(s)-(1(s)-phenylethyl-amino))-butyric acid in the stirred warm DMSO solution (50° C., dry, 40 mL) and added 25 mL of acetic acid to form a clear solution, then added the warm DMSO solution to the Erlenmeyer at an even dropwise rat. The suspension is then filtered through paper by suction and ethyl ether (125 mL). The filter cake is then suction to compact "dryness" over 30 min. The solids then transferred to room temperature and dried under full vacuum for 12 hours (85% yield).

Second purification of 3-methyl-3-nitro-(2(S)-(1(S)-phenylethyl-amino))-butyric acid 131 (Procedure is similar to the first precipitation above). A solution of diluted aq hydrochloric acid (3.0M, 40 mL), water (500 mL) and acetic acid (80 mL) is placed in a 1 L Erlenmeyer flask and stirred well as it is immersed in a 45-60° C. bath and warmed to 40° C. (internal). Another flask, to a solution of the 3-methyl-3-nitro-(2(s)-(1(s)-phenylethyl-amino))-butyric acid (5.10 g) in anhydrous DMSO (40 mL) is added acetic acid. The mixture is then warmed to 50° C. and added dropwise to the Erlenmeyer flask. Upon complete addition, the suspension is stirred and placed in a 0° C. bath to cool room temperature. The suspension is then filtered through paper by suction and rinsed with dilute aq hydrochloric acid (0.2M, 500 mL), water (1 L), isopropanol (40 mL) and diethyl ether (125 mL). The filter cake is then suctioned to compact "dryness" over 30 min. The filtered is then transferred to room temperature vacuum and dried under full vacuum for 14 hours. After that, the solids is dried at 50° C. under high vacuum for 3 hours to yield 131 as white powder (5.00 g, 98%). $^1$H NMR (300 MHz, DMSO-d$_6$) δ 1.21 (d, J=6.3 Hz, 3H), 1.43 (s, 3H), 1.45 (s, 3H), 3.62 (q, J=12.6 Hz, 1H), 7.17-7.31 (m, 5H); $^{13}$C NMR (75 MHz, DMSO-d$_6$) δ 22.48, 24.05, 25.60, 57.14, 65.50, 98.69, 127.62, 127.81, 128.91, 144.85, 173.06; MS (ESI, positive): m/z 267 [M+H$^+$].

Methyl (2S)-3-methyl-3-nitro-2-{[(1'S)-1'-phenylethyl]amino}butanoate (133): In an oven-dried 100 mL flask with a stir bar is charged with 131 (3.00 g, 11.3 mmol) and cesium carbonate (3.85 g, 11.82 mmol, 1.05 equiv) under argon with rapid string. Dimethylformamide (10 mL) is added rapidly and stirred for 10 min, with aid of sonication for 5 min. After the reaction mixture is cooled to 0° C., iodomethane (0.81 g, 13.00 mmol, 1.15 equiv) is added dropwise over 15 min. The reaction mixture is stirred under argon and at 0° C. for 1 h then is allowed to warm to ambient temperature with stirring is continued for 12 h. The reaction is washed with EtOAc and water into a separatory funnel containing EtOAc (100 mL), water (20 mL) and 3.0 M aq hydrochloric acid. The organic layer is separated. And the aqueous layer is adjusted pH to 7-8 and extracted with EtOAc (2×100 mL). The combined organic phases are washed with 3% Li$_2$SO$_4$ (3×30 mL), half-saturated aq NaHCO$_3$ (30 mL) and brine (30 mL) and dried over anhydrous Na$_2$SO$_4$. The solvent is concentrated to give amber oil (2.93 g, 93% yield). $^1$H NMR (300 MHz, CDCl$_3$) δ 1.33 (d, J=6.6 Hz, 3H), 1.49 (s, 3H), 1.54 (s, 3H), 2.06 (s, 1H), 3.60 (m, 1H), 3.75 (s, 3H), 7.21-7.35 (m, 5H); $^{13}$C NMR (75 MHz, CDCl$_3$) δ 22.39, 24.02, 25.12, 52.55, 57.39, 65.20, 89.33, 127.43, 127.75, 128.64, 143.67, 172.67; MS (ESI, positive): m/z 281 [M+H$^+$].

Methyl (2S)-3-amino-3-methyl-2-{[(1S)-1'-phenylethyl]amino}butanoate (134): 133 (2.83 g, 10.0 mmol) is dissolved in anhydrous THF (30 mL) and glacial acetic acid (45 mL) along with activated powdered molecular sieves 4 Å (3.4 g), and stirred mildly for 3 h under argon. The flask is then immersed in 0° C. bath and stirred well for 20 min. To the cold reaction mixture is added zinc dust (5.85 g, 90.0 mmol, 10.0 equiv). The mixture reaction is stirred at 0° C. for 2 h, and then allowed warm to ambient temperature with stirring continued for 16 h. The mixture is then diluted with THF (40 mL) and filtered through a celite pad with additional THF (100 mL) washing. The solution is rotary evaporated to yield a slightly yellow oily solid. This material is dissolved in 3:1 chloroform/isopropanol (100 mL) and 0.25 EDTA solutions at pH 10.5-11 (60 mL). Additional 4M NaOH solutions are added in portions to reach pH=10.5-11.0. The funnel contents are thoroughly shaken, and the aqueous phase separated. The organic phase is then washed with 0.25 EDTA pH=10.5-11.0 (50 mL), brine (40 mL), dried (Na$_2$SO$_4$), filtered and evaporated under reduced pressure, followed with additional heptane (3×40 mL) and evaporation to yield a light-amber oil, which is purified by CombiFlash (eluting with MeOH in DCM 0-7%) to afford 134 as colorless oil (1.763 g, 68.8% yield). $^1$H NMR (300 MHz, CDCl$_3$) δ 1.00 (s, 1H), 1.05 (s, 1H), 1.32 (d, J=6.6 Hz, 3H), 2.74 (s, 1H), 3.56 (q, J=13.2 1H), 3.71 (s, 3H), 7.21-7.30 (m, 5H); $^{13}$C NMR (75 MHz, CDCl$_3$) δ 25.68, 27.34, 27.90, 51.55, 51.81, 57.25, 68.54, 127.32, 128.58, 145.02, 176.05; MS (ESI, positive): m/z 251 [M+H$^+$].

Methyl (2S)-3-{[(tert-butoxy)carbonyl]amino}-3-methyl-2-{[(1'S)-1'-phenylethyl]amino}butanoate (135): 134 (1.70 g, 6.8 mmol) is dissolved in anhydrous THF (20 mL) under argon, and diisopropylethylamine (1.30 mL, 7.5 mmol, 1.10 equiv) is added to this solution. tert-Butylpyrocarbonate (1.78 g, 8.2 mmol, 1.20 equiv) is added. After stirring at room temperature for 16 h, the reaction mixture is dissolved in EtOAc (100 mL), and washed with water containing 1 eq HCl (0.3 M HCl, 20 mL), half saturated NaHCO$_3$ solution, 14% NH$_4$OH (30 mL), brine (50 mL), dried (Na$_2$SO$_4$), filtered and contracted under reduced pressure to yield the BOC-diamino-ester residue, which is purified by Combi-Flash (eluting with EtOAc in DCM 0-5%) to afford it as viscous oil (2.10 g, 88% yield). $^1$H NMR (300 MHz, CDCl$_3$) δ 1.27-1.37 (m, 18H), 1.99 (br s, 1H), 3.16 (br s, 1H), 3.55 (q, J=20.1 Hz, 1H), 3.73 (s, 3H), 4.93 (br s, 1H), 7.22-7.30 (m, 5H); $^{13}$C NMR (75 MHz, CDCl$_3$) δ 23.78, 24.17, 25.41, 28.59, 51.89, 54.37, 57.36, 66.07, 127.259, 127.47, 128.70, 144.72, 175.15.

Methyl (2S)-2-amino-3-{[(tert-butoxy)carbonyl]amino}-3-methyl butanoate (136): 135 (0.50 g, 1.4 mmol) is dissolved in anhydrous THF (10 mL) in 50 mL flask and placed under argon. Palladium hydroxide catalyst (0.18 g, 20 wt %) is rapidly weight and added to the flask. The flask is then filled with hydrogen and refilled. (−101 kpa). After 2 h, LC/MS showed the reaction is completed. The mixture is filtered through a celite pad, and the filtrate is condensed to dryness. The residue is purified by CombiFlash (eluting with 0-5% MeOH in DCM) to afford 34 as white solid (330 mg, 95% yield). $^1$H NMR (300 MHz, CDCl$_3$) δ 1.30 (s, 3H), 1.37 (s, 3H), 1.39 (s, 9H), 3.26 (br s, 2H), 3.71 (s, 3H), 3.87 (s, 1H), 4.95 (s, 1H); $^{13}$C NMR (75 MHz, CDCl$_3$) δ 24.15, 24.23, 28.55, 52.28, 54.77, 60.55, 79.77, 155.26, 173.41.

Methyl (2S)-2-({4'-[4'-(4'-aminophenyl)buta-1',3'-diyn-1'-yl]phenyl}formamido)-3'-{[(tert-butoxy)carbonyl]amino}-3-methylbutanoate (137). Following the procedure of 125a. 79.5% yield; $^1$H NMR (300 MHz, CD$_3$OD) δ 1.45 (m, 15H), 3.73 (s, 3H), 4.78 (d, J=6.9 Hz, 1H), 6.61 (d, J=8.1 Hz, 2H), 7.24 (d, J=8.4 Hz, 2H), 7.58 (d, J=8.1 Hz, 1H), 7.85 (d, J=8.1 Hz, 2H); $^{13}$C NMR (75 MHz, CD$_3$OD) δ 24.00, 26.13, 27.66, 51.56, 53.90, 62.09, 70.92, 76.86, 79.09, 79.48, 84.71, 108.32, 114.25, 126.14, 127.40, 132.22, 133.62, 133.88, 150.17, 157.30, 167.46, 170.89; MS (ESI, positive): m/z 490 [M+H$^+$].

Methyl (2S)-3-amino-2-({4'-[4'-(4'-aminophenyl)buta-1',3'-diyn-1'-yl]phenyl}formamido)-3-methylbutanoate (138). Following the procedure of 126a. 90.6% yield; $^1$H NMR (300 MHz, CD$_3$OD) δ 1.21 (s, 3H), 1.25 (s, 3H), 3.77 (s, 3H), 4.64 (s, 1H), 6.62 (d, J=8.7 Hz, 2H), 7.24 (d, J=8.7 Hz, 2H), 7.58 (d, J=8.4 Hz, 2H), 7.83 (d, J=8.4 Hz, 2H); $^{13}$C NMR (75 MHz, CD$_3$OD) δ 26.22, 26.71, 51.49, 52.00, 61.67, 70.72, 76.66, 78.95, 84.60, 108.25, 114.20, 126.08, 127.66, 132.07, 133.82, 150.26, 168.39, 171.48; MS (ESI, positive): m/z 390 [M+H$^+$].

CPD-040, (2S)-3-amino-2-({4'-[4'-(4'-aminophenyl)buta-1',3'-diyn-1-yl]phenyl}formamido)-N-hydroxy-3-methylbutanamide: Following the procedure of 127. 68.4% yield; $^1$H NMR (300 MHz, CD$_3$OD) δ 1.28 (s, 3H), 1.30 (s, 3H), 4.52 (s, 1H), 6.62 (d, J=8.4 Hz, 2H), 7.24 (d, J=8.4 Hz, 2H), 7.58 (d, J=8.4 Hz, 2H), 7.87 (d, J=8.1 Hz, 2H); $^{13}$C NMR (75 MHz, CD$_3$OD) δ 25.21, 25.83, 53.36, 57.58, 70.72, 76.73, 78.93, 84.65, 108.26, 114.20, 126.17, 127.67, 132.07, 133.71, 133.81, 150.25, 167.53, 168.08; HRMS: calculated for C$_{23}$H$_{22}$N$_3$O$_3$H$^+$ 391.1770. found 391.1767 [M+H]$^+$.

Example 29

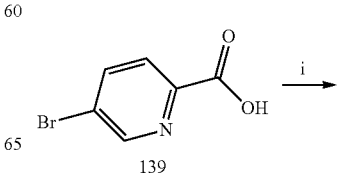

139

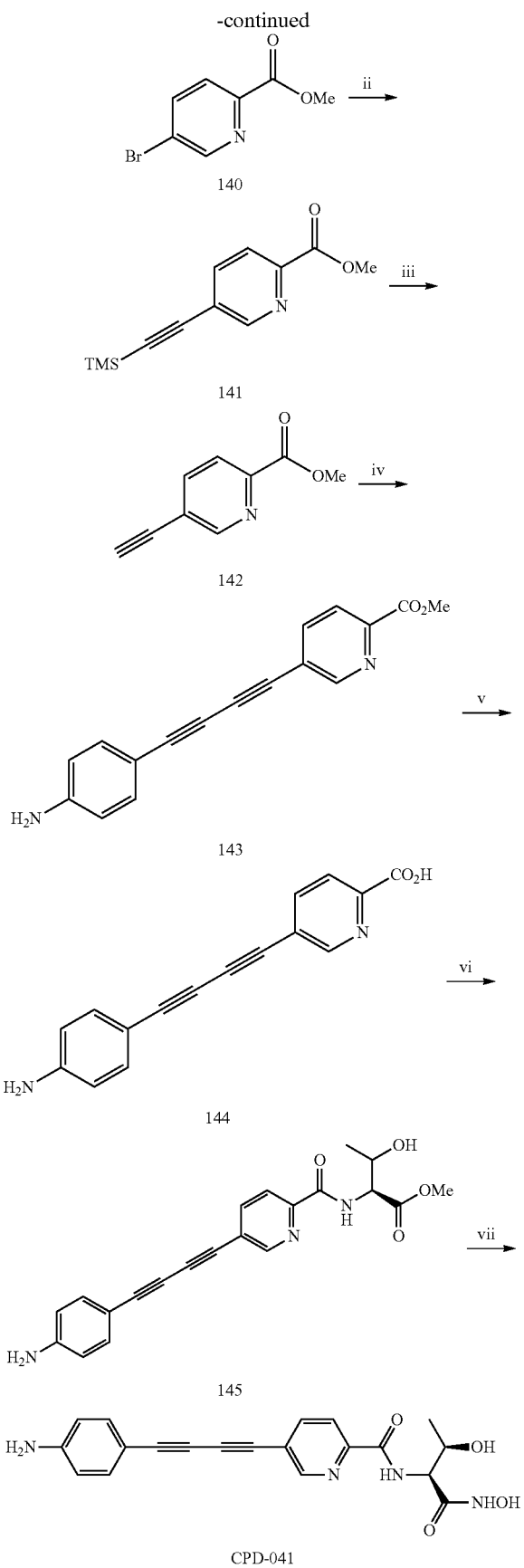

(i) (TMS)CHN$_2$, MeOH, benzene, 0° C. to room temperature, 1 h, 87%. (ii) (trimethylsily)acetylene, PdCl$_2$(PPh$_3$)$_2$, CuI, DIEA, THF, 70° C., 14 h, 95%. (iii) K$_2$CO$_3$, MeOH, room temperature, 40 min, 84%. (iv) 4-ethylnylaniline, Cu(OAc)$_2$, pyridine, MeOH, room temperature, 20 h. (v) 3N NaOH, MeOH, reflux, 40 min, 31% (from 142). (vi) EDC.HCl, HOBt, DIEA, DMF, 13, 0° C., 1 h, then room temperature, 36 h, 74%. (vii) hydroxylamine hydrochloride, 25% NaOMe/MeOH, THF, 0° C., 2 h, then room temperature, 16 h, 40%.

5-Bromopyridine-2-carboxylic acid (140): To an ice-cold solution of 139 (3.00 g, 15.0 mmol) dissolved in anhydrous MeOH (20 mL) and benzene (20 mL) is added dropwise (TMS)CHN$_2$ (2.5 ml, 5.0 mmol, 2.0 equiv), then is allowed to warm to ambient temperature with stirring is continued under argon for 1 h. The reaction is monitored by LC/MS and TLC. The resulting solution is condensed to dryness with a rotavapor, and the residue is purified by CombiFlash (eluting with 0-10% EtOAc in hexane) to give 140 as with solid (2.79 g, 87% yield). $^1$H NMR (300 MHz, CDCl$_3$) δ 3.93 (s, 3H), 7.56 (d, J=9.3 Hz, 1H), 8.10 (d, J=10.5 Hz, 1H), 8.93 (s, 1H); $^{13}$C NMR (300 MHz, CDCl$_3$) δ 52.88, 125.52, 128.28, 139.40, 147.03, 151.62, 165.23; MS (ESI, positive): m/z 490 [M+H$^+$].

Methyl 5-[2-(trimethylsilyl)ethynyl]pyridine-2-carboxylate (141): To an oven-dried round bottom flask equipped with a condenser and magnetic stir bar is added 140 (2.00 g, 9.30 mmol), bis(triphenylphosphine) palladium (II) dichloride (0.197 g, 0.28 mmol, 0.03 equiv) and copper (I) iodide (0.053 g, 0.28 mmol, 0.03 equiv). The vessel is then sealed with a rubber septum under argon, and then anhydrous THF (20 mL) and diisopropylethylamine (20 mL) is added. Finally, (trimethylsily)acetylene (1.80 mL, 13.0 mmol, 1.40 equiv) is added and the reaction mixture is heated to 70° C. in an oil bath for 14 h. The resulting yellow suspension is filtered through a celite pad, and the filtrate is condensed to dryness with a rotavapor, and the residue is treated with water (100 mL), extracted with EtOAc (3×100 mL). The combined extracts are washed with water (100 mL), brine (100 mL) and dried over anhydrous Na$_2$SO$_4$. The crude product is purified by flash chromatography (eluting with 0-10% EtOAc in hexane) to afford 141 (2.06 g, 95% yield) as white solid. It changed to brown solid in 10 min. (Caution: prevent from exposure to light!). $^1$H NMR (300 MHz, CDCl$_3$) δ 0.25 (s, 9H), 3.92 (s, 3H), 7.49 (d, J=8.7 Hz, 1H), 8.21 (d, J=10.5 Hz, 1H), 9.12 (s, 1H); $^{13}$C NMR (75 MHz, CDCl$_3$) δ 0.20, 52.72, 98.65, 103.22, 125.00, 126.96, 137.36, 146.77, 151.19, 165.44; MS (ESI, positive): m/z 224 [M+H$^+$].

Methyl 5-ethynylpyridine-2-carboxylate (142): 141 (2.00 g, 8.58 mmol) is dissolved in anhydrous MeOH (20 mL) at room temperature, and potassium carbonate (0.024 g, 0.17 mmol, 0.02 equiv) is added. The mixture is stirred for 40 min under argon at room temperature. Then the mixture reaction is evaporated in vacuum to afford the crude product, which is purified by flash chromatography (eluting with 0-10% MeOH in DCM) to afford 142 (1.61 g, 84% yield) as white solid. $^1$H NMR (300 MHz, CDCl$_3$) δ 3.30 (s, 1H), 3.92 (s, 3H), 7.52 (d, J=9.3 Hz, 1H), 8.23 (d, J=10.5 Hz, 1H), 9.13 (s, 1H); $^{13}$C NMR (75 MHz, CDCl$_3$) δ 52.79, 80.23, 82.43, 125.49, 127.20, 137.47, 146.07, 151.24, 165.31; MS (ESI, positive): m/z 162 [M+H$^+$].

Sodium 5-[4'-(4'-aminophenyl)buta-1',3'-diyn-1-yl]pyridine-2-carboxylate (144): Copper (II) acetate (1.36 g, 7.46 mmol, 2.0 equiv) is added at room temperature under stream of argon to a stirred solution of 142 (0.60 g, 3.73 mmol) and 4-ethylnylbenzenamine (2.18 g 18.63 mmol, 5.0 equiv)

dissolved in anhydrous pyridine (10 mL) and MeOH (10 mL). The reaction mixture is stirred at room temperature for 20 h. The resulting suspension is filtered, and the solid is washed with EtOAc (3×50 mL). The solid is dried under high vacuum for 12 h to afford as an orange powder, and then used for next step directly. 4N NaOH (10 mL) is added to a stirred solution of the crude methyl ester (600 mg) in MeOH (50 mL) at room temperature. Then reaction solution is heated to reflux for 40 min under argon. The reaction mixture turned clear. After all the starting material has been consumed monitored by TLC, the reaction mixture is cooled to room temperature, and the solvents are removed by evaporation under reduced pressure. The yellow solid is washed by water (3×50 mL), EtOAc (3×50 mL) to give a yellow solid (320 mg, 31% yield, for two steps), which is used for next step without future purification. $^1$H NMR (300 MHz, CD$_3$OD) δ 6.62 (d, J=8.4 Hz, 2H), 7.26 (d, J=8.7 Hz, 2H), 7.59 (d, J=9.0 Hz, 1H), 8.27 (d, J=10.2 Hz, 1H), 9.01 (s, 1H); $^{13}$C NMR (75 MHz, CD$_3$OD) δ 70.50, 75.996, 78.48, 85.59, 107.59, 114.17, 127.44, 133.09, 134.06, 137.62, 142.94, 150.69, 170.58; MS (ESI, positive): m/z 263 [M+H$^+$].

Methyl (2S,3R)-2-({5'-[4'-(4'-aminophenyl)buta-1',3'-diyn-1'-yl]pyridin-2'-yl}formamido)-3-hydroxybutanoate (145): Following the procedure of 125a. 74.5% yield; $^1$H NMR (300 MHz, CD$_3$OD) δ 1.25 (d, J=6.3 Hz, 3H), 3.78 (s, 3H), 4.37-4.41 (m, 1H), 4.70 (m, 1H), 6.62 (d, J=8.7 Hz, 2H), 7.28 (d, J=8.7 Hz, 2H), 7.69 (d, J=9.0 Hz, 1H), 8.26 (d, J=10.2 Hz, 1H), 8.99 (s, 1H); $^{13}$C NMR (75 MHz, CD$_3$OD) δ 19.24, 51.77, 58.95, 67.23, 70.40, 77.10, 78.18, 86.45, 107.30, 114.13, 127.66, 129.13, 134.16, 136.21, 144.82, 148.89, 150.79, 166.52, 171.18; MS (ESI, positive): m/z 378 [M+H$^+$].

CPD-041, (2S,3R)-2-({5-[4-(4-aminophenyl)buta-1,3-diyn-1-yl]pyridin-2-yl}formamido)-N,3-dihydroxybutanamide: Following the procedure of 127. 40.0% yield; $^1$H NMR (300 MHz, CDCl$_3$) δ 1.24 (d, J=6.3 Hz, 3H), 4.18-4.22 (m, 1H), 4.43 (d, J=5.4 Hz 1H), 6.62 (d, J=8.7 Hz, 2H), 7.28 (d, J=8.7 Hz, 2H), 7.68 (d, J=9.0 Hz, 1H), 8.27 (d, J=10.5 Hz, 1H), 8.99 (s, 1H); $^{13}$C NMR (75 MHz, CDCl$_3$) δ 19.13, 58.05, 67.13, 70.38, 77.06, 78.17, 86.42, 107.28, 114.12, 127.59, 129.15, 134.15, 136.22, 144.73, 148.96, 150.81, 166.15, 168.19; HRMS: calculated for C$_{20}$H$_{18}$N$_4$O$_4$ 378.1328. found 378.1328 M$^+$.

Example 30

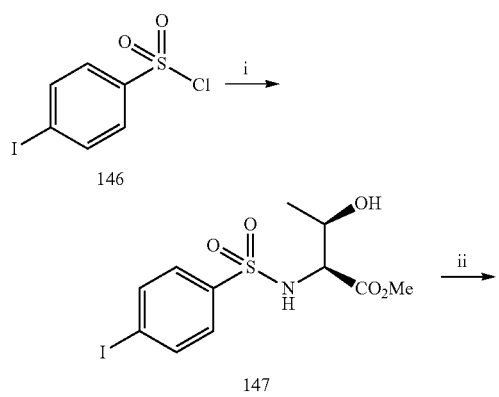

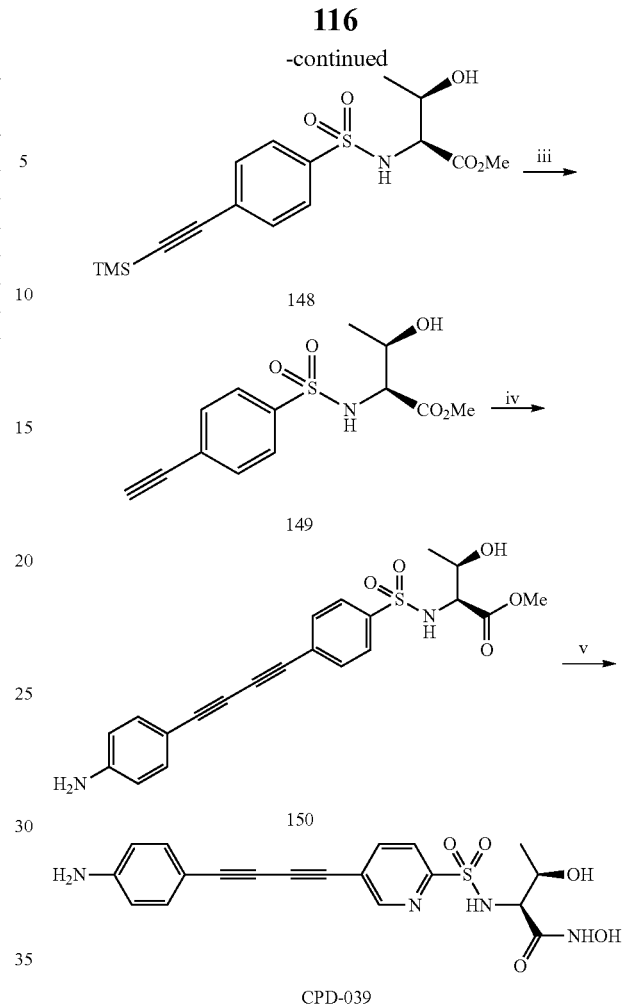

(i) L-threonine methyl ester, TEA, DCM, 0° C., 1 h, 91%.
(ii) PdCl$_2$(PPh$_3$)$_2$, CuI, TEA, THF, room temperature, 12 h, 87%. (iii) K$_2$CO$_3$, MeOH, room temperature, 40 min, 88%.
(iv) Cu(OAc)$_2$, pyrindine, MeOH, room temperature, 24 h, 58%. (v) hydroxylamine hydrochloride, NaOMe, THF, MeOH, 0° C., 2 h, then room temperature, 18 h, 56%.

Methyl (2S,3R)-3-hydroxy-2-[(4-iodobenzene)sulfonamido]butanoate (147): To an ice-cold solution of pipsylchloride (5.00 g, 16.5 mmol) and L-threonine methyl ester hydrochloride (4.20 g, 24.7 mmol, 1.5 equiv) dissolved in anhydrous DCM (50 mL), is added dropwise triethylamine (6.8 mL, 29.6 mmol, 3.0 equiv). After 1 h, TLC showed the reaction is completed. The reaction mixture is diluted with DCM (150 mL), and washed with 1 N HCl (30 mL), brine (30 mL) and dried over anhydrous Na$_2$SO$_4$. The crude product is purified by CombiFlash (eluting with 0-70% EtOAc in hexane) to give 147 as white solid (6.00 g, 91% yield). $^1$H NMR (300 MHz, CDCl$_3$) δ 1.22 (d, J=6.3 Hz, 3H), 2.26 (d, J=5.4 Hz, 1H), 3.54 (s, 3H), 3.83 (d, J=6.5 Hz, 1H), 4.17-4.22 (m, 1H), 5.71 (d, J=9.3 Hz, 1H), 7.52 (d, J=6.9 Hz, 2H), 7.85 (d, J=9.9 Hz, 2H); $^{13}$C NMR (75 MHz, CDCl$_3$) δ 20.13, 52.99, 61.14, 68.53, 100.46, 128.81, 138.48, 139.75, 170.82; MS (ESI, positive): m/z 400 [M+H$^+$].

Methyl (2S,3R)-3-hydroxy-2-({4'-[2'-(trimethylsily)ethynyl]benzene}sulfonamido)butanoate (148): 86.6% yield; $^1$H NMR (300 MHz, CDCl$_3$) δ 0.25 (s, 9H), 1.24 (d, J=6.3 Hz, 3H), 2.64 (d, J=5.7 Hz, 1H), 3.51 (s, 3H), 3.82 (d J=4.9 Hz, 1H), 4.15-4.20 (m, 1H), 5.91 (d, J=9.0 Hz, 1H), 7.54 (d, J=8.4 Hz, 2H), 7.76 (d, J=8.1 Hz, 2H); $^{13}$C NMR (75 MHz, CDCl$_3$) δ 0.02, 20.06, 52.94, 61.22, 68.52, 98.82, 103.312, 127.27, 128.14, 132.53, 139.44, 170.87; MS (ESI, positive): m/z 370 [M+H]$^+$.

Methyl (2S,3R)-2-[(4'-ethynylbenzene)sulfonamido]-3-hydroxybutanoate (149): 88.2% yield; $^1$H NMR (300 MHz, CDCl$_3$) δ 1.27 (d, J=7.2 Hz, 3H), 2.39 (d, J=5.1 Hz, 1H), 3.26 (s, 1H), 3.53 (s, 3H), 3.85 (d, J=6.3 Hz, 1H), 4.17-4.21 (m, 1H), 5.78 (d, J=8.4 Hz, 1H), 7.59 (d, J=7.8 Hz, 2H), 7.80 (d, J=7.8 Hz, 2H); $^{13}$C NMR (75 MHz, CDCl$_3$) δ 20.10, 52.94, 61.18, 68.54, 81.05, 82.16, 127.16, 127.38, 132.80, 139.97, 170.84; MS (ESI, positive): m/z 298 [M+H]$^+$.

Methyl (2S,3R)-2-({4'-[4'-(4'-aminophenyl)buta-1',3'-diyn-1-yl]benzene}sulfonamido)-3-hydroxybutanoate (150): 58% yield; $^1$H NMR (300 MHz, CDCl$_3$) δ 1.26 (d, J=6.3 Hz, 3H), 2.48 (br s, 1H), 3.52 (s, 3H), 3.84 (s, J=6.3 Hz, 1H), 3.99 (br s, 2H), 4.15-4.19 (m, 1H), 5.82 (d, J=7.8 Hz, 1H), 6.59 (d, J=7.8 Hz, 2H), 7.33 (d, J=7.8 Hz, 2H), 7.57 (d, J=7.8 Hz, 2H), 7.77 (d, J=7.8 Hz); $^{13}$C NMR (75 MHz, CDCl$_3$) δ 20.10, 52.96, 61.21, 68.52, 71.83, 78.47, 79.07, 85.34, 110.09, 114.89, 127.40, 132.87, 134.50, 139.55, 148.25, 170.86; MS (ESI, positive): m/z 413 [M+H]$^+$.

CPD-039, (2S,3R)-2-({4'-[4'-(4'-aminophenyl)buta-1',3'-diyn-1'-yl]benzene}sulfonamido)-N,3-dihydroxybutanamide: 56.4% yield; $^1$H NMR (300 MHz, CD$_3$OD) δ 1.06 (d, J=6.3 Hz, 3H), 3.56 (d, J=5.1 Hz, 1H), 3.89-3.93 (m, 1H), 6.62 (d, J=8.7 Hz, 2H), 7.25 (d, J=9.0 Hz, 2H), 7.61 (d, J=8.7 Hz, 2H), 7.83 (d, J=8.7 Hz, 2H); $^{13}$C NMR (75 MHz, CD$_3$OD) δ 18.47, 60.54, 67.80, 70.62, 77.32, 78.48, 85.09, 108.06, 114.21, 126.94, 127.15, 132.48, 133.89, 140.59, 150.36, 167.50; HRMS: calculated for C$_{20}$H$_{19}$N$_3$O$_5$SH$^+$ 414.1124. found 414.1117 [M+H]$^+$.

Example 31

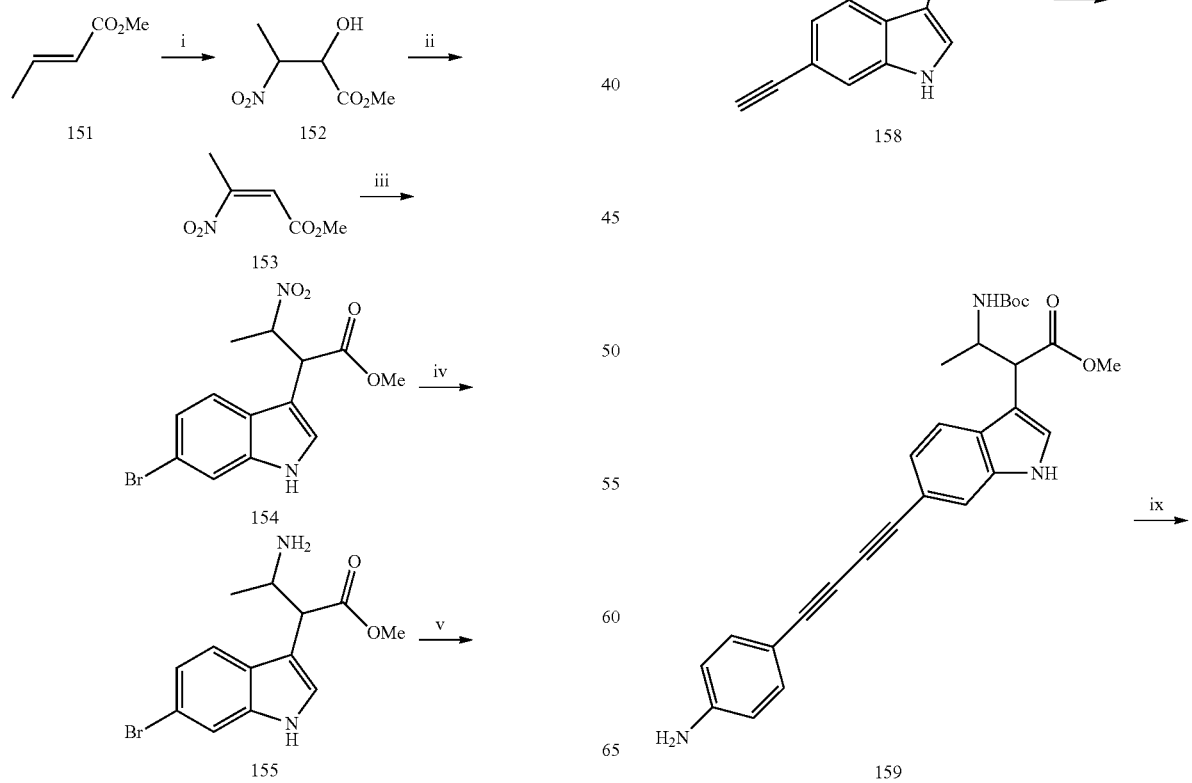

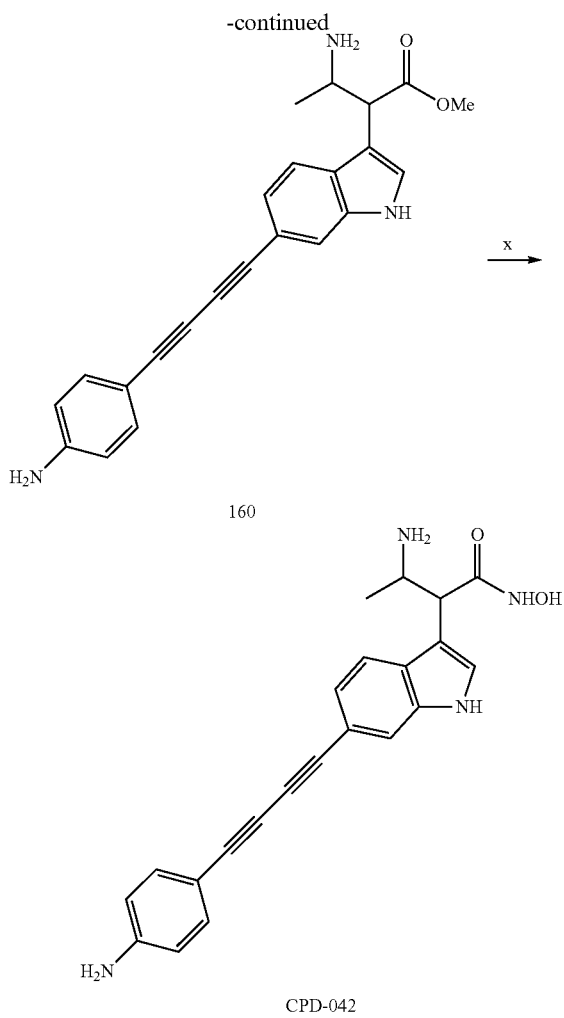

CPD-042

(i) CAN, CH₃CN, NaNO₂, 0° C. to room temperature, 16 h, 42%. (ii) MsCl, TEA, DCM, 40° C., 4 h, 77%. (iii) 6-Brominidole, basic Al, 60° C., 5 h, 70%. (iv) Zn, AcOH, 4 Å, 0° C., 2 h, then room temperature, 15 h, 92%. (v) (Boc)₂O, DIEA, THF, room temperature, 16 h, 94%. (vi) PdCl₂(PPh₃)₂, CuI, TEA, 70° C., 16 h, 88%. (vii) K₂CO₃, MeOH, room temperature, 15 h, 85%. (viii) Cu(OAc)₂, pyridine/MeOH, 4-ethynylbenzenamine, room temperature, 24 h, 50%. (ix) TFA, DCM, 0° C., 2 h, and then room temperature 14 h, 72%. (x) hydroxylamine hydrochloride, NaOMe, THF, MeOH, 0° C., 2 h, then room temperature, 48 h, 26%.

Methyl 2-hydroxy-3-nitrobutanoate (152): To a stirred solution of methyl (2E)-but-2-enoate (1.60 g, 16.4 mmol) in anhydrous CH₃CN (80 mL) are added CAN (26.30 g, 48.0 mmol, 3.0 equiv) and NaNO₂ (1.13 g, 48.0 mmol, 3.0 equiv) at 0° C. under argon. The reaction mixture is vigorously stirred at room temperature for 18 h. The resulting yellow suspension is condensed to dryness with a rotavapor, and the residue is treated with water (100 mL). The mixture is extracted with EtOAc (3×70 mL). The combined extracts are washed with saturated NaHCO₃ (50 mL), brine (50 mL) and dried (anhydrous Na₂SO₄). The crude product is purified by CombiFlash (eluting with 10-30% EtOAc in hexane) to give 152 (1.10 g, 42% yield) as colorless liquid. ¹H NMR (300 MHz, CDCl₃) δ 1.20 (d, J=6.0 Hz, 3H), 3.84 (br s, 1H), 3.85 (br s, 3H), 5.47-5.16 (m, 2H); ¹³C NMR (75 MHz, CDCl₃) δ 11.81, 11.93, 53.82, 53.96, 87.05, 87.11, 87.77, 87.82, 163.14 163.23; MS (ESI, positive): m/z 186 [M+Na]⁺.

Methyl (2Z)-3-nitrobut-2-enoate (153): To a stirred solution of nitro alcohol 152 (2.50 g, 15.3 mmol) in anhydrous CH₂Cl₂ (20 mL) are added MeSO₂Cl (3.19 mL, 45.9 mmol, 3.0 equiv), triethylamine (6.38 mL, 45.9 mmol, 3.0 equiv) at 40° C. in under argon for 4 h. After the reaction is completed (monitored by LC/MS), the mixture is poured into ice water and extracted with CH₂Cl₂ (3×70 mL). The combined organic layers are washed with water (50 mL), brine (50 mL) and dried (anhydrous Na₂SO₄). Evaporation of the solvent (200 torr, 30° C.) gives the crude product, which is purified by CombiFlash (eluting with 0-7% EtOAc in hexane) to afford 153 (1.70 g, 77% yield) as green liquid. ¹H NMR (300 MHz, CDCl₃) δ 2.54 (s, 3H), 3.79 (s, 3H), 7.01 (s, 1H); ¹³C NMR (75 MHz, CDCl₃) δ 14.11, 52.71, 121.07, 160.30, 164.75; MS (ESI, positive): m/z 146 [M+H⁺].

Methyl 2-(6'-bromo-1'H-indol-3'-yl)-3-nitrobutanoate (154): To a mixture of 6-brominidole (1.00 g, 5.10 mmol) and nitroalkene 153 (1.70 g, 11.72 mmol, 1.4 equiv) is added activated basic alumina (6.12 g) at room temperature under argon. The reaction mixture is warm to 60° C. for 5 h. The result solid is directly loaded into silica gel column and purified by CombiFlash (eluting with 10-30% EtOAc in hexane) to afford 154 (1.20 g, 70% yield) as brown foam. ¹H NMR (300 MHz, CDCl₃) δ 1.41 (d, J=7.2 Hz, 2H), 1.72 (d, J=6.6 Hz, 1H), 3.66 (s, 2H), 3.71 (s, 1H), 4.46 (q, J=23.4 Hz, 1H), 5.28-5.34 (m, 1H), 7.13 (d, J=2.7 Hz, 1H), 7.21-7.27 (m, 1H), 7.43-7.53 (m, 2H), 8.62 (d, J=34.2 Hz, 1H); ¹³C NMR (75 MHz, CDCl₃) δ 18.42, 47.03, 47.71, 53.01, 83.42, 85.03, 108.08, 108.52, 114.78. 114.97, 116.37, 116.63, 120.25, 123.82, 124.01, 124.70, 125.02, 137.06, 137.32, 171.05, 172.13.

Methyl 3-amino-2-(6-bromo-1H-indol-3-yl)butanoate (155): Following the procedure of 134: 92% yield; ¹H NMR (300 MHz, CDCl₃) δ 1.02 (d, J=6.3 Hz, 2H), 1.20 (d, J=4.8 Hz, 1H), 1.51 (br s, 2H), 3.68 (s, 2H), 3.68 (s, 1H), 7.14-7.26 (m, 2H), 7.47-7.59 (m, 2H), 8.94 (d, J=33.3 Hz, 1H); ¹³C NMR (75 MHz, CDCl₃) δ 21.79, 22.12, 49.48, 49.90, 52.00, 52.16, 52.32, 111.02, 112.14, 114.47, 115.97, 120.67, 120.83, 123.26, 123.38, 123.63, 124.27, 125.81, 126.17, 137.18, 174.16, 174.43.

Methyl 2-(6'-bromo-1'H-indol-3'-yl)-3'-{[(tert-butoxy)carbonyl]amino}butanoate (156): Following the procedure of 135.94% yield; ¹H NMR (300 MHz, CDCl₃) δ 1.18 (q, J=20.1 Hz, 3H), 1.35 (d, J=33.3 Hz, 9H), 3.69 (d, J=4.8 Hz, 3H), 4.06 (d, J=6.0 Hz, 1H), 4.30-4.37 (m, 1H), 4.69 (br s, 1H), 5.04 (d, J=9.0 Hz, 1H), 7.18 (t, J=21.0 Hz, 2H), 7.49 (t, J=18.3 Hz, 2H), 8.87 (d, J=12.6 Hz, 1H); ¹³C NMR (75 MHz, CDCl₃) δ 19.43, 28.57, 48.18, 49.16, 52.29, 79.73, 110.57, 114.53, 115.82, 120.42, 123.21, 124.27, 126.10, 137.02, 155.55, 173.69.

Methyl 3-{[(tert-butoxy)carbonyl]amino}-2-{6'-[2'-(trimethylsilyl)ethynyl]-1'H-indol-3'-yl}butanoate (157): Following the procedure of 141.88% yield; ¹H NMR (300 MHz, CDCl₃) δ 0.25 (s, 9H), 1.18 (m, 3H), 1.37 (d, J=19.2 Hz, 9H), 3.66 (d, J=3.0 Hz, 3H), 4.07 (d, J=2.7 Hz, 1H), 4.29-4.35 (m, 1H), 5.05 (d, J=9.3 Hz, 1H), 7.19-7.26 (m, 2H), 7.49-7.55 (m, 2H), 9.10 (d, J=7.2 Hz, 1H); ¹³C NMR (75 MHz, CDCl₃) δ 0.37, 19.26, 28.52, 48.15, 49.14, 52.24, 79.69, 92.47, 107.09, 110.44, 115.65, 116.38, 118.93, 123.83, 125.50, 125.69, 127.51, 135.68, 155.57, 173.36, 173.77; MS (ESI, positive): m/z 451 [M+H⁺].

Methyl 3-{[(tert-butoxy)carbonyl]amino}-2-(6'-ethynyl-1'H-indol-3'-yl)butanoate (158): Following the procedure of 142. 85.0% yield; ¹H NMR (300 MHz, CDCl₃) δ 1.17 (q, J=27.6 Hz, 3H), 1.37 (d, J=20.4 Hz, 9H), 3.04 (s, 1H), 3.66

(d, J=3.6 Hz, 3H), 4.01 (d, J=7.2 Hz, 1H), 4.30-4.36 (m, 1H), 5.09 (d, J=9.3 Hz, 1H), 7.23 (t, J=19.8 Hz, 2H), 7.49 (s, 1H), 7.55 (t, J=18.3 Hz, 1H), 9.22 (d, J=11.1 Hz, 1H); $^{13}$C NMR (75 MHz, CDCl$_3$) δ 19.32, 28.50, 48.25, 52.26, 75.95, 79.71, 85.45, 110.44, 115.25, 115.89, 119.08, 123.80, 125.62, 125.79, 127.65, 135.70, 155.63, 173.38, 173.77; MS (ESI, positive): m/z 335 [M+H$^+$].

Methyl 2-{6'-[4'-(4'-aminophenyl)buta-1',3'-diyn-1'-yl]-1'H-indol-3'-yl}-3'-{[(tert-butoxy)carbonyl]amino}butanoate (159): Following the procedure of 143. 50.3% yield; $^1$H NMR (300 MHz, CDCl$_3$) δ 1.18 (q, J=21.0 Hz, 3H), 1.38 (d, J=18.0 Hz, 9H), 3.69 (d, J=3.3 Hz, 3H), 3.91 (br s, 2H), 4.10 (d, J=5.1 Hz, 1H), 4.29-4.34 (m, 1H), 5.00 (d, J=9.3 Hz, 1H), 6.58 (d, J=7.8 Hz, 2H), 7.24-7.27 (m, 2H), 7.33 (d, J=7.8 Hz, 2H), 7.53 (s, 1H), 7.58 (t, J=11.1 Hz, 1H), 8.80 (d, J=11.7 Hz, 1H); $^{13}$C NMR (75 MHz, CDCl$_3$) δ 19.35, 28.52, 48.07, 49.16, 52.32, 72.70, 73.41, 79.74, 82.55, 82.81, 110.87, 111.07, 114.92, 115.34, 116.15, 119.24, 124.26, 125.81, 127.89, 134.24, 135.62, 147.72, 155.72, 155.72, 155.53, 173.26, 173.67; MS (ESI, positive): m/z 472 [M+H$^+$].

Methyl 3-amino-2-{6'-[4'-(4'-aminophenyl)buta-1',3'-diyn-1'-yl]-1'H-indol-3'-yl}butanoate (160): Following the procedure of 126c. 72.6% yield; $^1$H NMR (300 MHz, CDCl$_3$) δ 1.02 (d, J=6.3 Hz, 2H), 1.19 (d, J=6.0 Hz, 1H), 1.61 (br s, 2 Hz), 3.66 (d, J=6.6 Hz, 3H), 6.58 (d, J=8.4 Hz, 2H), 7.27-7.25 (m, 2H), 7.32 (d, J=6.9 Hz, 2H), 7.52 (d, J=4.2 Hz, 1H), 7.63 (q, J=20.7 Hz, 1H), 8.77 (s, 0.6H), 8.88 (s, 0.4H); $^{13}$C NMR (75 MHz, CDCl$_3$) δ 21.77, 22.08, 49.57, 49.99, 51.91, 52.17, 72.68, 73.47, 82.57, 82.70, 111.07, 111.40, 112.53, 114.90, 115.50, 119.46, 119.60, 124.30, 124.35, 125.10, 125.74, 127.52, 127.90, 134.25, 135.78, 147.71, 174.14, 174.42; MS (ESI, positive): m/z 765 [2M+Na]$^+$.

CPD-042, 3-amino-2-{6'-[4'-(4'-aminophenyl)buta-1',3'-diyn-1'-yl]-1'H-indol-3'-yl}-N-hydroxybutanamide: Following the procedure of 127.26% yield; $^1$H NMR (300 MHz, CD$_3$OD) δ 1.28 (d, J=6.0 Hz, 2H), 1.39 (d, J=6.3 Hz, 1H), 3.86-3.95 (m, 2H), 6.62 (d, J=8.4 Hz, 2H), 7.17-7.18 (m, 1H), 7.23 (d, J=8.7 Hz, 2H), 7.48 (d, J=6.3 Hz, 1H), 7.44 (s, 0.33H), 7.51 (s, 0.67H), 7.57 (s, 1H), 7.64 (d, J=8.4 Hz, 0.33H), 7.76 (d, J=8.4 Hz, 0.67H); $^{13}$C NMR (75 MHz, CD$_3$OD) δ 16.84, 29.56, 49.53. 71.37, 72.79, 81.59, 82.27, 107.89, 109.22, 112.14, 114.32, 115.88, 118.60, 119.08, 123.44, 126.84, 127.36, 127.54, 133.55, 136.48, 149.71, 169.59; HRMS: calculated for O$_{22}$H$_{20}$N$_4$O$_2$ 372.1586. found 372.1584 M$^+$.

Example 32

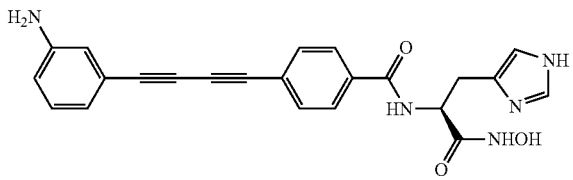

CPD-015, (2S)-2-({4'-[4'-(3'-aminophenyl)buta-1',3'-diyn-1'-yl]phenyl}formamido)-N-hydroxy-3'-(1'H-imidazol-4'-yl)propanamide Followed the procedure of CPD-012: Methyl (2S)-2-({4-[4-(3-aminophenyl)buta-1,3-diyn-1-yl]phenyl}formamido)-3-(1H-imidazol-4-yl)propanoate. 19.4% yield; $^1$H NMR (300 MHz, CD$_3$OD) δ 3.12 (q, 2H, J=20.7 Hz), 3.71 (s, 3H), 4.84 (q, 1H, J=14.4 Hz), 6.73-6.76 (m, 1H), 6.83-6.84 (m, 2H), 7.07 (t, J=16.2 Hz, 1H), 7.50-7.58 (m, 3H), 7.77 (q, J=14.7 Hz 3H) 7.87 (s, 1H); $^{13}$C NMR (75 MHz, CD$_3$OD) δ 28.75, 51.75, 53.60, 71.92, 75.82, 78.29, 79.59, 80.13, 83.34, 116.76, 118.19, 121.81, 125.41, 127.54, 129.23, 131.93, 132.31, 133.86, 134.19, 148.17, 167.92, 172.28; MS (ESI, positive): m/z 413 [M+H]$^+$.

CPD-015, (2S)-2-({4'-[4'-(3'-aminophenyl)buta-1',3'-diyn-1'-yl]phenyl}formamido)-N-hydroxy-3-(1'H-imidazol-4'-yl)propanamide: 75.0% yield; $^1$H NMR (300 MHz, CD$_3$OD) δ 3.12 (q, J=18.6 Hz 2H), 4.21 (d, J=6.9 Hz, 1H), 4.74 (t, J=13.8 Hz, 1H), 6.73-6.82 (m, 1H), 6.82-6.84 (m, 2H), 6.92 (br s, 1H), 7.08 (t, J=15.6 Hz, 1H) 7.55-7.62 (m, 3H), 7.69-7.72 (m, 1H), 7.78 (t, J=15.6 Hz, 1H); $^{13}$C NMR (75 MHz, CD$_3$OD) δ 29.42, 52.22, 67.95, 71.82, 75.73, 79.53, 83.30, 116.74, 118.16, 121.72, 125.35, 127.61, 128.70, 129.19, 131.25, 131.85, 132.23, 134.26, 148.23, 167.72. 169.29; HRMS: calculated for C$_{23}$H$_{18}$N$_5$O$_3$H$^+$ 414.1566. found 414.1571 [M+H]$^+$.

Example 33

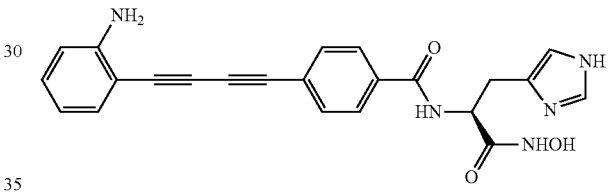

CPD-016, (2S)-2-({4'-[4'-(2'-aminophenyl)buta-1',3'-diyn-1'-yl]phenyl}formamido)-N-hydroxy-3'-(1'H-imidazol-4'-yl)propanamid Followed the procedure of CPD-013: Methyl (2S)-2-({4'-[4'-(2'-aminophenyl)buta-1',3'-diyn-1'-yl]phenyl}formamido)-3-(1H-imidazol-4-yl)propanoate. 25.8% yield; $^1$H NMR (300 MHz, CD$_3$OD) δ 3.14-3.22 (m, 2H), 3.17 (s, 3H), 4.86 (q, J=8.7 Hz, 1H), 6.59 (t, J=15.9 Hz, 1H), 6.74 (d, J=8.7 Hz, 1H), 6.90 (br s, 1H), 7.12 (t, J=13.8 Hz, 1H), 7.25 (d, J=9.3 Hz, 1H), 7.53-7.60 (m, 3H), 7.79 (d, J=8.4 Hz, 2H); $^{13}$C NMR (75 MHz, CD$_3$OD) δ 28.73, 51.70, 53.60, 73.62, 75.88, 77.79, 78.29, 80.23, 81.01, 104.99, 114.52, 117.03, 125.54, 127.53, 130.88, 132.16, 132.81, 134.12, 135.26, 151.15, 167.91, 172.25; MS (ESI, positive): m/z 413 [M+H]$^+$.

CPD-016, (2S)-2-({4'-[4'-(2'-aminophenyl)buta-1',3'-diyn-1'-yl]phenyl}formamido)-N-hydroxy-3'-(1'H-imidazol-4'-yl)propanamide: 51.0% yield, 60% pure; $^1$H NMR (300 MHz, CD$_3$OD) δ 3.09-3.15 (m, 2H), 4.74 (t, J=13.8 Hz, 1H), 6.59 (t, J=13.8 Hz, 1H), 6.74 (d, J=8.1 Hz, 1H), 6.92 (br s, 1H), 7.128 (t, J=14.1 Hz, 1H), 7.25 (d, J=6.3 Hz, 1H), 7.55-7.62 (m, 3H), 7.69-7.81 (m, 2H); $^{13}$C NMR (75 MHz, CD$_3$OD) δ 29.44, 52.17, 67.95, 75.82, 77.75, 80.19, 80.10, 104.98, 114.52, 117.01, 125.49, 127.60, 128.70, 130.87, 131.24, 132.11, 132.80, 134.15, 151.17, 167.73, 169.24; HRMS: calculated for C$_{23}$H$_{18}$N$_5$O$_3$H$^+$ 414.1566. found 414.1565 [M+H]$^+$.

Example 34

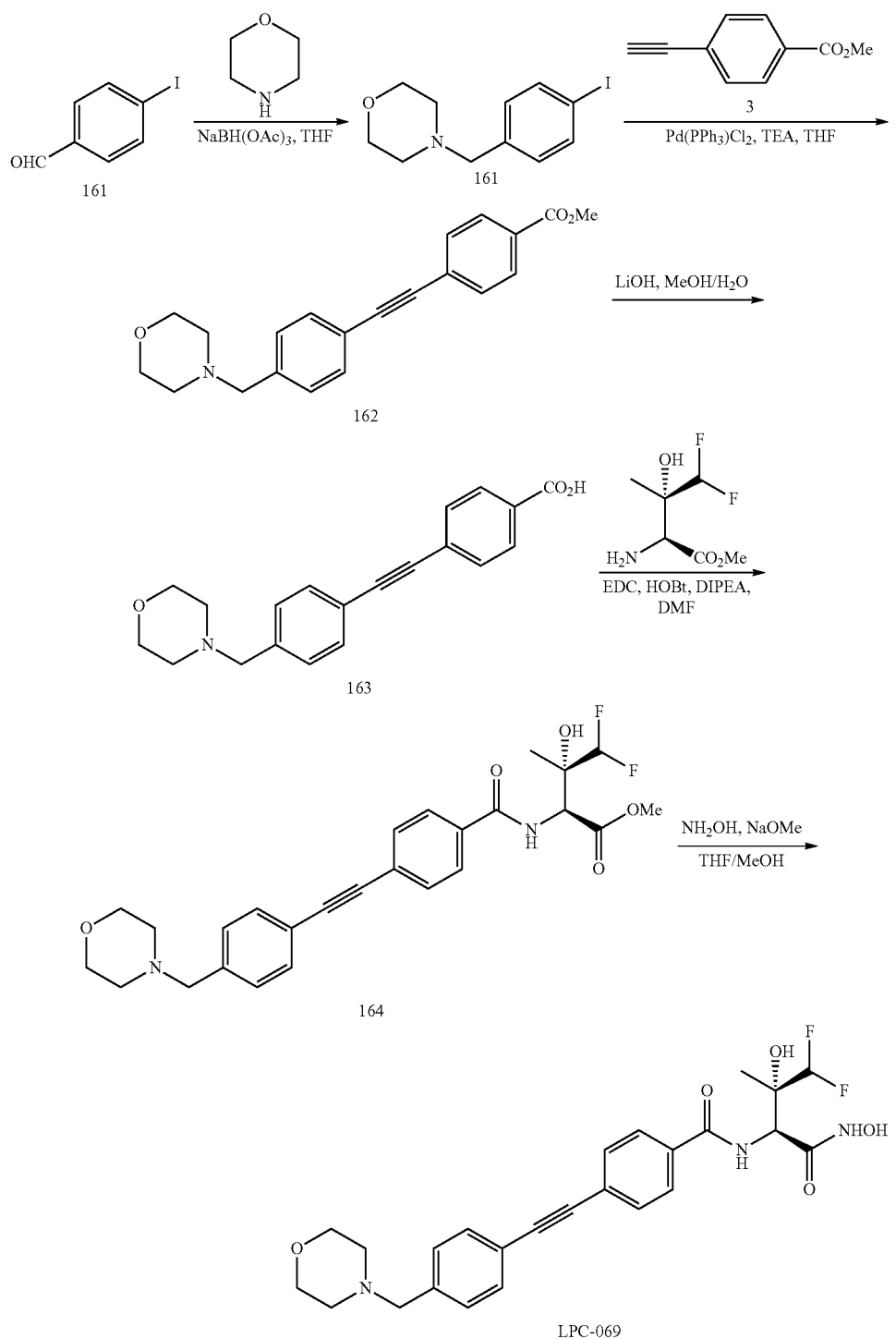

To a solution of 4-iodobenzylaldehyde (2.00, 8.6 mmol, 1.00 equiv) and morpholine (0.94 g, 10.8 mmol, 1.25 equiv) in anhydrous THF (30 mL) is added NaBH(OAc)$_3$ (2.76 g, 12.04 mmol, 1.40 equiv) at 0° C. under argon. The reaction mixture is then warmed to room temperature and stirred for 18 h. The solvent is concentrated to dryness. The residue is diluted with sat. Na$_2$CO$_3$ (50 mL). And the mixture solution is extracted with EtOAc (3×80 mL). The combined extracts are washed with water (30 mL), brine (30 mL), and dried over anhydrous Na$_2$SO$_4$. Evaporation of the solvent affords the crude product, which is purified by CombiFlash (eluting with 0-15% MeOH in DCM) to afford 161 (2.28 mg, 87% yield) as white solid.

To an oven-dried round bottom flask equipped with water cooled west condenser and magnetic stir bar are added the compound 161 (1.03 g, 3.41 mmol, 1.00 equiv), bis(triphenylphosphine) palladium (II) dichloride (29 mg, 0.041 mmol, 0.01 equiv) and copper (I) iodide (15 mg, 0.08 mmol, 0.02 equiv.). The vessel is then sealed with a rubber septum under argon and are added anhydrous THF (30 mL) and TEA (0.72 mL, 5.12 mmol, 1.5 equiv). Finally, compound 3 (0.60 g, 3.75 mmol, 1.1 equiv) is added. The reaction mixture is stirred at room temperature for 22 h. The resulting dark solution is condensed to dryness with a rotavapor, and the residue is treated with water (50 mL), extracted with EtOAc (3×80 mL). The combined extracts are washed with water (50 mL) and brine (anhydrous $Na_2SO_4$). The crude products are purified by flash chromatography (eluting with 0-50% EtOAc in hexane) to afford 162 (0.91 g, 80%) yellow solid.

To a solution of methyl ester 162 (335 mg, 1.0 mmol, 1.00 equiv) in methanol (8 mL) is added a solution of LiOH in water (42 mg, 1.05 mmol, 1.05 equiv, 4 ml of water The reaction mixture is stirred at reflux for 4 h under argon. Then the solution is cooled to room temperature and concentrated to dryness. The residue is diluted with water (30 mL). And 1 N HCl is added to pH to 4. The suspension solution is then filtered. The white solid is washed with water (30 ml), then dried under high vacuum to give compound 163 (300 mg, 93%), which is going to next step without further purification.

To a solution of acid 163 (100 mg, 0.31 mmol) in anhydrous DMF (5 mL) is added difluoro amine 75 mg, 0.34 mmol, 1.1 equiv), EDC.HCl (72 mg, 0.37 mmol, 1.2 equiv), HOBt (51 mg, 0.34 mmol, 1.2 equiv) at room temperature under argon. The mixture is cooled to 0° C., DIEA (0.28 mL, 1.56 mmol, 5.00 equiv) is added. The reaction mixture is stirred at 0° C. for 2 hours, then is allowed to warm to room temperature for 14 hours. The yellow solution is then concentrated to dryness. The residue is treated with water (30 mL), extracted with EtOAc (3×50 mL). The combined extracts are washed with water (30 mL), brine (30 mL), and dried (anhydrous $Na_2SO_4$). The crude product is purified by CombiFlash (eluting with MeOH in DCM 0-1.5%) to give 164 (120 mg, 79% yield) as yellow solid.

To an ice-cold solution of 164 (100 mg, 0.21 mmol) dissolved in anhydrous THF (1 mL) and MeOH (1 mL) is added hydroxylamine hydrochloride (43 mg, 0.63 mmol, 3.0 equiv) followed by 25% sodium methoxide in methanol solution (0.24 mL, 1.05 mmol, 5.0 equiv). The reaction mixture is stirred under argon and at 0° C. for 2 h, then allowed to warm to ambient temperature with the stirring is continued overnight (14 h). The resulting yellow suspension is condensed to dryness with a rotavapor, and the residue is treated water (20 mL) and saturated $NH_4Cl$ (2 mL), extracted with EtOAc (3×80 mL). The combined extracts are washed with water (30 mL), brine (30 mL), and dried over anhydrous $Na_2SO_4$. Evaporation of the solvent affords the crude product, which is purified by CombiFlash (eluting with 0-15% MeOH in DCM) to afford CPD-069 (60 mg, 60% yield) as yellow solid.

Example 35

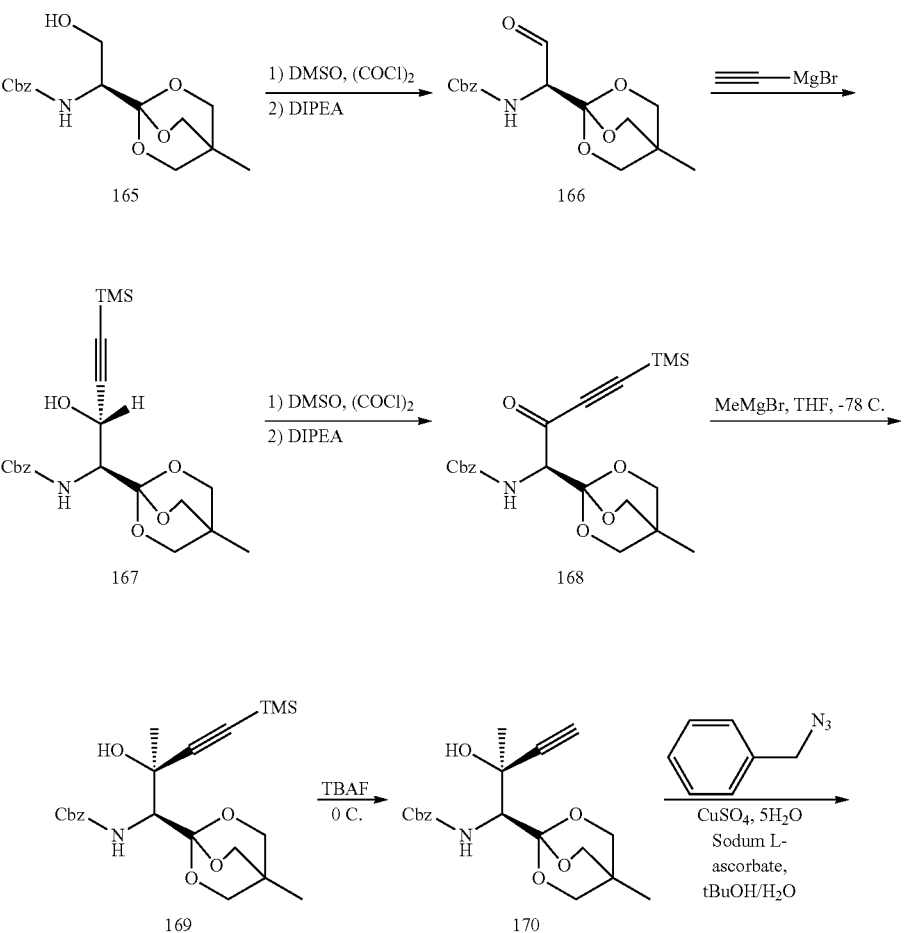

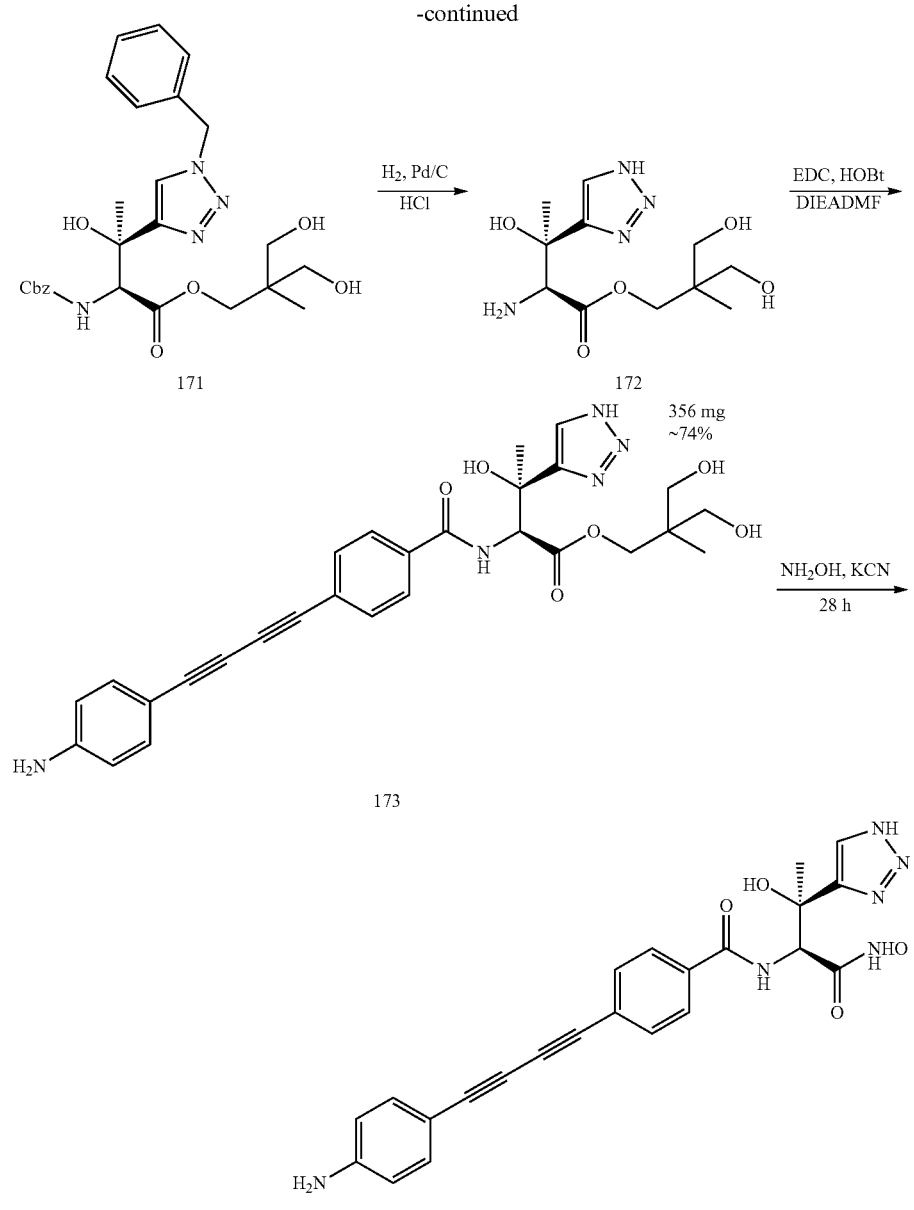

To an isopropylmagnesium bromide in 2-methyl THF (2.90 M) (10.7 mL, 31.2 mmol, 4.00 equiv) is added TMS ethynheyl (4.41 mL, 31.2 mmol, 4.00 equiv) at 0° C. Then the reaction mixture is warmed to room temperature and stirred under argon for 2 h. Then a solution of compound 166 (2.50 g, 7.78 mmol, 1.00 equiv) in THF (8 mL) is added. The reaction mixture is stirred at room temperature for 2 h. It is quenched by added sat.NH$_4$Cl (pH to 7). The mixture is extracted with EtOAc (3×100 mL). The combined extracts are washed with water (80 mL), brine (80 mL), and dried over anhydrous Na$_2$SO$_4$. Evaporation of the solvent affords the crude product, which is purified by CombiFlash (eluting with 0-15% MeOH in DCM) to afford 167 (2.20 g, 70% yield) as white foam. $^1$H NMR (300 MHz, CDCl$_3$) δ 0.12 (s, 9H), 0.81 (s, 3H), 3.09 (s, 1H), 3.92 (s, 6H), 4.12 (d, J=10.2 Hz, 1H), 4.90 (s, 1H), 5.13 (dd, J$_1$=21.0 Hz, J$_2$=12.3 Hz, 2H), 5.45 (d, J=10.5 Hz, 1H), 7.32-7.36 (m, 5H); $^{13}$C NMR (75 MHz, CDCl$_3$) δ −0.27, 14.25, 30.65, 57.62, 62.11, 66.91, 72.74, 72.89, 89.99, 102.66, 108.31, 127.98, 128.06, 128.43, 136.53. 156.43; LC/MS m/s [M+H]$^+$ 420.2

Compound 167 (0.80 g, 1.91 mmol) is dissolved in anhydrous DCM (40 mL) under argon and cooled to −78° C. in flask I. Oxalyl chloride (0.39 mL, 3.05 mmol, 1.6 equiv) is added to anhydrous DCM (40 mL) in a separate flask II under argon and cooled to −78° C. Anhydrous DMSO (0.48 mL, 6.30 mmol, 3.30 equiv) is added to the oxalyl chloride solution (flask II), and the mixture stirred at −78° C. for 15 min. The alcohol solution is transferred by syringe at −78° C. to the flask II over a period of 20 min. The resulting cloudy white mixture is stirred for 2 h at −78° C. DIPEA (1.65 mL, 9.55 mmol, 5.0 equiv) is added and the solution is stirred for 30 min at −78° C. and 10 min at 0° C. Ice-cold DCM (100 mL) is added, and the solution is washed with ice-cold 3% NH$_4$Cl (3×50 mL), brine (100 mL), dried (anhydrous Na$_2$SO$_4$). The crude product is purified by CombiFlash (eluting with 0-50% EtOAc in hexane) to give compound 168 (0.62 g, 80% yield) as white foam. $^1$H NMR (300 MHz, CDCl$_3$) δ 0.01 (s, 9H), 0.58 (s, 3H) 3.69 (s, 6H), 4.45 (d, J=9.3 Hz, 1H), 4.89 (s, 2H), 5.40 (d, J=9.0 Hz, 1H), 7.04-7.13 (m, 5H); $^{13}$C NMR (75 MHz, CDCl$_3$) δ −0.84, 14.21, 30.80, 63.88, 67.17, 72.93, 101.23, 102.11, 106.88, 128.12, 128.47, 136.16, 155.72, 181.35; LC/MS m/s [M+H]$^+$ 418.1

Compound 168 (140 mg, 0.33 mmol) is dissolved in anhydrous THF (5 mL) under argon. A solution of methyl magnesium bromide in THF (1.4 M, 1.2 mL, 1.65 mmol, 5.0 equiv) is added quickly by syringe at −78 C and stirred vigorously. After 2 h, the reaction mixture is quenched by sat. NH$_4$Cl (pH=7) and is stirred for an additional 15 min. The mixture is extracted with EtOAc (3×50 mL). The combined organic layers are washed with brine (50 mL), dried (anhydrous Na$_2$SO$_4$). The crude product is purified by CombiFlash (eluting with 0-50% EtOAc in hexane) to give 169 (0.1 g, 74% yield) as white solid. $^1$H NMR (300 MHz, CDCl$_3$) δ 0.16 (s, 9H), 0.81 (s, 3H), 1.47 (s, 3H), 3.72 (s, 1H), 3.90 (s, 6H), 4.05 (d, J=10.5 Hz, 1H), 5.13 (s, 2H), 5.27 (d, J=9.6 Hz, 1H), 7.27-7.35 (m, 5H); $^{13}$C NMR (75 MHz, CDCl$_3$) δ −0.03, 14.30, 27.38, 30.57, 60.23, 66.92, 68.45, 72.40, 88.53, 107.31, 108.83, 127.97, 128.02, 128.46, 136.50, 156.55; LC/MS m/s [M+H]$^+$ 434.2

To a solution of compound 169 (50 mg, 0.115 mmol, 1.0 equiv) in THF (5 mL) is added TBAF (30.0 mg, 0.115 mmol, 1.0 equiv) at 0° C. under argon. The reaction mixture is stirred at 0° C. for 5 min. Then it is concentrated to dryness. The crude product is purified by CombiFlash (eluting with 0-50% EtOAc in hexane) to give 170 (38 mg, 90% yield) as white solid. $^1$H NMR (300 MHz, CDCl$_3$) δ 0.81 (s, 3H), 1.50 (s, 3H), 2.48 (s, 1H), 3.81 (s, 1H), 3.92 (s, br, 6H), 4.07 (d, J=11.1 Hz, 1H), 5.19 (dd, J$_1$=18.6 Hz, J$_2$=12.3 Hz, 2H), 5.29 (d, J=10.5 Hz, 1H), 7.28-7.35 (m, 5H); $^{13}$C NMR (75 MHz, CDCl$_3$) δ; LC/MS m/s [M+H]$^+$ 362.2

To a solution of 170 (410 mg, 1.14 mmol, 1.00 equiv) and benzyl azide (151 mg, 1.14 mmol, 1.00 equiv) in a cosolvent t-BuOH/H$_2$O (1:1) (4 mL) is added a solution of sodium ascorbate (22.6 mg, 0.114 mmol, 0.1 equiv) in 0.5 mL of water and a solution of CuSO$_4$ (14.23 mg, 0.057 mmol, 0.05 equiv) in 0.5 mL of water. The reaction mixture is stirred at room temperature under argon for 24 h. Evaporation of the solvents affords the crude product, which is purified by CombiFlash (eluting with MeOH in DCM 0-5%) to give 171 (520 mg, 92%) as white foam. $^1$H NMR (300 MHz, CDCl$_3$) δ 0.71 (s, 3H), 1.62 (s, 3H), 1.81 (s, 1H), 3.07 (s, 1H), 3.15 (s, 1H), 3.43 (s, br, 4H), 4.02 (s, 2H), 4.16 (s, 1H), 4.60 (d, J=9.3 Hz, 1H), 5.10 (s, 2H), 5.46 (s, 2H), 5.92 (d, J=9.0 Hz, 1H), 7.23-7.45 (m, 10H); $^{13}$C NMR (75 MHz, CDCl$_3$) δ 16.85, 26.09, 40.27, 54.33, 61.79, 67.00, 67.27, 67.41, 68.10, 77.81, 121.02, 128.15, 128.19, 128.30, 128.56, 128.93, 129.20, 134.13, 135.92, 151.70, 156.59, 170.97; LC/MS m/s [M+H]$^+$ 513.2

To a solution of 171 (336 mg, 0.656 mmol) in anhydrous MeOH (10 mL) is added 10% Pd/C (30 mg). The reaction mixture is stirred under a balloon of hydrogen. After 1 h, LC/MS showed that the Cbz group is deprotected. Then 1 mL of 4 M HCl in dioxane is added. The reaction mixture is stirred for another 18 h. The resulting solution is filtered through a pad of celite and washed with MeOH (20 mL). The filtrate is concentrated to dryness to afford the 172 as white solid, which is going to next step without the further purification. $^1$H NMR (300 MHz, CD$_3$OD) δ 0.83 (s, 3H), 1.91 (s, 3H), 3.37-3.42 (m, 4H), 4.11 (dd, J$_1$=75.6 Hz, J$_2$=10.8 Hz, 2H), 4.51 (s, 1H), 8.39 (s, 1H); $^{13}$C NMR (75 MHz, CD$_3$OD) δ 15.56, 26.08, 40.35, 61.44, 64.00, 68.64, 69.40, 125.68, 146.41, 165.99; LC/MS m/s [M+H]$^+$ 289.2

To a stirred mixture of 172 (210 mg, 0.582 mml, 1.05 equiv) and acid 6 (144 mg, 0.554 mmol, 1.00 equiv, prepared as in Example 1) in anhydrous DMF (5 mL) is added N-ethyl-N'-(3-dimethylaminopropyl)carbodiimide hydrochloride (EDC hydrochloride) (149 mg 0.776 mmol, 1.40 equiv), 1-hydroxybenzotriazole (HOBt) (105 mg, 0.776 mmol, 1.40 equiv) at room temperature. The mixture is cooled with an ice-bath, and diisopropylethylamine (DIEA) (0.99 mL, 5.44 mmol, 10.0 equiv) is added. The whole reaction mixture is stirred under argon and at 0° C. for 1 h, then allowed to warm to temperature with the stirring is continued for additional 36 h. The resulting yellow solution is condensed to dryness with a rotavapor, and the residue is treated with water (50 mL), extracted with EtOAc (3×50 mL). The combined extracts are washed with brine (50 mL), and dried over anhydrous Na$_2$SO$_4$. Evaporation of the solvent affords the crude product, which is purified by CombiFlash (eluting with 0-10% MeOH in DCM) to afford 173 (130 mg, 44% yield) as yellow solid. LC/MS m/s [M+H]$^+$ 532.2

CPD-072: compound 173 (110 mg, 0.21 mmol) is taken into 2.0 mL of MeOH. 50% aq hydroxylamine (0.20 mL, 3.0 mmol, 30 equiv) is added and followed by potassium cyanide (10.0 mg, 0.10 mmol, 1.5 equiv) at room temperature under argon. The reaction mixture is stirred room temperature for 20 h. Then the yellow solution is concentrated to dryness. The residue is treated water (5 mL), washed with EtOAc (10 mL). The precipitate is then washed with milliQ water (3×30 mL), dried under high vacuum to give CPD-072 (55.0 mg, 66% yield) as yellow solid. LC/MS m/s [M+H]$^+$ 445.2

Example 36

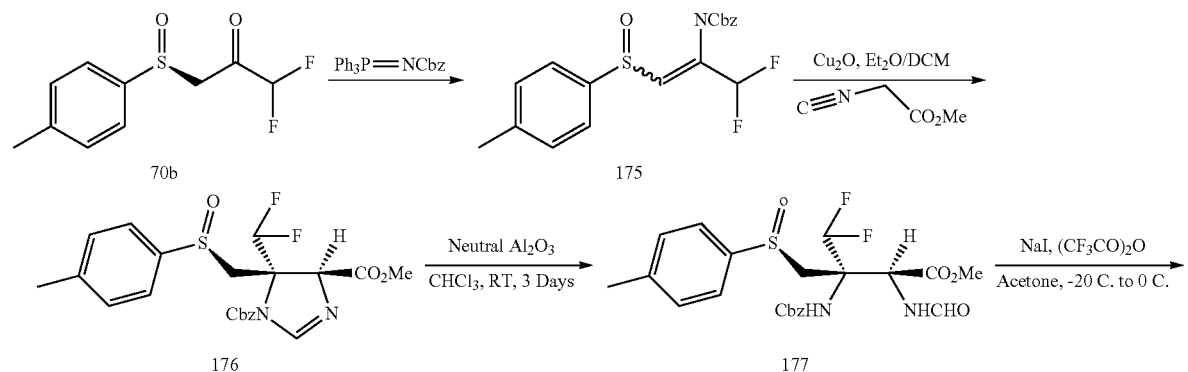

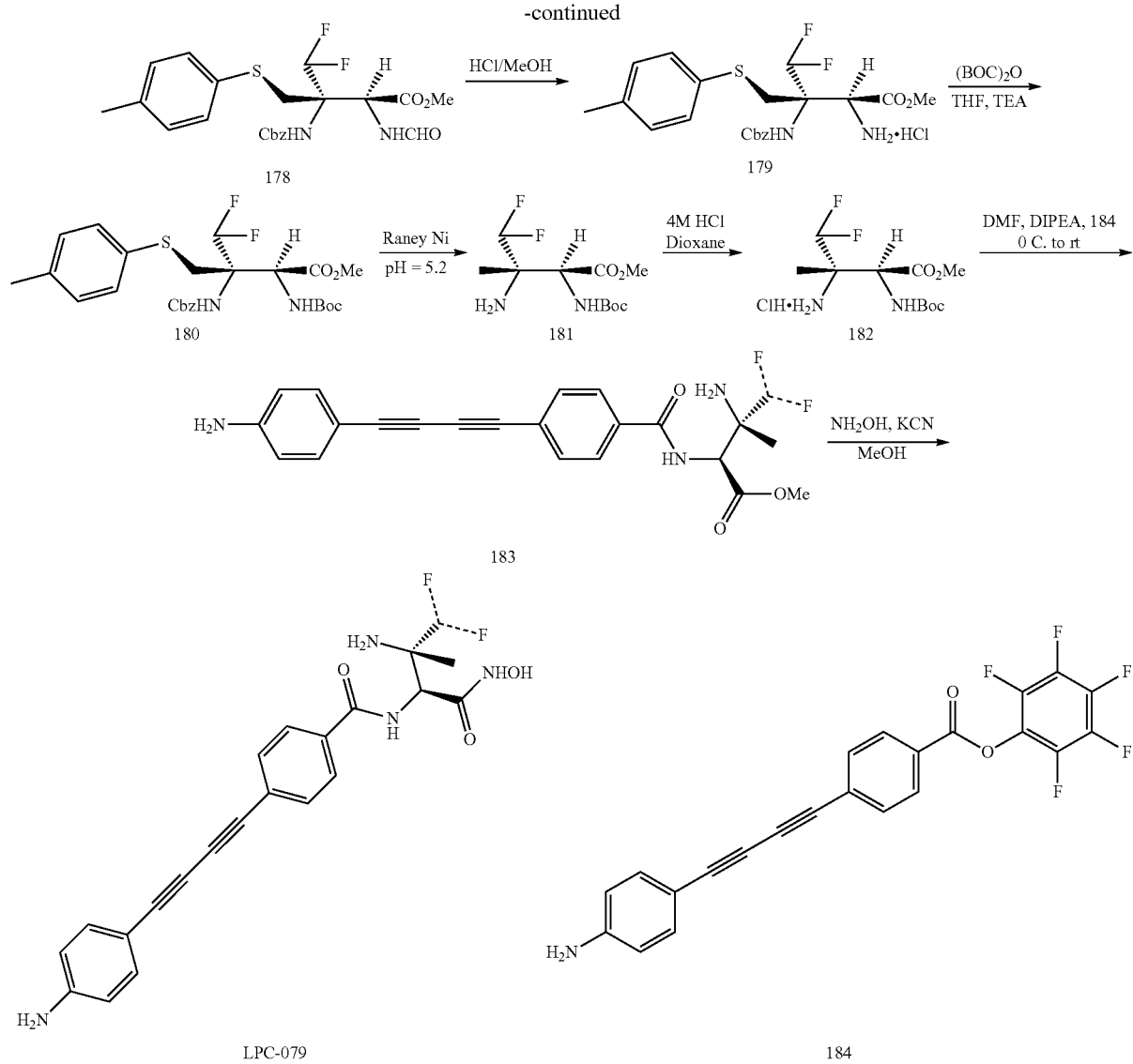

To a solution of benzyl chloroformate (20.0 g, 0.117 mol, 1.00 equiv) in anhydrous acetone (300 mL) is added sodium azide (11.4 g, 0.176 mol, 1.5 equiv). Then a solution of PPh$_3$ (30.74 g, 0.117 mol, 1.00 equiv) in anhydrous DCM (100 mL) is dropwise added in 1.5 h at 0° C. under argon. The reaction mixture is stirred at 0° C. for additional 30 min. Then the white suspension is filtered and washed with DCM (100 mL). The filtrate is concentrated to dryness to afford the crude product, which is purified by crystallization from EtOAc and hexanes to give compound 174 (29.27 g, 60%) as white solid. $^1$H NMR (300 MHz, CDCl$_3$) δ 5.06 (s, 2H), 7.23 (m, 4H), 7.40-7.46 (m, 6H), 7.51-7.56 (m, 3H), 7.740-7.76 (m, 7H); $^{13}$C NMR (75 MHz, CDCl$_3$) δ 67.32, 127.34, 127.41, 128.06, 128.11, 128.53, 128.61, 128.76, 132.31, 132.35, 133.00, 133.13, 137.82, 161.65;

175: To a solution of compound 70b (3.30 g, 14.22 mmol, 1.00 equiv) in anhydrous benzene (60 mL) is added iminophosphorane 174 (5.85 g, 14.22 mmol, 1.00 equiv). Then the reaction mixture is stirred at reflux for 40 h. The yellow solution is cooled to room temperature. Evaporation of the solvent is affords the crude product, which is purified by CombiFlash (eluting with EtOAc in hexanes 0-50%) to give the compound 175 (4.1 g, 80%) as white solid. $^1$H NMR (300 MHz, CDCl$_3$) δ 2.42 (s, 3H), 5.15 (s, 2H), 5.70 (s, 1H), 7.06 (t, J=109.4 Hz, 1H), 7.32-7.39 (m, 7H), 7.59 (j=8.1 Hz, 2H), 9.96 (s, 1H); $^{13}$C NMR (75 MHz, CDCl$_3$) δ 21.49, 67.78, 105.04, 108.27, 109.26, (109.14, 109.26, 109.38), 111.48, 125.09, 128.32, 128.49, 128.60, 130.46, 135.35, 139.46, (139.65, 139.96, 140.28), 142.78, 152.36; LC/MS m/s [M+H]$^+$ 366.2

To a solution of 175 (2.00 g, 5.48 mmol, 1.00 equiv) in anhydrous Diethyl ether (300 mL) and DCM (80 mL) is added Cu$_2$O (0.568 g, 3.97 mmol, 0.10 equiv) at −20° C. under argon. The reaction mixture is then dropwise added methyl isocyanoacetate (7.82 g, 79.44 mmol, 2.00 equiv). The reaction mixture is stirred at −20° C. for 3 hours, then is allowed to warm to room temperature for 40 hours. The mixture solution is concentrated to dryness. The crude product is purified by CombiFlash (eluting with EtOAc in hexane 0-60%) to give the 176 (6.6 g, less polar one) as white solid. $^1$H NMR (300 MHz, CDCl$_3$) δ 2.41 (s, 3H), 3.59 (dd, J$_1$=117.9 Hz, J$_2$=13.8 Hz, 2H), 3.88 (s, 3H), 5.30 (dd, J₁=30.9 Hz, J₂=12.0 Hz, 2H), 5.27 (s, 1H), 6.45 (t, J=114.0 Hz, 1H), 7.31-7.54 (m, 9H), 7.73 (s, 1H); $^{13}$C NMR (75 MHz, CDCl₃) δ 21.39, 53.11, 55.19, (67.43, 67.83, 68.23), 69.07, 70.92, 112.57, 123.89, 128.35, 128.72, 130.12, 134.64, 140.69, 141.89, 149.32, 149.99, 169.29; LC/MS m/s [M+H]⁺ 465.2

To a solution of 176 (4.83 g, 10.41 mmol, 1.00 equiv) in CHCl₃ (100 mL) is added neutral Aluminum oxide (10.61 g, 20.82 mmol, 10.00 equiv) and milliQ water (0.37 g, 20.82 mmol, 2.00 equiv). The reaction mixture is stirred at room temperature under argon for 3 days. Evaporation of the solvent is afford the crude product, which is purified by CombiFlash (eluting with MeOH in DCM 0-2%) to give 177 (4.0 g, 80%) as white solid. The compound 177 (4.0 g) is crystallized from EtOAc/Hexanes to give optical pure compound (3.0 g, 60%). LC/MS m/s [M+H]⁺ 483.2

To a solution of 177 (2.5 g, 5.19 g mmol, 100 equiv) in acetone (60 mL) is added sodium iodide (1.87 g, 12.45 mmol, 2.4 equiv) at 0° C. under argon. A solution of trifluoroacetatic anhydride (1.19 mL in 2 mL acetone) is added dropwise in 8 min. The reaction mixture is stirred at 0° C. for 30 min, then is quenched by ice cold water (30 mL). The mixture is extracted with EtOAc (3×80 mL). The combined organic layers are washed with sat. Na₂S₂O₃ (3×40 mL), water (30 mL), brine (30 mL) and dried (anhydrous Na₂SO₄). The crude product is purified by Combi-Flash (eluting with MeOH in DCM 0-5%) to give 178 (2.1 g, 86%) as colorless oil. $^{1}$H NMR (300 MHz, CDCl₃) δ 2.30 (s, 3H), 3.65 (dd, J₁=55.2 Hz, J₂=14.1 Hz, 2H), 3.65 (s, 3H), 3.71 (s, 1H), 4.99 (dd, J₁=26.4 Hz, J₂=12.3 Hz, 2H), 5.37 (d, J=9.9 Hz, 1H), 6.08 (s, 1H), 6.42 (t, J=111.0 Hz, 1H), 7.10 (d, J=8.1 Hz, 2H), 7.26-7.37 (m, 7H), 8.21 (s, 1H); $^{13}$C NMR (75 MHz, CDCl₃) δ 21.06, 36.83, 52.29, 53.01, (60.92, 61.21, 61.49), 67.29, (110.76, 114.07, 117.37), 127.92, 127.98, 128.32, 128.39, 128.57, 130.01, 130.15, 131.44, 131.67, 131.98, 135.70, 137.72, 155.42, 160.99, 168.97; LC/MS m/s [M+H]⁺ 467.2

To a solution of 178 (500 mg, 1.1 mmol, 1.00 equiv) in methanol (5 mL) is added 3M HCl in MeOH (2 mL). The reaction mixture is stirred at room temperature for 18 hours. Then the mixture is concentrated to dryness to afford 179 as white solid, which is going to next step without purification. $^{1}$H NMR (300 MHz, CDCl₃) δ 2.24 (s, 3H), 3.67 (s, 3H), 3.61-3.87 (m, 2H), 5.03 (s, 2H), 5.05 (s, 1H), 6.20 (s, 1H), 6.56 (t, J=108.9 Hz, 1H), 7.03 (d, J=7.2 Hz, 2H), 7.24-7.37 (m, 7 h), 9.34 (s, br, 2H); $^{13}$C NMR (75 MHz, CDCl₃) δ 21.00, 35.50, 53.71, 54.73, (60.84, 61.12, 61.40), 67.61, 105.01, (110.74, 114.08, 117.40), 128.13, 128.43, 129.95, 130.77, 131.37, 135.73, 137.47, 135.35, 166.09; LC/MS m/s [M+H]⁺ 439.1.

To a solution of 179 (150 mg, 0.32 mmol, 1.00 equiv) in anhydrous THF (8 mL) is added TEA (0.089 mL, 0.64 mmol, 2.00 equiv) at 0° C., then (Boc)₂O (76 mg, 0.35 mmol, 1.10 equiv) is added. The reaction mixture is stirred at 0° C. for 30 min. Then it is allowed to warm to room temperature for 14 h. The resulting solution is concentrated to dryness. The residue is diluted with water (30 mL). The mixture solution is extracted with EtOAc (3×50 mL). The combined organic layers are washed with water (30 mL), brine (30 mL) and dried over (anhydrous Na₂SO₄). Evaporation of the solvent is affords the crude product, which is purified by CombiFlash (eluting with EtOAc in Hexanes 0-25%) to give 180 (0.167 g, 97%) as colorless oil. $^{1}$H NMR (300 MHz, CDCl₃) δ 1.45 (s, 9H), 2.30 (s, 3H), 3.67 (dd, J₁=84.6 Hz, J₂=13.8 Hz, 2H), 3.69 (s, 2H), 4.96 (dd, J₁=27.6 Hz, J₂=2.3 Hz, 2H), 4.96 (s, 1H), 5.76 (d, J=9.3 Hz, 1H), 6.45 (t, J=111.0 hz, 1H), 7.09 (d, J=7.5 Hz, 2H) 7.29-7.38 (m, 7H); $^{13}$C NMR (75 MHz, CDCl₃) δ 28.22, 36.35, 52.87, 55.20, 60.37, (61.44, 61.71, 61.99), 67.03, 80.67, 105.00, (111.25, 114.56, 117.88), 127.88, 128.21, 128.51, 129.87, 137.80, 135.83, 137.45, 155.01, 155.30, 170.17; LC/MS m/s [M+H]⁺ 539.2

To a solution of 180 (150 mg, 0.28 mmol, 1.00 equiv) in acetate buffer (pH 5.2) and MeOH (1:2, 15 mL) is added Raney Ni (suspension in methanol, 5 mL) followed by addition of sodium hyphophite monohydrate (0.35 g in milliQ water 1 mL) immediately. The reaction mixture is stirred at room temperature for 3 hours under argon. The mixture is filtered through a celite pad and washed with MeOH (50 ml). The filtrate is concentrated to dryness. The residue is treated with water (30 mL), extracted with EtOAc (3×80 mL). The combined organic layers are washed with water (30 mL), 10% NaHCO₃ (2×30 mL), brine (30 mL), and dried (anhydrous Na₂SO₄). The crude product is purified by CombiFlash (eluting with MeOH in DCM 0-10%) to give 181 (66 mg, 85%) as colorless oil. $^{1}$H NMR (300 MHz, CDCl₃) δ 1.15 (s, 3H), 1/41 (s, 9H), 1.48 (br, 2H), 3.74 (s, 3H), 4.32 (d, J=8.1 Hz, 1H), 5.57 (d, J=8.4 Hz, 1H), 5.67 (t, J=113.1 Hz, 1H); $^{13}$C NMR (75 MHz, CDCl₃) δ 28.17, 52.35, (56.19, 56.48, 56.77), 57.02, 80.39, (113.22, 116.49, 119.76), 155.43, 171.67; LC/MS m/s [M+H]⁺ 283.2

To a solution of 181 (300 mg, 1.06 mmol, 1.00 equiv) in anhydrous dioxane (4 mL) is added 4 M HCl in dioxane (8 mL). The reaction mixture is stirred at room temperature for 14 h. Evaporation of the solvent is affords the 182, which is going to next step without further purification. LC/MS m/s [M+H]⁺ 183.1

To a solution of 182 (96 mg, 0.37 mmol, 1.00 equiv) in anhydrous DMF (5 mL) is added DIEA (0.340 mL, 1.98 mmol, 5.00 equiv). The mixture is cooled to 0° C. Compound 184 (172 mg, 0.42 mmol, 1.10 equiv) is added. The reaction mixture is stirred at 0° C. for 2 hours, and then is allowed to warm to room temperature for 14 hours. The yellow solution is then concentrated to dryness. The residue is treated with water (30 mL), extracted with EtOAc (3×30 mL). The combined extracts are washed with water (30 mL), brine (30 mL), and dried (anhydrous Na₂SO₄). The crude product is purified by CombiFlash (eluting with MeOH in DCM 0-5%) to give 183 (65 mg, 83%) as a yellow solid. $^{1}$H NMR (300 MHz, CDCl₃) δ 1.26 (s, 3H), 1.68 (s, br, 2H), 3.80 (s, 3H), 3.96 (s, br, 2H), 4.80 (d, J=7.8 Hz, 1H), 5.73 (t, J=113.1 Hz, 1H), 6.58 (d, J=9.0 Hz, 2H), 7.24 (d, J=8.1 Hz, 1H), 7.32 (d, J=8.7 Hz, 2H), 7.56 (d, J=8.4 Hz, 2H), 7.76 (d, J=8.7 Hz, 2H); $^{13}$C NMR (75 MHz, CDCl₃) δ 19.46, 52.67, 55.87, (56.31, 56.58, 56.86), 71.75, 77.25, 79.63, 84.45, 105.00, 110.09, (113.20, 116.47, 119.75), 114.59, 126.23, 127.20, 132.50, 132.97, 134.19, 147.88, 165.51, 170.61; LC/MS m/s [M+H]⁺ 426.2

To an ice-cold solution of 184 (50 mg, 0.12 mmol, 1.00 equiv) dissolved in anhydrous MeOH (2 mL) is added KCN (10 mg, 0.15 mmol, 1.27 equiv). The mixture is the cooled to 0° C., and 2 mL of 50% NH₂OH aq is added. The reaction mixture is stirred at 0° C. for 4 h, then allowed to warm to ambient temperature with the stirring is continued overnight (14 h). The resulting yellow solvent is condensed to dryness with a rotavapor, and the residue is treated with water (20 mL), and extracted with EtOAc (3×50 mL). The combined extracts are washed with water (30 mL), brine (30 mL), and dried over anhydrous Na₂SO₄. Evaporation of the solvent affords the crude product, which is purified by CombiFlash (eluting with 0-10% MeOH in DCM) to give CPD-079 (39.2 mg, 80%) as a yellow solid. ¹H NMR (300 MHz, CD₃OD) δ 1.26 (s, 3H), 4.72 (s, 1H), 5.77 (t, J=112.5 Hz, 1H), 6.61 (d, J=8.4 Hz, 1H), 7.24 (d, J=8.4 Hz, 2H), 7.56 (d, J=8.1 Hz, 2H), 7.84 (d, J=8.1 Hz, 2H); ¹³C NMR (75 MHz, CD₃OD) δ 17.81, 53.31, 56.56, 70.55, 76.51, 78.76, 84.41, 108.10, 114.02, 125.93, 127.41, 131.86, 133.60, 143.96, 149.33, 149.95, 166.29, 167.57; LC/MS m/s [M+H]⁺ 427.3

Example 37

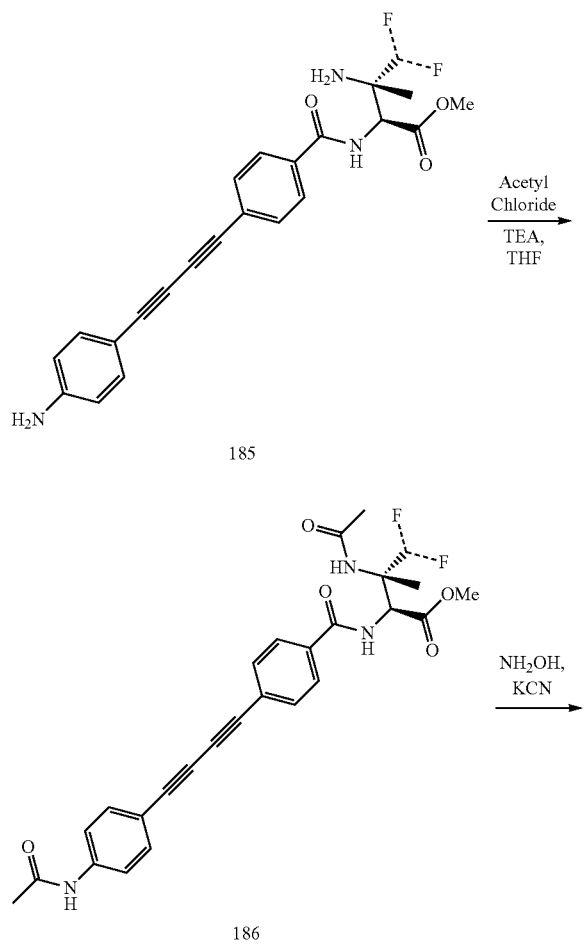

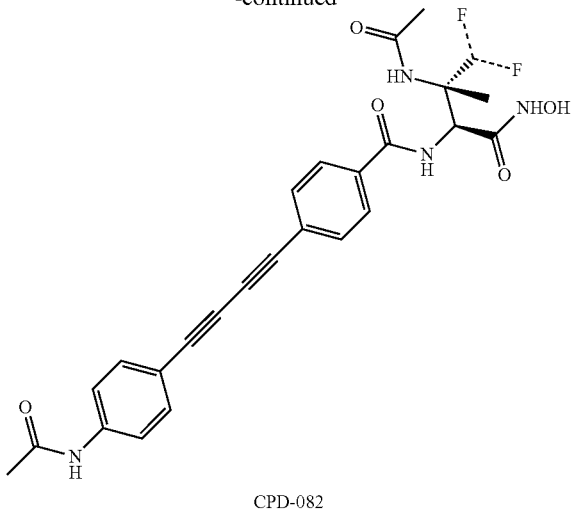

CPD-082

To a solution of starting material methyl 185 (20 mg, 47.1 µmol, 1.00 equiv) in anhydrous THF (1 mL) is added TEA (20 µL, 141.1 µmol, 3.00 equiv) at room temperature under argon. The mixture is cooled to 0° C.; Acetyl chloride (7 µL, 98.8 µmol, 2.10 equiv) is added. The reaction mixture is stirred at 0° C. for 1 h, then allowed to warm to ambient temperature with the stirring is continued overnight (20 h). The resulting yellow suspension is condensed to dryness with a rotavapor, and the residue is treated water (20 mL), extracted with EtOAc (3×50 mL). The combined extracts are ished with water (30 mL), brine (30 mL), and dried over anhydrous Na₂SO₄. Evaporation of the solvent afforded the crude product, which is purified by CombiFlash (eluting with 0-7% MeOH in DCM) to afford 186 (19.7 mg, 83%) as off yellow solid. ¹H NMR (300 MHz, CDCl₃) δ 1.58 (s, 3H), 2.05 (s, 3H), 2.17 (s, 3H), 3.75 (s, 3H), 5.09 (d, J=8.7 Hz, 1H), 5.92 (s, 1H), 6.60 (d, J=8.4 Hz, 2H), 7.46-7.53 (m, 4H), 7.59 (d, J=8.1 Hz, 2H), 7.65 (s, 1H), 7.86 (d, J=8.4 Hz, 2H), 9.07 (d, J=9.0 Hz, 1H); ¹³C NMR (75 MHz, CDCl₃) δ 17.64, 23.55, 24.66, 52.74, 53.42 57.55, (59.57, 59.86, 60.19), 73.32, 80.45, 82.75, 108.65, 111.94, 115.23, 116.79, 119.36, 125.72, 127.33, 132.68, 133.13, 133.49, 139.06, 166.23, 168.49, 169.31, 172.90; LC/MS m/s [M+H]⁺ 510.2

To an ice-cold solution of 186 (18 mg, 35.4 µmol, 1.00 equiv) dissolved in MeOH (1 mL) is added KCN (5 mg, 75 µmol, 2.0 equiv). The mixture is the cooled to 0° C., 2 mL of 50% NH₂OH aq is added. The reaction mixture is stirred at 0° C. for 4 h, then allowed to warm to ambient temperature with the stirring is continued overnight (20 h). The resulting yellow solvent is condensed to dryness with a rotavapor, and the residue is treated water (20 mL), extracted with EtOAc (3×50 mL). The combined extracts are ished with water (30 mL), brine (30 mL), and dried over anhydrous Na₂SO₄. Evaporation of the solvent afforded the crude product, which is purified by CombiFlash (eluting with 0-10% MeOH in DCM) to afford CPD-082, N-((2S,3S)-3-acetamido-4,4-difluoro-1-(hydroxyamino)-3-methyl-1-oxobutan-2-yl)-4-((4-acetamidophenyl)buta-1,3-diynyl) benzamide, (8 mg, 44%) as a yellow solid. ¹H NMR (300 MHz, CD₃OD) δ 1.48 (s, 3H), 2.02 (s, 3H), 2.14 (s, 3H), 6.75 (t, J=113.4 Hz, 1H), 7.49 (d, J=8.4 Hz, 2H), 7.60-7.65 (m, 4H), 7.89 (d, J=8.4 Hz, 2H); ¹³C NMR (75 MHz, CD₃OD) δ 15.40, 21.56, 22.53, 31.33, 55.56, 72.16, 75.60, 79.56, 82.26, 105.00, 112.48, 115.75, 119.27, 125.41, 127.26, 132.19, 132.87, 133.50, 140.03, 165.42, 166.56, 170.35, 174.35; LC/MS m/s [M+H]⁺ 511.3.

Example 38
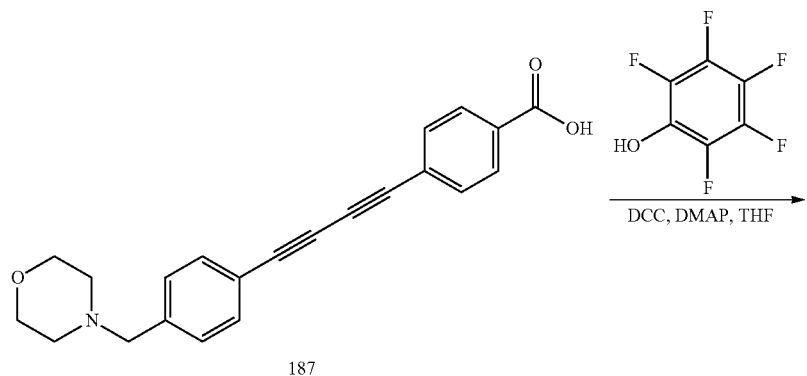
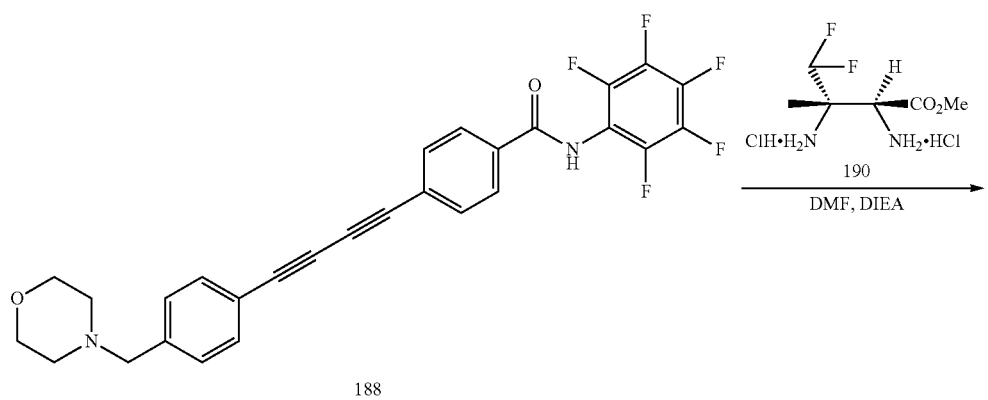
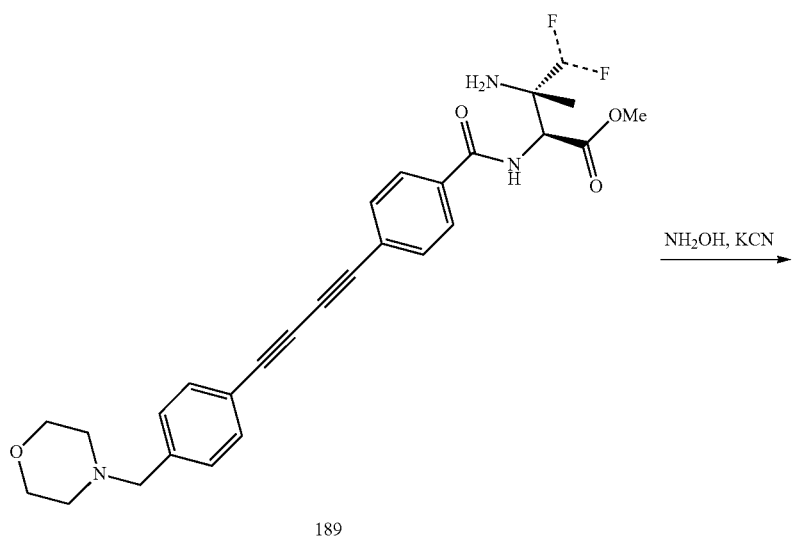

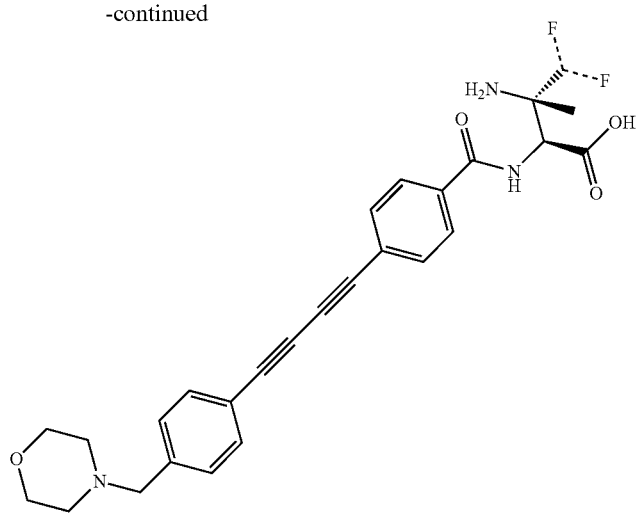

CPD-084

To a solution of 187 (65 mg, 0.18 mmol, 1.00 equiv) in anhydrous THF (8 mL) is added 2, 3, 4, 5, 6-pentafluorophenol (92 mg, 0.54 mmol, 3.00 equiv). Then the mixture is cooled to 0° C. DCC (40 mg, 0.198 mmol, 1.1 equiv) and DMAP (6.5 mg, 0.054 mmol, 0.3 equiv) are added. The reaction mixture is stirred at 0° C. for 4 h, then allowed to warm to ambient temperature with the stirring is continued overnight (20 h). The resulting suspension is filtered and ished with 20 mL of EtOAc. The filtrate is condensed to dryness with a rotavapor, and the residue is treated water (20 mL), extracted with EtOAc (3×30 mL). The combined extracts are ished with water (30 mL), brine (30 mL), and dried over anhydrous $Na_2SO_4$. Evaporation of the solvent afforded the crude product, which is purified by CombiFlash (eluting with 0-2% MeOH in DCM) to afford 188 (77 mg, 81%) as a yellow solid. $^1$H NMR (300 MHz, CDCl$_3$) δ; 2.43-2.46 (m, 4H), 3.51 (s, 2H), 3.70-3.73 (m, 4H), 7.33 (d, J=8.4 Hz, 2H), 7.50 (d, J=8.4 Hz, 2H); $^{13}$C NMR (75 MHz, CDCl$_3$) δ 24.93, 33.94, 53.61, 63.04, 66.94, 73.27, 78.15, 79.85, 83.87, 119.96, 126.79, 128.54, 129.20, 130.61, 132.57, 132.73, 139.99, 161.87; LC/MS m/s [M+H]$^+$ 511.1.

To a solution of 190 (33 mg, 0.131 mmol, 1.00 equiv) in anhydrous DMF (2 mL) is added DIEA (0.23 mL, 1.31 mmol, 10.00 equiv) is added. The mixture is cooled to 0° C. Compound 188 (70 mg, 0.14 mmol, 1.08 equiv) is added. The reaction mixture is stirred at 0° C. for 2 hours, and then is allowed to warm to room temperature for 14 hours. The yellow solution is then concentrated to dryness. The residue is treated with water (30 mL), extracted with EtOAc (3×30 mL). The combined extracts are ished with water (30 mL), brine (30 mL), and dried (anhydrous $Na_2SO_4$). The crude product is purified by CombiFlash (eluting with MeOH in DCM 0-5%) to give 189 (50 mg, 75%) as a yellow solid. $^1$H NMR (300 MHz, CDCl$_3$) δ 1.26 (s, 3H), 2.41-2.44 (m, 4H), 3.49 (s, 2H), 3.68-3.71 (m, 4H), 3.80 (s, 3H), 4.80 (d, J=7.8 Hz, 1H), 5.73 (t, J=112.8 Hz, 1H), 7.24 (d, J=8.1 Hz, 1H), 7.31 (d, J=8.1 Hz, 2H), 7.46 (d, J=8.4 Hz, 2H), 7.58 (d, J=8.4 Hz, 2H), 7.78 (d, J=8.4 Hz, 2H); $^{13}$C NMR (75 MHz, CDCl$_3$) δ 19.47, 52.65, 53.61, 55.85, (55.88, 56.56, 56.86), 63.05, 66.96, 73.42, 76.56, 80.26, 82.96, 116.46, 120.13, 125.72, 127.26, 129.15, 132.51, 132.65, 133.39, 139.84, 166.39, 170.61; LC/MS m/s [M+H]$^+$ 510.3.

To an ice-cold solution of 189 (40 mg, 0.078 mmol, 1.00 equiv) dissolved in anhydrous MeOH (1 mL) is added KCN (10 mg, 0.15 mmol, 2.0 equiv). The mixture is the cooled to 0° C., 2 mL of 50% $NH_2OH$ aq is added. The reaction mixture is stirred at 0° C. for 4 h, then allowed to warm to ambient temperature with the stirring is continued overnight (14 h). The resulting yellow solvent is condensed to dryness with a rotavapor, and the residue is treated water (20 mL), extracted with EtOAc (3×50 mL). The combined extracts are ished with water (30 mL), brine (30 mL), and dried over anhydrous $Na_2SO_4$. Evaporation of the solvent afforded the crude product, which is purified by CombiFlash (eluting with 0-10% MeOH in DCM) to afford CPD-084, (2S,3S)-3-amino-4,4-difluoro-3-methyl-2-(4-((4-(morpholinomethyl)phenyl)buta-1,3-diynyl)benzamido)butanoic acid, (30 mg, 75%) as a yellow solid. LC/MS m/s [M+H]$^+$ 512.3.

Example 39

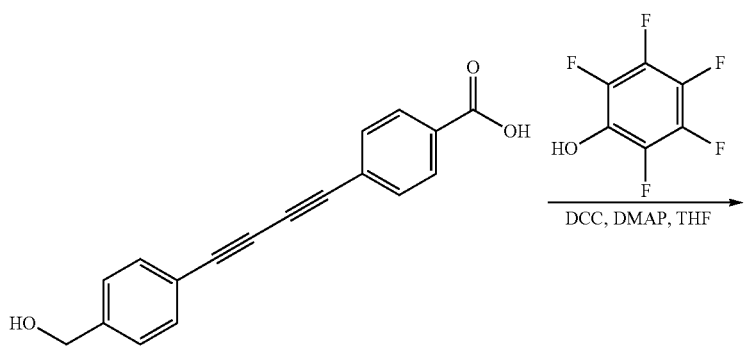

191

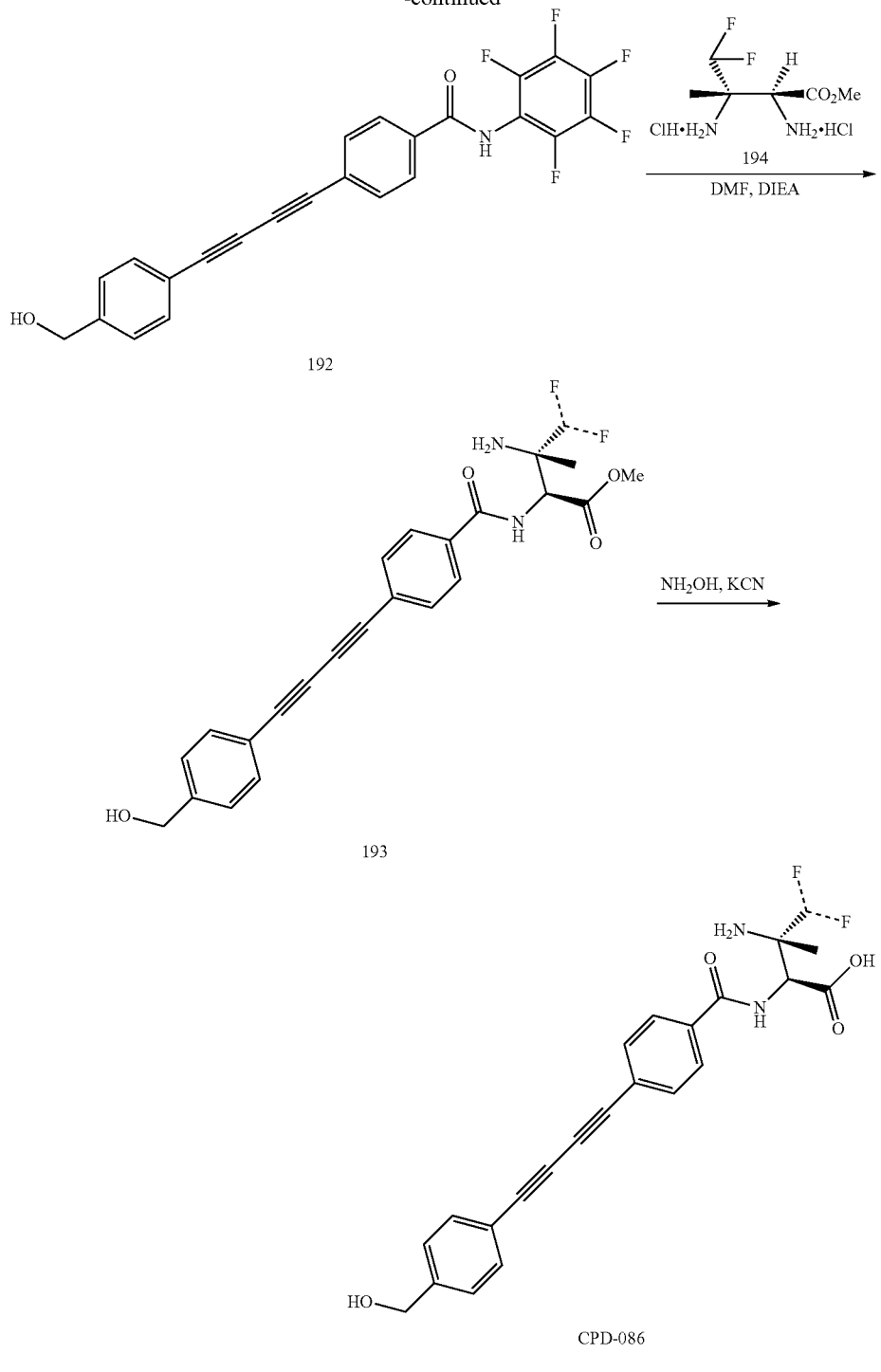

CPD-086

To a solution of 191 (60 mg, 0.217 mmol, 1.00 equiv) in anhydrous THF (8 mL) is added 2, 3, 4, 5, 6-pentafluorophenol (112 mg, 0.652 mmol, 3.00 equiv). Then the mixture is cooled to 0° C. DCC (49 mg, 0.239 mmol, 1.1 equiv) and DMAP (8 mg, 0.065 mmol, 0.3 equiv) are added. The reaction mixture is stirred at 0° C. for 4 h, then allowed to warm to ambient temperature with the stirring is continued overnight (20 h). The resulting suspension is filtered and ished with 20 mL of EtOAc. The filtrate is condensed to dryness with a rotavapor, and the residue is treated water (20 mL), extracted with EtOAc (3×30 mL). The combined extracts are ished with water (30 mL), brine (30 mL), and dried over anhydrous $Na_2SO_4$. Evaporation of the solvent afforded the crude product, which is purified by CombiFlash (eluting with 0-2% MeOH in DCM) to afford 192 (75 mg, 81%) as a yellow solid. LC/MS m/s [M+H]$^+$ 442.1.

To a solution of 194 (33 mg, 0.131 mmol, 1.00 equiv) in anhydrous DMF (2 mL) is added DIEA (0.23 mL, 1.31 mmol, 10.00 equiv) is added. The mixture is cooled to 0° C. Compound 192 (65 mg, 0.157 mmol, 1.08 equiv) is added.

The reaction mixture is stirred at 0° C. for 2 hours, and then is allowed to warm to room temperature for 14 hours. The yellow solution is then concentrated to dryness. The residue is treated with water (30 mL), extracted with EtOAc (3×30 mL). The combined extracts are ished with water (30 mL), brine (30 mL), and dried (anhydrous Na$_2$SO$_4$). The crude product is purified by CombiFlash (eluting with MeOH in DCM 0-5%) to give 193 as a yellow solid. LC/MS m/s [M+H]$^+$ 441.3.

To an ice-cold solution of 193 (0.078 mmol, 1.00 equiv) dissolved in MeOH (1 mL) is added KCN (0.15 mmol, 2.0 equiv). The mixture is the cooled to 0° C., 2 mL of 50% NH$_2$OH aq is added. The reaction mixture is stirred at 0° C. for 4 h, then allowed to warm to ambient temperature with the stirring is continued overnight (14 h). The resulting yellow solvent is condensed to dryness with a rotavapor, and the residue is treated water (20 mL), extracted with EtOAc (3×50 mL). The combined extracts are ished with water (30 mL), brine (30 mL), and dried over anhydrous Na$_2$SO$_4$. Evaporation of the solvent afforded the crude product, which is purified by CombiFlash (eluting with 0-10% MeOH in DCM) to afford CPD-086, (2S,3S)-3-amino-4,4-difluoro-2-(4-((4-(hydroxymethyl)phenyl)buta-1,3-diynyl)benzamido)-3-methylbutanoic acid, as a yellow solid. LC/MS m/s [M+H]$^+$ 442.1.

Examples 40-274

The following compounds can be prepared essentially according to the procedures set forth above, with modifications where necessary of the starting materials to provide the desired product.

| Ex. No. | Structure | Name |
|---|---|---|
| 40 | 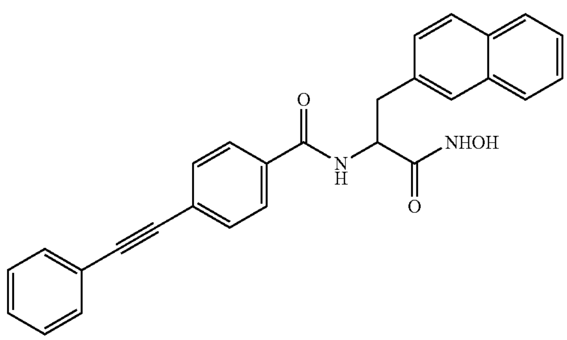 | N-(1-(hydroxyamino)-3-(naphthalen-2-yl)-1-oxopropan-2-yl)-4-(phenylethynyl)benzamide |
| 41 | 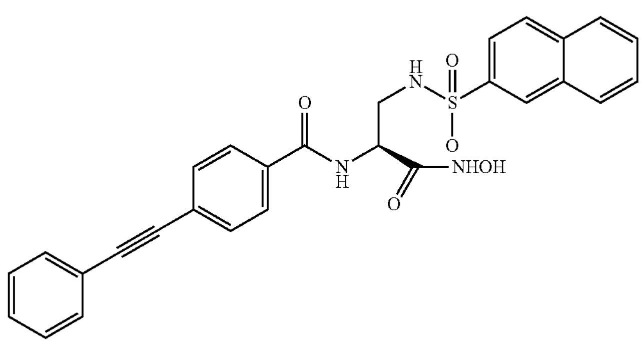 | (S)-N-(1-(hydroxyamino)-3-(naphthalene-2-sulfonamido)-1-oxopropan-2-yl)-4-(phenylethynyl)benzamide |
| 42 | 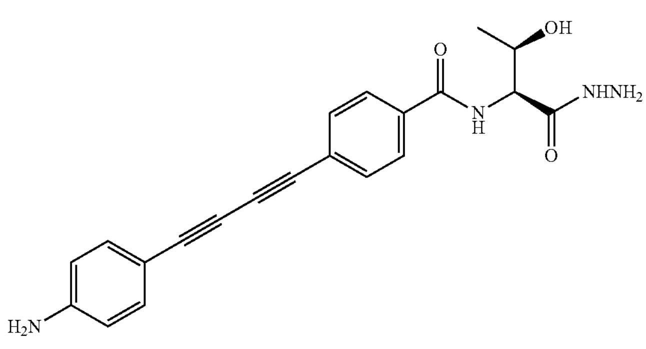 [SMILES: C[C@@H](O)[C@H](NC(=O)c1ccc(C#CC#Cc2ccc(N)cc2)cc1)C(=O)NN] | 4-((4-aminophenyl)buta-1,3-diynyl)-N-((2S,3R)-1-hydrazinyl-3-hydroxy-1-oxobutan-2-yl)benzamide (CPD-045) |

-continued

| Ex. No. | Structure | Name |
|---|---|---|
| 43 | 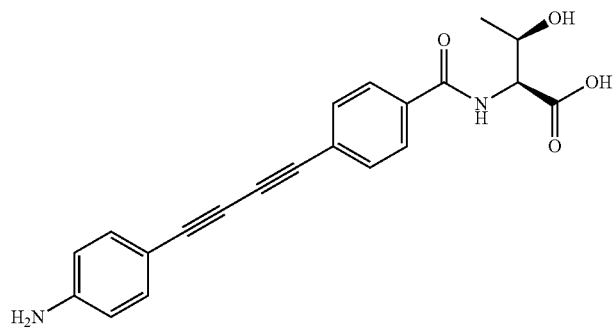 [SMILES: C[C@@H](O)[C@H](NC(=O)c1ccc(C#CC#Cc2ccc(N)cc2)cc1)C(=O)O] | (2S,3R)-2-(4-((4-aminophenyl)buta-1,3-diynyl)benzamido)-3-hydroxybutanoic acid (CPD-046) |
| 44 | 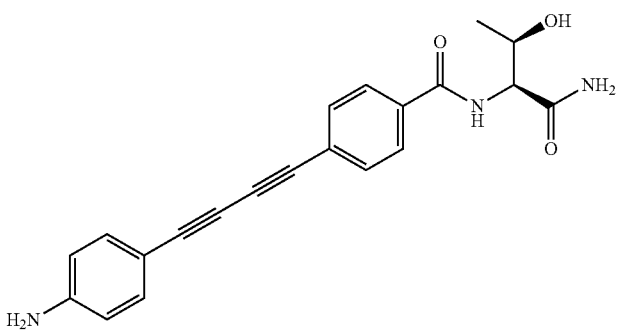 [SMILES: C[C@@H](O)[C@H](NC(=O)c1ccc(C#CC#Cc2ccc(N)cc2)cc1)C(N)=O] | N-((2S,3R)-1-amino-3-hydroxy-1-oxobutan-2-yl)-4-((4-aminophenyl)buta-1,3-diynyl)benzamide (CPD-047) |
| 45 | 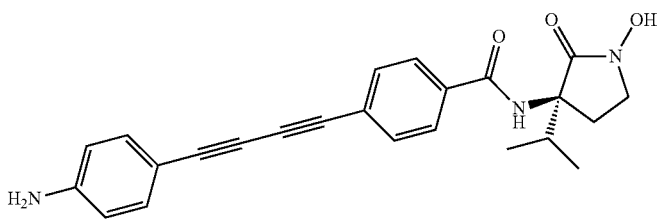 [SMILES: CC(C)[C@@]1(NC(=O)c2ccc(C#CC#Cc3ccc(N)cc3)cc2)CCN(O)C1=O] | (S)-4-((4-aminophenyl)buta-1,3-diynyl)-N-(1-hydroxy-3-isopropyl-2-oxopyrrolidin-3-yl)benzamide (CPD-048) |
| 46 | 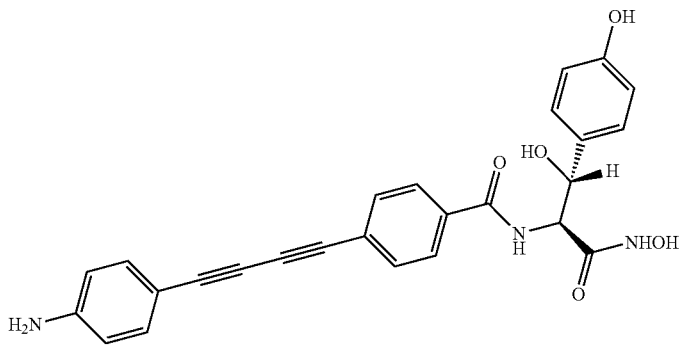 | 4-((4-aminophenyl)buta-1,3-diynyl)-N-((1R,2S)-1-hydroxy-3-(hydroxyamino)-1-(4-hydroxyphenyl)-3-oxopropan-2-yl)benzamide (CPD-049) |
| 47 | 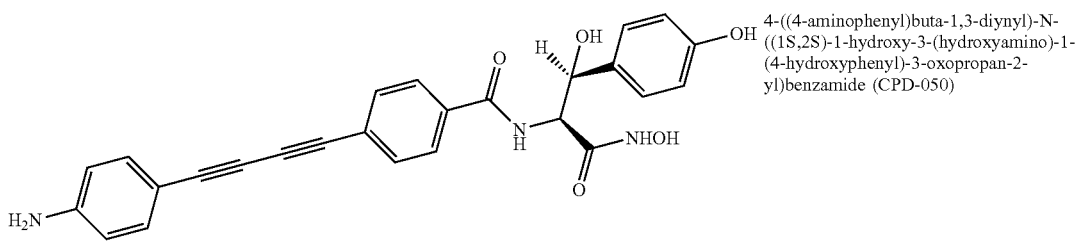 | 4-((4-aminophenyl)buta-1,3-diynyl)-N-((1S,2S)-1-hydroxy-3-(hydroxyamino)-1-(4-hydroxyphenyl)-3-oxopropan-2-yl)benzamide (CPD-050) |

-continued

| Ex. No. | Structure | Name |
|---|---|---|
| 48 | 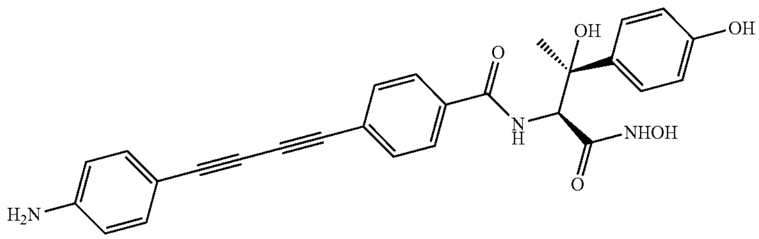 | 4-((4-aminophenyl)buta-1,3-diynyl)-N-((2S)-3-hydroxy-1-(hydroxyamino)-3-(4-hydroxyphenyl)-1-oxobutan-2-yl)benzamide (CPD-051) |
| 49 | 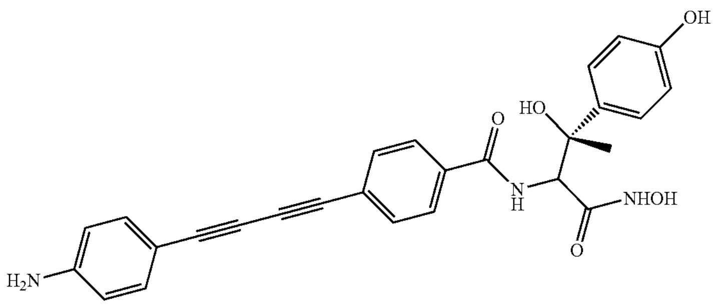 | 4-((4-aminophenyl)buta-1,3-diynyl)-N-((3R)-3-hydroxy-1-(hydroxyamino)-3-(4-hydroxyphenyl)-1-oxobutan-2-yl)benzamide (CPD-052) |
| 50 | 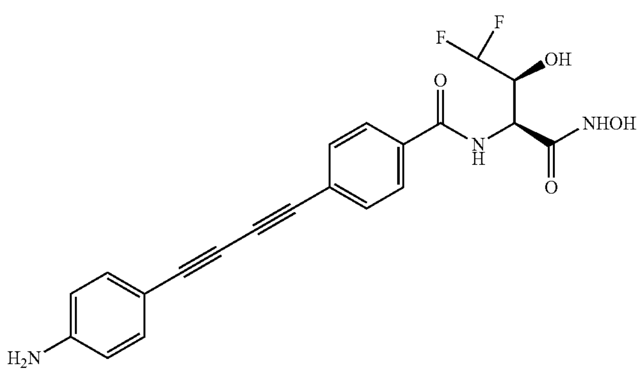 | 4-((4-aminophenyl)buta-1,3-diynyl)-N-((2S,3S)-4,4-difluoro-3-hydroxy-1-(hydroxyamino)-1-oxobutan-2-yl)benzamide (CPD-056) |
| 51 | 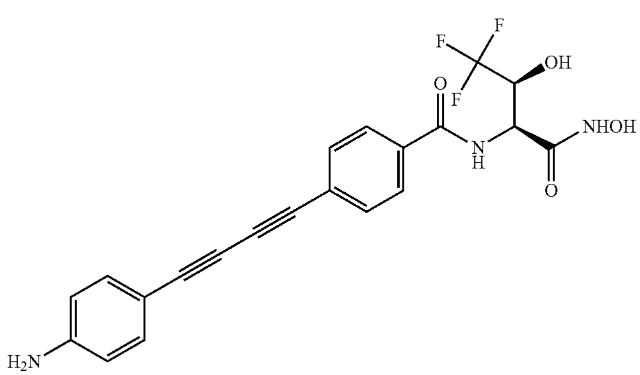 | 4-((4-aminophenyl)buta-1,3-diynyl)-N-((2S,3S)-4,4,4-trifluoro-3-hydroxy-1-(hydroxyamino)-1-oxobutan-2-yl)benzamide (CPD-057) |

-continued

| Ex. No. | Structure | Name |
|---|---|---|
| 52 | 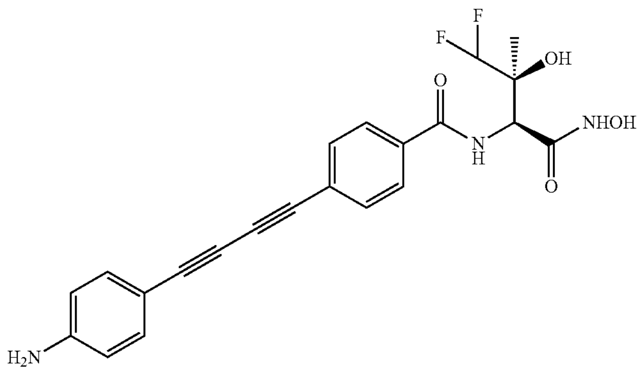 | 4-((4-aminophenyl)buta-1,3-diynyl)-N-((2S,3S)-4,4-difluoro-3-hydroxy-1-(hydroxyamino)-3-methyl-1-oxobutan-2-yl)benzamide (CPD-058) |
| 53 | 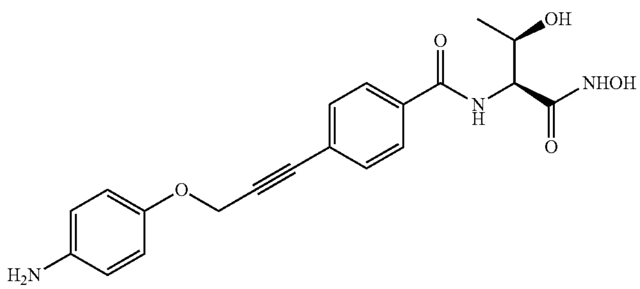 | 4-(3-(4-aminophenoxy)prop-1-ynyl)-N-((2S,3R)-3-hydroxy-1-(hydroxyamino)-1-oxobutan-2-yl)benzamide (CPD-059) |
| 54 | 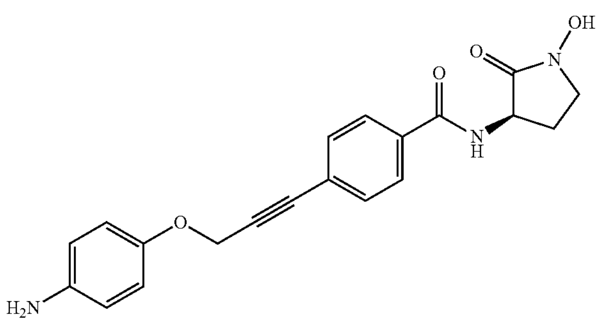 [SMILES: Nc1ccc(OCC#Cc2ccc(C(=O)N[C@@H]3CCN(O)C3=O)cc2)cc1] | (R)-4-(3-(4-aminophenoxy)prop-1-ynyl)-N-(1-hydroxy-2-oxopyrrolidin-3-yl)benzamide (CPD-060) |
| 55 | 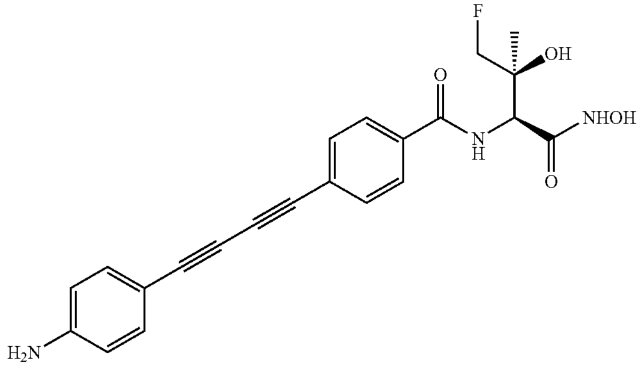 | 4-((4-aminophenyl)buta-1,3-diynyl)-N-((2S,3S)-4-fluoro-3-hydroxy-1-(hydroxyamino)-3-methyl-1-oxobutan-2-yl)benzamide (CPD-061) |

-continued

| Ex. No. | Structure | Name |
|---|---|---|
| 56 | 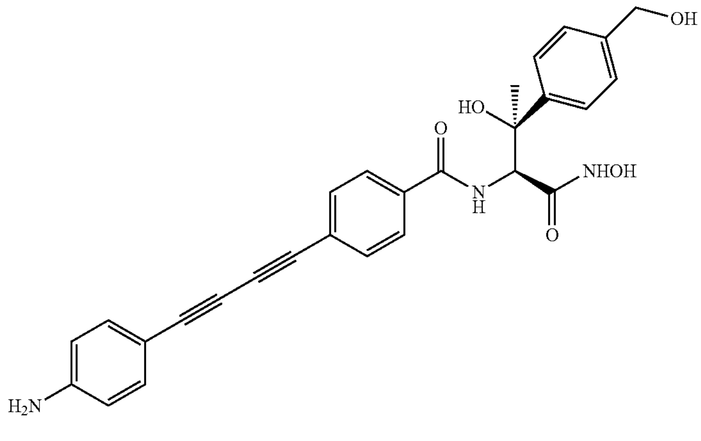 | 4-((4-aminophenyl)buta-1,3-diynyl)-N-((2S,3S)-3-hydroxy-1-(hydroxyamino)-3-(4-(hydroxymethyl)phenyl)-1-oxobutan-2-yl)benzamide (CPD-062) |
| 57 | 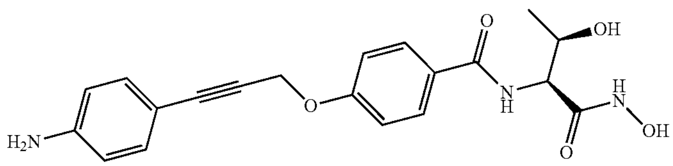 [SMILES: C[C@@H](O)[C@H](NC(=O)c1ccc(OCC#Cc2ccc(N)cc2)cc1)C(=O)NO] | 4-(3-(4-aminophenyl)prop-2-ynyloxy)-N-((2S,3R)-3-hydroxy-1-(hydroxyamino)-1-oxobutan-2-yl)benzamide (CPD-063) |
| 58 | 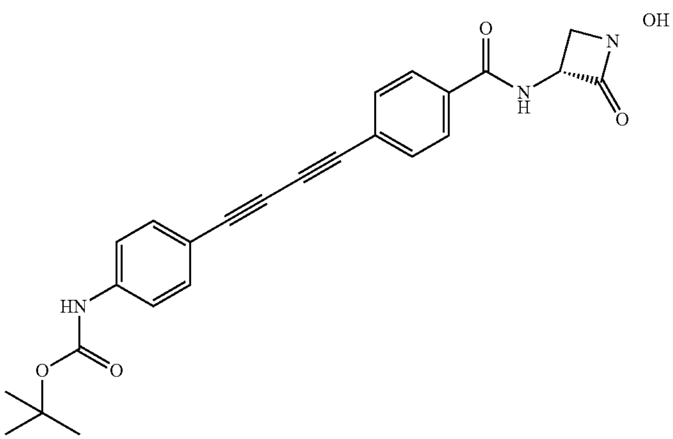 | (R)-tert-butyl 4-((4-(1-hydroxy-2-oxoazetidin-3-ylcarbamoyl)phenyl)buta-1,3-diynyl)phenylcarbamate (CPD-064) |
| 59 | 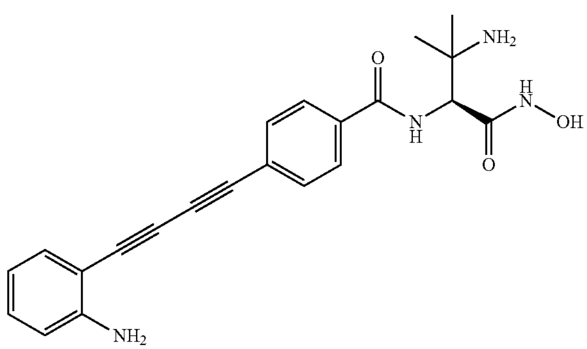 | (S)-N-(3-amino-1-(hydroxyamino)-3-methyl-1-oxobutan-2-yl)-4-((2-aminophenyl)buta-1,3-diynyl)benzamide (CPD-065) |

| Ex. No. | Structure | Name |
|---|---|---|
| 60 | 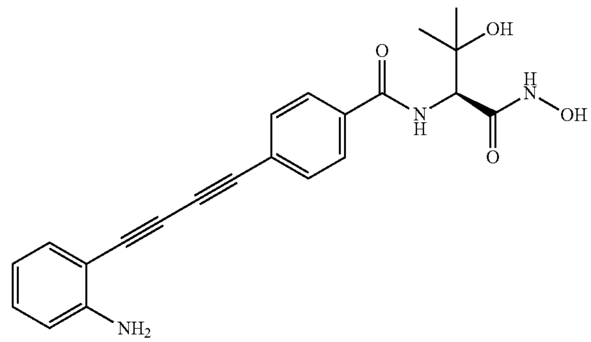 [SMILES: CC(C)(O)[C@H](NC(=O)c1ccc(C#CC#Cc2ccccc2N)cc1)C(=O)NO] | (S)-4-((2-aminophenyl)buta-1,3-diynyl)-N-(3-hydroxy-1-(hydroxyamino)-3-methyl-1-oxobutan-2-yl)benzamide (CPD-066) |
| 61 | 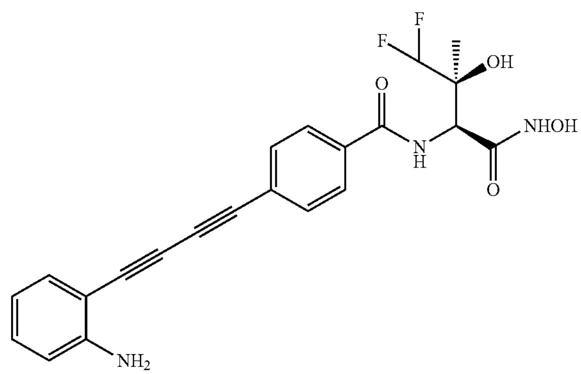 | 4-((2-aminophenyl)buta-1,3-diynyl)-N-((2S,3S)-4,4-difluoro-3-hydroxy-1-(hydroxyamino)-3-methyl-1-oxobutan-2-yl)benzamide (CPD-067) |
| 62 | 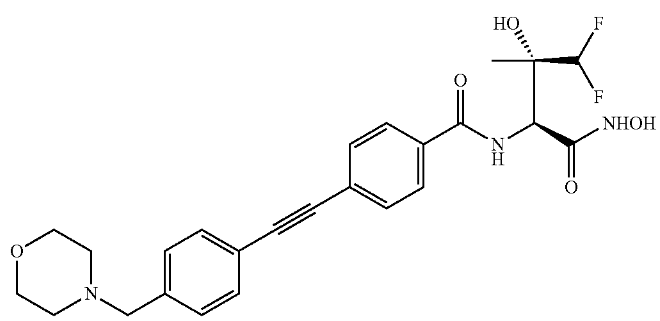 | N-((2S,3S)-4,4-difluoro-3-hydroxy-1-(hydroxyamino)-3-methyl-1-oxobutan-2-yl)-4-((4-(morpholinomethyl)phenyl)ethynyl)benzamide (CPD-069) |
| 63 | 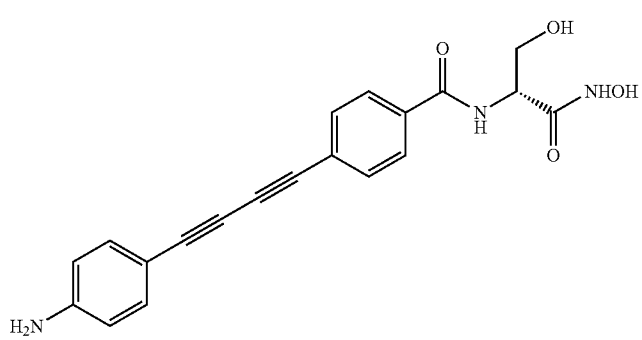 | (R)-4-((4-aminophenyl)buta-1,3-diynyl)-N-(3-hydroxy-1-(hydroxyamino)-1-oxopropan-2-yl)benzamide (CPD-070) |

| Ex. No. | Structure | Name |
|---|---|---|
| 64 | 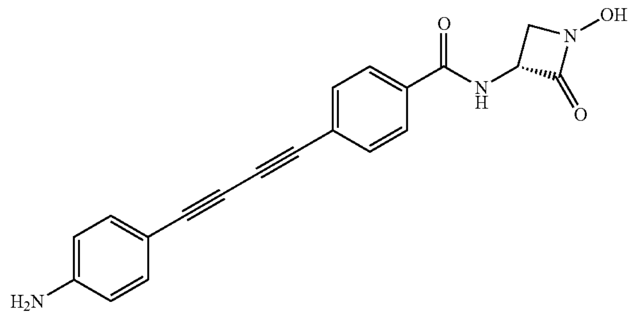 [SMILES: Nc1ccc(C#CC#Cc2ccc(C(=O)N[C@@H]3CN(O)C3=O)cc2)cc1] | (R)-4-((4-aminophenyl)buta-1,3-diynyl)-N-(1-hydroxy-2-oxoazetidin-3-yl)benzamide (CPD-071) |
| 65 | 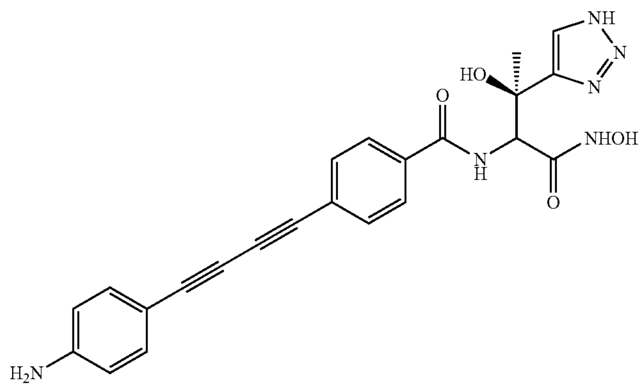 | 4-((4-aminophenyl)buta-1,3-diynyl)-N-((3R)-3-hydroxy-1-(hydroxyamino)-1-oxo-3-(1H-1,2,3-triazol-4-yl)butan-2-yl)benzamide (CPD-072) |
| 66 | 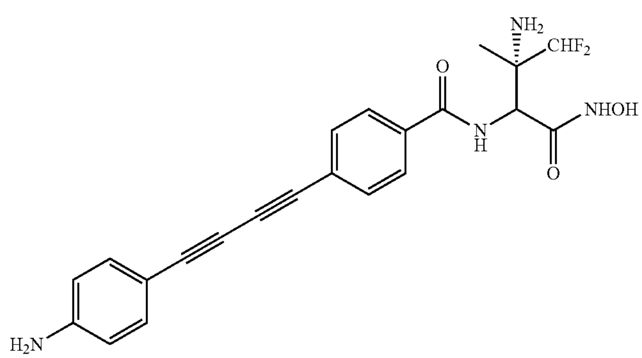 | N-((3S)-3-amino-4,4-difluoro-1-(hydroxyamino)-3-methyl-1-oxobutan-2-yl)-4-((4-aminophenyl)buta-1,3-diynyl)benzamide (CPD-079) |
| 67 | 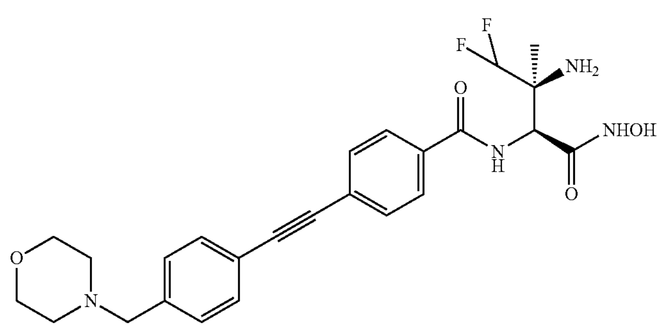 | N-((2S,3S)-3-amino-4,4-difluoro-1-(hydroxyamino)-3-methyl-1-oxobutan-2-yl)-4-((4-(morpholinomethyl)phenyl)ethynyl)benzamide (CPD-080) |

| Ex. No. | Structure | Name |
|---|---|---|
| 68 | 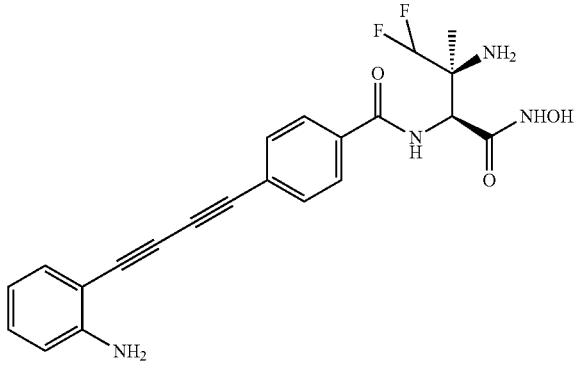 | N-((2S,3S)-3-amino-4,4-difluoro-1-(hydroxyamino)-3-methyl-1-oxobutan-2-yl)-4-((2-aminophenyl)buta-1,3-diynyl)benzamide (CPD-081) |
| 69 | 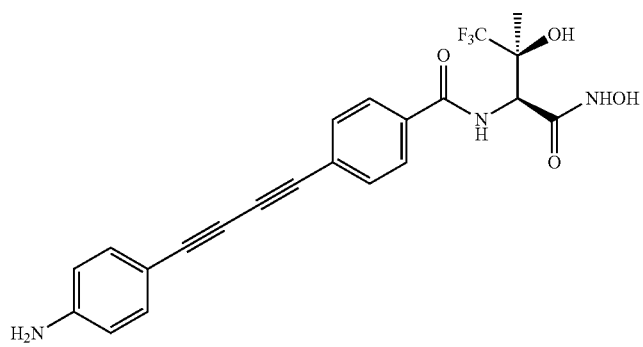 | 4-((4-aminophenyl)buta-1,3-diynyl)-N-((2S,3S)-4,4,4-trifluoro-3-hydroxy-1-(hydroxyamino)-3-methyl-1-oxobutan-2-yl)benzamide (CPD-083) |
| 70 | 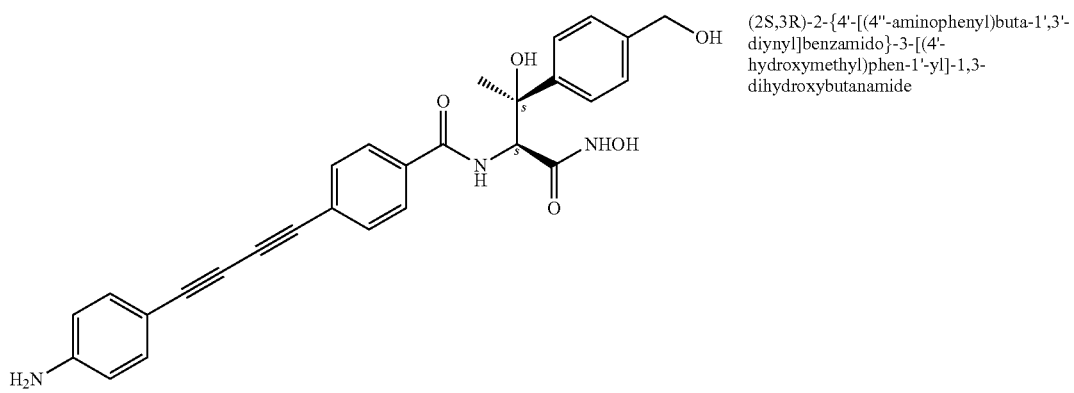 | (2S,3R)-2-{4'-[(4''-aminophenyl)buta-1',3'-diynyl]benzamido}-3-[(4'-hydroxymethyl)phen-1'-yl]-1,3-dihydroxybutanamide |
| 71 | 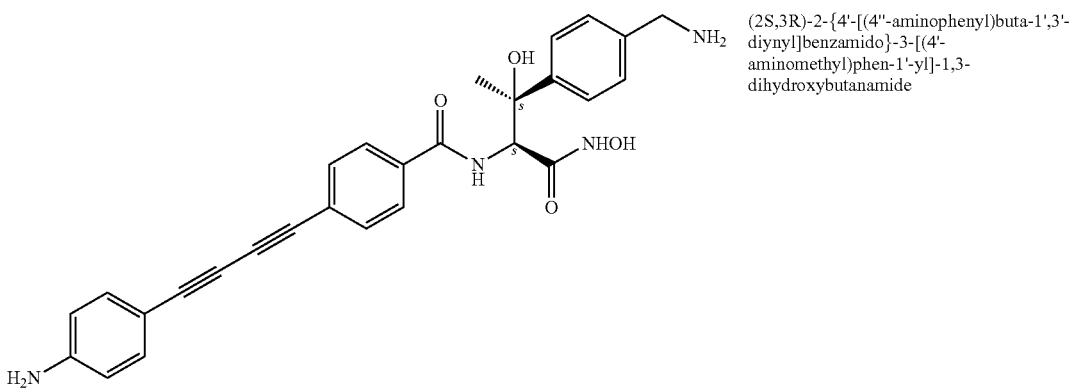 | (2S,3R)-2-{4'-[(4''-aminophenyl)buta-1',3'-diynyl]benzamido}-3-[(4'-aminomethyl)phen-1'-yl]-1,3-dihydroxybutanamide |

| Ex. No. | Structure | Name |
|---|---|---|
| 72 | 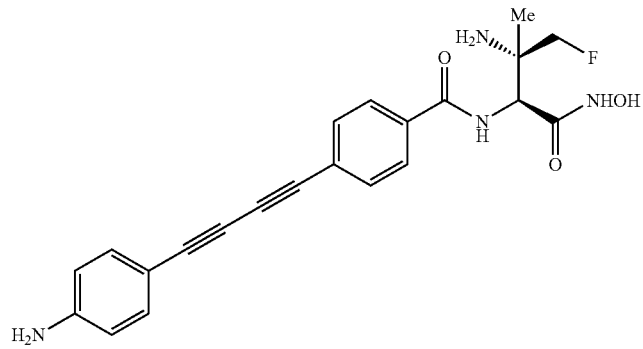 | (2S,3R)-3-amino-2-{4'-[(4''-aminophenyl)buta-1',3'-diynyl]benzamido}-3-fluoromethyl-1,3-dihydroxybutanamide |
| 73 | 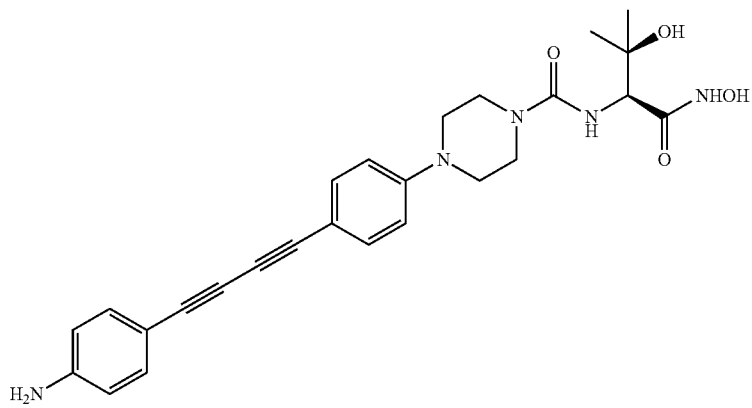 | (2S,3R)-2-{4'-[(4''-aminophenyl)buta-1',3'-diynyl]phenyl-4'-piperizine-4'-carboxamido}-1,3-dihydroxybutanamide |
| 74 | 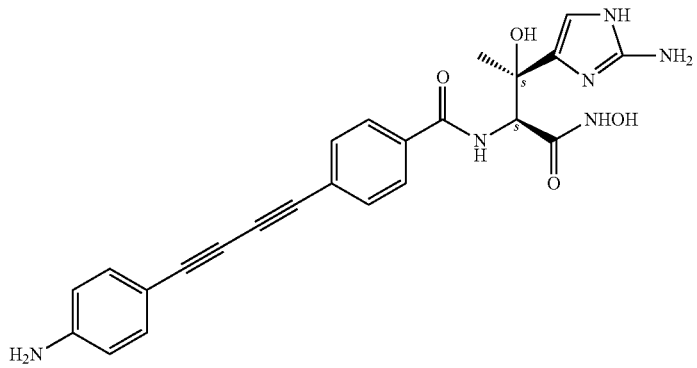 | (2S,3R)-2-{4'-[(4''-aminophenyl)buta-1',3'-diynyl]benzamido}-3-[(2'-amino)imidazol-5'-yl]-1,3-dihydroxybutanamide |
| 75 | 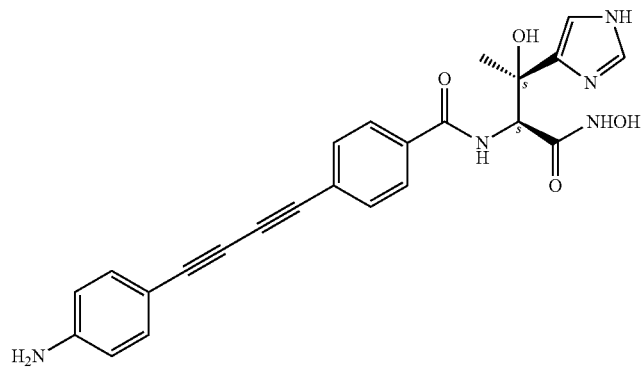 | (2S,3R)-2-{4'-[(4''-aminophenyl)buta-1',3'-diynyl]benzamido}-3-(imidazol-5'-yl]-1,3-dihydroxybutanamide |

| Ex. No. | Structure | Name |
|---|---|---|
| 76 | 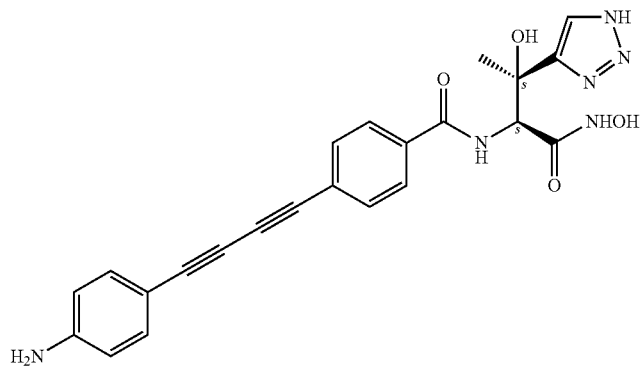 | (2S,3R)-2-{4'-[(4''-aminophenyl)buta-1',3'-diynyl]benzamido}-3-(triazol-5'-yl)-1,3-dihydroxybutanamide |
| 77 | 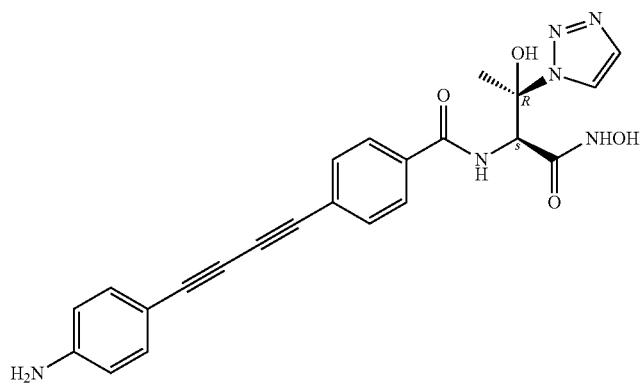 | (2S,3R)-2-{4'-[(4''-aminophenyl)buta-1',3'-diynyl]benzamido}-3-(triazol-1'-yl)-1,3-dihydroxybutanamide |
| 78 | 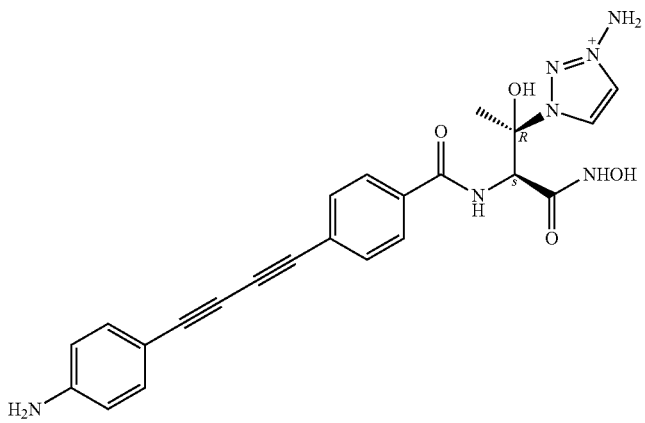 | (2S,3R)-2-{4'-[(4''-aminophenyl)buta-1',3'-diynyl]benzamido}-3-(3'-amminium-triazol-1'-yl]-1,3-dihydroxybutanamide |
| 79 | 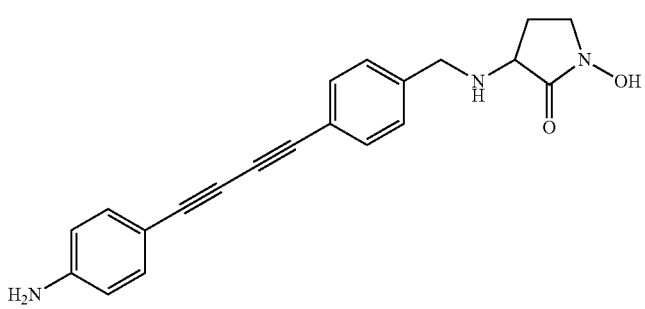 [SMILES: Nc1ccc(C#CC#Cc2ccc(CNC3CCN(O)C3=O)cc2)cc1] | 1-hydroxy-3-{N-[(4''-aminophenyl)buta-1',3'-diynyl]benzyl}-2-pyrrolidone |

-continued
| Ex. No. | Structure | Name |
|---|---|---|
| 80 | 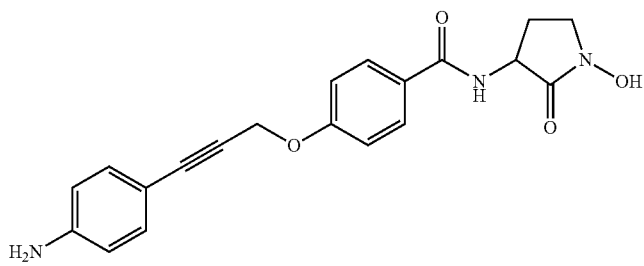 [SMILES: Nc1ccc(C#CCOc2ccc(C(=O)NC3CCN(O)C3=O)cc2)cc1] | 1-hydroxy-3-{4'-[(4''-aminophenyl)prop-2-ynyloxy]benzamido}-2-pyrrolidone |
| 81 | 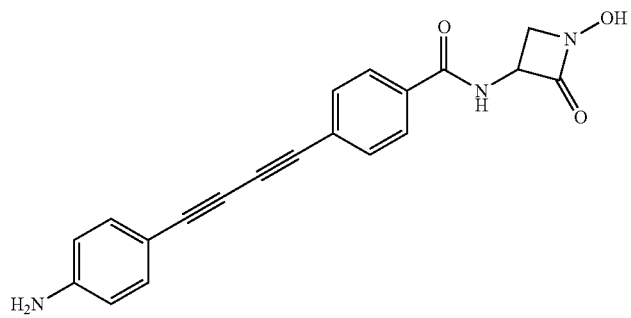 | 1-hydroxy-3-{4'-[(4''-aminophenyl)buta-1',3'-diynyl]benzamido}-2-lactam |
| 82 | 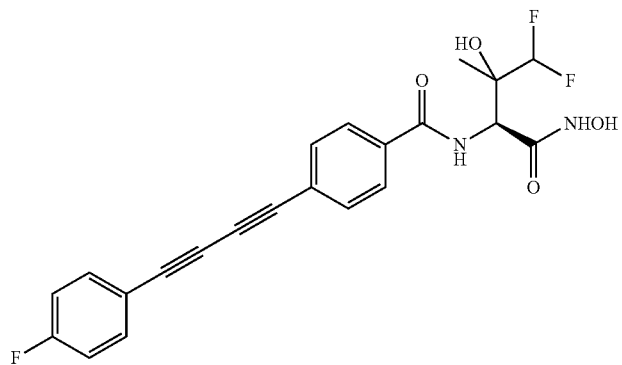 | N-((2S)-4,4-difluoro-3-hydroxy-1-(hydroxyamino)-3-methyl-1-oxobutan-2-yl)-4-((4-fluorophenyl)buta-1,3-diynyl)benzamide |
| 83 | 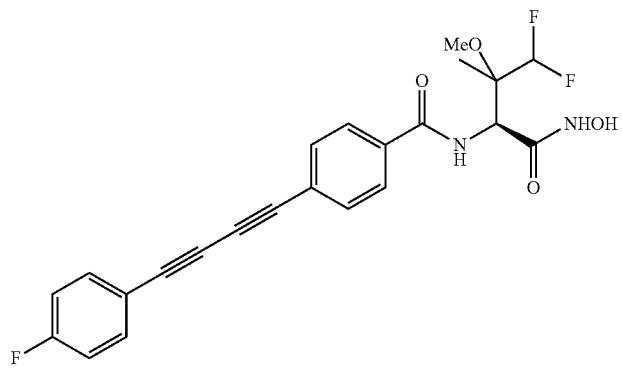 | N-((2S)-4,4-difluoro-1-(hydroxyamino)-3-methoxy-3-methyl-1-oxobutan-2-yl)-4-((4-fluorophenyl)buta-1,3-diynyl)benzamide |

-continued

| Ex. No. | Structure | Name |
|---|---|---|
| 84 | 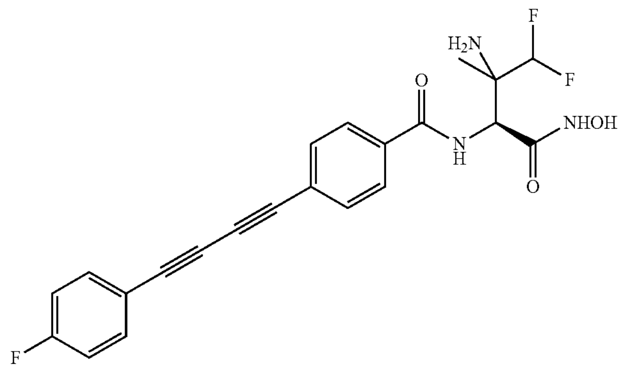 | N-((2S)-3-amino-4,4-difluoro-1-(hydroxyamino)-3-methyl-1-oxobutan-2-yl)-4-((4-fluorophenyl)buta-1,3-diynyl)benzamide |
| 85 | 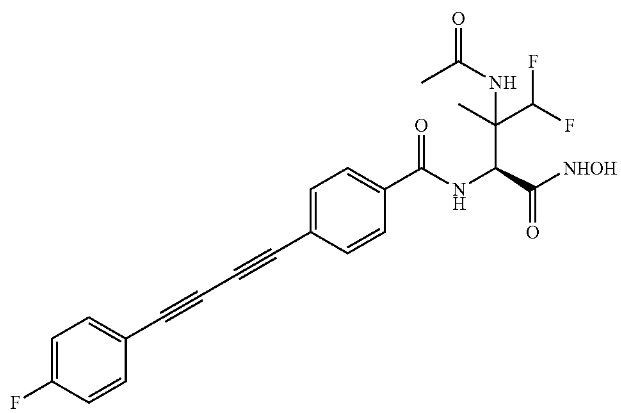 | N-((2S)-3-acetamido-4,4-difluoro-1-(hydroxyamino)-3-methyl-1-oxobutan-2-yl)-4-((4-fluorophenyl)buta-1,3-diynyl)benzamide |
| 86 | 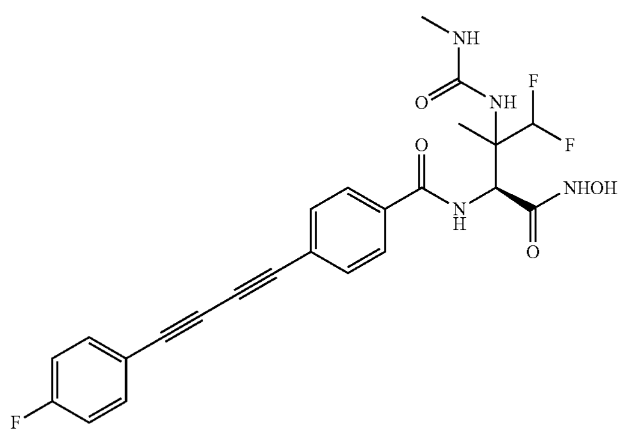 | N-((2S)-4,4-difluoro-1-(hydroxyamino)-3-methyl-3-(3-methylureido)-1-oxobutan-2-yl)-4-((4-fluorophenyl)buta-1,3-diynyl)benzamide |
| 87 | 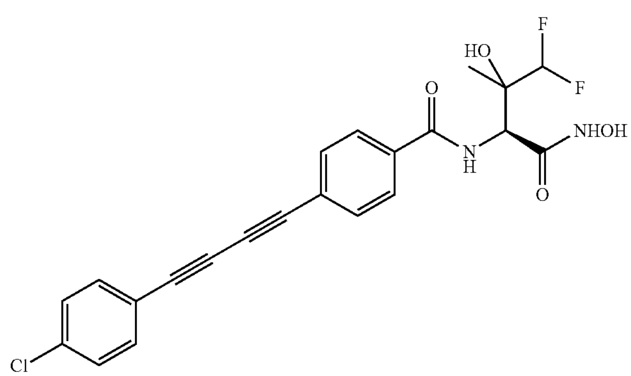 | 4-((4-chlorophenyl)buta-1,3-diynyl)-N-((2S)-4,4-difluoro-3-hydroxy-1-(hydroxyamino)-3-methyl-1-oxobutan-2-yl)benzamide |

| Ex. No. | Structure | Name |
|---|---|---|
| 88 | 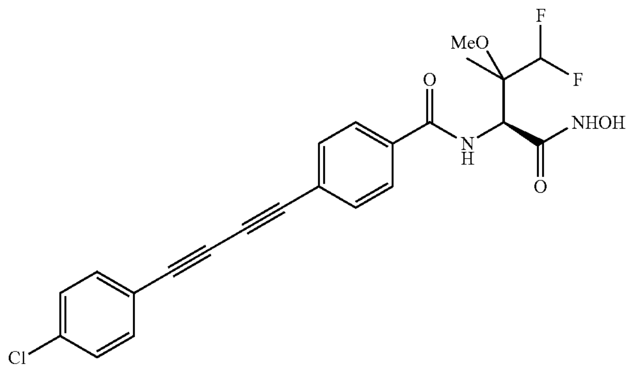 | 4-((4-chlorophenyl)buta-1,3-diynyl)-N-((2S)-4,4-difluoro-1-(hydroxyamino)-3-methoxy-3-methyl-1-oxobutan-2-yl)benzamide |
| 89 | 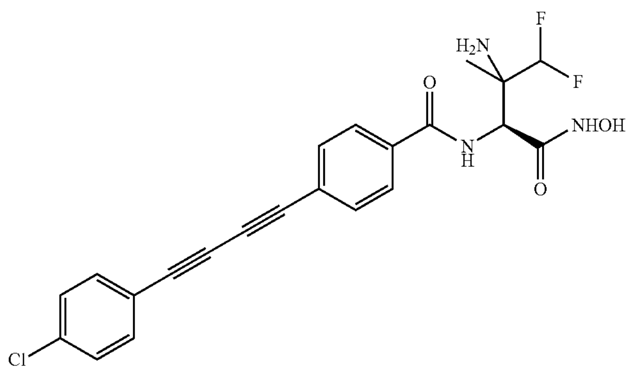 | N-((2S)-3-amino-4,4-difluoro-1-(hydroxyamino)-3-methyl-1-oxobutan-2-yl)-4-((4-chlorophenyl)buta-1,3-diynyl)benzamide |
| 90 | 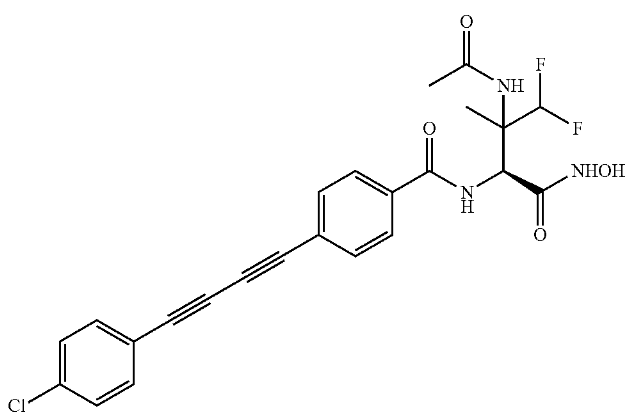 | N-((2S)-3-acetamido-4,4-difluoro-1-(hydroxyamino)-3-methyl-1-oxobutan-2-yl)-4-((4-chlorophenyl)buta-1,3-diynyl)benzamide |
| 91 | 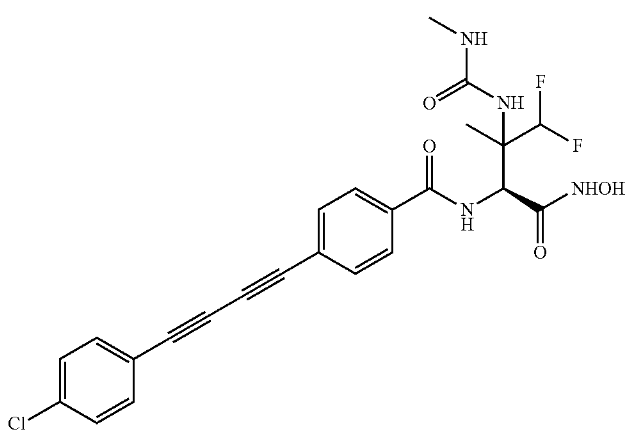 | 4-((4-chlorophenyl)buta-1,3-diynyl)-N-((2S)-4,4-difluoro-1-(hydroxyamino)-3-methyl-3-(3-methylureido)-1-oxobutan-2-yl)benzamide |

| Ex. No. | Structure | Name |
|---|---|---|
| 92 | 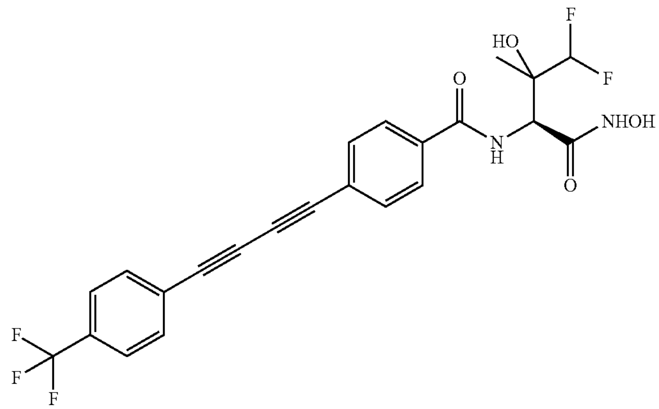 | N-((2S)-4,4-difluoro-3-hydroxy-1-(hydroxyamino)-3-methyl-1-oxobutan-2-yl)-4-((4-(trifluoromethyl)phenyl)buta-1,3-diynyl)benzamide |
| 93 | 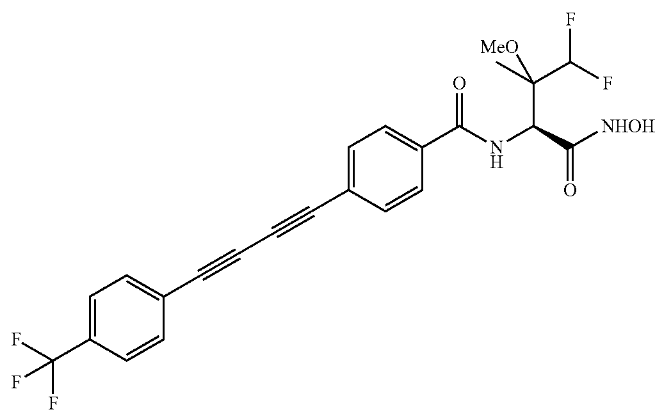 | N-((2S)-4,4-difluoro-1-(hydroxyamino)-3-methoxy-3-methyl-1-oxobutan-2-yl)-4-((4-(trifluoromethyl)phenyl)buta-1,3-diynyl)benzamide |
| 94 | 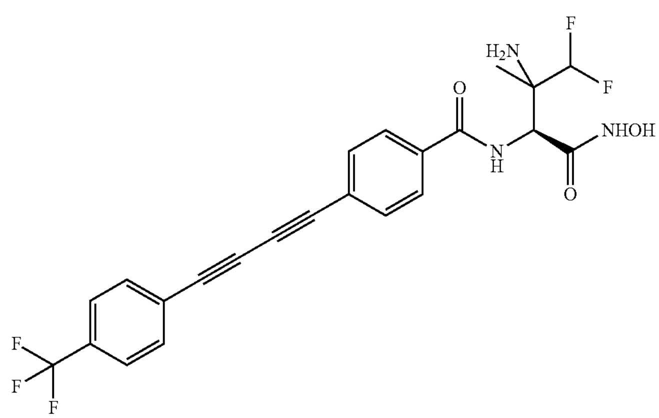 | N-((2S)-3-amino-4,4-difluoro-1-(hydroxyamino)-3-methyl-1-oxobutan-2-yl)-4-((4-(trifluoromethyl)phenyl)buta-1,3-diynyl)benzamide |

| Ex. No. | Structure | Name |
|---|---|---|
| 95 | 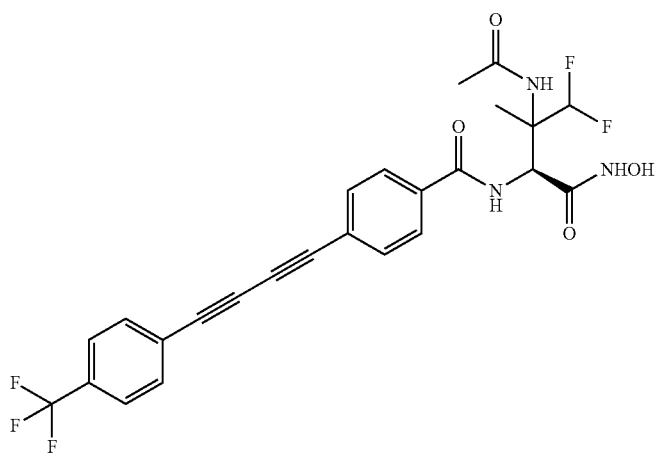 | N-((2S)-3-acetamido-4,4-difluoro-1-(hydroxyamino)-3-methyl-1-oxobutan-2-yl)-4-((4-(trifluoromethyl)phenyl)buta-1,3-diynyl)benzamide |
| 96 | 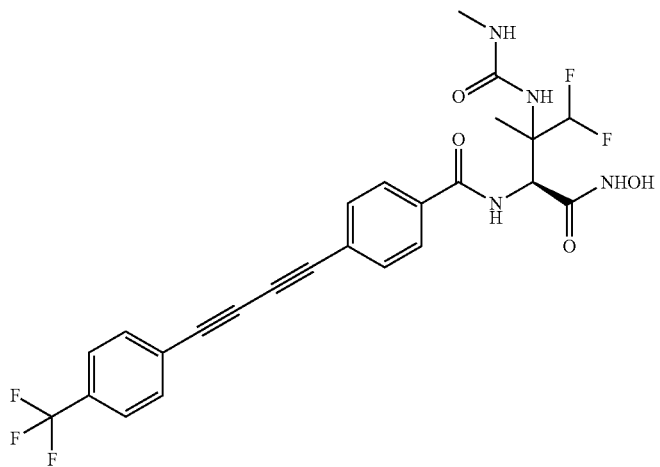 | N-((2S)-4,4-difluoro-1-(hydroxyamino)-3-methyl-3-(3-methylureido)-1-oxobutan-2-yl)-4-((4-(trifluoromethyl)phenyl)buta-1,3-diynyl)benzamide |
| 97 | 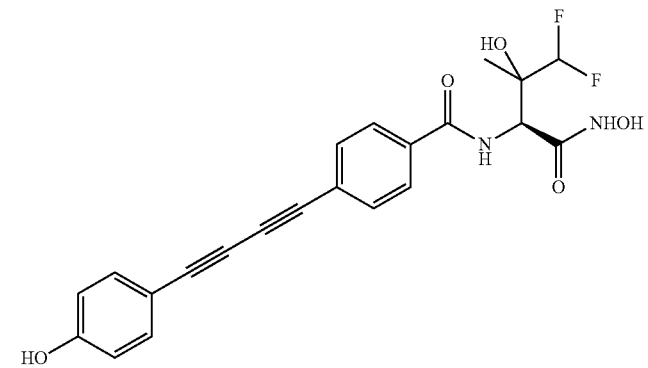 | N-((2S)-4,4-difluoro-3-hydroxy-1-(hydroxyamino)-3-methyl-1-oxobutan-2-yl)-4-((4-hydroxyphenyl)buta-1,3-diynyl)benzamide |

-continued

| Ex. No. | Structure | Name |
|---|---|---|
| 98 | 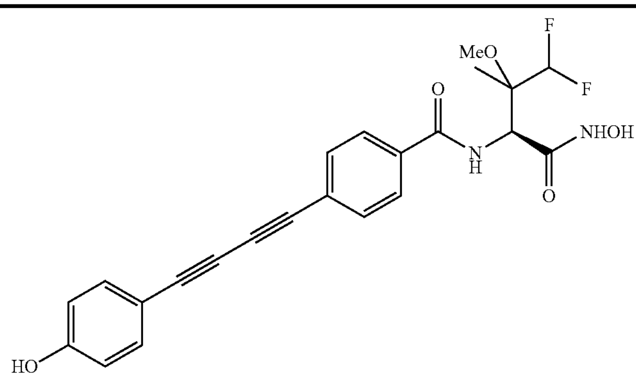 | N-((2S)-4,4-difluoro-1-(hydroxyamino)-3-methoxy-3-methyl-1-oxobutan-2-yl)-4-((4-hydroxyphenyl)buta-1,3-diynyl)benzamide |
| 99 | 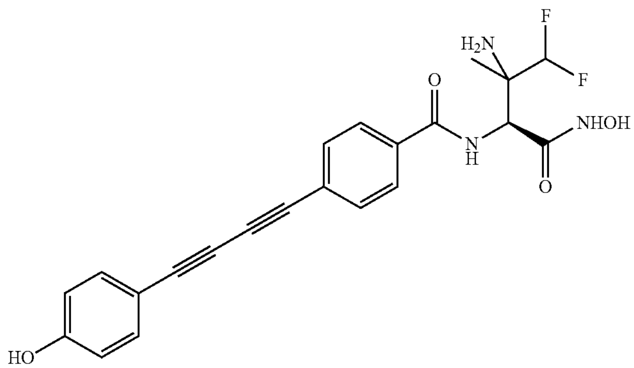 | N-((2S)-3-amino-4,4-difluoro-1-(hydroxyamino)-3-methyl-1-oxobutan-2-yl)-4-((4-hydroxyphenyl)buta-1,3-diynyl)benzamide |
| 100 | 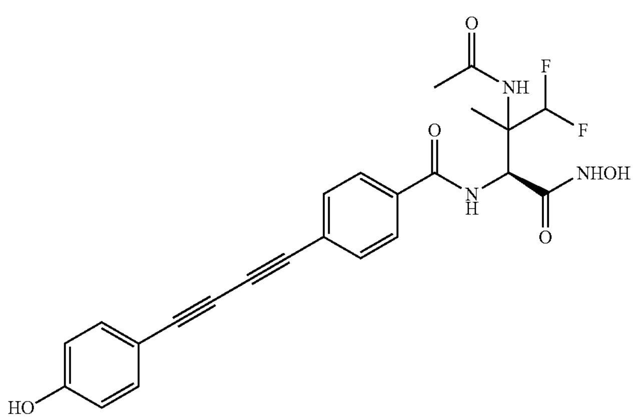 | N-((2S)-3-acetamido-4,4-difluoro-1-(hydroxyamino)-3-methyl-1-oxobutan-2-yl)-4-((4-hydroxyphenyl)buta-1,3-diynyl)benzamide |
| 101 | 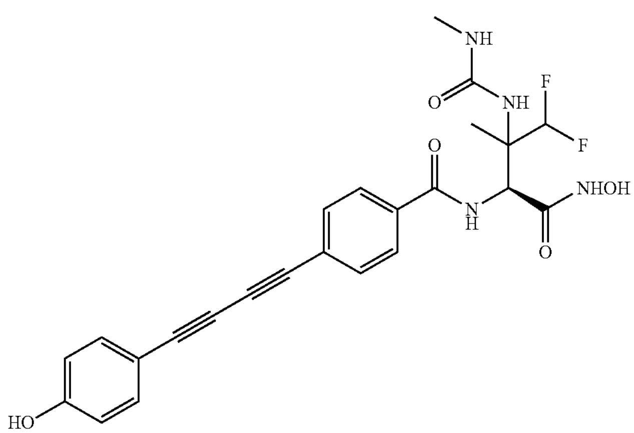 | N-((2S)-4,4-difluoro-1-(hydroxyamino)-3-methyl-3-(3-methylureido)-1-oxobutan-2-yl)-4-((4-hydroxyphenyl)buta-1,3-diynyl)benzamide |

-continued

| Ex. No. | Structure | Name |
|---|---|---|
| 102 | 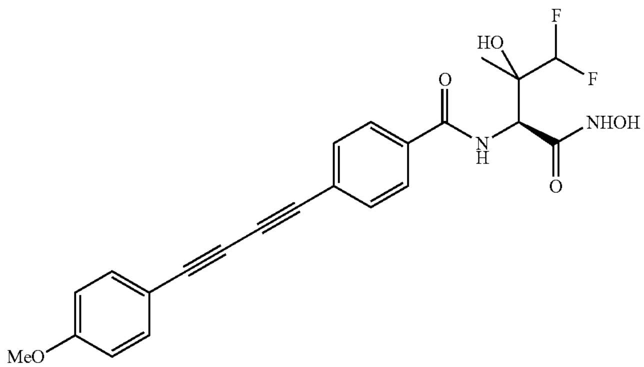 | N-((2S)-4,4-difluoro-3-hydroxy-1-(hydroxyamino)-3-methyl-1-oxobutan-2-yl)-4-((4-methoxyphenyl)buta-1,3-diynyl)benzamide |
| 103 | 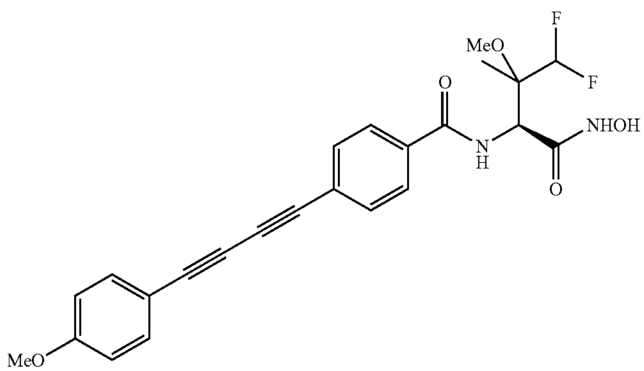 | N-((2S)-4,4-difluoro-1-(hydroxyamino)-3-methoxy-3-methyl-1-oxobutan-2-yl)-4-((4-methoxyphenyl)buta-1,3-diynyl)benzamide |
| 104 | 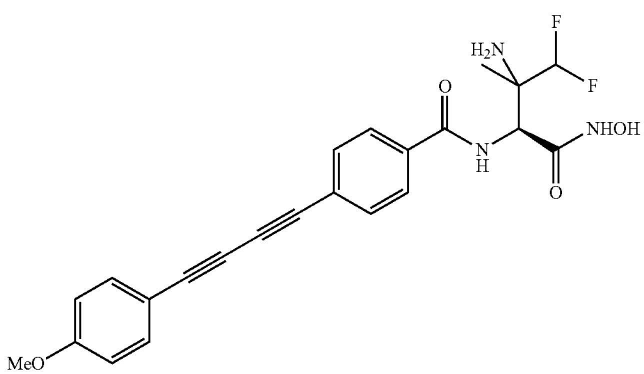 | N-((2S)-3-amino-4,4-difluoro-1-(hydroxyamino)-3-methyl-1-oxobutan-2-yl)-4-((4-methoxyphenyl)buta-1,3-diynyl)benzamide |
| 105 | 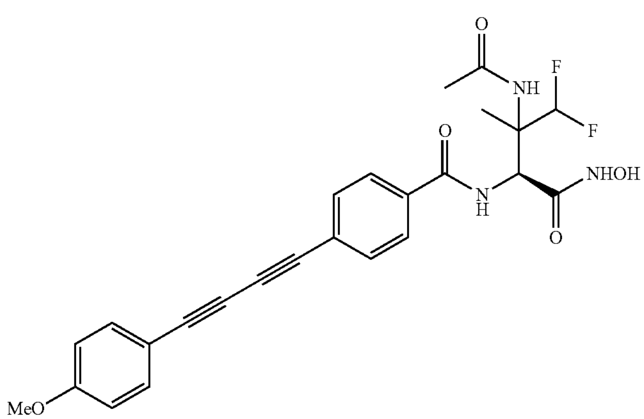 | N-((2S)-3-acetamido-4,4-difluoro-1-(hydroxyamino)-3-methyl-1-oxobutan-2-yl)-4-((4-methoxyphenyl)buta-1,3-diynyl)benzamide |

| Ex. No. | Structure | Name |
|---|---|---|
| 106 | 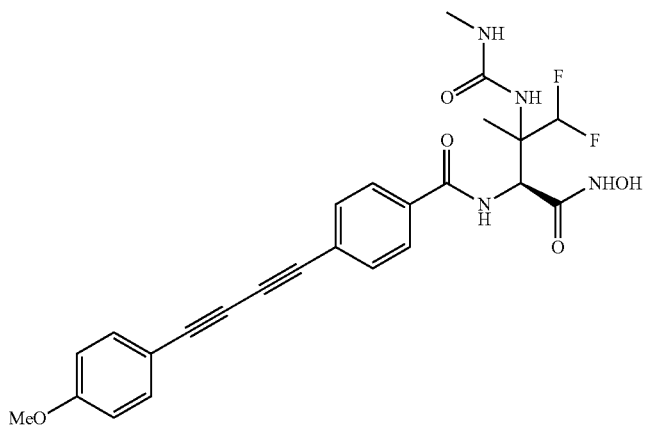 | N-((2S)-4,4-difluoro-1-(hydroxyamino)-3-methyl-3-(3-methylureido)-1-oxobutan-2-yl)-4-((4-methoxyphenyl)buta-1,3-diynyl)benzamide |
| 107 | 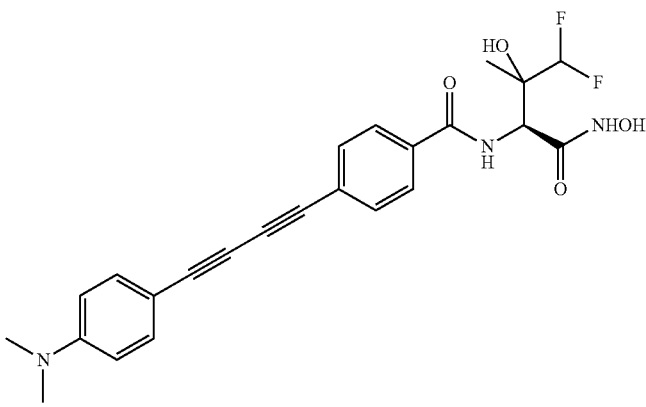 | N-((2S)-4,4-difluoro-3-hydroxy-1-(hydroxyamino)-3-methyl-1-oxobutan-2-yl)-4-((4-(dimethylamino)phenyl)buta-1,3-diynyl)benzamide |
| 108 | 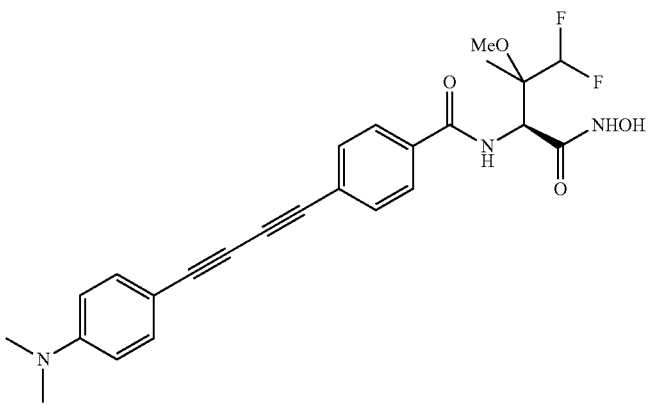 | N-((2S)-4,4-difluoro-1-(hydroxyamino)-3-methoxy-3-methyl-1-oxobutan-2-yl)-4-((4-(dimethylamino)phenyl)buta-1,3-diynyl)benzamide |

-continued
| Ex. No. | Structure | Name |
|---|---|---|
| 109 | 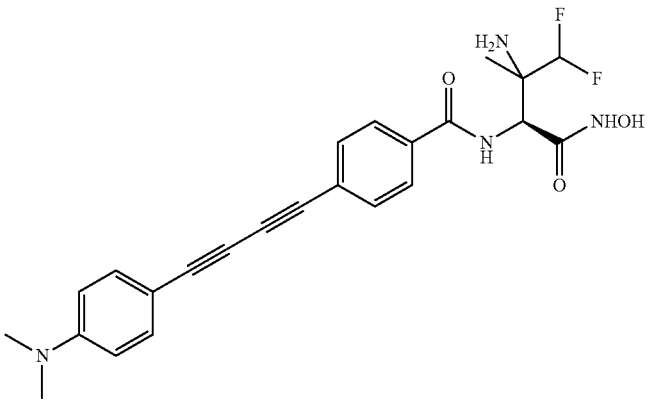 | N-((2S)-3-amino-4,4-difluoro-1-(hydroxyamino)-3-methyl-1-oxobutan-2-yl)-4-((4-(dimethylamino)phenyl)buta-1,3-diynyl)benzamide |
| 110 | 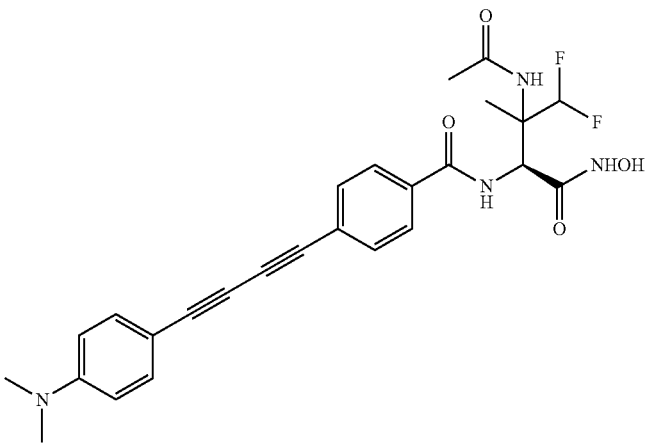 | N-((2S)-3-acetamido-4,4-difluoro-1-(hydroxyamino)-3-methyl-1-oxobutan-2-yl)-4-((4-(dimethylamino)phenyl)buta-1,3-diynyl)benzamide |
| 111 | 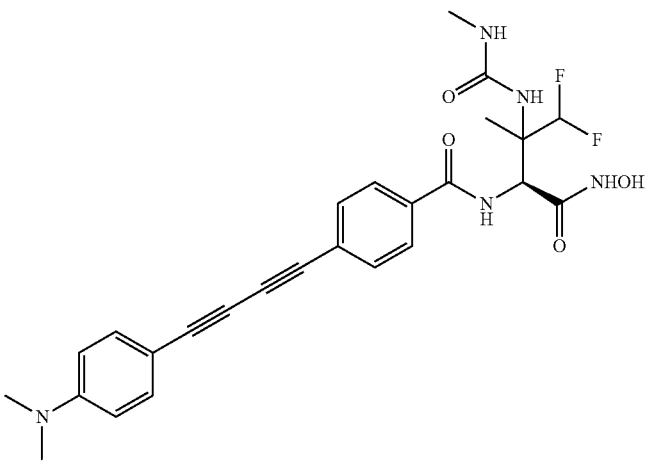 | N-((2S)-4,4-difluoro-1-(hydroxyamino)-3-methyl-3-(3-methylureido)-1-oxobutan-2-yl)-4-((4-(dimethylamino)phenyl)buta-1,3-diynyl)benzamide |

| Ex. No. | Structure | Name |
|---|---|---|
| 112 | 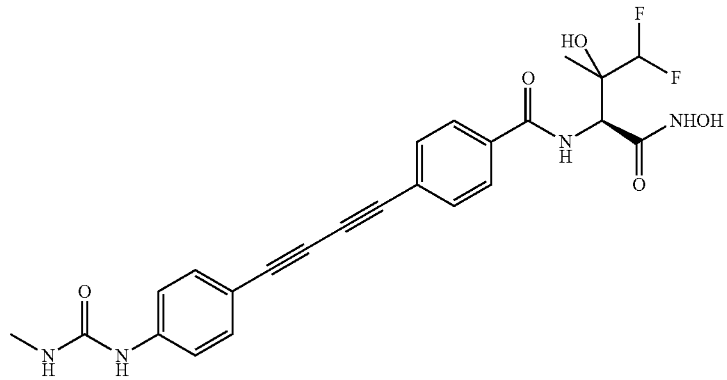 | N-((2S)-4,4-difluoro-3-hydroxy-1-(hydroxyamino)-3-methyl-1-oxobutan-2-yl)-4-((4-(3-methylureido)phenyl)buta-1,3-diynyl)benzamide |
| 113 | 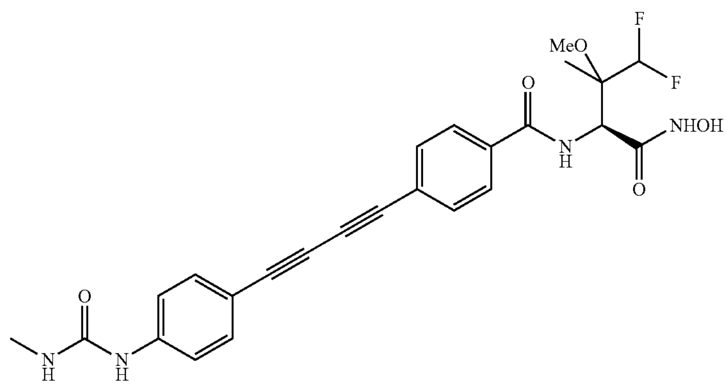 | N-((2S)-4,4-difluoro-1-(hydroxyamino)-3-methoxy-3-methyl-1-oxobutan-2-yl)-4-((4-(3-methylureido)phenyl)buta-1,3-diynyl)benzamide |
| 114 | 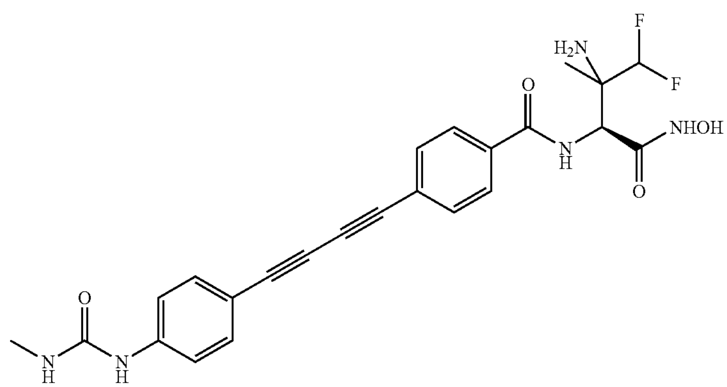 | N-((2S)-3-amino-4,4-difluoro-1-(hydroxyamino)-3-methyl-1-oxobutan-2-yl)-4-((4-(3-methylureido)phenyl)buta-1,3-diynyl)benzamide |
| 115 | 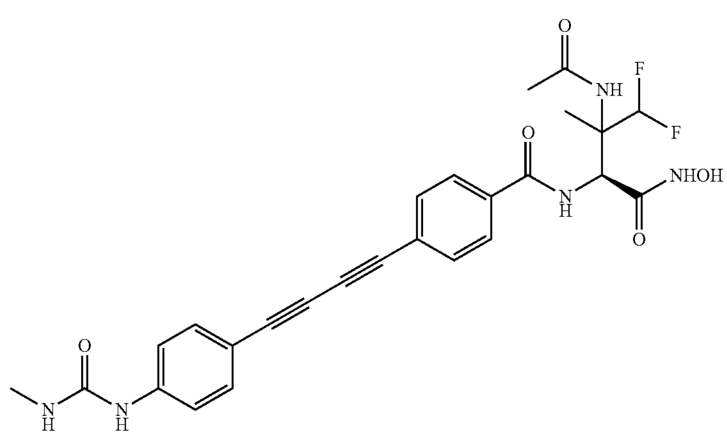 | N-((2S)-3-acetamido-4,4-difluoro-1-(hydroxyamino)-3-methyl-1-oxobutan-2-yl)-4-((4-(3-methylureido)phenyl)buta-1,3-diynyl)benzamide |

-continued

| Ex. No. | Structure | Name |
|---|---|---|
| 116 | 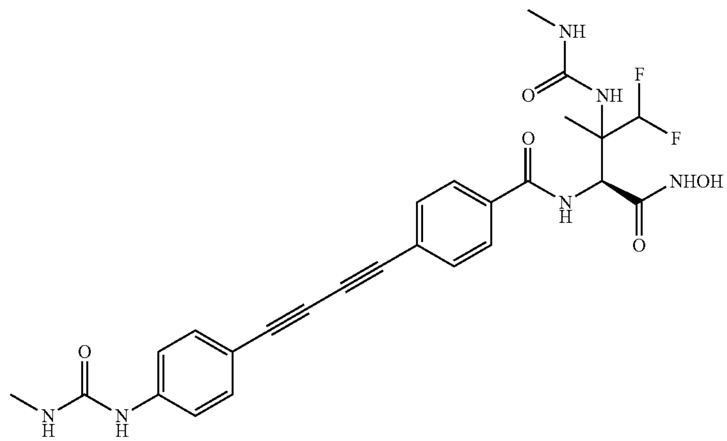 | N-((2S)-4,4-difluoro-1-(hydroxyamino)-3-methyl-3-(3-methylureido)-1-oxobutan-2-yl)-4-((4-(3-methylureido)phenyl)buta-1,3-diynyl)benzamide |
| 117 | 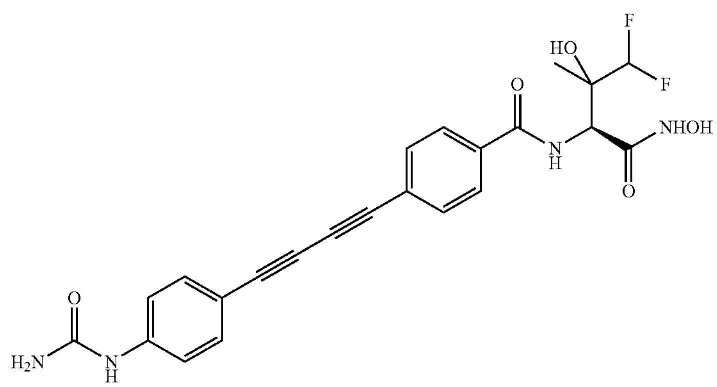 | N-((2S)-4,4-difluoro-3-hydroxy-1-(hydroxyamino)-3-methyl-1-oxobutan-2-yl)-4-((4-ureidophenyl)buta-1,3-diynyl)benzamide |
| 118 | 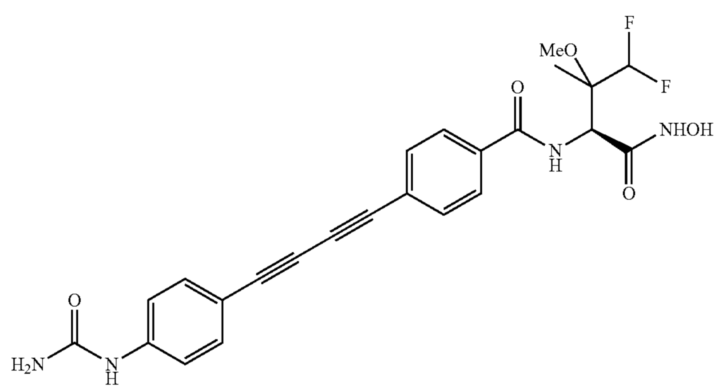 | N-((2S)-4,4-difluoro-1-(hydroxyamino)-3-methoxy-3-methyl-1-oxobutan-2-yl)-4-((4-ureidophenyl)buta-1,3-diynyl)benzamide |
| 119 | 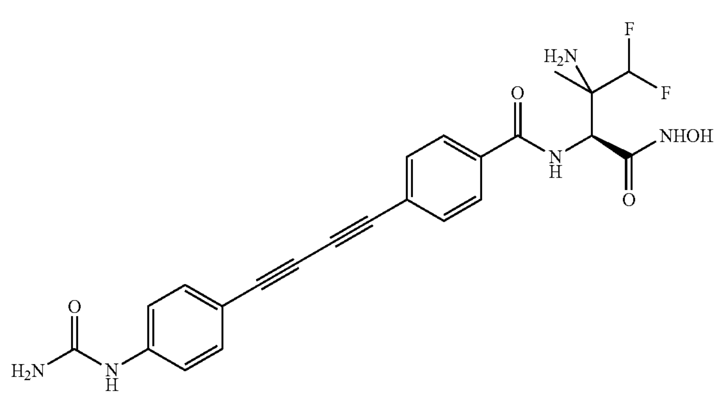 | N-((2S)-3-amino-4,4-difluoro-1-(hydroxyamino)-3-methyl-1-oxobutan-2-yl)-4-((4-ureidophenyl)buta-1,3-diynyl)benzamide |

| Ex. No. | Structure | Name |
|---|---|---|
| 120 | 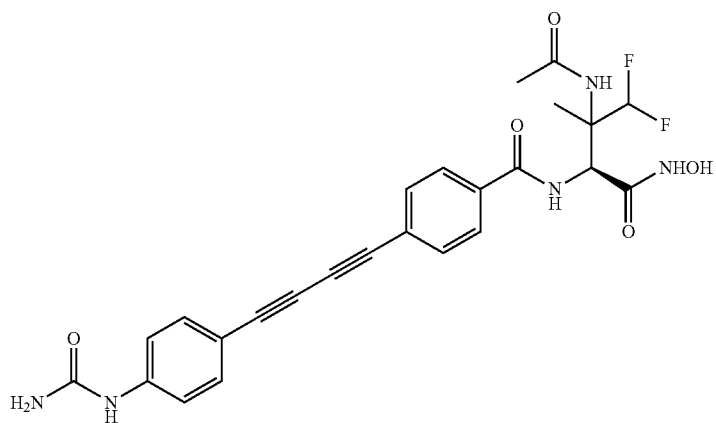 | N-((2S)-3-acetamido-4,4-difluoro-1-(hydroxyamino)-3-methyl-1-oxobutan-2-yl)-4-((4-ureidophenyl)buta-1,3-diynyl)benzamide |
| 121 | 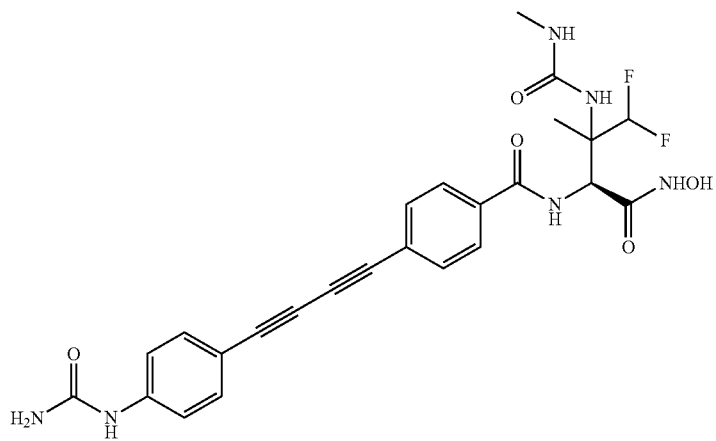 | N-((2S)-4,4-difluoro-1-(hydroxyamino)-3-methyl-3-(3-methylureido)-1-oxobutan-2-yl)-4-((4-ureidophenyl)buta-1,3-diynyl)benzamide |
| 122 | 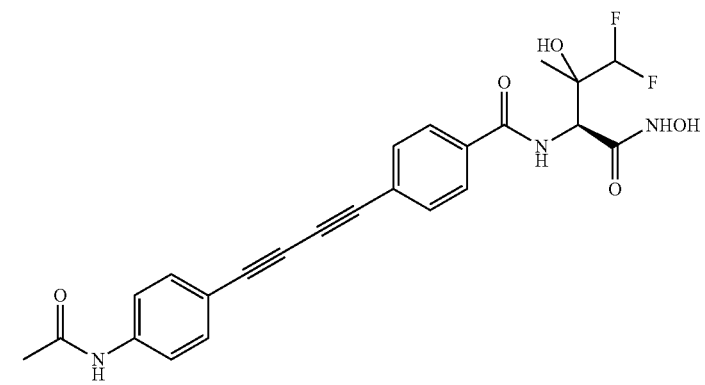 | 4-((4-acetamidophenyl)buta-1,3-diynyl)-N-((2S)-4,4-difluoro-3-hydroxy-1-(hydroxyamino)-3-methyl-1-oxobutan-2-yl)benzamide |

-continued

| Ex. No. | Structure | Name |
|---|---|---|
| 123 | 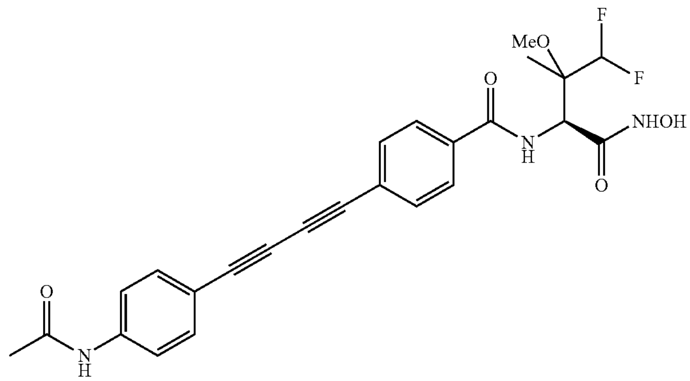 | 4-((4-acetamidophenyl)buta-1,3-diynyl)-N-((2S)-4,4-difluoro-1-(hydroxyamino)-3-methoxy-3-methyl-1-oxobutan-2-yl)benzamide |
| 124 | 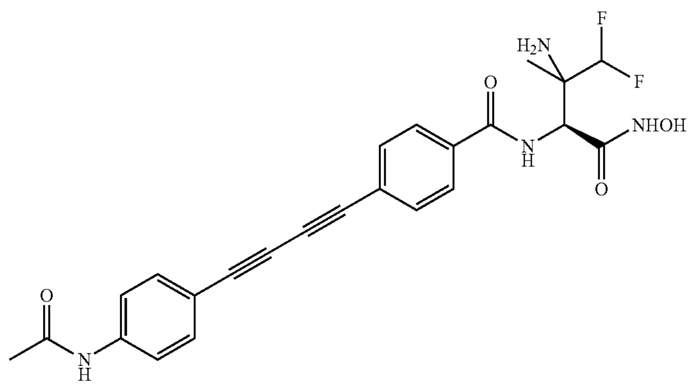 | 4-((4-acetamidophenyl)buta-1,3-diynyl)-N-((2S)-3-amino-4,4-difluoro-1-(hydroxyamino)-3-methyl-1-oxobutan-2-yl)benzamide |
| 125 | 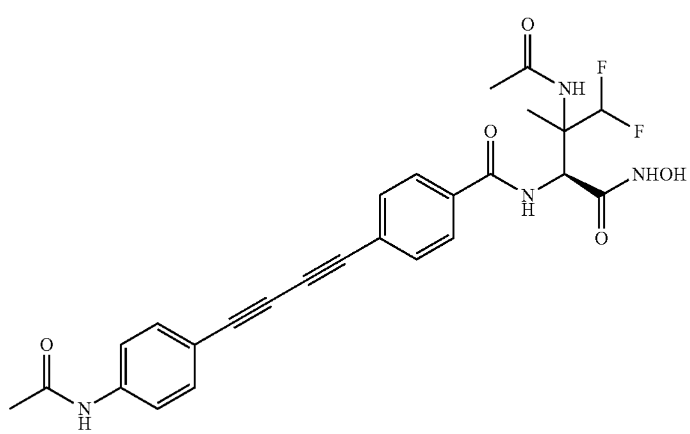 | N-((2S)-3-acetamido-4,4-difluoro-1-(hydroxyamino)-3-methyl-1-oxobutan-2-yl)-4-((4-acetamidophenyl)buta-1,3-diynyl)benzamide |

-continued

| Ex. No. | Structure | Name |
|---|---|---|
| 126 | 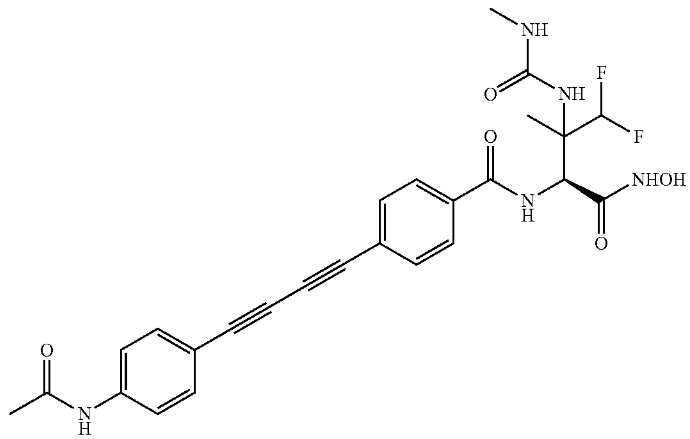 | 4-((4-acetamidophenyl)buta-1,3-diynyl)-N-((2S)-4,4-difluoro-1-(hydroxyamino)-3-methyl-3-(3-methylureido)-1-oxobutan-2-yl)benzamide |
| 127 | 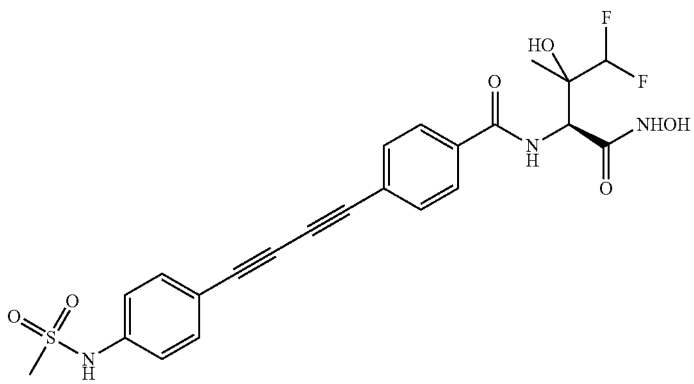 | N-((2S)-4,4-difluoro-3-hydroxy-1-(hydroxyamino)-3-methyl-1-oxobutan-2-yl)-4-((4-(methylsulfonamido)phenyl)buta-1,3-diynyl)benzamide |
| 128 | 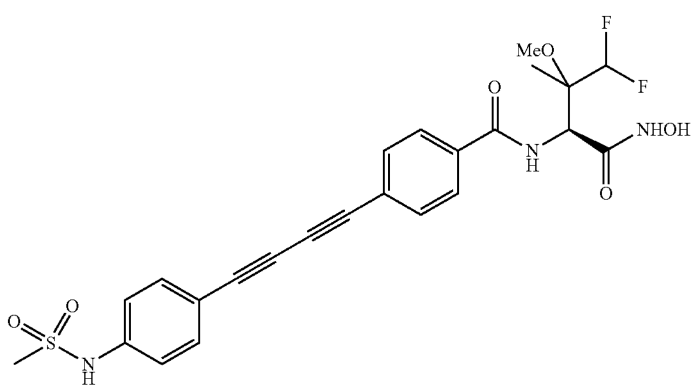 | N-((2S)-4,4-difluoro-1-(hydroxyamino)-3-methoxy-3-methyl-1-oxobutan-2-yl)-4-((4-(methylsulfonamido)phenyl)buta-1,3-diynyl)benzamide |
| 129 | 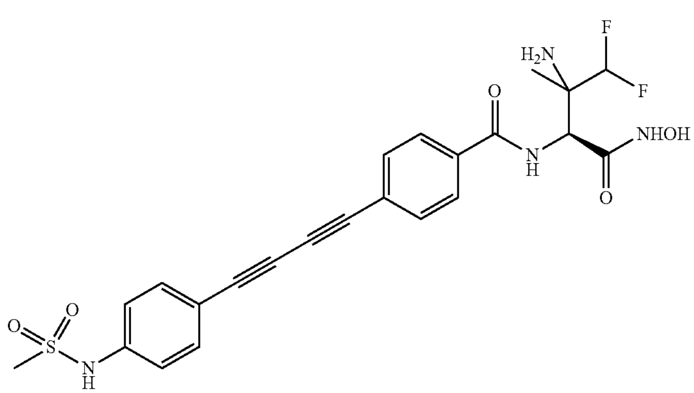 | N-((2S)-3-amino-4,4-difluoro-1-(hydroxyamino)-3-methyl-1-oxobutan-2-yl)-4-((4-(methylsulfonamido)phenyl)buta-1,3-diynyl)benzamide |

-continued
| Ex. No. | Structure | Name |
|---|---|---|
| 130 | 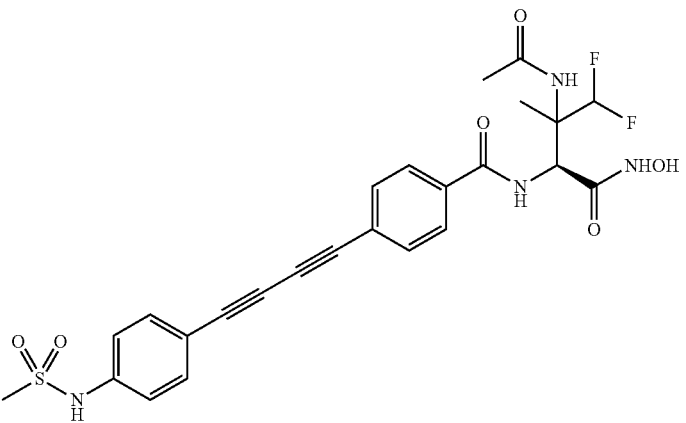 | N-((2S)-3-acetamido-4,4-difluoro-1-(hydroxyamino)-3-methyl-1-oxobutan-2-yl)-4-((4-(methylsulfonamido)phenyl)buta-1,3-diynyl)benzamide |
| 131 | 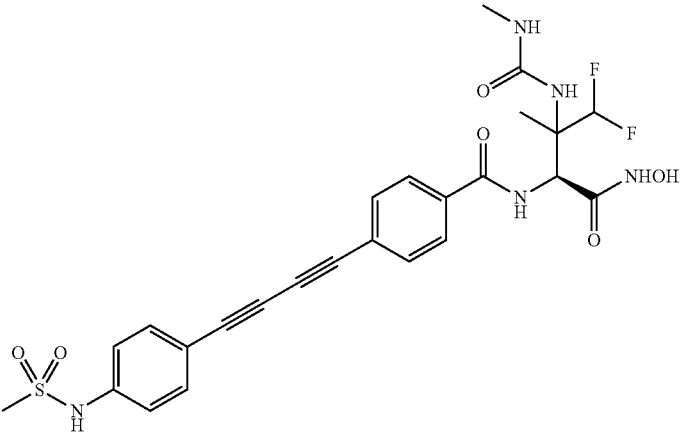 | N-((2S)-4,4-difluoro-1-(hydroxyamino)-3-methyl-3-(3-methylureido)-1-oxobutan-2-yl)-4-((4-(methylsulfonamido)phenyl)buta-1,3-diynyl)benzamide |
| 132 | 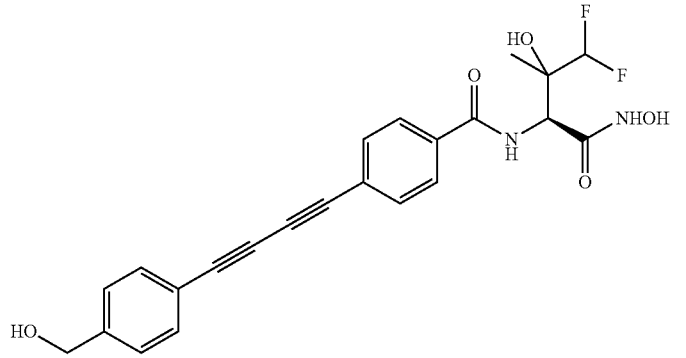 | N-((2S)-4,4-difluoro-3-hydroxy-1-(hydroxyamino)-3-methyl-1-oxobutan-2-yl)-4-((4-(hydroxymethyl)phenyl)buta-1,3-diynyl)benzamide |

| Ex. No. | Structure | Name |
|---|---|---|
| 133 | 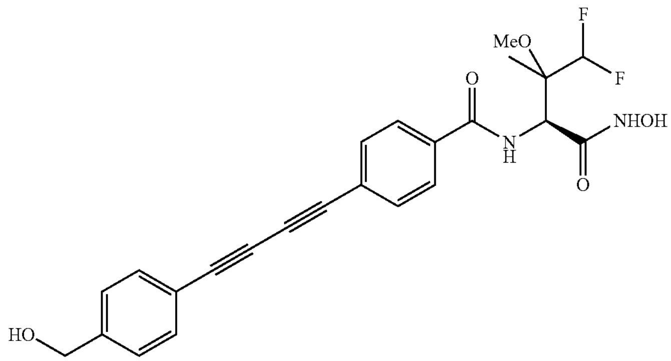 | N-((2S)-4,4-difluoro-1-(hydroxyamino)-3-methoxy-3-methyl-1-oxobutan-2-yl)-4-((4-(hydroxymethyl)phenyl)buta-1,3-diynyl)benzamide |
| 134 | 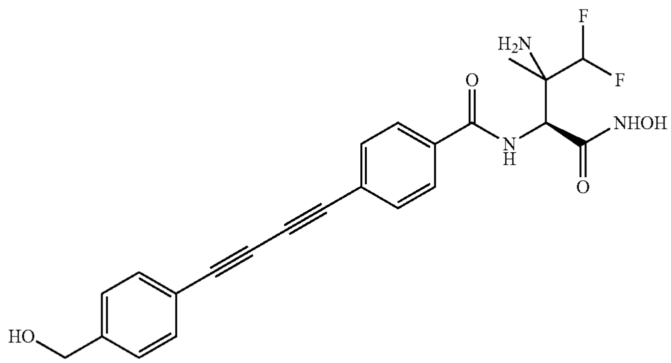 | N-((2S)-3-amino-4,4-difluoro-1-(hydroxyamino)-3-methyl-1-oxobutan-2-yl)-4-((4-(hydroxymethyl)phenyl)buta-1,3-diynyl)benzamide |
| 135 | 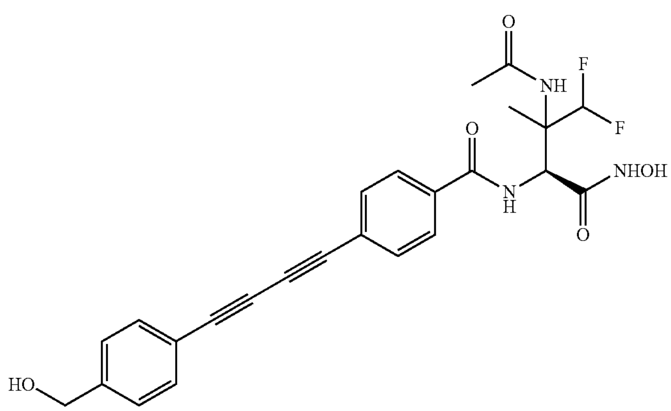 | N-((2S)-3-acetamido-4,4-difluoro-1-(hydroxyamino)-3-methyl-1-oxobutan-2-yl)-4-((4-(hydroxymethyl)phenyl)buta-1,3-diynyl)benzamide |
| 136 | 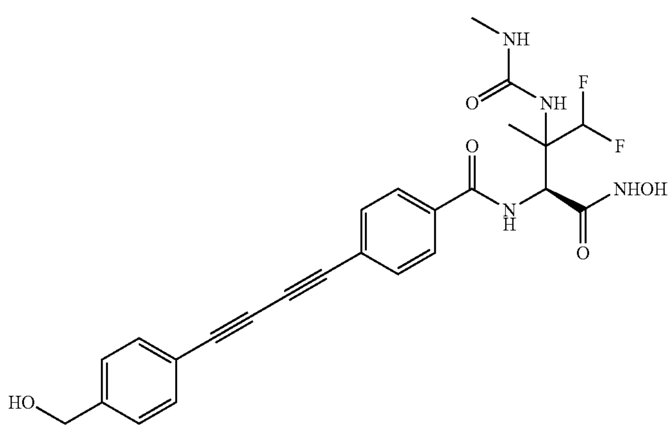 | N-((2S)-4,4-difluoro-1-(hydroxyamino)-3-methyl-3-(3-methylureido)-1-oxobutan-2-yl)-4-((4-(hydroxymethyl)phenyl)buta-1,3-diynyl)benzamide |

-continued

| Ex. No. | Structure | Name |
|---|---|---|
| 137 | 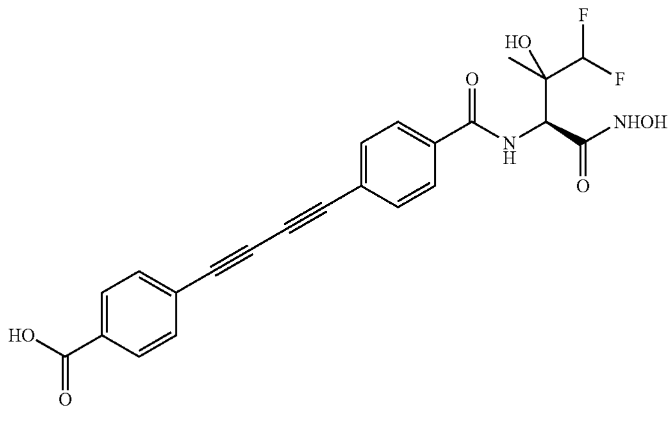 | 4-((4-((2S)-4,4-difluoro-3-hydroxy-1-(hydroxyamino)-3-methyl-1-oxobutan-2-ylcarbamoyl)phenyl)buta-1,3-diynyl)benzoic acid |
| 138 | 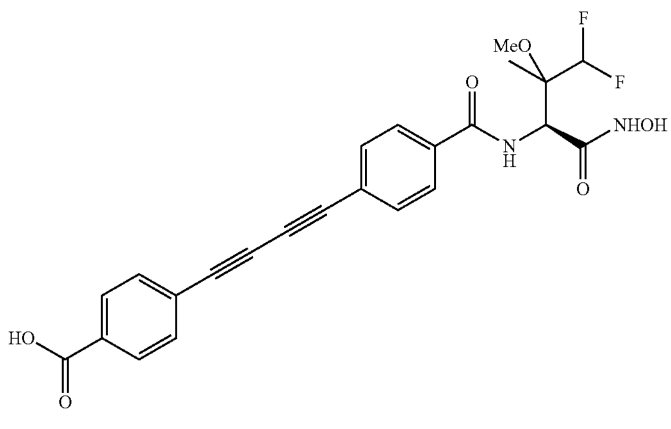 | 4-((4-((2S)-4,4-difluoro-1-(hydroxyamino)-3-methoxy-3-methyl-1-oxobutan-2-ylcarbamoyl)phenyl)buta-1,3-diynyl)benzoic acid |
| 139 | 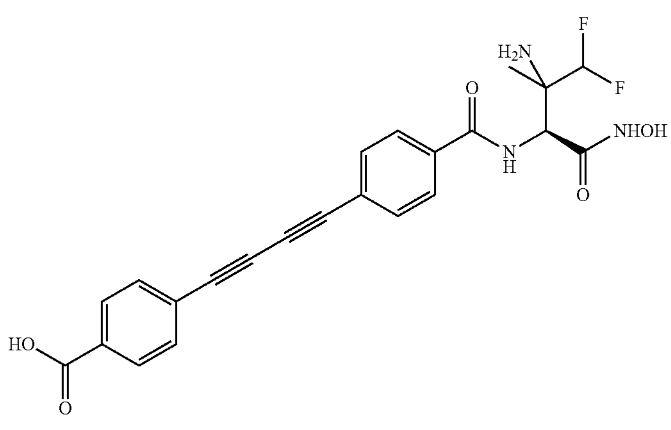 | 4-((4-((2S)-3-amino-4,4-difluoro-1-(hydroxyamino)-3-methyl-1-oxobutan-2-ylcarbamoyl)phenyl)buta-1,3-diynyl)benzoic acid |

| Ex. No. | Structure | Name |
|---|---|---|
| 140 | 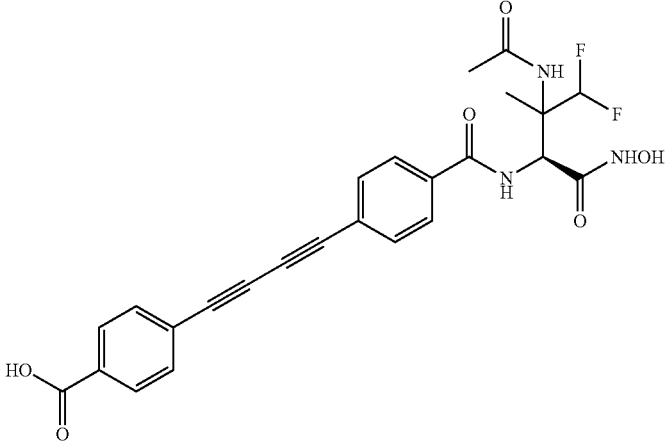 | 4-((4-((2S)-3-acetamido-4,4-difluoro-1-(hydroxyamino)-3-methyl-1-oxobutan-2-ylcarbamoyl)phenyl)buta-1,3-diynyl)benzoic acid |
| 141 | 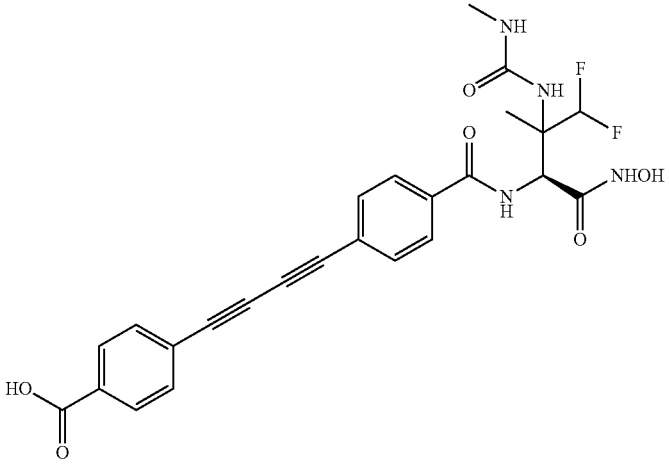 | 4-((4-((2S)-4,4-difluoro-1-(hydroxyamino)-3-methyl-3-(3-methylureido)-1-oxobutan-2-ylcarbamoyl)phenyl)buta-1,3-diynyl)benzoic acid |
| 142 | 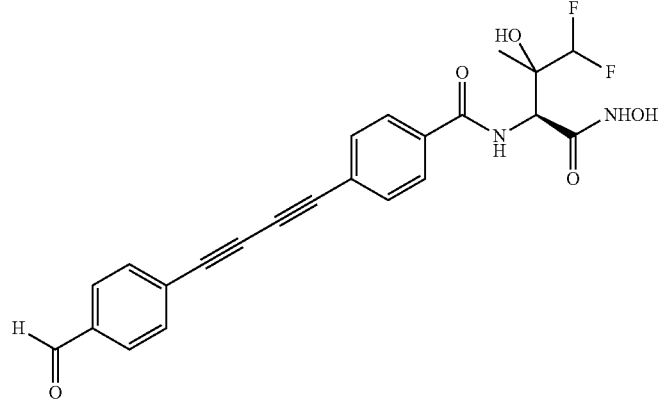 | N-((2S)-4,4-difluoro-3-hydroxy-1-(hydroxyamino)-3-methyl-1-oxobutan-2-yl)-4-((4-formylphenyl)buta-1,3-diynyl)benzamide |

| Ex. No. | Structure | Name |
| --- | --- | --- |
| 143 | 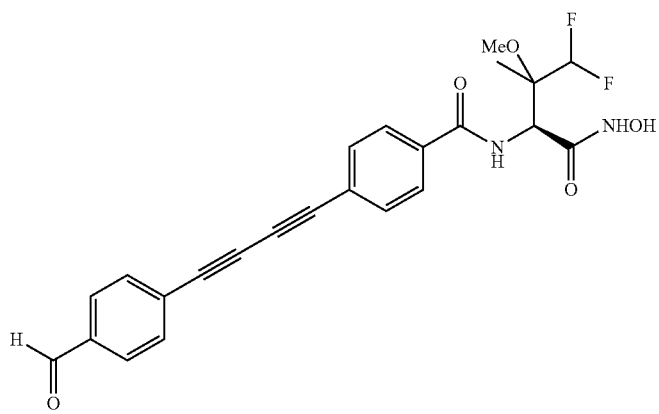 | N-((2S)-4,4-difluoro-1-(hydroxyamino)-3-methoxy-3-methyl-1-oxobutan-2-yl)-4-((4-formylphenyl)buta-1,3-diynyl)benzamide |
| 144 | 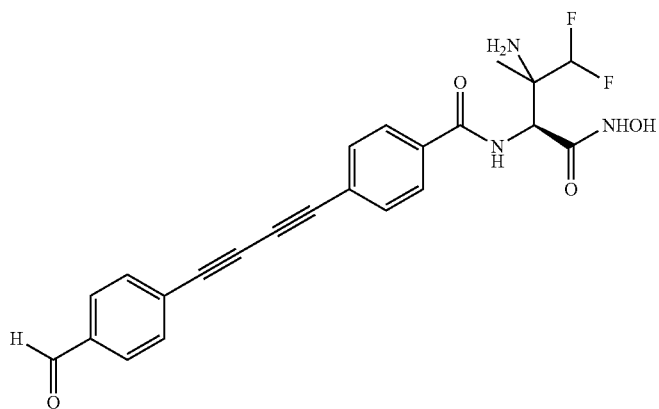 | N-((2S)-3-amino-4,4-difluoro-1-(hydroxyamino)-3-methyl-1-oxobutan-2-yl)-4-((4-formylphenyl)buta-1,3-diynyl)benzamide |
| 145 | 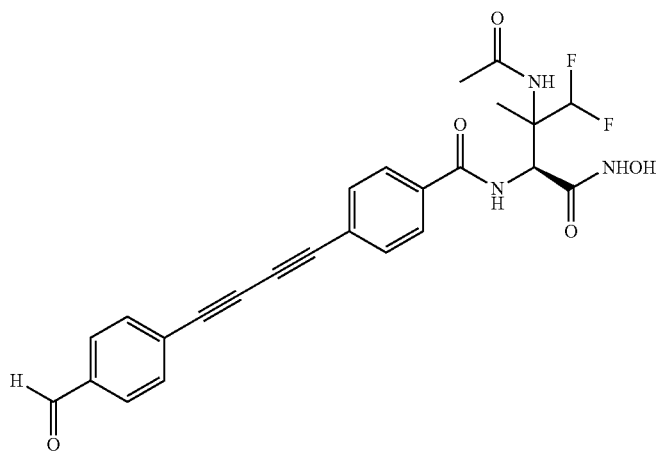 | N-((2S)-3-acetamido-4,4-difluoro-1-(hydroxyamino)-3-methyl-1-oxobutan-2-yl)-4-((4-formylphenyl)buta-1,3-diynyl)benzamide |

-continued

| Ex. No. | Structure | Name |
|---|---|---|
| 146 | 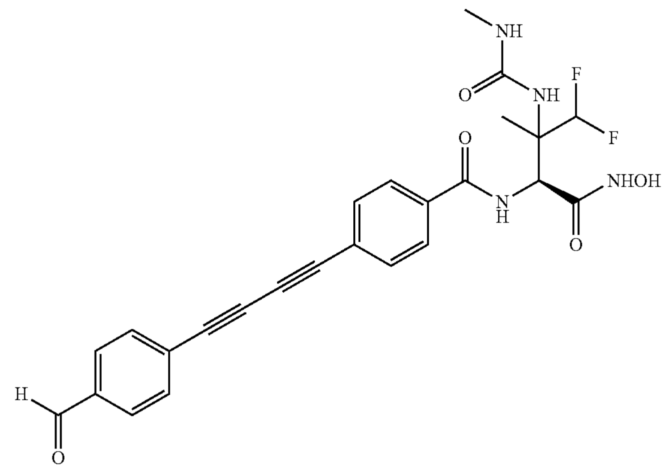 | N-((2S)-4,4-difluoro-1-(hydroxyamino)-3-methyl-3-(3-methylureido)-1-oxobutan-2-yl)-4-((4-formylphenyl)buta-1,3-diynyl)benzamide |
| 147 | 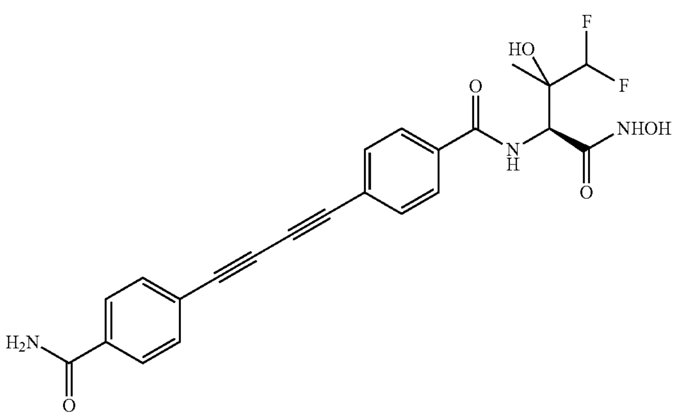 | 4-((4-carbamoylphenyl)buta-1,3-diynyl)-N-((2S)-4,4-difluoro-3-hydroxy-1-(hydroxyamino)-3-methyl-1-oxobutan-2-yl)benzamide |
| 148 | 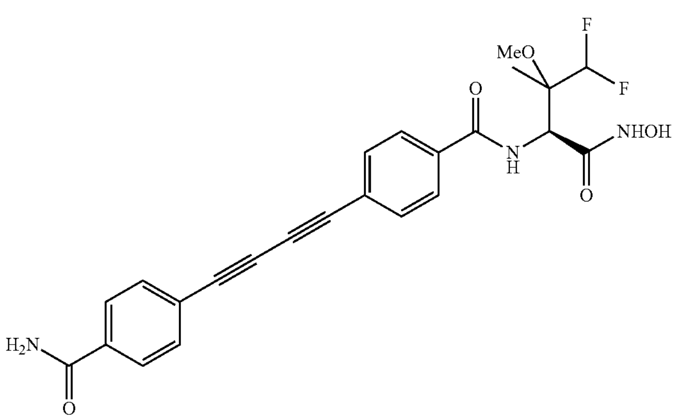 | 4-((4-carbamoylphenyl)buta-1,3-diynyl)-N-((2S)-4,4-difluoro-1-(hydroxyamino)-3-methoxy-3-methyl-1-oxobutan-2-yl)benzamide |

-continued
| Ex. No. | Structure | Name |
|---|---|---|
| 149 | 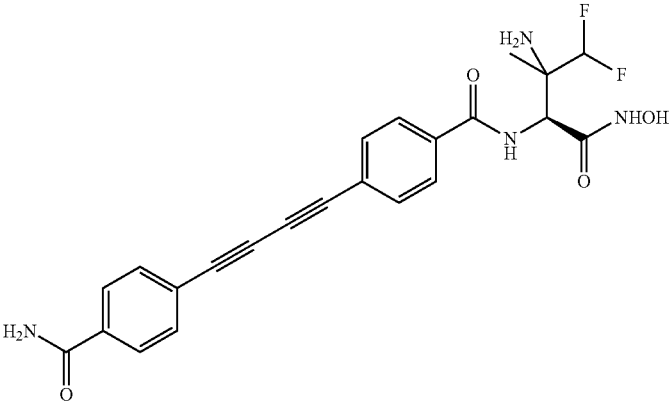 | N-((2S)-3-amino-4,4-difluoro-1-(hydroxyamino)-3-methyl-1-oxobutan-2-yl)-4-((4-carbamoylphenyl)buta-1,3-diynyl)benzamide |
| 150 | 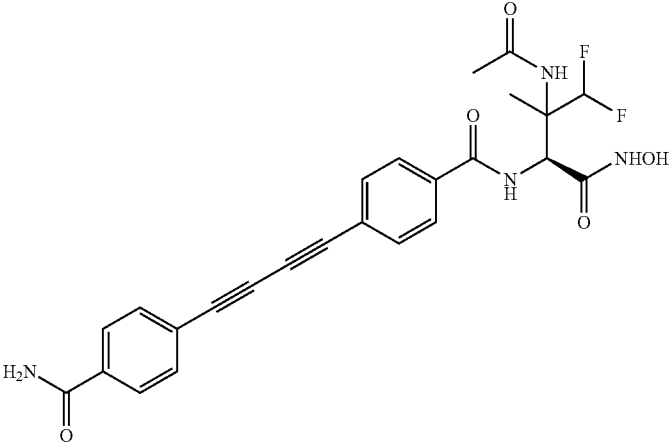 | N-((2S)-3-acetamido-4,4-difluoro-1-(hydroxyamino)-3-methyl-1-oxobutan-2-yl)-4-((4-carbamoylphenyl)buta-1,3-diynyl)benzamide |
| 151 | 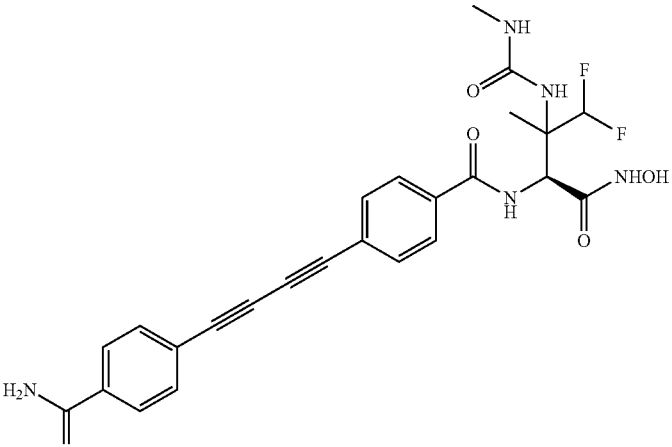 | 4-((4-carbamoylphenyl)buta-1,3-diynyl)-N-((2S)-4,4-difluoro-1-(hydroxyamino)-3-methyl-3-(3-methylureido)-1-oxobutan-2-yl)benzamide |

| Ex. No. | Structure | Name |
|---|---|---|
| 152 | 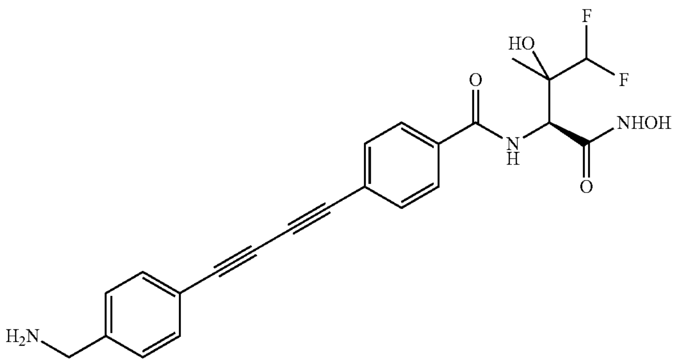 | 4-((4-(aminomethyl)phenyl)buta-1,3-diynyl)-N-((2S)-4,4-difluoro-3-hydroxy-1-(hydroxyamino)-3-methyl-1-oxobutan-2-yl)benzamide |
| 153 | 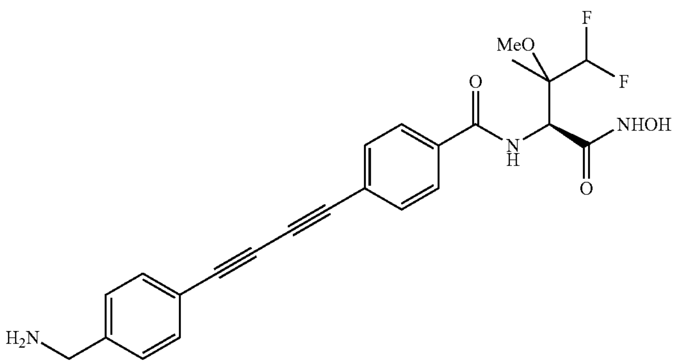 | 4-((4-(aminomethyl)phenyl)buta-1,3-diynyl)-N-((2S)-4,4-difluoro-1-(hydroxyamino)-3-methoxy-3-methyl-1-oxobutan-2-yl)benzamide |
| 154 | 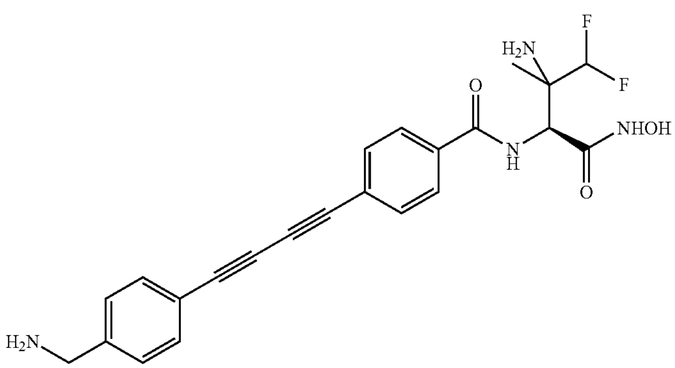 | N-((2S)-3-amino-4,4-difluoro-1-(hydroxyamino)-3-methyl-1-oxobutan-2-yl)-4-((4-(aminomethyl)phenyl)buta-1,3-diynyl)benzamide |
| 155 | 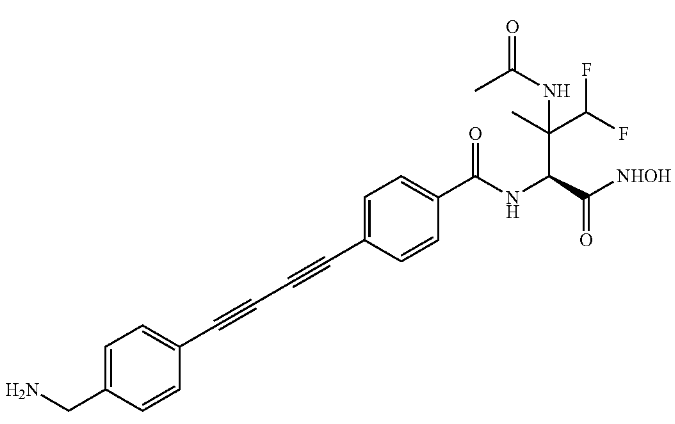 | N-((2S)-3-acetamido-4,4-difluoro-1-(hydroxyamino)-3-methyl-1-oxobutan-2-yl)-4-((4-(aminomethyl)phenyl)buta-1,3-diynyl)benzamide |

| Ex. No. | Structure | Name |
|---|---|---|
| 156 | 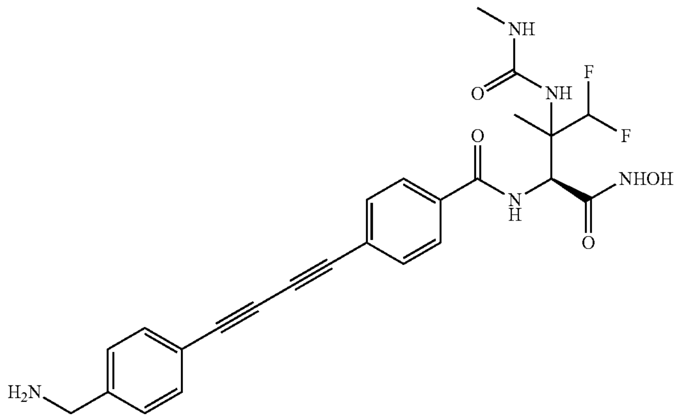 | 4-((4-(aminomethyl)phenyl)buta-1,3-diynyl)-N-((2S)-4,4-difluoro-1-(hydroxyamino)-3-methyl-3-(3-methylureido)-1-oxobutan-2-yl)benzamide |
| 157 | 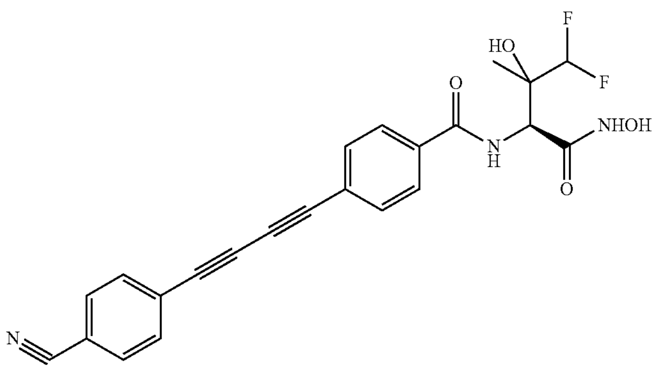 | 4-((4-cyanophenyl)buta-1,3-diynyl)-N-((2S)-4,4-difluoro-3-hydroxy-1-(hydroxyamino)-3-methyl-1-oxobutan-2-yl)benzamide |
| 158 | 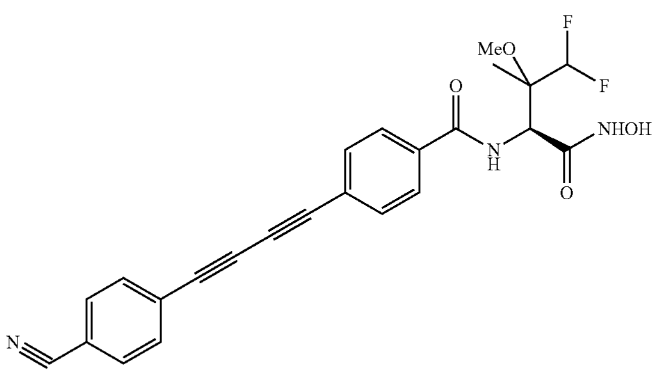 | 4-((4-cyanophenyl)buta-1,3-diynyl)-N-((2S)-4,4-difluoro-1-(hydroxyamino)-3-methoxy-3-methyl-1-oxobutan-2-yl)benzamide |
| 159 | 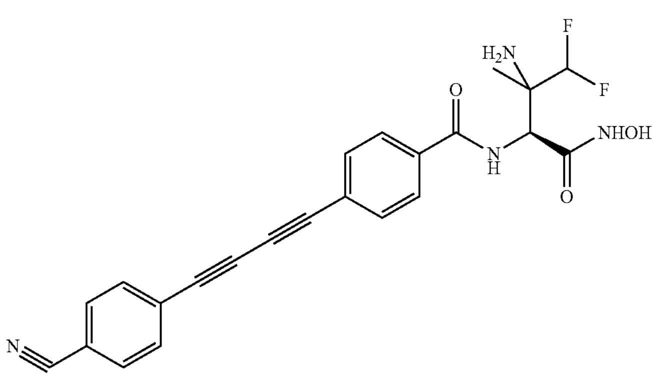 | N-((2S)-3-amino-4,4-difluoro-1-(hydroxyamino)-3-methyl-1-oxobutan-2-yl)-4-((4-cyanophenyl)buta-1,3-diynyl)benzamide |

-continued

| Ex. No. | Structure | Name |
|---|---|---|
| 160 | 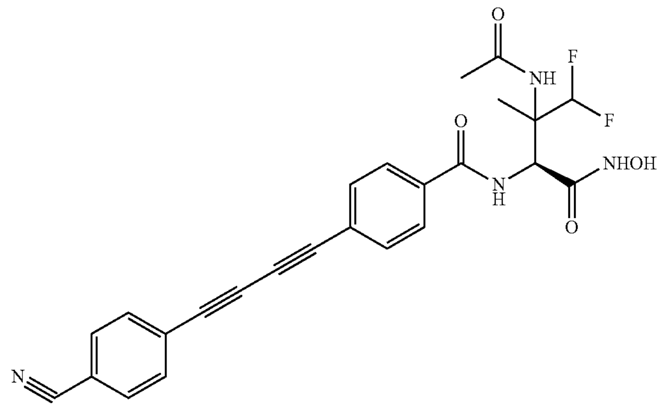 | N-((2S)-3-acetamido-4,4-difluoro-1-(hydroxyamino)-3-methyl-1-oxobutan-2-yl)-4-((4-cyanophenyl)buta-1,3-diynyl)benzamide |
| 161 | 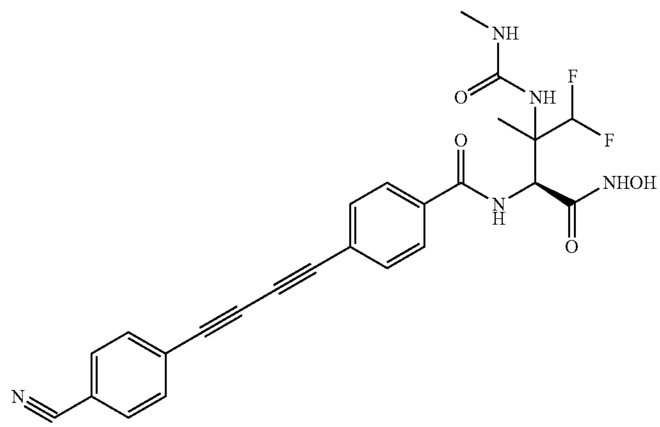 | 4-((4-cyanophenyl)buta-1,3-diynyl)-N-((2S)-4,4-difluoro-1-(hydroxyamino)-3-methyl-3-(3-methylureido)-1-oxobutan-2-yl)benzamide |
| 162 | 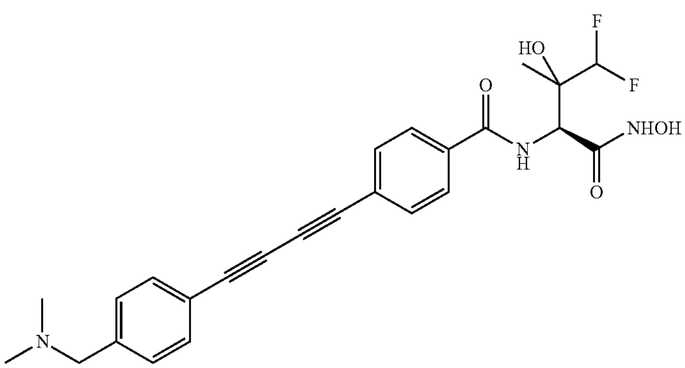 | N-((2S)-4,4-difluoro-3-hydroxy-1-(hydroxyamino)-3-methyl-1-oxobutan-2-yl)-4-((4-((dimethylamino)methyl)phenyl)buta-1,3-diynyl)benzamide |
| 163 | 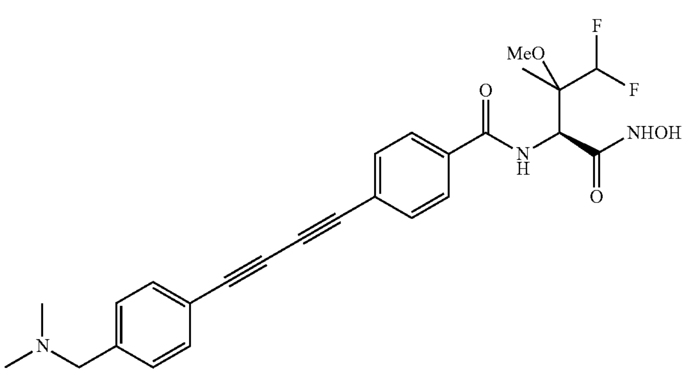 | N-((2S)-4,4-difluoro-1-(hydroxyamino)-3-methoxy-3-methyl-1-oxobutan-2-yl)-4-((4-((dimethylamino)methyl)phenyl)buta-1,3-diynyl)benzamide |

-continued

| Ex. No. | Structure | Name |
|---|---|---|
| 164 | 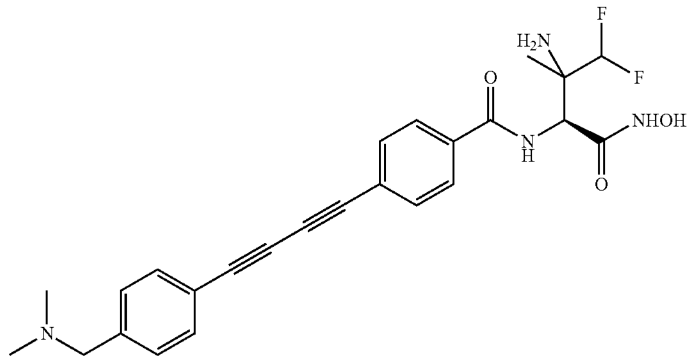 | N-((2S)-3-amino-4,4-difluoro-1-(hydroxyamino)-3-methyl-1-oxobutan-2-yl)-4-((4-((dimethylamino)methyl)phenyl)buta-1,3-diynyl)benzamide |
| 165 | 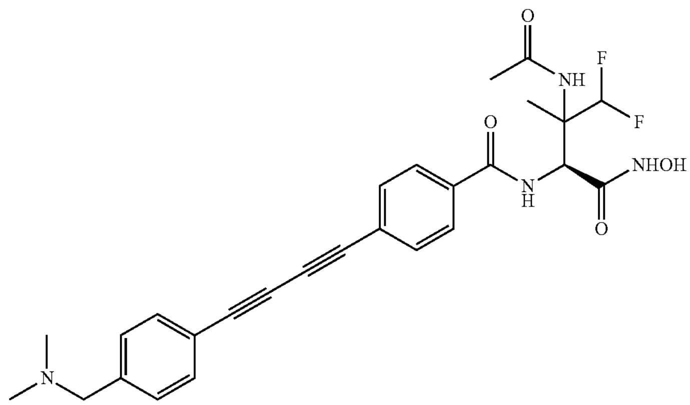 | N-((2S)-3-acetamido-4,4-difluoro-1-(hydroxyamino)-3-methyl-1-oxobutan-2-yl)-4-((4-((dimethylamino)methyl)phenyl)buta-1,3-diynyl)benzamide |
| 166 | 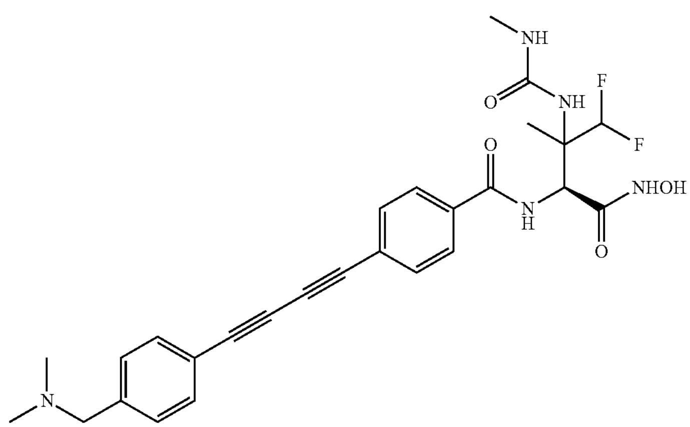 | N-((2S)-4,4-difluoro-1-(hydroxyamino)-3-methyl-3-(3-methylureido)-1-oxobutan-2-yl)-4-((4-((dimethylamino)methyl)phenyl)buta-1,3-diynyl)benzamide |
| 167 | 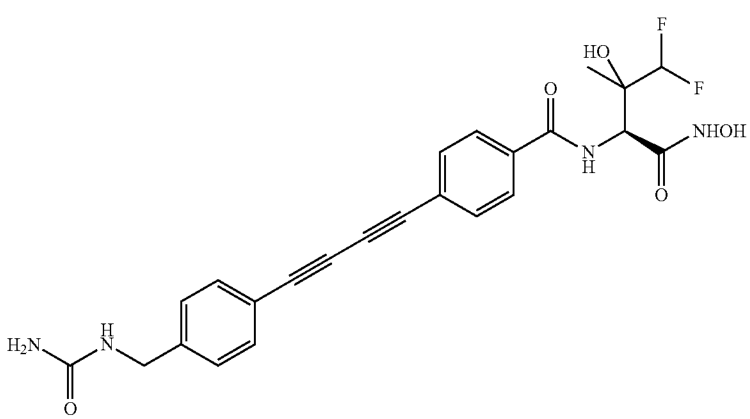 | N-((2S)-4,4-difluoro-3-hydroxy-1-(hydroxyamino)-3-methyl-1-oxobutan-2-yl)-4-((4-(ureidomethyl)phenyl)buta-1,3-diynyl)benzamide |

-continued
| Ex. No. | Structure | Name |
|---|---|---|
| 168 | 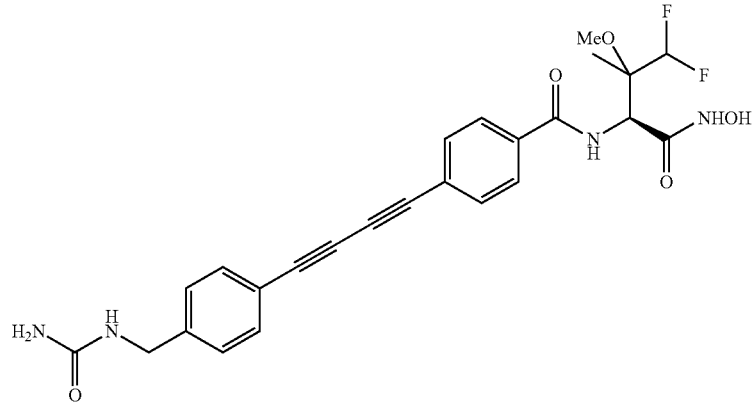 | N-((2S)-4,4-difluoro-1-(hydroxyamino)-3-methoxy-3-methyl-1-oxobutan-2-yl)-4-((4-(ureidomethyl)phenyl)buta-1,3-diynyl)benzamide |
| 169 | 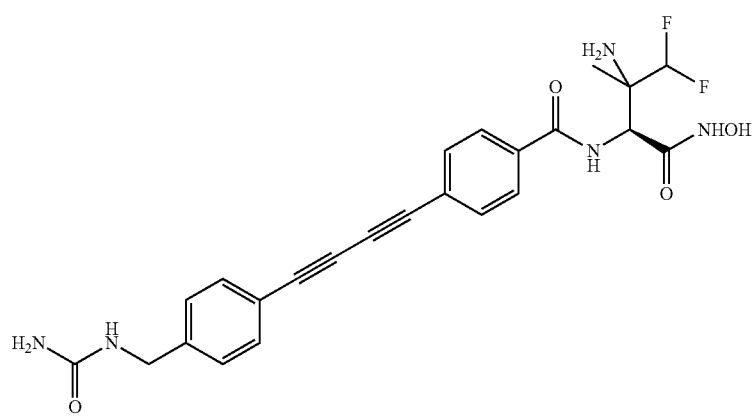 | N-((2S)-3-amino-4,4-difluoro-1-(hydroxyamino)-3-methyl-1-oxobutan-2-yl)-4-((4-(ureidomethyl)phenyl)buta-1,3-diynyl)benzamide |
| 170 | 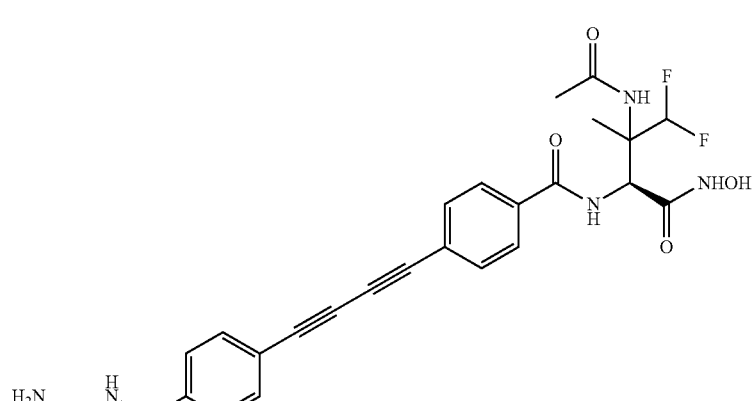 | N-((2S)-3-acetamido-4,4-difluoro-1-(hydroxyamino)-3-methyl-1-oxobutan-2-yl)-4-((4-(ureidomethyl)phenyl)buta-1,3-diynyl)benzamide |

-continued

| Ex. No. | Structure | Name |
|---|---|---|
| 171 | 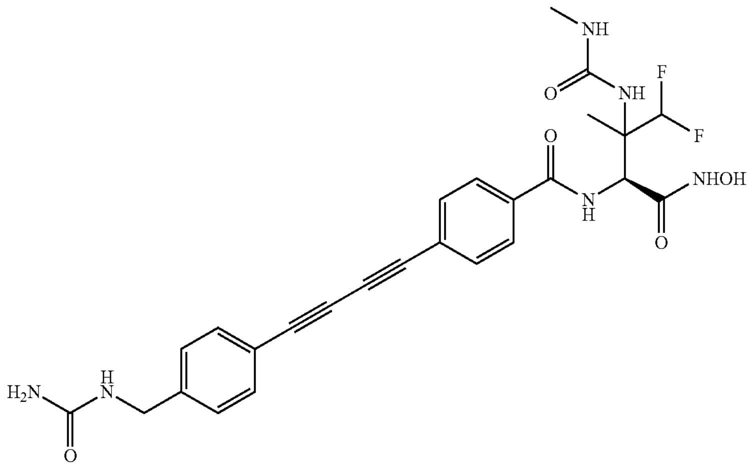 | N-((2S)-4,4-difluoro-1-(hydroxyamino)-3-methyl-3-(3-methylureido)-1-oxobutan-2-yl)-4-((4-(ureidomethyl)phenyl)buta-1,3-diynyl)benzamide |
| 172 | 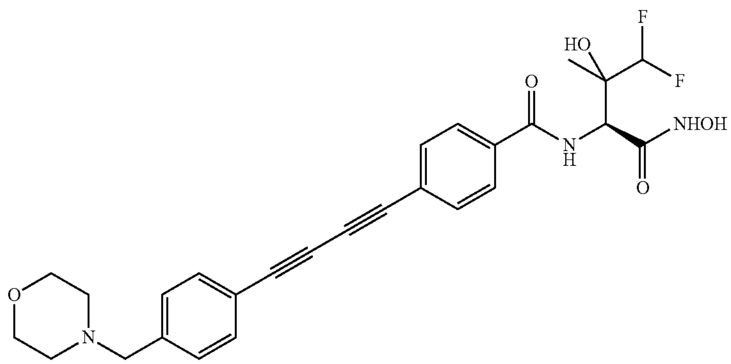 | N-((2S)-4,4-difluoro-3-hydroxy-1-(hydroxyamino)-3-methyl-1-oxobutan-2-yl)-4-((4-(morpholinomethyl)phenyl)buta-1,3-diynyl)benzamide |
| 173 | 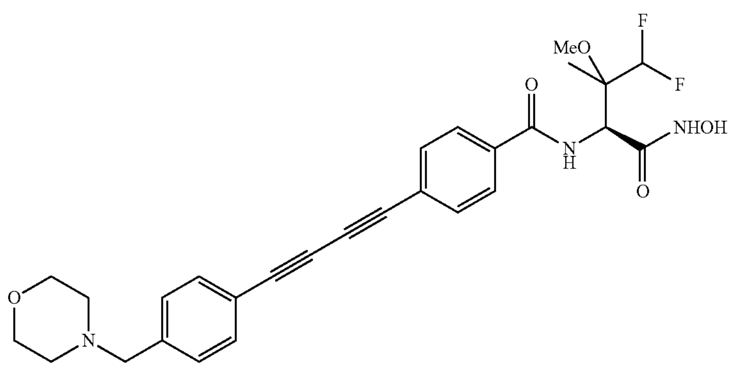 | N-((2S)-4,4-difluoro-1-(hydroxyamino)-3-methoxy-3-methyl-1-oxobutan-2-yl)-4-((4-(morpholinomethyl)phenyl)buta-1,3-diynyl)benzamide |
| 174 | 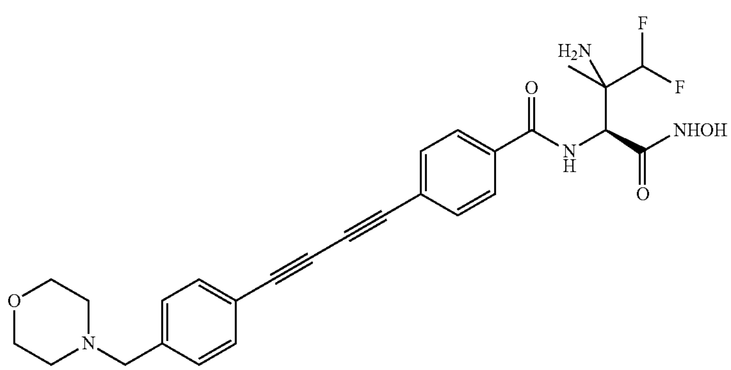 | N-((2S)-3-amino-4,4-difluoro-1-(hydroxyamino)-3-methyl-1-oxobutan-2-yl)-4-((4-(morpholinomethyl)phenyl)buta-1,3-diynyl)benzamide |

-continued

| Ex. No. | Structure | Name |
|---|---|---|
| 175 | 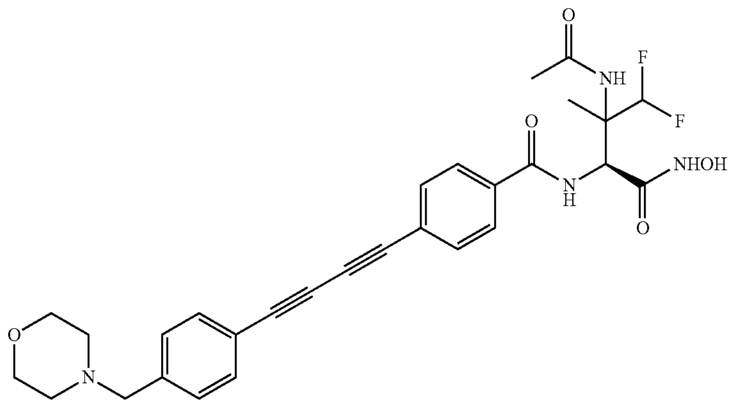 | N-((2S)-3-acetamido-4,4-difluoro-1-(hydroxyamino)-3-methyl-1-oxobutan-2-yl)-4-((4-(morpholinomethyl)phenyl)buta-1,3-diynyl)benzamide |
| 176 | 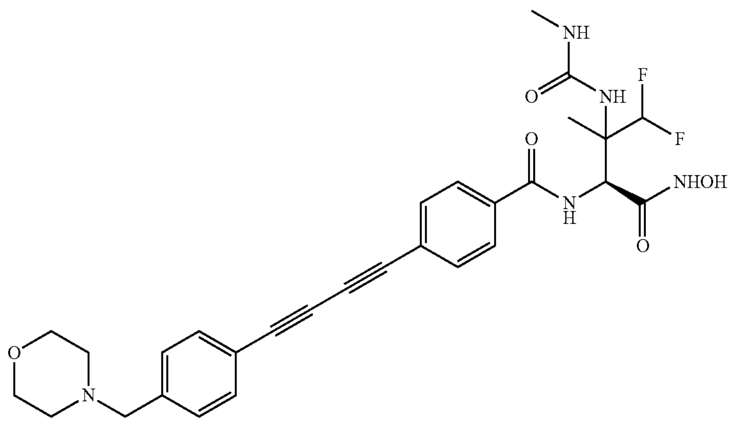 | N-((2S)-4,4-difluoro-1-(hydroxyamino)-3-methyl-3-(3-methylureido)-1-oxobutan-2-yl)-4-((4-(morpholinomethyl)phenyl)buta-1,3-diynyl)benzamide |
| 177 | 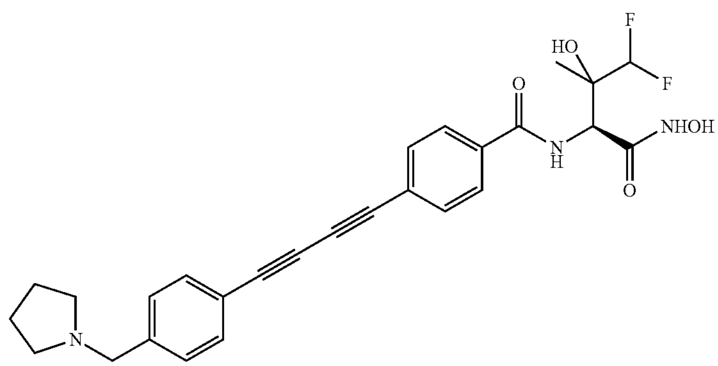 | N-((2S)-4,4-difluoro-3-hydroxy-1-(hydroxyamino)-3-methyl-1-oxobutan-2-yl)-4-((4-(pyrrolidin-1-ylmethyl)phenyl)buta-1,3-diynyl)benzamide |
| 178 | 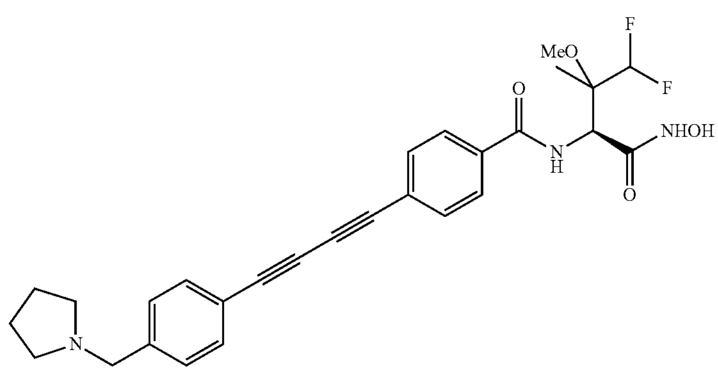 | N-((2S)-4,4-difluoro-1-(hydroxyamino)-3-methoxy-3-methyl-1-oxobutan-2-yl)-4-((4-(pyrrolidin-1-ylmethyl)phenyl)buta-1,3-diynyl)benzamide |

-continued

| Ex. No. | Structure | Name |
|---|---|---|
| 179 | 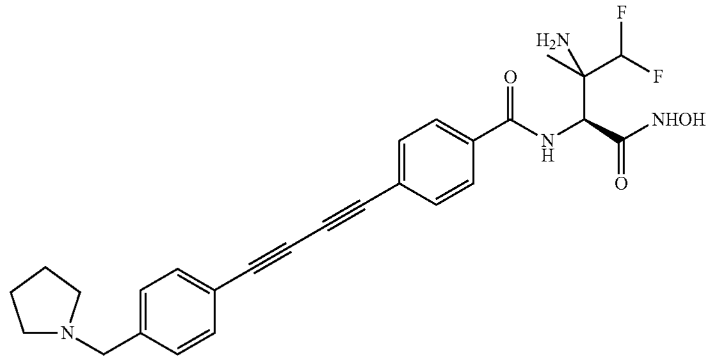 | N-((2S)-3-amino-4,4-difluoro-1-(hydroxyamino)-3-methyl-1-oxobutan-2-yl)-4-((4-(pyrrolidin-1-ylmethyl)phenyl)buta-1,3-diynyl)benzamide |
| 180 | 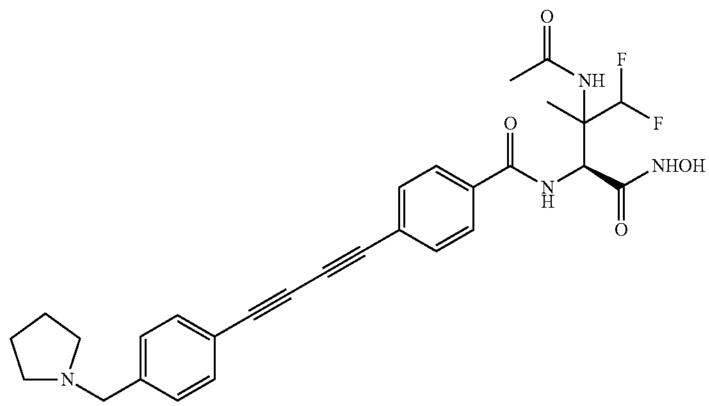 | N-((2S)-3-acetamido-4,4-difluoro-1-(hydroxyamino)-3-methyl-1-oxobutan-2-yl)-4-((4-(pyrrolidin-1-ylmethyl)phenyl)buta-1,3-diynyl)benzamide |
| 181 | 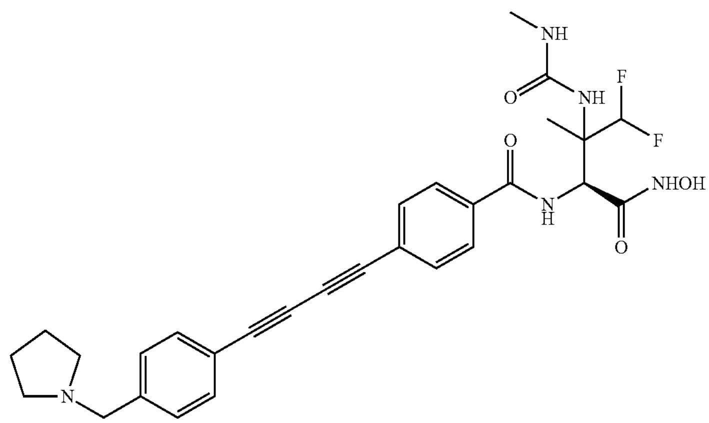 | N-((2S)-4,4-difluoro-1-(hydroxyamino)-3-methyl-3-(3-methylureido)-1-oxobutan-2-yl)-4-((4-(pyrrolidin-1-ylmethyl)phenyl)buta-1,3-diynyl)benzamide |
| 182 | 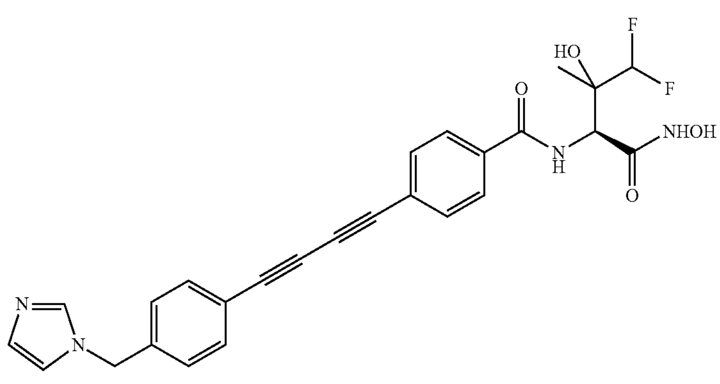 | 4-((4-((1H-imidazol-1-yl)methyl)phenyl)buta-1,3-diynyl)-N-((2S)-4,4-difluoro-3-hydroxy-1-(hydroxyamino)-3-methyl-1-oxobutan-2-yl)benzamide |

US 9,738,604 B2

-continued

| Ex. No. | Structure | Name |
|---|---|---|
| 183 | 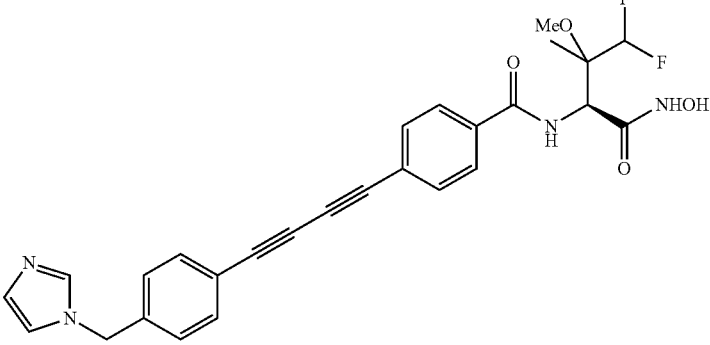 | 4-((4-((1H-imidazol-1-yl)methyl)phenyl)buta-1,3-diynyl)-N-((2S)-4,4-difluoro-1-(hydroxyamino)-3-methoxy-3-methyl-1-oxobutan-2-yl)benzamide |
| 184 | 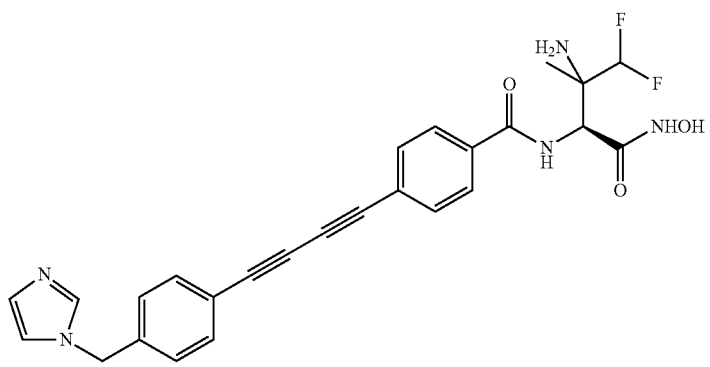 | 4-((4-((1H-imidazol-1-yl)methyl)phenyl)buta-1,3-diynyl)-N-((2S)-3-amino-4,4-difluoro-1-(hydroxyamino)-3-methyl-1-oxobutan-2-yl)benzamide |
| 185 | 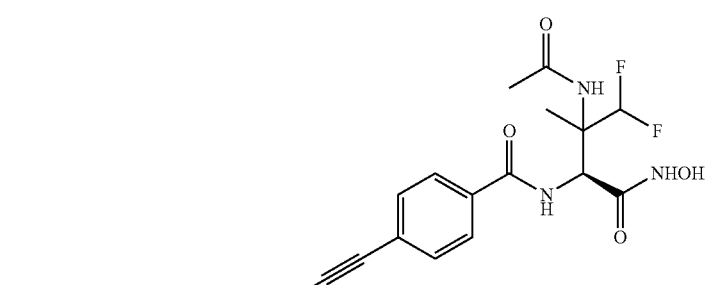 | 4-((4-((1H-imidazol-1-yl)methyl)phenyl)buta-1,3-diynyl)-N-((2S)-3-acetamido-4,4-difluoro-1-(hydroxyamino)-3-methyl-1-oxobutan-2-yl)benzamide |
| 186 | 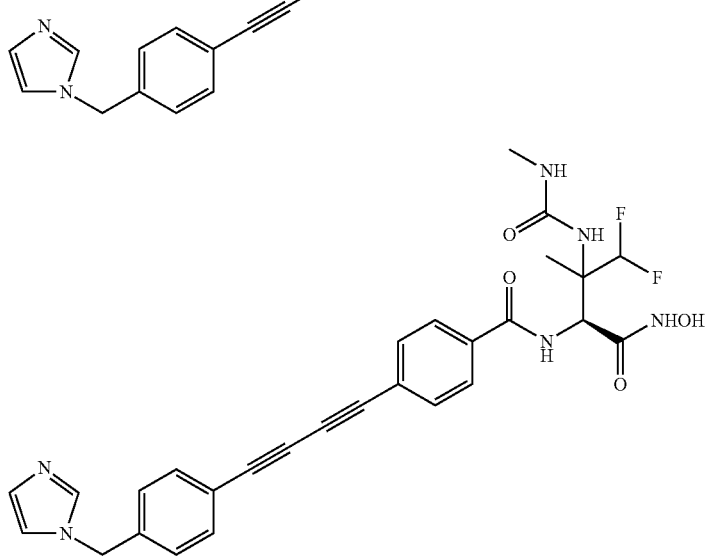 | 4-((4-((1H-imidazol-1-yl)methyl)phenyl)buta-1,3-diynyl)-N-((2S)-4,4-difluoro-1-(hydroxyamino)-3-methyl-3-(3-methylureido)-1-oxobutan-2-yl)benzamide |

-continued

| Ex. No. | Structure | Name |
|---|---|---|
| 187 | 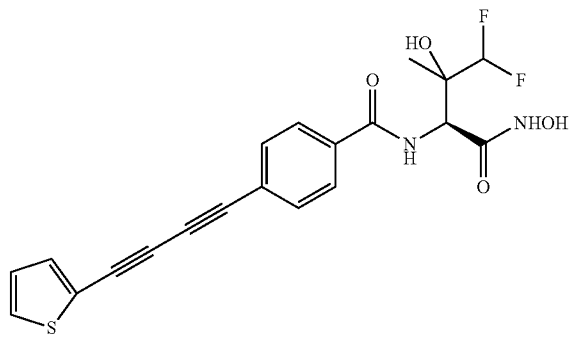 | N-((2S)-4,4-difluoro-3-hydroxy-1-(hydroxyamino)-3-methyl-1-oxobutan-2-yl)-4-(thiophen-2-ylbuta-1,3-diynyl)benzamide |
| 188 | 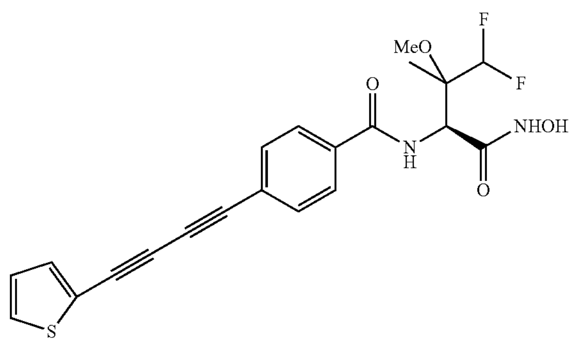 | N-((2S)-4,4-difluoro-1-(hydroxyamino)-3-methoxy-3-methyl-1-oxobutan-2-yl)-4-(thiophen-2-ylbuta-1,3-diynyl)benzamide |
| 189 | 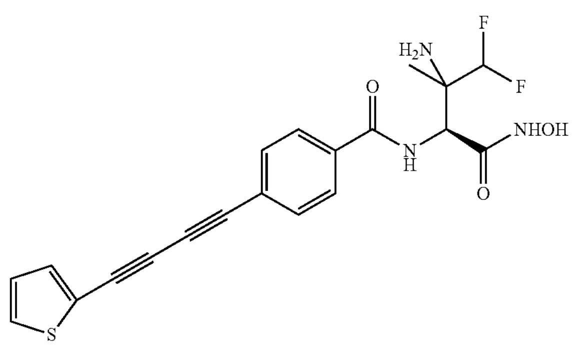 | N-((2S)-3-amino-4,4-difluoro-1-(hydroxyamino)-3-methyl-1-oxobutan-2-yl)-4-(thiophen-2-ylbuta-1,3-diynyl)benzamide |
| 190 | 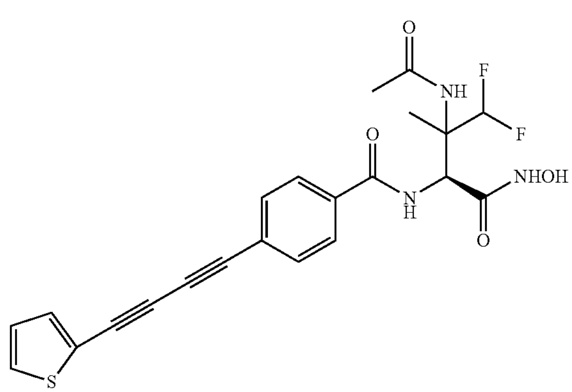 | N-((2S)-3-acetamido-4,4-difluoro-1-(hydroxyamino)-3-methyl-1-oxobutan-2-yl)-4-(thiophen-2-ylbuta-1,3-diynyl)benzamide |

-continued

| Ex. No. | Structure | Name |
|---|---|---|
| 191 | 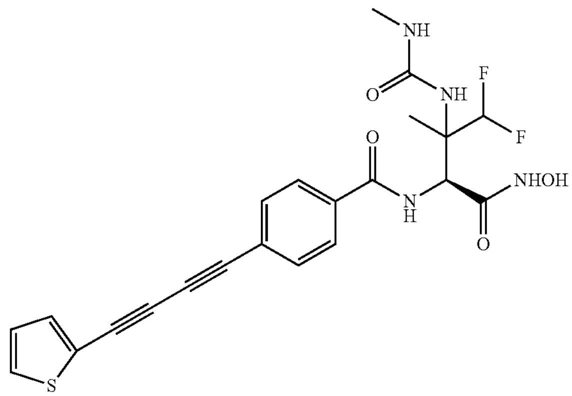 | N-((2S)-4,4-difluoro-1-(hydroxyamino)-3-methyl-3-(3-methylureido)-1-oxobutan-2-yl)-4-(thiophen-2-ylbuta-1,3-diynyl)benzamide |
| 192 | 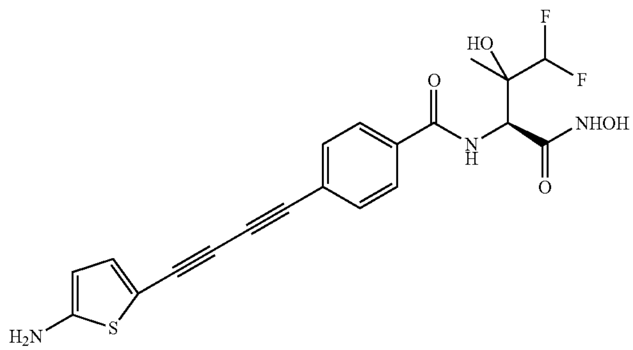 | 4-((5-aminothiophen-2-yl)buta-1,3-diynyl)-N-((2S)-4,4-difluoro-3-hydroxy-1-(hydroxyamino)-3-methyl-1-oxobutan-2-yl)benzamide |
| 193 | 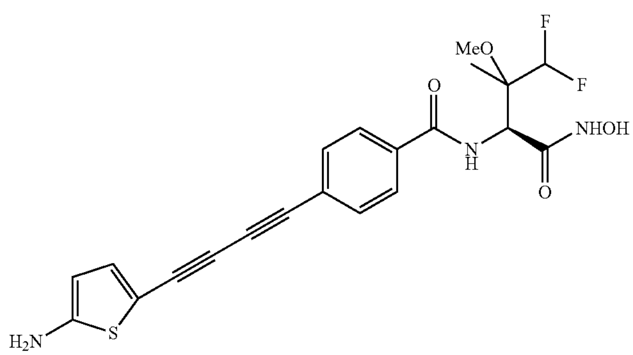 | 4-((5-aminothiophen-2-yl)buta-1,3-diynyl)-N-((2S)-4,4-difluoro-1-(hydroxyamino)-3-methoxy-3-methyl-1-oxobutan-2-yl)benzamide |
| 194 | 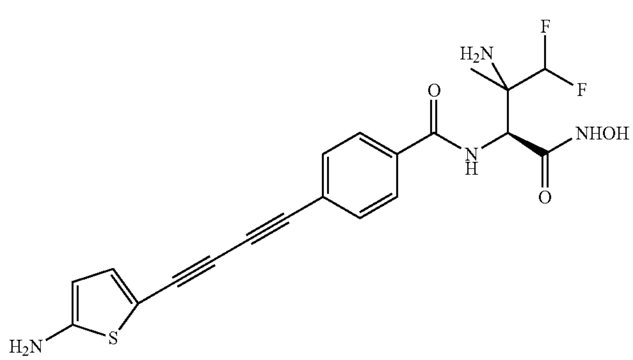 | N-((2S)-3-amino-4,4-difluoro-1-(hydroxyamino)-3-methyl-1-oxobutan-2-yl)-4-((5-aminothiophen-2-yl)buta-1,3-diynyl)benzamide |

| Ex. No. | Structure | Name |
|---|---|---|
| 195 | 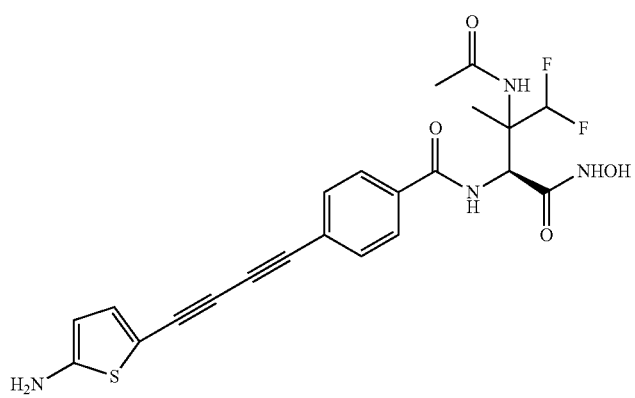 | N-((2S)-3-acetamido-4,4-difluoro-1-(hydroxyamino)-3-methyl-1-oxobutan-2-yl)-4-((5-aminothiophen-2-yl)buta-1,3-diynyl)benzamide |
| 196 | 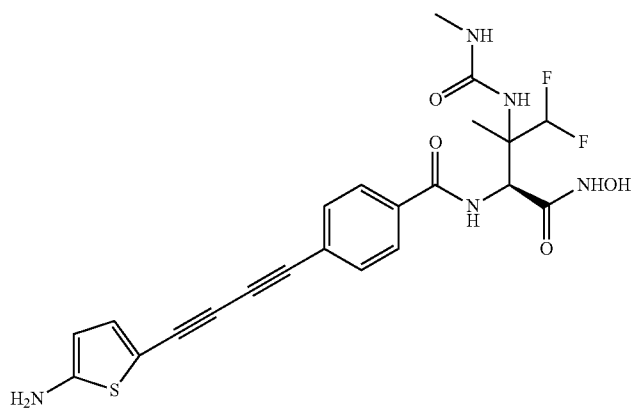 | 4-((5-aminothiophen-2-yl)buta-1,3-diynyl)-N-((2S)-4,4-difluoro-1-(hydroxyamino)-3-methyl-3-(3-methylureido)-1-oxobutan-2-yl)benzamide |
| 197 | 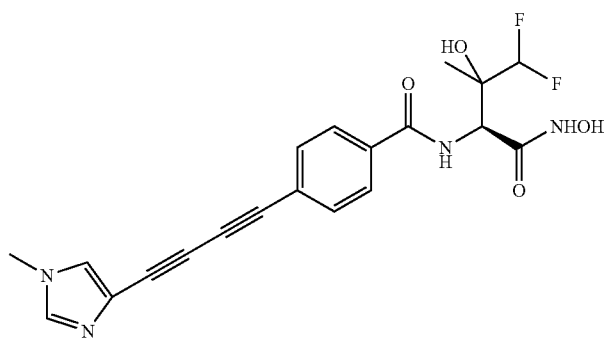 | N-((2S)-4,4-difluoro-3-hydroxy-1-(hydroxyamino)-3-methyl-1-oxobutan-2-yl)-4-((1-methyl-1H-imidazol-4-yl)buta-1,3-diynyl)benzamide |
| 198 | 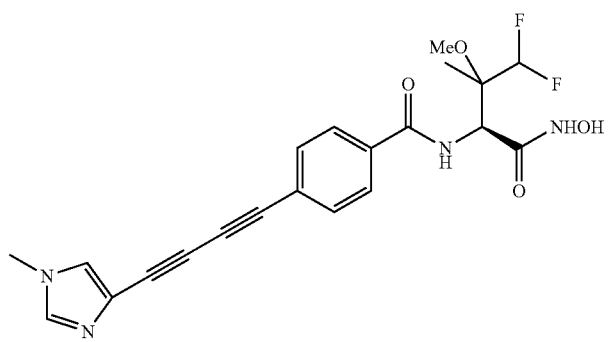 | N-((2S)-4,4-difluoro-1-(hydroxyamino)-3-methoxy-3-methyl-1-oxobutan-2-yl)-4-((1-methyl-1H-imidazol-4-yl)buta-1,3-diynyl)benzamide |

-continued

| Ex. No. | Structure | Name |
|---|---|---|
| 199 | 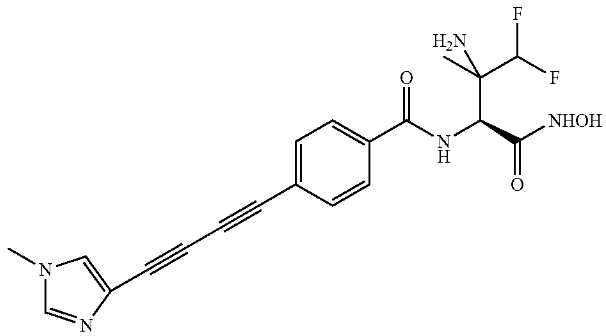 | N-((2S)-3-amino-4,4-difluoro-1-(hydroxyamino)-3-methyl-1-oxobutan-2-yl)-4-((1-methyl-1H-imidazol-4-yl)buta-1,3-diynyl)benzamide |
| 200 | 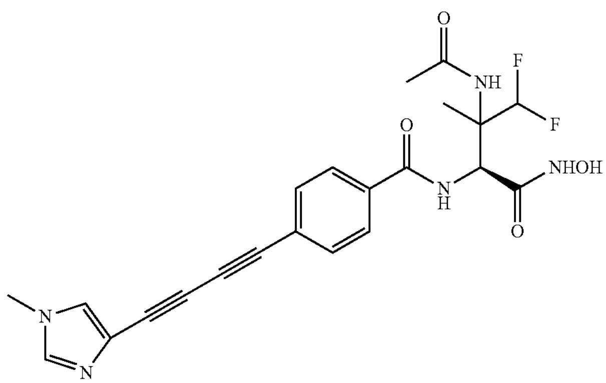 | N-((2S)-3-acetamido-4,4-difluoro-1-(hydroxyamino)-3-methyl-1-oxobutan-2-yl)-4-((1-methyl-1H-imidazol-4-yl)buta-1,3-diynyl)benzamide |
| 201 | 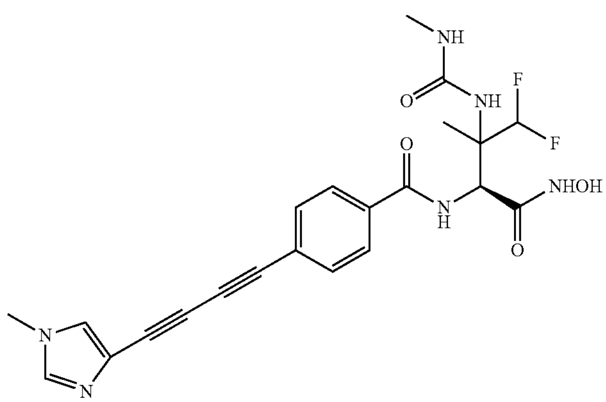 | N-((2S)-4,4-difluoro-1-(hydroxyamino)-3-methyl-3-(3-methylureido)-1-oxobutan-2-yl)-4-((1-methyl-1H-imidazol-4-yl)buta-1,3-diynyl)benzamide |
| 202 | 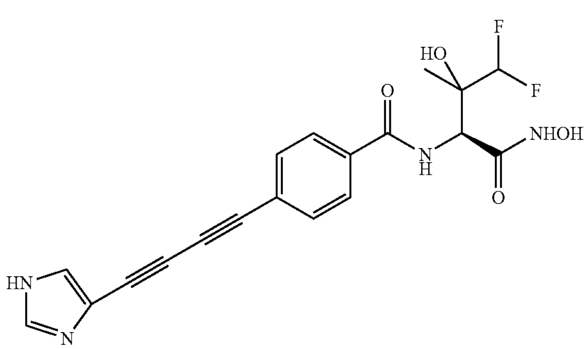 | 4-((1H-imidazol-4-yl)buta-1,3-diynyl)-N-((2S)-4,4-difluoro-3-hydroxy-1-(hydroxyamino)-3-methyl-1-oxobutan-2-yl)benzamide |

| Ex. No. | Structure | Name |
|---|---|---|
| 203 | 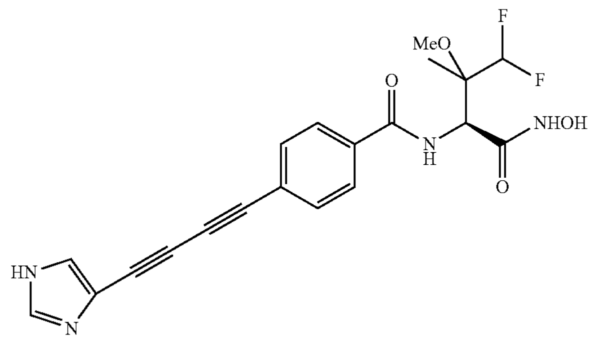 | 4-((1H-imidazol-4-yl)buta-1,3-diynyl)-N-((2S)-4,4-difluoro-1-(hydroxyamino)-3-methoxy-3-methyl-1-oxobutan-2-yl)benzamide |
| 204 | 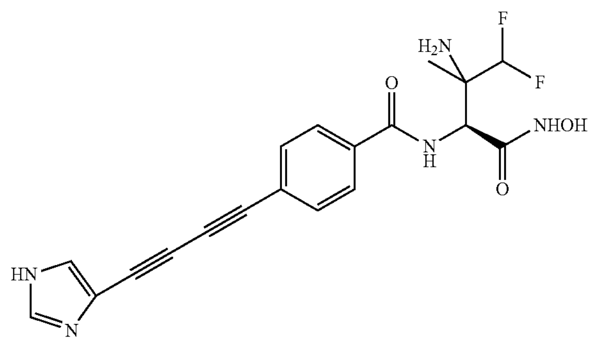 | 4-((1H-imidazol-4-yl)buta-1,3-diynyl)-N-((2S)-3-amino-4,4-difluoro-1-(hydroxyamino)-3-methyl-1-oxobutan-2-yl)benzamide |
| 205 | 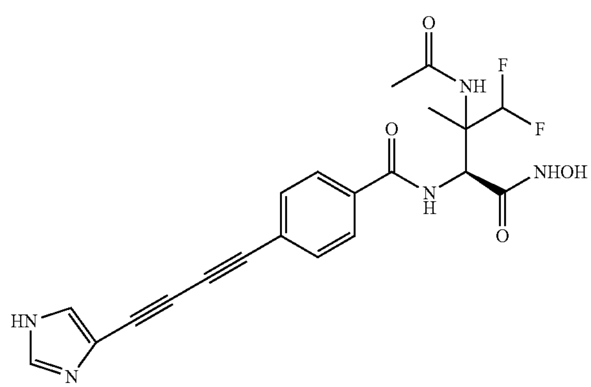 | 4-((1H-imidazol-4-yl)buta-1,3-diynyl)-N-((2S)-3-acetamido-4,4-difluoro-1-(hydroxyamino)-3-methyl-1-oxobutan-2-yl)benzamide |
| 206 | 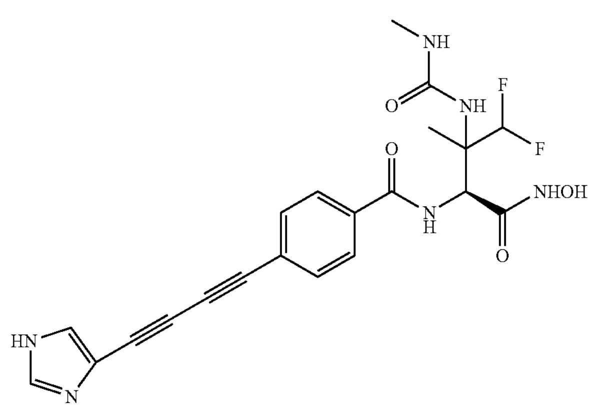 | 4-((1H-imidazol-4-yl)buta-1,3-diynyl)-N-((2S)-4,4-difluoro-1-(hydroxyamino)-3-methyl-3-(3-methylureido)-1-oxobutan-2-yl)benzamide |

-continued

| Ex. No. | Structure | Name |
|---|---|---|
| 207 | 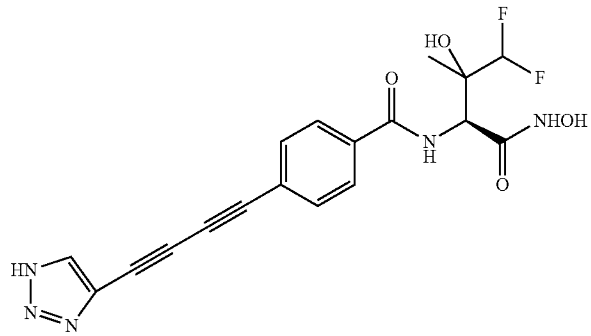 | 4-((1H-1,2,3-triazol-4-yl)buta-1,3-diynyl)-N-((2S)-4,4-difluoro-3-hydroxy-1-(hydroxyamino)-3-methyl-1-oxobutan-2-yl)benzamide |
| 208 | 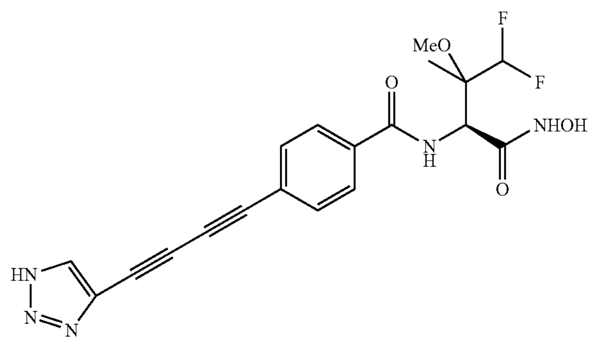 | 4-((1H-1,2,3-triazol-4-yl)buta-1,3-diynyl)-N-((2S)-4,4-difluoro-1-(hydroxyamino)-3-methoxy-3-methyl-1-oxobutan-2-yl)benzamide |
| 209 | 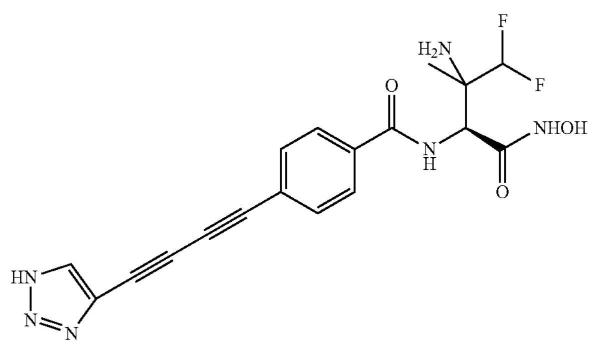 | 4-((1H-1,2,3-triazol-4-yl)buta-1,3-diynyl)-N-((2S)-3-amino-4,4-difluoro-1-(hydroxyamino)-3-methyl-1-oxobutan-2-yl)benzamide |
| 210 | 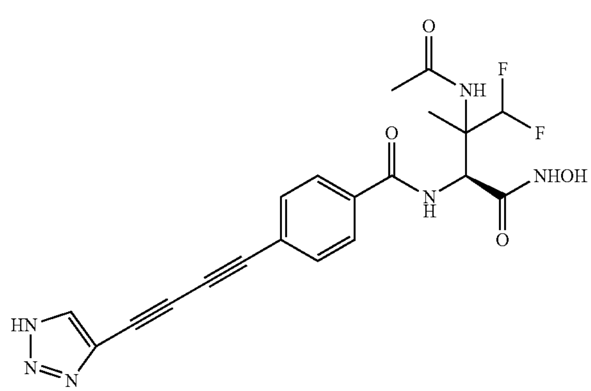 | 4-((1H-1,2,3-triazol-4-yl)buta-1,3-diynyl)-N-((2S)-3-acetamido-4,4-difluoro-1-(hydroxyamino)-3-methyl-1-oxobutan-2-yl)benzamide |

-continued

| Ex. No. | Structure | Name |
|---|---|---|
| 211 | 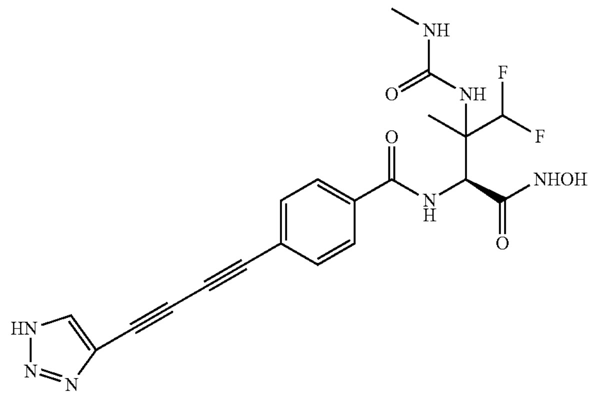 | 4-((1H-1,2,3-triazol-4-yl)buta-1,3-diynyl)-N-((2S)-4,4-difluoro-1-(hydroxyamino)-3-methyl-3-(3-methylureido)-1-oxobutan-2-yl)benzamide |
| 212 | 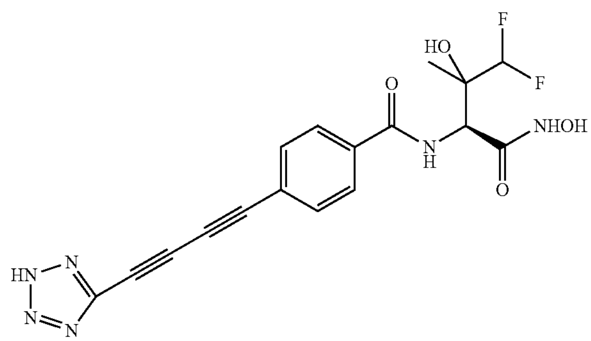 | 4-((2H-tetrazol-5-yl)buta-1,3-diynyl)-N-((2S)-4,4-difluoro-3-hydroxy-1-(hydroxyamino)-3-methyl-1-oxobutan-2-yl)benzamide |
| 213 | 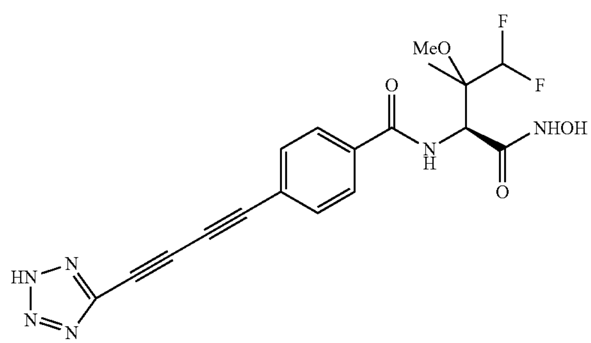 | 4-((2H-tetrazol-5-yl)buta-1,3-diynyl)-N-((2S)-4,4-difluoro-1-(hydroxyamino)-3-methoxy-3-methyl-1-oxobutan-2-yl)benzamide |
| 214 | 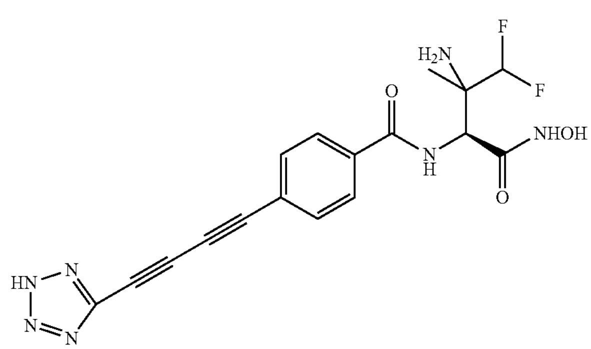 | 4-((2H-tetrazol-5-yl)buta-1,3-diynyl)-N-((2S)-3-amino-4,4-difluoro-1-(hydroxyamino)-3-methyl-1-oxobutan-2-yl)benzamide |

| Ex. No. | Structure | Name |
|---|---|---|
| 215 | 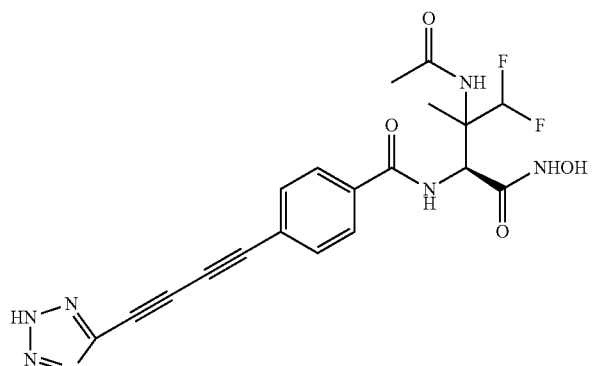 | 4-((2H-tetrazol-5-yl)buta-1,3-diynyl)-N-((2S)-3-acetamido-4,4-difluoro-1-(hydroxyamino)-3-methyl-1-oxobutan-2-yl)benzamide |
| 216 | 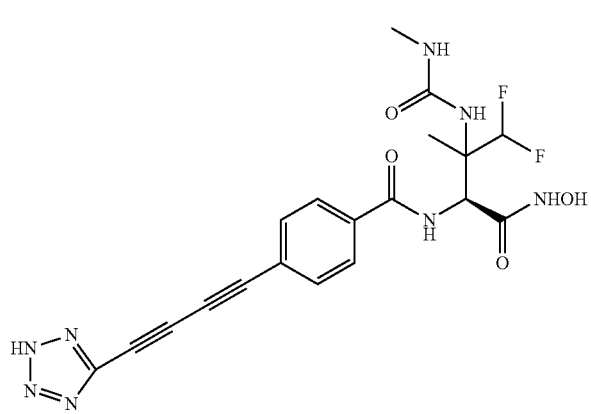 | 4-((2H-tetrazol-5-yl)buta-1,3-diynyl)-N-((2S)-4,4-difluoro-1-(hydroxyamino)-3-methyl-3-(3-methylureido)-1-oxobutan-2-yl)benzamide |
| 217 | 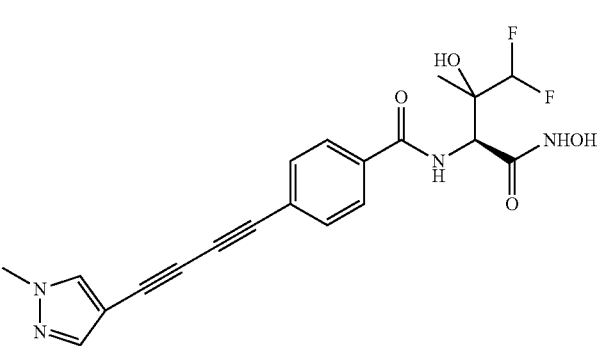 | N-((2S)-4,4-difluoro-3-hydroxy-1-(hydroxyamino)-3-methyl-1-oxobutan-2-yl)-4-((1-methyl-1H-pyrazol-4-yl)buta-1,3-diynyl)benzamide |
| 218 | 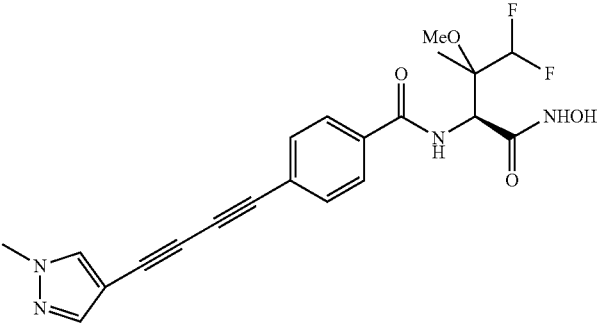 | N-((2S)-4,4-difluoro-1-(hydroxyamino)-3-methoxy-3-methyl-1-oxobutan-2-yl)-4-((1-methyl-1H-pyrazol-4-yl)buta-1,3-diynyl)benzamide |

| Ex. No. | Structure | Name |
|---|---|---|
| 219 | 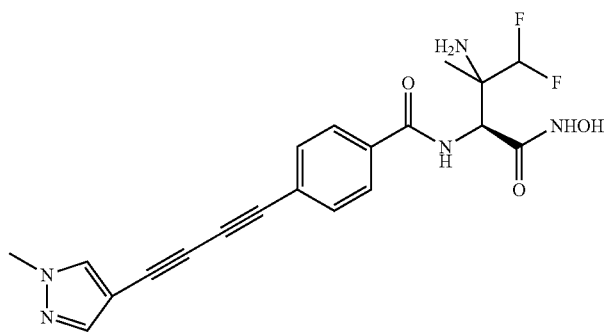 | N-((2S)-3-amino-4,4-difluoro-1-(hydroxyamino)-3-methyl-1-oxobutan-2-yl)-4-((1-methyl-1H-pyrazol-4-yl)buta-1,3-diynyl)benzamide |
| 220 | 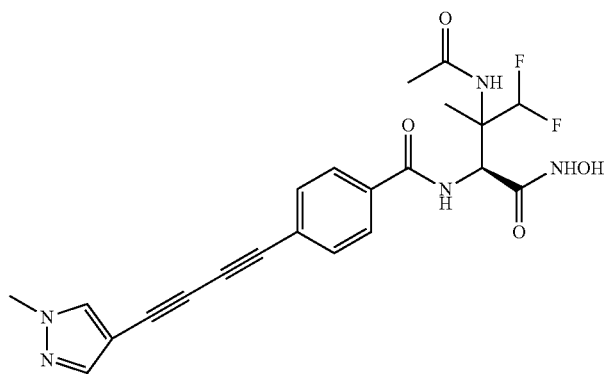 | N-((2S)-3-acetamido-4,4-difluoro-1-(hydroxyamino)-3-methyl-1-oxobutan-2-yl)-4-((1-methyl-1H-pyrazol-4-yl)buta-1,3-diynyl)benzamide |
| 221 | 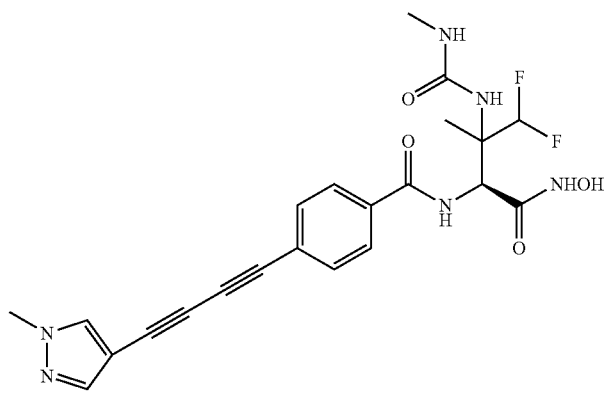 | N-((2S)-4,4-difluoro-1-(hydroxyamino)-3-methyl-3-(3-methylureido)-1-oxobutan-2-yl)-4-((1-methyl-1H-pyrazol-4-yl)buta-1,3-diynyl)benzamide |
| 222 | 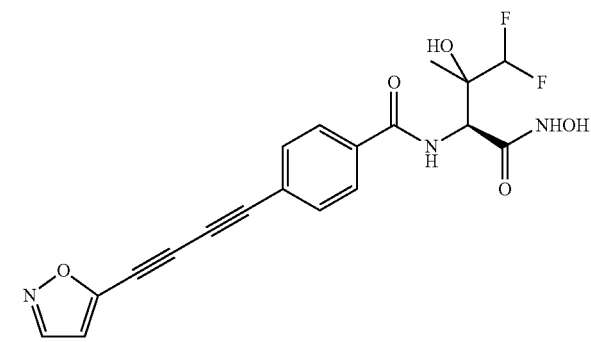 | N-((2S)-4,4-difluoro-3-hydroxy-1-(hydroxyamino)-3-methyl-1-oxobutan-2-yl)-4-(isoxazol-5-ylbuta-1,3-diynyl)benzamide |

| Ex. No. | Structure | Name |
|---|---|---|
| 223 | 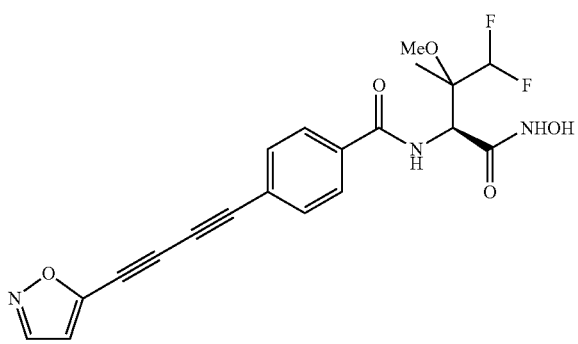 | N-((2S)-4,4-difluoro-1-(hydroxyamino)-3-methoxy-3-methyl-1-oxobutan-2-yl)-4-(isoxazol-5-ylbuta-1,3-diynyl)benzamide |
| 224 | 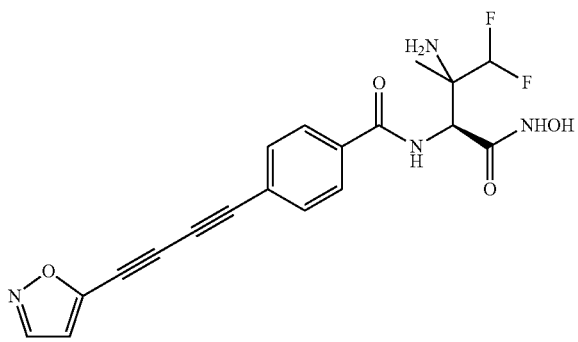 | N-((2S)-3-amino-4,4-difluoro-1-(hydroxyamino)-3-methyl-1-oxobutan-2-yl)-4-(isoxazol-5-ylbuta-1,3-diynyl)benzamide |
| 225 | 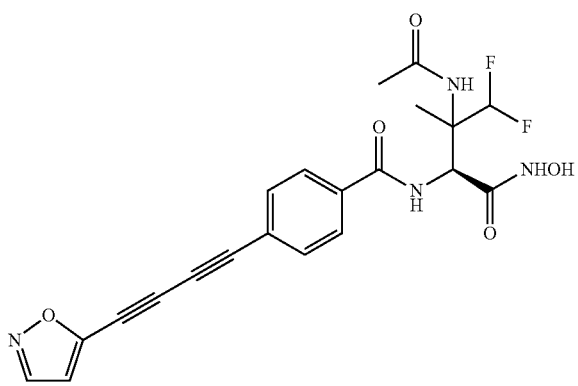 | N-((2S)-3-acetamido-4,4-difluoro-1-(hydroxyamino)-3-methyl-1-oxobutan-2-yl)-4-(isoxazol-5-ylbuta-1,3-diynyl)benzamide |
| 226 | 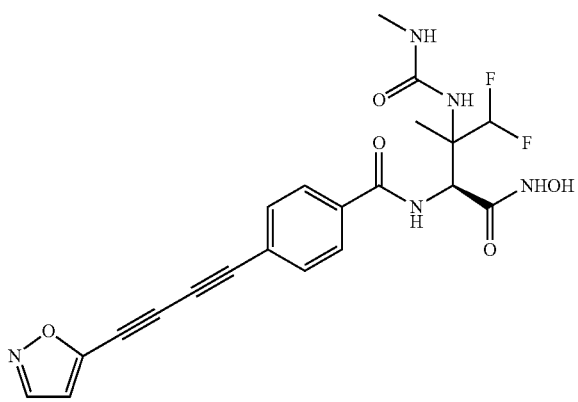 | N-((2S)-4,4-difluoro-1-(hydroxyamino)-3-methyl-3-(3-methylureido)-1-oxobutan-2-yl)-4-(isoxazol-5-ylbuta-1,3-diynyl)benzamide |

-continued

| Ex. No. | Structure | Name |
|---|---|---|
| 227 | 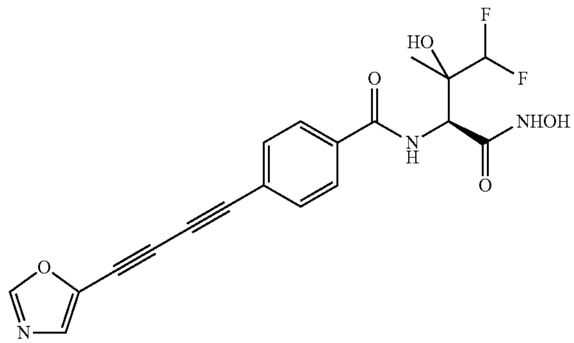 | N-((2S)-4,4-difluoro-3-hydroxy-1-(hydroxyamino)-3-methyl-1-oxobutan-2-yl)-4-(oxazol-5-ylbuta-1,3-diynyl)benzamide |
| 228 | 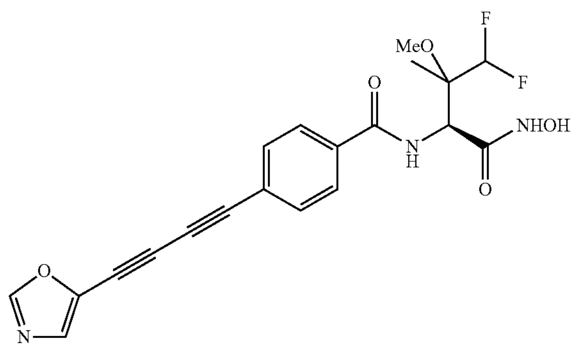 | N-((2S)-4,4-difluoro-1-(hydroxyamino)-3-methoxy-3-methyl-1-oxobutan-2-yl)-4-(oxazol-5-ylbuta-1,3-diynyl)benzamide |
| 229 | 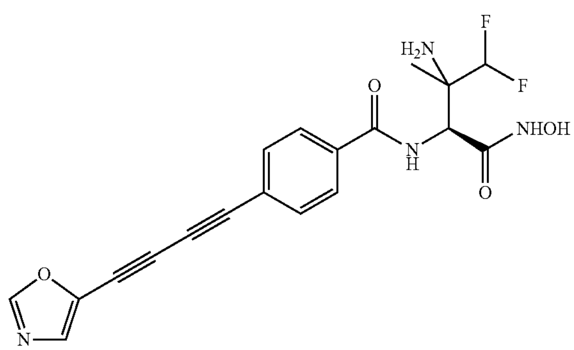 | N-((2S)-3-amino-4,4-difluoro-1-(hydroxyamino)-3-methyl-1-oxobutan-2-yl)-4-(oxazol-5-ylbuta-1,3-diynyl)benzamide |
| 230 | 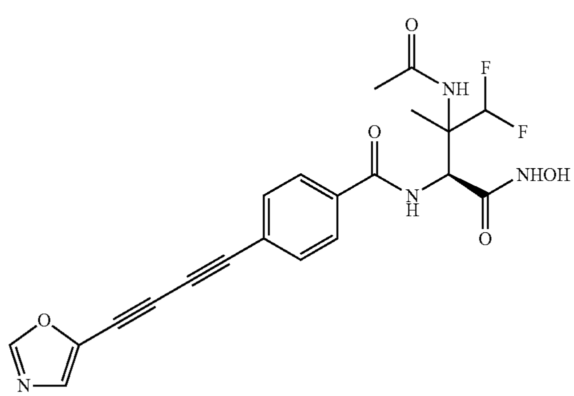 | N-((2S)-3-acetamido-4,4-difluoro-1-(hydroxyamino)-3-methyl-1-oxobutan-2-yl)-4-(oxazol-5-ylbuta-1,3-diynyl)benzamide |

-continued

| Ex. No. | Structure | Name |
|---|---|---|
| 231 | 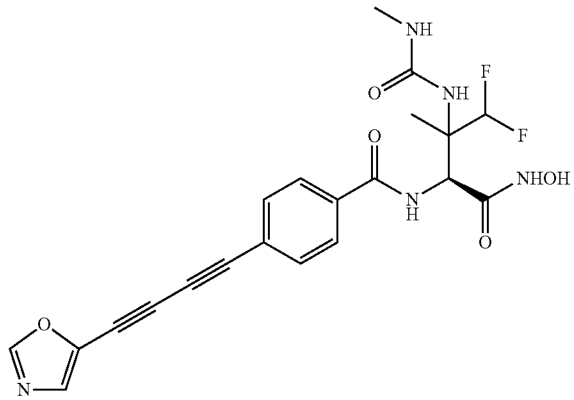 | N-((2S)-4,4-difluoro-1-(hydroxyamino)-3-methyl-3-(3-methylureido)-1-oxobutan-2-yl)-4-(oxazol-5-ylbuta-1,3-diynyl)benzamide |
| 232 | 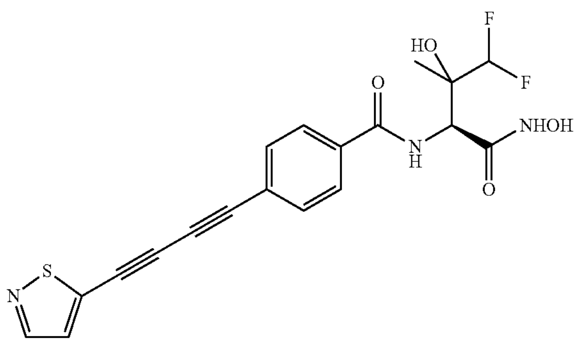 | N-((2S)-4,4-difluoro-3-hydroxy-1-(hydroxyamino)-3-methyl-1-oxobutan-2-yl)-4-(isothiazol-5-ylbuta-1,3-diynyl)benzamide |
| 233 | 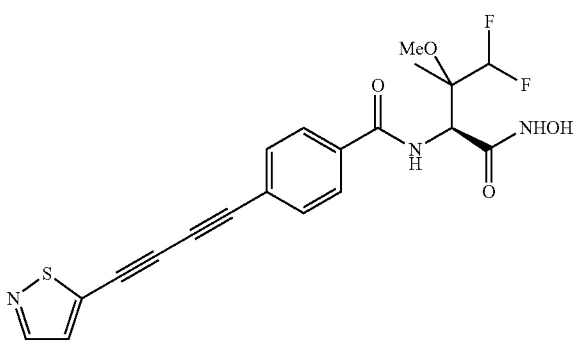 | N-((2S)-4,4-difluoro-1-(hydroxyamino)-3-methoxy-3-methyl-1-oxobutan-2-yl)-4-(isothiazol-5-ylbuta-1,3-diynyl)benzamide |
| 234 | 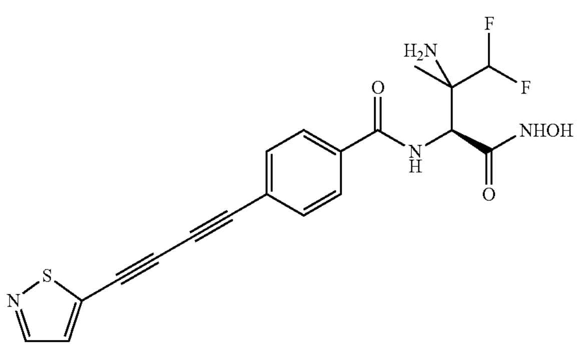 | N-((2S)-3-amino-4,4-difluoro-1-(hydroxyamino)-3-methyl-1-oxobutan-2-yl)-4-(isothiazol-5-ylbuta-1,3-diynyl)benzamide |

| Ex. No. | Structure | Name |
|---|---|---|
| 235 | 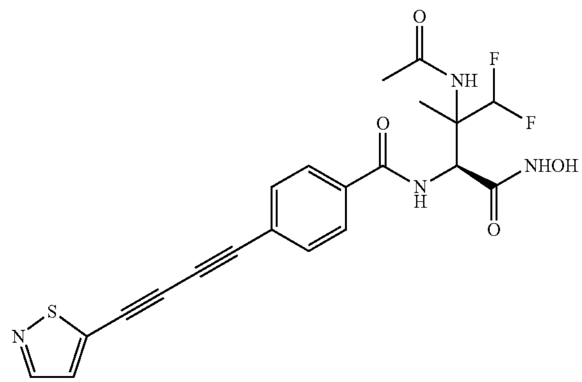 | N-((2S)-3-acetamido-4,4-difluoro-1-(hydroxyamino)-3-methyl-1-oxobutan-2-yl)-4-(isothiazol-5-ylbuta-1,3-diynyl)benzamide |
| 236 | 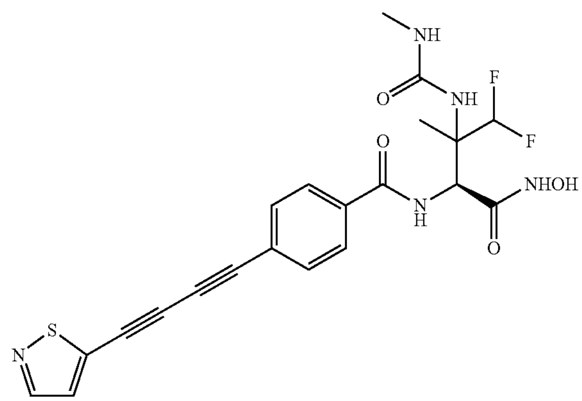 | N-((2S)-4,4-difluoro-1-(hydroxyamino)-3-methyl-3-(3-methylureido)-1-oxobutan-2-yl)-4-(isothiazol-5-ylbuta-1,3-diynyl)benzamide |
| 237 | 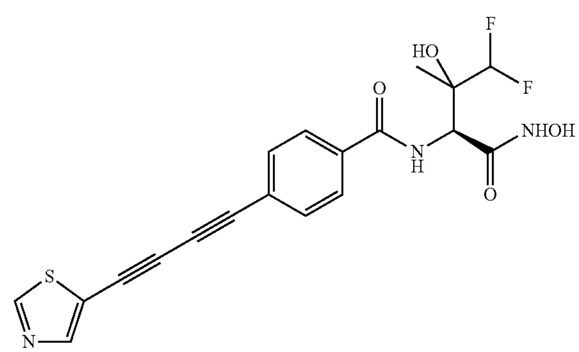 | N-((2S)-4,4-difluoro-3-hydroxy-1-(hydroxyamino)-3-methyl-1-oxobutan-2-yl)-4-(thiazol-5-ylbuta-1,3-diynyl)benzamide |
| 238 | 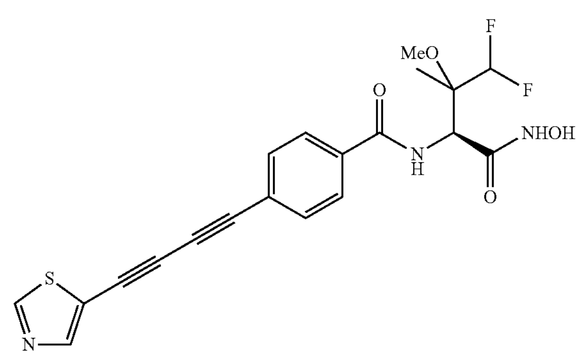 | N-((2S)-4,4-difluoro-1-(hydroxyamino)-3-methoxy-3-methyl-1-oxobutan-2-yl)-4-(thiazol-5-ylbuta-1,3-diynyl)benzamide |

| Ex. No. | Structure | Name |
|---|---|---|
| 239 | 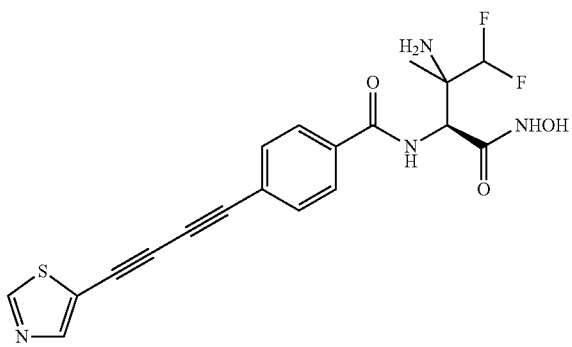 | N-((2S)-3-amino-4,4-difluoro-1-(hydroxyamino)-3-methyl-1-oxobutan-2-yl)-4-(thiazol-5-ylbuta-1,3-diynyl)benzamide |
| 240 | 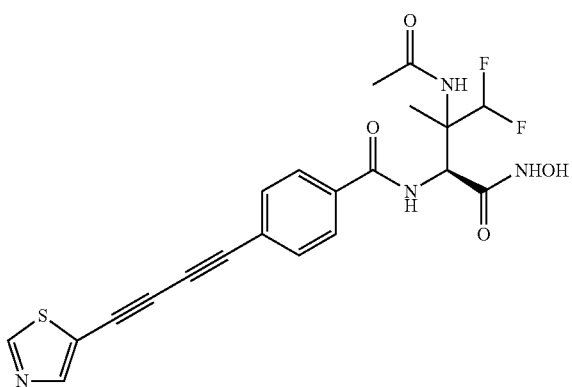 | N-((2S)-3-acetamido-4,4-difluoro-1-(hydroxyamino)-3-methyl-1-oxobutan-2-yl)-4-(thiazol-5-ylbuta-1,3-diynyl)benzamide |
| 241 | 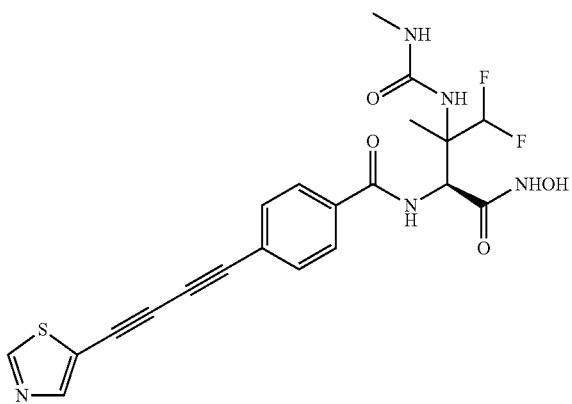 | N-((2S)-4,4-difluoro-1-(hydroxyamino)-3-methyl-3-(3-methylureido)-1-oxobutan-2-yl)-4-(thiazol-5-ylbuta-1,3-diynyl)benzamide |
| 242 | 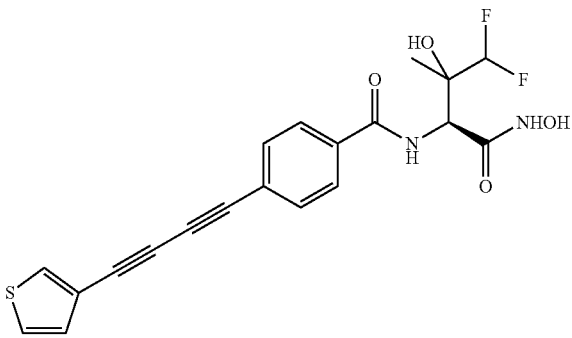 | N-((2S)-4,4-difluoro-3-hydroxy-1-(hydroxyamino)-3-methyl-1-oxobutan-2-yl)-4-(thiophen-3-ylbuta-1,3-diynyl)benzamide |

| Ex. No. | Structure | Name |
|---|---|---|
| 243 | 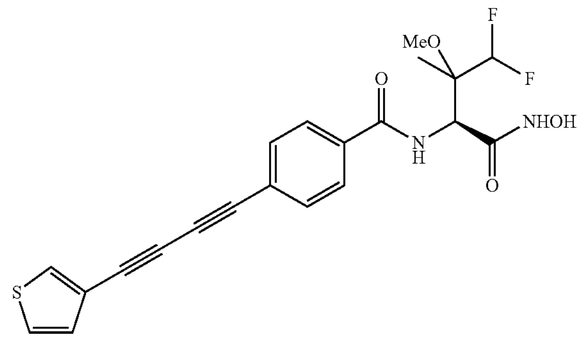 | N-((2S)-4,4-difluoro-1-(hydroxyamino)-3-methoxy-3-methyl-1-oxobutan-2-yl)-4-(thiophen-3-ylbuta-1,3-diynyl)benzamide |
| 244 | 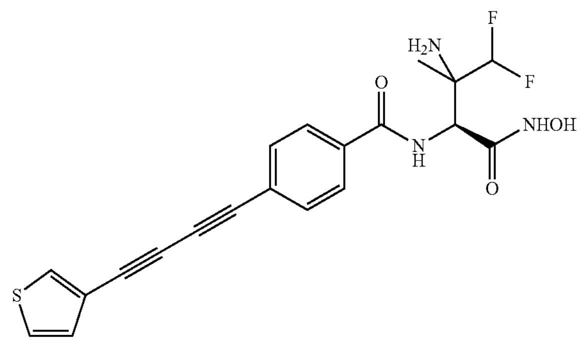 | N-((2S)-3-amino-4,4-difluoro-1-(hydroxyamino)-3-methyl-1-oxobutan-2-yl)-4-(thiophen-3-ylbuta-1,3-diynyl)benzamide |
| 245 | 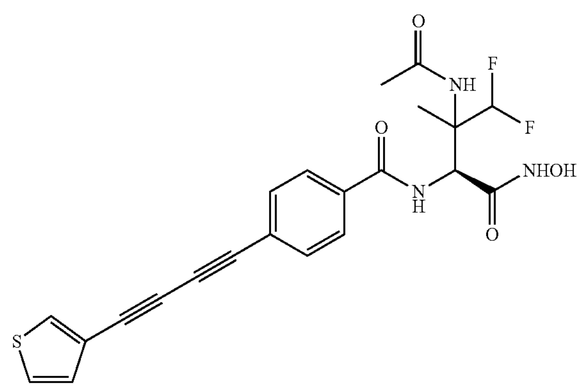 | N-((2S)-3-acetamido-4,4-difluoro-1-(hydroxyamino)-3-methyl-1-oxobutan-2-yl)-4-(thiophen-3-ylbuta-1,3-diynyl)benzamide |
| 246 | 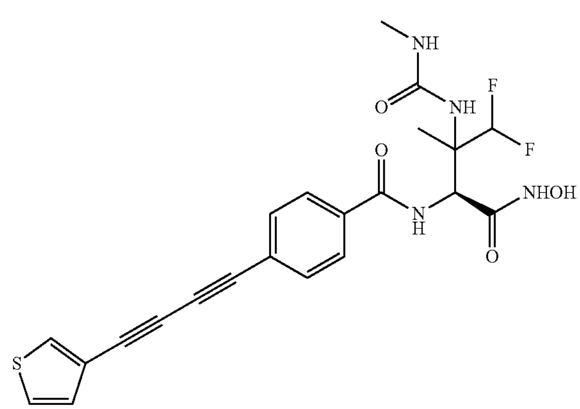 | N-((2S)-4,4-difluoro-1-(hydroxyamino)-3-methyl-3-(3-methylureido)-1-oxobutan-2-yl)-4-(thiophen-3-ylbuta-1,3-diynyl)benzamide |

| Ex. No. | Structure | Name |
|---|---|---|
| 247 | 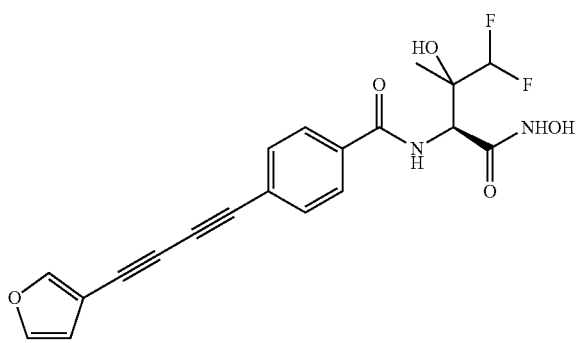 | N-((2S)-4,4-difluoro-3-hydroxy-1-(hydroxyamino)-3-methyl-1-oxobutan-2-yl)-4-(furan-3-ylbuta-1,3-diynyl)benzamide |
| 248 | 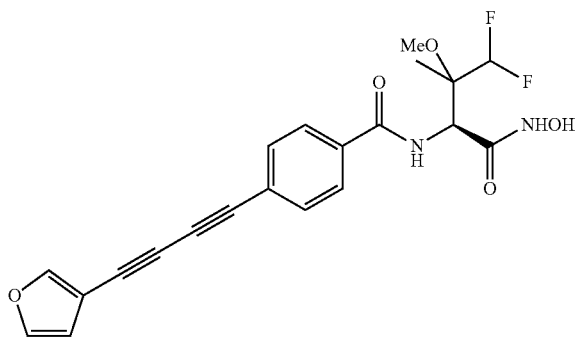 | N-((2S)-4,4-difluoro-1-(hydroxyamino)-3-methoxy-3-methyl-1-oxobutan-2-yl)-4-(furan-3-ylbuta-1,3-diynyl)benzamide |
| 249 | 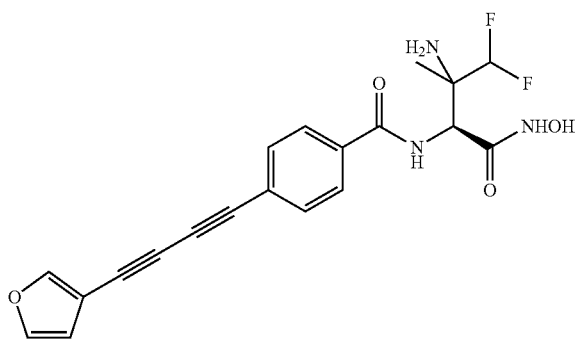 | N-((2S)-3-amino-4,4-difluoro-1-(hydroxyamino)-3-methyl-1-oxobutan-2-yl)-4-(furan-3-ylbuta-1,3-diynyl)benzamide |
| 250 | 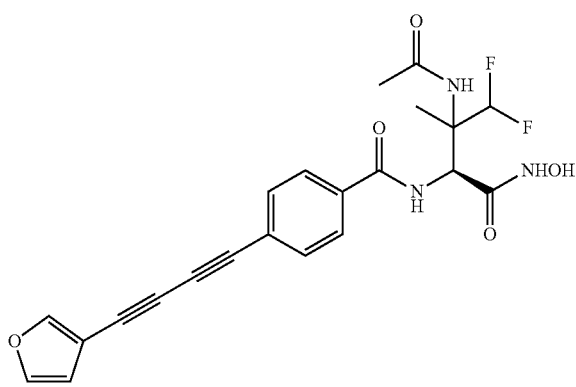 | N-((2S)-3-acetamido-4,4-difluoro-1-(hydroxyamino)-3-methyl-1-oxobutan-2-yl)-4-(furan-3-ylbuta-1,3-diynyl)benzamide |

-continued

| Ex. No. | Structure | Name |
|---|---|---|
| 251 | 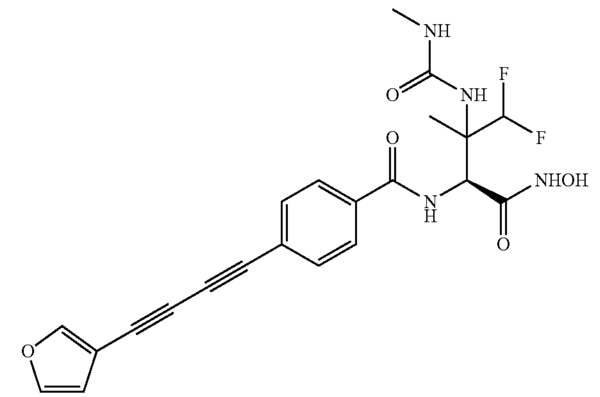 | N-((2S)-4,4-difluoro-1-(hydroxyamino)-3-methyl-3-(3-methylureido)-1-oxobutan-2-yl)-4-(furan-3-ylbuta-1,3-diynyl)benzamide |
| 252 | 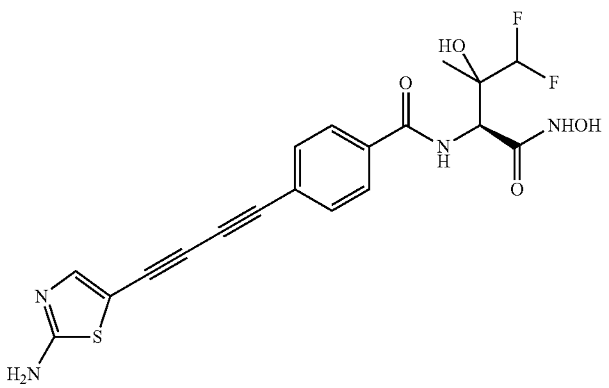 | 4-((2-aminothiazol-5-yl)buta-1,3-diynyl)-N-((2S)-4,4-difluoro-3-hydroxy-1-(hydroxyamino)-3-methyl-1-oxobutan-2-yl)benzamide |
| 253 | 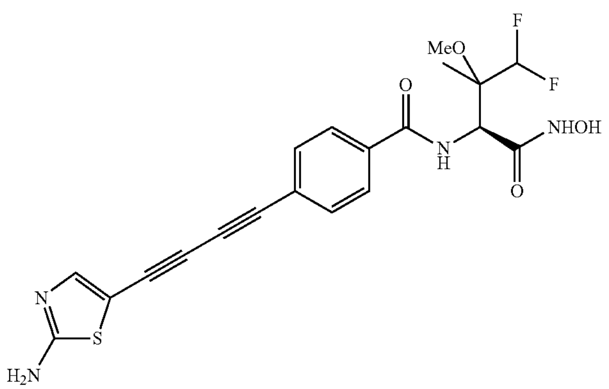 | 4-((2-aminothiazol-5-yl)buta-1,3-diynyl)-N-((2S)-4,4-difluoro-1-(hydroxyamino)-3-methoxy-3-methyl-1-oxobutan-2-yl)benzamide |
| 254 | 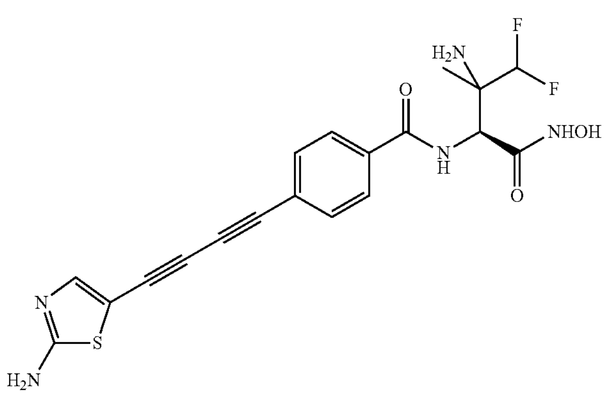 | N-((2S)-3-amino-4,4-difluoro-1-(hydroxyamino)-3-methyl-1-oxobutan-2-yl)-4-((2-aminothiazol-5-yl)buta-1,3-diynyl)benzamide |

| Ex. No. | Structure | Name |
|---|---|---|
| 255 | 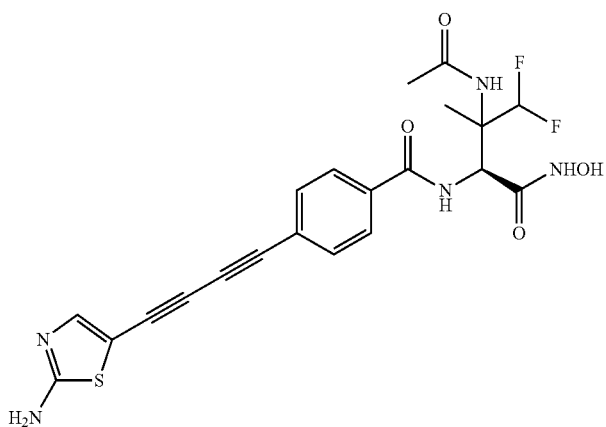 | N-((2S)-3-acetamido-4,4-difluoro-1-(hydroxyamino)-3-methyl-1-oxobutan-2-yl)-4-((2-aminothiazol-5-yl)buta-1,3-diynyl)benzamide |
| 256 | 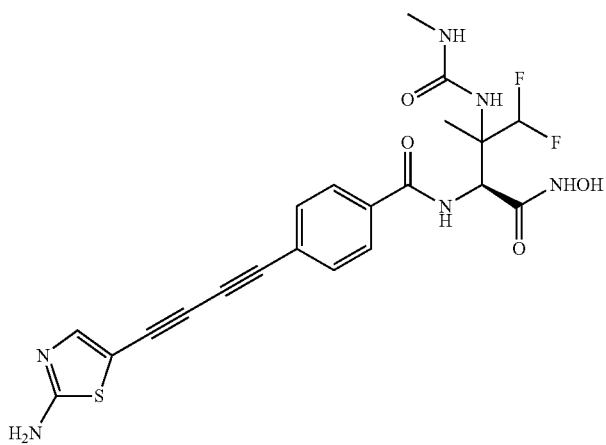 | 4-((2-aminothiazol-5-yl)buta-1,3-diynyl)-N-((2S)-4,4-difluoro-1-(hydroxyamino)-3-methyl-3-(3-methylureido)-1-oxobutan-2-yl)benzamide |
| 257 | 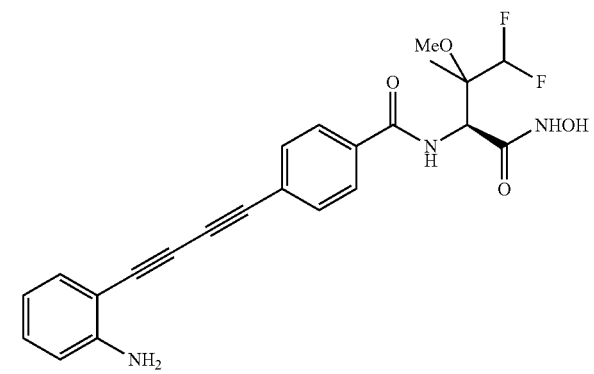 | 4-((2-aminophenyl)buta-1,3-diynyl)-N-((2S)-4,4-difluoro-1-(hydroxyamino)-3-methoxy-3-methyl-1-oxobutan-2-yl)benzamide |

| Ex. No. | Structure | Name |
|---|---|---|
| 258 | 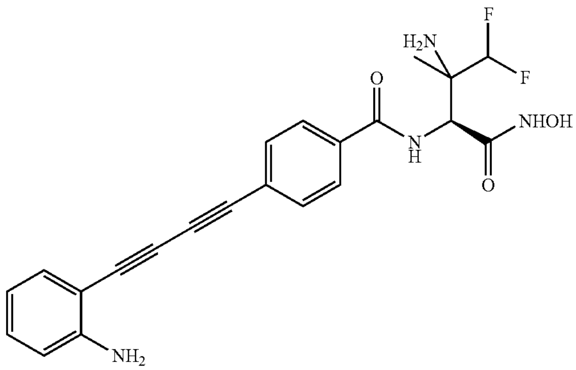 | N-((2S)-3-amino-4,4-difluoro-1-(hydroxyamino)-3-methyl-1-oxobutan-2-yl)-4-((2-aminophenyl)buta-1,3-diynyl)benzamide |
| 259 | 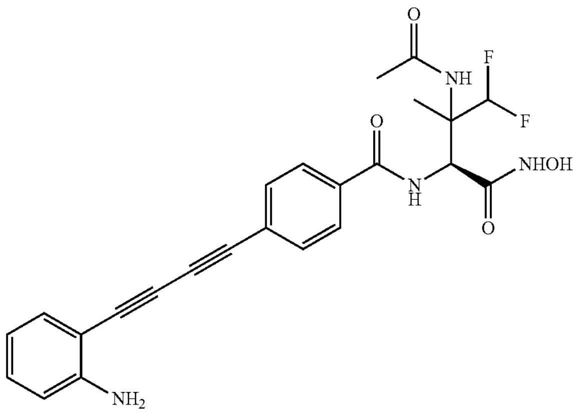 | N-((2S)-3-acetamido-4,4-difluoro-1-(hydroxyamino)-3-methyl-1-oxobutan-2-yl)-4-((2-aminophenyl)buta-1,3-diynyl)benzamide |
| 260 | 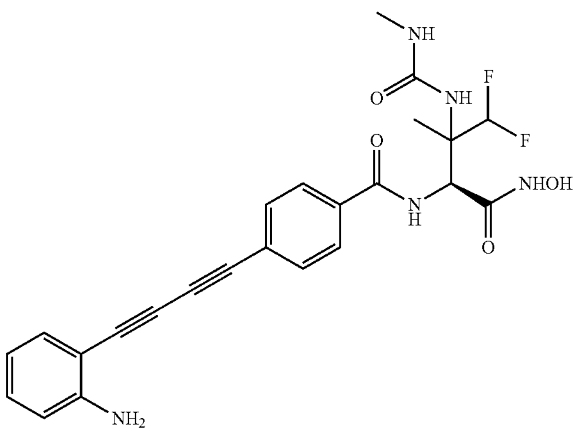 | 4-((2-aminophenyl)buta-1,3-diynyl)-N-((2S)-4,4-difluoro-1-(hydroxyamino)-3-methyl-3-(3-methylureido)-1-oxobutan-2-yl)benzamide |
| 261 | 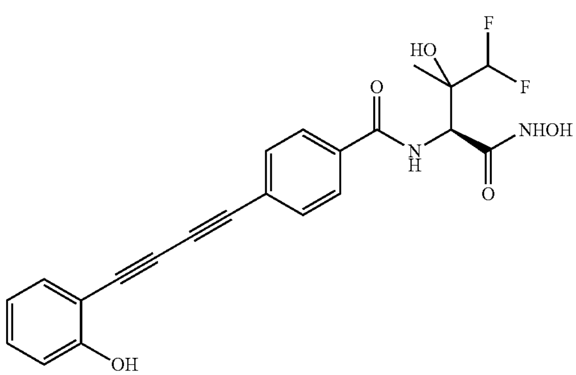 | N-((2S)-4,4-difluoro-3-hydroxy-1-(hydroxyamino)-3-methyl-1-oxobutan-2-yl)-4-((2-hydroxyphenyl)buta-1,3-diynyl)benzamide |

| Ex. No. | Structure | Name |
|---|---|---|
| 262 | 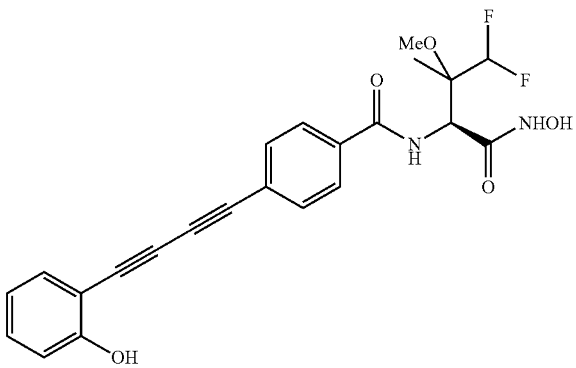 | N-((2S)-4,4-difluoro-1-(hydroxyamino)-3-methoxy-3-methyl-1-oxobutan-2-yl)-4-((2-hydroxyphenyl)buta-1,3-diynyl)benzamide |
| 263 | 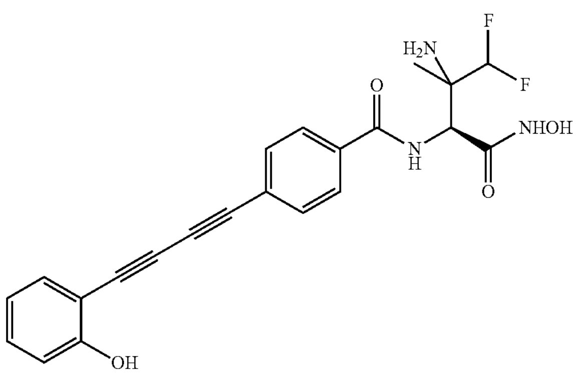 | N-((2S)-3-amino-4,4-difluoro-1-(hydroxyamino)-3-methyl-1-oxobutan-2-yl)-4-((2-hydroxyphenyl)buta-1,3-diynyl)benzamide |
| 264 | 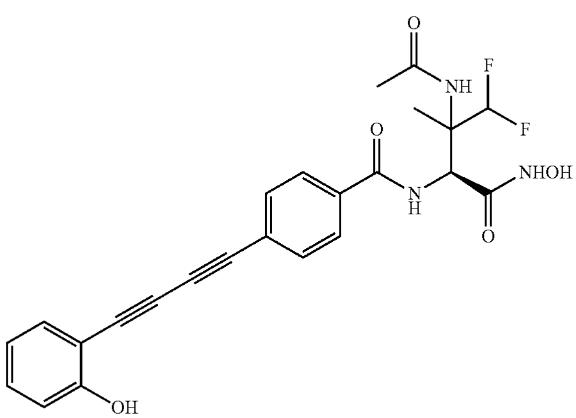 | N-((2S)-3-acetamido-4,4-difluoro-1-(hydroxyamino)-3-methyl-1-oxobutan-2-yl)-4-((2-hydroxyphenyl)buta-1,3-diynyl)benzamide |
| 265 | 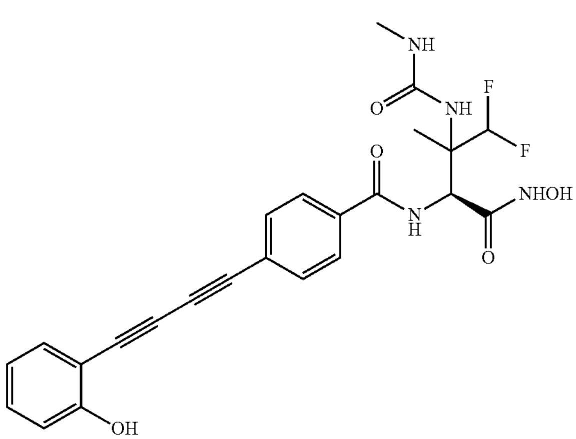 | N-((2S)-4,4-difluoro-1-(hydroxyamino)-3-methyl-3-(3-methylureido)-1-oxobutan-2-yl)-4-((2-hydroxyphenyl)buta-1,3-diynyl)benzamide |

-continued

| Ex. No. | Structure | Name |
|---|---|---|
| 266 | 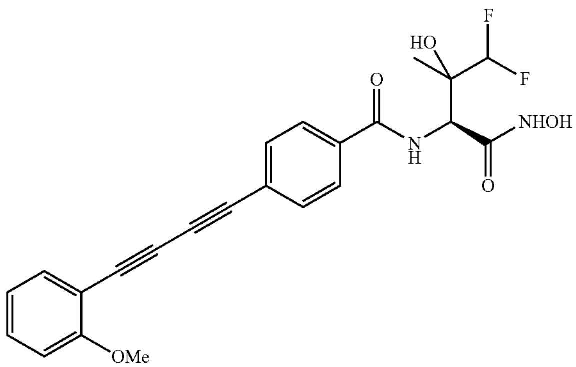 | N-((2S)-4,4-difluoro-3-hydroxy-1-(hydroxyamino)-3-methyl-1-oxobutan-2-yl)-4-((2-methoxyphenyl)buta-1,3-diynyl)benzamide |
| 267 | 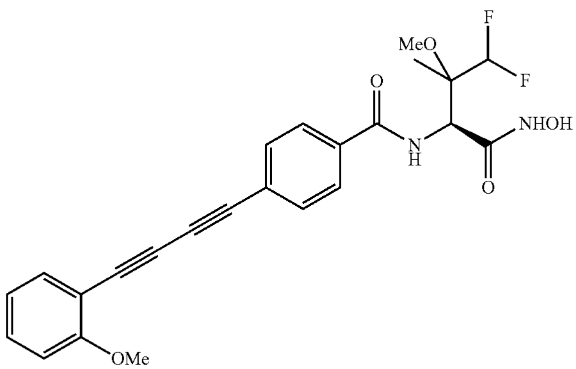 | N-((2S)-4,4-difluoro-1-(hydroxyamino)-3-methoxy-3-methyl-1-oxobutan-2-yl)-4-((2-methoxyphenyl)buta-1,3-diynyl)benzamide |
| 268 | 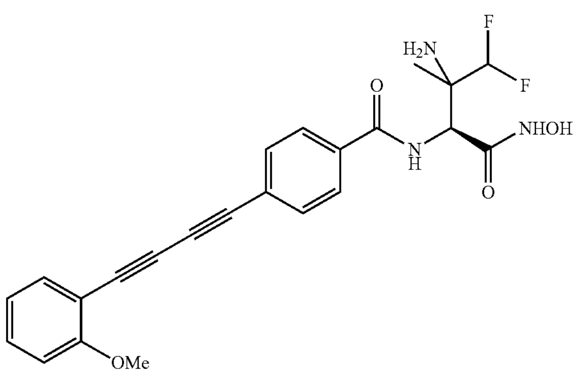 | N-((2S)-3-amino-4,4-difluoro-1-(hydroxyamino)-3-methyl-1-oxobutan-2-yl)-4-((2-methoxyphenyl)buta-1,3-diynyl)benzamide |
| 269 | 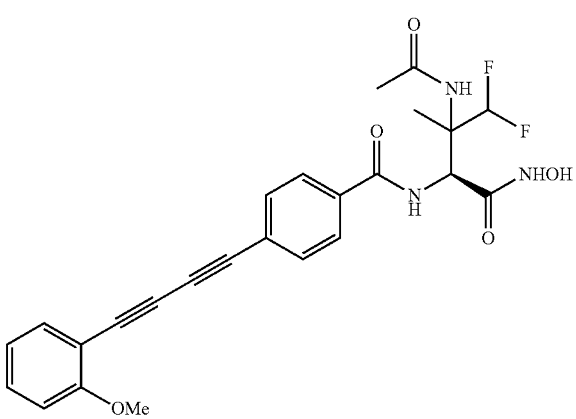 | N-((2S)-3-acetamido-4,4-difluoro-1-(hydroxyamino)-3-methyl-1-oxobutan-2-yl)-4-((2-methoxyphenyl)buta-1,3-diynyl)benzamide |

| Ex. No. | Structure | Name |
|---|---|---|
| 270 | 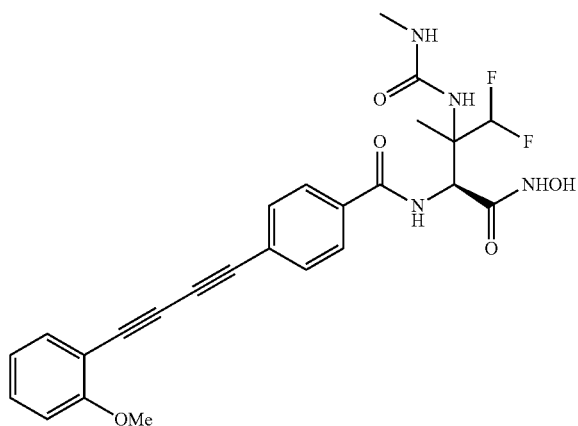 | N-((2S)-4,4-difluoro-1-(hydroxyamino)-3-methyl-3-(3-methylureido)-1-oxobutan-2-yl)-4-((2-methoxyphenyl)buta-1,3-diynyl)benzamide |
| 271 | 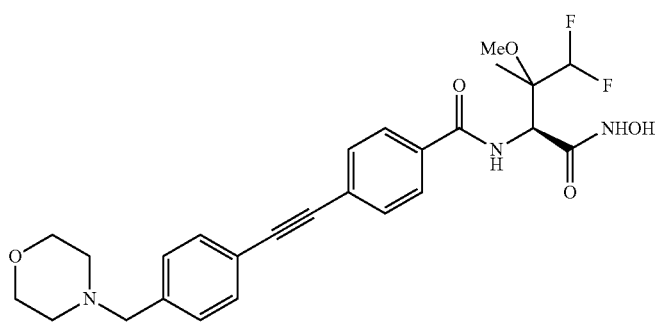 | N-((2S)-4,4-difluoro-1-(hydroxyamino)-3-methoxy-3-methyl-1-oxobutan-2-yl)-4-((4-(morpholinomethyl)phenyl)ethynyl)benzamide |
| 272 | 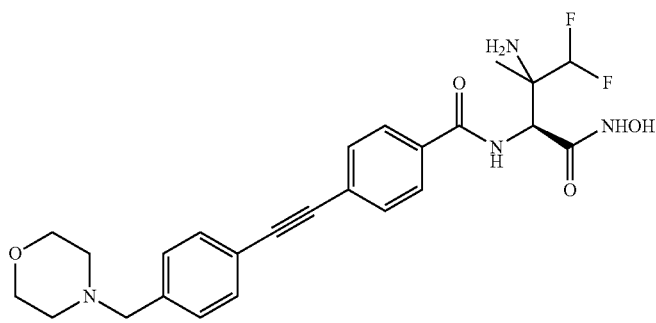 | N-((2S)-3-amino-4,4-difluoro-1-(hydroxyamino)-3-methyl-1-oxobutan-2-yl)-4-((4-(morpholinomethyl)phenyl)ethynyl)benzamide |
| 273 | 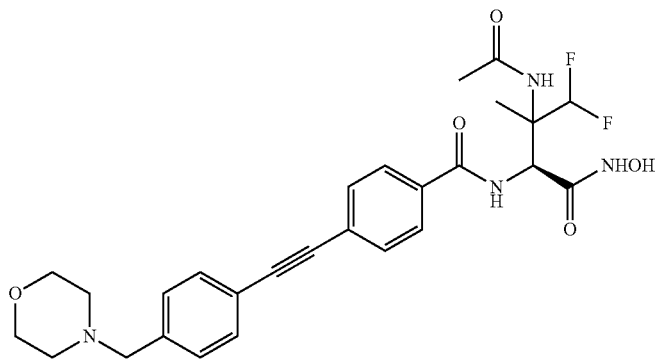 | N-((2S)-3-acetamido-4,4-difluoro-1-(hydroxyamino)-3-methyl-1-oxobutan-2-yl)-4-((4-(morpholinomethyl)phenyl)ethynyl)benzamide |

| Ex. No. | Structure | Name |
|---|---|---|
| 274 | 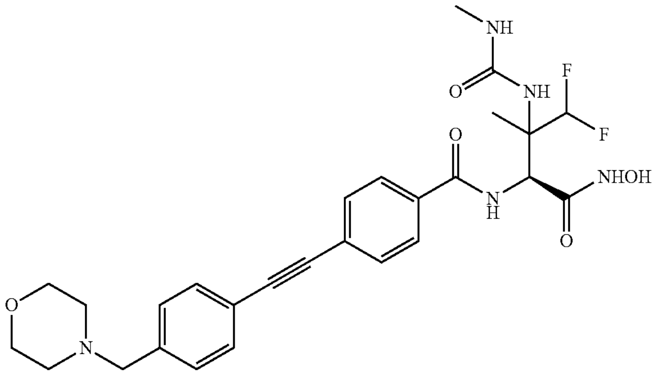 | N-((2S)-4,4-difluoro-1-(hydroxyamino)-3-methyl-3-(3-methylureido)-1-oxobutan-2-yl)-4-((4-(morpholinomethyl)phenyl)ethynyl)benzamide |

Example 275

Biological Examples

Protein Purification

Plasmids encoding wild-type *E. coli* LpxC, *P. aeruginosa* LpxC (residues 1-299) with a C40S mutation, and *A. aeolicus* LpxC lacking the eight C-terminal amino acids and containing a C181A mutation (1-274) are prepared following established procedures. An *E. coli* LpxC construct lacking the C-terminal five amino acids (1-300) is prepared by using the QuikChange site-directed mutagenesis kit (Stratagene) from the full-length *E. coli* LpxC gene. LpxC proteins are overexpressed in BL21(DE3)STAR cells (Invitrogen) grown in LB media and purified using anion-exchange (Q-Sepharose Fast Flow, Amersham) and size exclusion (Sephacryl S-200 HR, Amersham) chromatography. Purified proteins are concentrated and buffer-exchanged into 25 mM HEPES, pH 7.0, with 100 mM KCl and 0.1 mM ZnSO$_4$. For the EcLpxC proteins, 2 mM dithiothreitol is added to all the purification buffers. All proteins samples for enzymatic assay and crystallography are stored at –80° C.

Enzymatic Inhibition Assay

UDP-3-O—[(R)-3-hydroxymyristoyl]-N-acetylglucosamine and [α-$^{32}$P]UDP-3-O—[(R)-3-hydroxymyristoyl]-N-acetylglucosamine are prepared as previously described. Assays of LpxC activity are performed at 30° C. in 25 mM sodium phosphate, pH 7.4, 1 mg/mL bovine serum albumin, 100 mM KCl and 2 mM DTT, in the presence of 5 µM substrate and 0.2 nM EcLpxC, unless noted otherwise. 10% DMSO is included and held constant in assay mixtures. Initial velocities are calculated from the linear portion of reaction progress curves (<10% conversion of substrate to product).

$K_M$ and $V_{max}$ values are determined by varying the substrate concentration from 0.5 to 50 µM. Data is analyzed using an Eadie-Hofstee plot and by a nonlinear curve-fitting program (KaleidaGraph, Synergy Software); the resultant values are nearly identical within experimental errors. To determine a K, value, the compound concentrations are varied from 12.5 pM to 15 nM, or from 0.8 pM to 51 nM. Fractional activity ($u_i/u_0$) versus the compound concentration is plotted and fitted to calculate a $K_i^{app}$ value using the Morrison equation:

$$\frac{v_i}{v_0} = 1 - \frac{([E]_T + [I]_T + K_I^{app}) - \sqrt{([E]_T + [I]_T + K_I^{app})^2 - 4[E]_T[I]_T}}{2[E]_T}$$

where $u_i$ is the initial velocity of the reaction in the presence of the inhibitor, $u_0$ is the initial velocity of the reaction in the absence of the inhibitor, $[E]_T$ is the total enzyme concentration, and $[I]_T$ is the total inhibitor concentration. A $K_I$ value is calculated using: $K_I=K_I^{app}/(1+[S]/K_M)$, where [S] is the substrate concentration. All measurements are done in triplicates.

Construction of *E. coli* W3110PA

*P. aeruginosa* lpxC is used to replace *E. coli* chromosomal lpxC. A linear PCR product containing the *P. aeruginosa* ORF with flanking sequences containing 33 bps of DNA complementary to the upstream 5' region of *E. coli* lpxC and 45 bps of DNA complementary to the downstream 3' region of *E. coli* lpxC, is amplified from a plasmid carrying *P. aeruginosa* lpxC using primers pa-LpxC-5' (5'-TCG GTT GGA TAG GTA ATT TGG CGA GAT AAT ACG ATG ATC AAA CAA CGC ACC TTG AAG AAC ATC-3') and pa-LpxC-3' (5'-GTG CCA GAT TTG CCA GTC GAA TTT TAT ACG ACA GTA TAA ATG TCG CTA CAC TGC CGC CGC C-3'). This PCR product is gel purified and then electroporated into *E. coli* DY330 cells, which carry λ-red recombinases, using a Bio-Rad Gene Pulser II set to 2.5 kV, 25 µF, and 400Ω. While DY330 cannot survive on the LB/agar plate supplemented with 15 µg/mL of the compound of disclosure, cells wherein *E. coli* lpxC replaced with *P. aeruginosa* lpxC can survive on this media. Transformants are therefore selected directly using the compound of disclosure without introducing a closely linked resistance cassette for a different antibiotic marker. Genomic DNA from resistant colonies is isolated, and the region around lpxC amplified with primers 300-up-lpxC (5'-ACA AAC GTC CTG AAA TCA CTC TGG TG-3') and 300-down-lpxC (5'-TCC CTA ATA AGA GAT GCG GCC AGA A-3'), and sequenced with primers paLpxC-361-5' (5'-GAG CAG GAA GCT GCC AA-3') and paLpxC-581-3' (5'-GTA CTC GAT GTC GCG CA-3'). One clone in which PalpxC had replaced chromosomal EclpxC is selected and grown at 30° C. This strain is used to generate P1 vir lysate, which is used to transduce chromosomal PalpxC into the chromosome of *E. coli* W3110. Transduced cells are plated on LB/agar containing 15 µg/mL of the compound of disclosure and 10 mM sodium citrate. The resulting colonies are purified 3 times on this media. Genomic DNA from resistant colonies is isolated, and the region around lpxC is amplified with the primers 300-up-lpxC and 300-down-lpxC, and sequenced with paLpxC-361-5' and paLpxC-581-3'. The colony that harbored the *P. aeruginosa* lpxC knock-in is named as W3110PA.

Minimum Inhibitory Concentration (MIC)

MICs are determined according to the NCCLS protocol using 96-well plates. Briefly, diluted bacterial cells ($10^6$ cells/mL) are added into each well of the 96-well plates containing LB medium with 5% DMSO and various concentrations of the compound of disclosure. After incubation of the plates for 22 hours at 37° C., [4,5-dimethylthiazol-2-yl]-2,5-diphenyltetrazolium bromide solution (MTT) is added (final concentration, 0.2 mg/mL) and incubated at 37° C. for another 3 hrs. MIC is determined as the lowest concentration of an antibiotic that prevented color change (yellow to purple).

The antibiotic activities of several exemplary compounds useful in the methods of the disclosure are evaluated by measurements of minimum inhibitory concentrations (MICs) using wild-type *E. coli* (W3110), *P. aeruginosa* (PAO1), and modified *E. coli* strains with the native lpxC gene replaced by that of *R. leguminosarum* (W3110RL) or *P. aeruginosa* (W3110PA).

Compounds disclosed herein have MIC values generally ranging from about 0.01 µg/ml to about 400 µg/ml.

MIC value key for values listed in Table 1:
A: <1 µg/mL
B: 1-10 µg/mL
C: 11-50 µg/mL
D: 51-100 µg/mL
E: >100 µg/mL.

TABLE 1

| Compound | E. coli W3110 | E. coli W3110RL | P. aeruginosa (PAO1) | E. coli W3110PA |
|---|---|---|---|---|
| (structure) | B | E | E | E |
| (structure) | A | E | B | A |
| (structure) | C | E | E | E |
| (structure) | A | E | A | A |
| CPD-007 | B | E | B | B |
| CPD-009 | A | B | A | A |
| CPD-011 | A | B | A | A |

TABLE 1-continued

| Compound | E. coli W3110 | E. coli W3110RL | P. aeruginosa (PAO1) | E. coli W3110PA |
|---|---|---|---|---|
| CPD-012 | A | B | A | A |
| CPD-013 | A | C | B | A |
| CPD-014 | A | E | B | B |
| CPD-015 | A | E | B | D |
| CPD-016 | B | E | E | D |
| CPD-017 | C | E | E | E |
| CPD-018 | B | E | C | D |
| CPD-019 | D | E | E | E |
| CPD-020 | A | B | C | B |
| CPD-021 | B | E | B | C |
| CPD-022 | A | D | B | A |
| CPD-023 | A | C | D | B |
| CPD-024 | A | E | D | C |
| CPD-025 | B | E | D | E |
| CPD-026 | B | E | E | E |
| CPD-027 | A | C | B | B |
| CPD-028 | A | E | E | E |
| CPD-029 | B | E | E | E |
| CPD-030 | C | E | E | E |
| CPD-031 | C | E | E | E |
| CPD-032 | C | D | C | C |
| CPD-033 | B | E | C | B |
| CPD-034 | C | D | C | D |
| CPD-035 | A | C | A | B |
| CPD-036 | B | E | A | B |
| CPD-037 | A | B | A | A |
| CPD-038 | A | D | A | B |
| CPD-039 | B | E | D | D |
| CPD-040 | A | B | A | A |
| CPD-041 | A | C | B | B |
| CPD-042 | B | D | D | D |
| CPD-043 | A | D | D | D |
| CPD-044 | A | D | D | D |
| CPD-045 | B | D | D | D |
| CPD-046 | B | D | D | D |
| CPD-047 | B | D | D | D |
| CPD-048 | B | D | D | D |
| CPD-049 | B | D | C | D |
| CPD-050 | A | C | B | A |
| CPD-051 | A | D | A | A |
| CPD-052 | A | D | B | B |
| CPD-053 | A | D | A | A |
| CPD-054 | B | D | C | C |
| CPD-055 | B | D | C | C |
| CPD-056 | A | B | A | A |
| CPD-057 | A | D | A | A |
| CPD-058 | A | A | A | A |
| CPD-059 | B | D | C | C |
| CPD-060 | B | D | C | C |
| CPD-061 | A | D | B | B |
| CPD-062 | A | D | B | A |
| CPD-069 | A | | B | |
| CPD-071 | B | | D | |
| CPD-072 | A | | A | |
| CPD-079 | A | | A | |
| CPD-080 | A | | A | |

The antibiotic activities of several exemplary compounds useful in the methods of the disclosure are evaluated by measurements of minimum inhibitory concentrations (MICs) using two N. gonorrhoeae strains: FA19 (a drug-sensitive strain) and 35/02 (drug-resistant strain.) FA19 is an isolate from uncomplicated infection and was lyophilized in 1962. 35/02 displays intermediate-level resistance to extended spectrum cephalosporins such as ceftriaxone (MIC=0.12 µg/ml) and cefixime (MIC=0.28 µg/ml) and high-level resistance to penicillin (MIC=6 µg/ml). The strain is being sequenced to elucidate the mechanisms involved in high-level chromosomally mediated resistance.

Compounds disclosed herein have MIC values generally ranging from about 0.01 µg/ml to about 10 µg/ml.

MIC value key for values listed in Table 2:

A: <0.1 µg/mL
B: 0.1-1 µg/mL
C: 2-4 µg/mL
D: 5-7 µg/mL
E: 8 µg/mL

TABLE 2

| Compound | N. gonorrhoeae FA 19 | 35/02 |
|---|---|---|
| [Structure shown] | E | E |
| CPD-011 | C | D |
| CPD-013 | B | C |
| CPD-040 | C | D |
| CPD-065 | B | C |
| CPD-066 | B | C |
| CPD-067 | A | B |

Disk Diffusion Assay

An assay was performed on two strains of *Acinetobacter Baumannii*: antibiotic susceptible strain (Sus. A.b. Isolate), and multidrug-resistant strains (MDR A.b. Isolate). 2 μg of compound is added per disc, which is 6 mm in diameter. Activity is measured as the diameter (in mm) of the growth inhibition. The results are summarized in Table 3, where A is no detectable inhibition, B is 6-10 mm, C is 11-15 mm, D is ≥16.

TABLE 3

| Compound | Sus. A.b. Isolate | MDR A.b. Isolate |
|---|---|---|
| CPD-011 | A | A |
| CPD-012 | A | A |
| CPD-013 | A | A |
| CPD-037 | C | B |
| CPD-040 | B | B |
| CPD-051 | A | A |
| CPD-058 | C | C |
| CPD-067 | B | B |
| Ciprofloxacin | D | A |
| Carbenicillin | A | A |
| Chloramphenicol | B | A |
| Imipenem | D | A |
| Ceftriaxone | A | A |
| Tetracycline | B | A |
| Polymyxin B | B | B |

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A method of treating a Gram-negative bacterial infection in a subject in need of such treatment, the method comprising administering to the subject an effective amount of a compound of the formula:

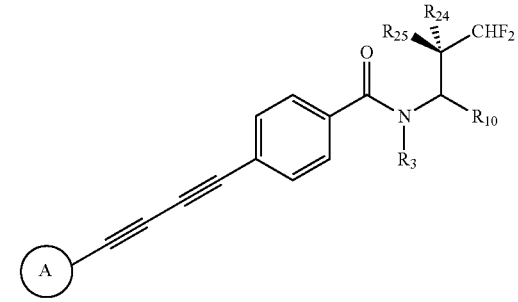

or a pharmaceutically acceptable salt thereof, wherein
$R_{24}$ is selected from the group consisting of —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), hydroxy($C_1$-$C_6$ alkyl), alkoxy($C_1$-$C_6$ alkyl), amino($C_1$-$C_6$ alkyl), —NHCO($C_1$-$C_6$ alkyl), —NHCONH$_2$, —NHCONH($C_1$-$C_6$ alkyl), —OCO($C_1$-$C_6$ alkyl); and
$R_{25}$ is $C_1$-$C_6$ alkyl;
$R_{10}$ is —CONH$_2$, —CON($C_1$-$C_6$ alkyl), —CON($C_1$-$C_6$ alkyl)$_2$, —CONH—OH, —CONH—NH$_2$, —CO$_2$H, or —CO$_2$($C_1$-$C_6$ alkyl);
$R_3$ is hydrogen or $C_1$-$C_6$ alkyl;
A is phenyl optionally substituted with $R_8$, or monocyclic heteroaryl having 5-6 members and optionally substituted with $R_8$; and
each $R_8$ is independently selected from the group consisting of halogen, —NO$_2$, —CN, $C_1$-$C_6$ alkyl, $C_1$-$C_6$ haloalkyl, —NH$_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —SH, —S($C_1$-$C_6$ alkyl), oxo, hydroxy ($C_1$-$C_6$ alkyl), alkoxy($C_1$-$C_6$ alkyl), amino($C_1$-$C_6$ alkyl), —CH$_2$—NH($C_1$-$C_6$ alkyl), —CH$_2$—N($C_1$-$C_6$ alkyl)$_2$, —CONH$_2$, —CON($C_1$-$C_6$ alkyl), —CON($C_1$-$C_6$ alkyl)$_2$, —CONH—OH, —CONH—NH$_2$, —COH, —CO$_2$H, —CO$_2$($C_1$-$C_6$ alkyl), —OCO($C_1$-$C_6$ alkyl), —NHCO($C_1$-$C_6$ alkoxy), —NHCO($C_1$-$C_6$ alkyl), —NHCONH$_2$, —NHCONH($C_1$-$C_6$ alkyl), —NHC(=NH)NH$_2$, —NH—S(O)$_{0-2}$—($C_1$-$C_6$ alkyl), —NH—S(O)$_{0-2}$-aryl, heterocyclyl($C_1$-$C_6$ alkyl), —CH$_2$—NHCONH$_2$, —CH$_2$—NHCONH (C$_1$-C$_6$ alkyl), and —CH$_2$—OCO(C$_1$-C$_6$ alkyl).

2. A method according to claim 1, wherein A is phenyl optionally substituted with R$_8$, where R$_8$ is selected from the group consisting of halogen, —NO$_2$, —NH$_2$, —NH(C$_1$-C$_6$ alkyl), —N(C$_1$-C$_6$ alkyl)$_2$, —OH, C$_1$-C$_6$ alkoxy, and C$_1$-C$_6$ haloalkoxy.

3. A method according to claim 1, wherein
R$_{24}$ is selected from the group consisting of —OH, —NH$_2$, C$_1$-C$_6$ alkoxy, and amino(C$_1$-C$_6$ alkyl);
R$_{10}$ is —CONH$_2$, —CON(C$_1$-C$_6$ alkyl), —CON(C$_1$-C$_6$ alkyl)$_2$, —CONH—OH, or —CONH—NH$_2$; and
R$_8$ is selected from the group consisting of is halogen, —NO$_2$, —ON, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, C$_1$-C$_6$ haloalkoxy, hydroxy(C$_1$-C$_6$ alkyl), alkoxy(C$_1$-C$_6$ alkyl), amino(C$_1$-C$_6$ alkyl), —CH$_2$—NH(C$_1$-C$_6$ alkyl), —CH$_2$—N(C$_1$-C$_6$ alkyl)$_2$, —CONH$_2$, —CON(C$_1$-C$_6$ alkyl), —CON(C$_1$-C$_6$ alkyl)$_2$, —COH, —CO$_2$H, —NHCO(C$_1$-C$_6$ alkoxy), —NHCO(C$_1$-C$_6$ alkyl), —NHCONH$_2$, —NHCONH(C$_1$-C$_6$ alkyl), —NH—S(O)$_{0-2}$—(C$_1$-C$_6$ alkyl), heterocyclyl(C$_1$-C$_6$ alkyl), —CH$_2$—NHCONH$_2$, —CH$_2$—NHCONH(C$_1$-C$_6$ alkyl), and —CH$_2$—OCO(C$_1$-C$_6$ alkyl).

4. A method according to claim 1, wherein R$_8$ is selected from the group consisting of halogen, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, hydroxy(C$_1$-C$_6$ alkyl), amino(C$_1$-C$_6$ alkyl), —CH$_2$—NH(C$_1$-C$_6$ alkyl), —CH$_2$—N(C$_1$-C$_6$ alkyl)$_2$, —CONH$_2$, —CON(C$_1$-C$_6$ alkyl), —CON(C$_1$-C$_6$ alkyl)$_2$, —COH, —CO$_2$H, —NHCO(C$_1$-C$_6$ alkyl), —NHCONH$_2$, —NHCONH(C$_1$-C$_6$ alkyl), —NH—S(O)$_{0-2}$—(C$_1$-C$_6$ alkyl), heteroaryl(C$_1$-C$_6$ alkyl), heterocyclyl(C$_1$-C$_6$ alkyl), —CH$_2$—NHCONH$_2$, and —CH$_2$—NHCONH(C$_1$-C$_6$ alkyl).

5. A method according to claim 4, wherein R$_8$ is selected from the group consisting of is halogen, —CN, C$_1$-C$_6$ alkyl, C$_1$-C$_6$ haloalkyl, —NH$_2$, —NH(C$_1$-C$_6$ alkyl), —N(C$_1$-C$_6$ alkyl)$_2$, —OH, C$_1$-C$_6$ alkoxy, —CONH$_2$, —COH, —CO$_2$H, —NHCO(C$_1$-C$_6$ alkyl), —NHCONH$_2$, —NHCONH(C$_1$-C$_6$ alkyl), and —NH—S(O)$_{0-2}$—(C$_1$-C$_6$ alkyl).

6. A method according to claim 2, wherein
R$_{24}$ is selected from the group consisting of —NH$_2$, —NH(C$_1$-C$_6$ alkyl), —OH, C$_1$-C$_6$ alkoxy, —SH, —S(C$_1$-C$_6$ alkyl), hydroxy(C$_1$-C$_6$ alkyl), amino(C$_1$-C$_6$ alkyl), —NHCONH$_2$, and —NHCONH(C$_1$-C$_6$ alkyl);
R$_{25}$ is C$_1$-C$_3$ alkyl; and
R$_{10}$ is —CONH$_2$, —CON(C$_1$-C$_6$ alkyl), —CON(C$_1$-C$_6$ alkyl)$_2$, —CONH—OH, —CONH—NH$_2$, —CO$_2$H, or —CO$_2$(C$_1$-C$_6$ alkyl).

7. A method according to claim 6, wherein R$_{25}$ is methyl.

8. A method according to claim 6, wherein R$_{10}$ is —CONH—OH, —CONH—NH$_2$, or —CO$_2$H.

9. A method according to claim 8, wherein R$_{10}$ is —CONH—OH.

10. A method according to claim 6, wherein R$_3$ is hydrogen and R$_{24}$ is —OH or —NH$_2$.

11. A method according to claim 1, which is:
N-(3-acetamido-4,4-difluoro-1-(hydroxyamino)-3-methyl-1-oxobutan-2-yl)-4-((4-acetamidophenyl)buta-1,3-diynyl)benzamide;
4-((4-aminophenyl)buta-1,3-diynyl)-N-(4,4-difluoro-3-hydroxy-1-(hydroxyamino)-3-methyl-1-oxobutan-2-yl)benzamide;
4-((2-aminophenyl)buta-1,3-diynyl)-N-(4,4-difluoro-3-hydroxy-1-(hydroxyamino)-3-methyl-1-oxobutan-2-yl)benzamide;
N-(3-amino-4,4-difluoro-1-(hydroxyamino)-3-methyl-1-oxobutan-2-yl)-4-((4-aminophenyl)buta-1,3-diynyl)benzamide;
N-(3-amino-4,4-difluoro-1-(hydroxyamino)-3-methyl-1-oxobutan-2-yl)-4-((2-aminophenyl)buta-1,3-diynyl)benzamide;
N-(4,4-difluoro-3-hydroxy-1-(hydroxyamino)-3-methyl-1-oxobutan-2-yl)-4-((4-fluorophenyl)buta-1,3-diynyl)benzamide;
N-(4,4-difluoro-1-(hydroxyamino)-3-methoxy-3-methyl-1-oxobutan-2-yl)-4-((4-fluorophenyl)buta-1,3-diynyl)benzamide;
N-(3-amino-4,4-difluoro-1-(hydroxyamino)-3-methyl-1-oxobutan-2-yl)-4-((4-fluorophenyl)buta-1,3-diynyl)benzamide;
N-(3-acetamido-4,4-difluoro-1-(hydroxyamino)-3-methyl-1-oxobutan-2-yl)-4-((4-fluorophenyl)buta-1,3-diynyl)benzamide;
N-(4,4-difluoro-1-(hydroxyamino)-3-methyl-3-(3-methylureido)-1-oxobutan-2-yl)-4-((4-fluorophenyl)buta-1,3-diynyl)benzamide;
4-((4-chlorophenyl)buta-1,3-diynyl)-N-(4,4-difluoro-3-hydroxy-1-(hydroxyamino)-3-methyl-1-oxobutan-2-yl)benzamide;
4-((4-chlorophenyl)buta-1,3-diynyl)-N-(4,4-difluoro-1-(hydroxyamino)-3-methoxy-3-methyl-1-oxobutan-2-yl)benzamide;
N-(3-amino-4,4-difluoro-1-(hydroxyamino)-3-methyl-1-oxobutan-2-yl)-4-((4-chlorophenyl)buta-1,3-diynyl)benzamide;
N-(3-acetamido-4,4-difluoro-1-(hydroxyamino)-3-methyl-1-oxobutan-2-yl)-4-((4-chlorophenyl)buta-1,3-diynyl)benzamide;
4-((4-chlorophenyl)buta-1,3-diynyl)-N-(4,4-difluoro-1-(hydroxyamino)-3-methyl-3-(3-methylureido)-1-oxobutan-2-yl)benzamide;
N-(4,4-difluoro-3-hydroxy-1-(hydroxyamino)-3-methyl-1-oxobutan-2-yl)-4-((4-(trifluoromethyl)phenyl)buta-1,3-diynyl)benzamide;
N-(4,4-difluoro-1-(hydroxyamino)-3-methoxy-3-methyl-1-oxobutan-2-yl)-4-((4-(trifluoromethyl)phenyl)buta-1,3-diynyl)benzamide;
N-(3-amino-4,4-difluoro-1-(hydroxyamino)-3-methyl-1-oxobutan-2-yl)-4-((4-(trifluoromethyl)phenyl)buta-1,3-diynyl)benzamide;
N-(3-acetamido-4,4-difluoro-1-(hydroxyamino)-3-methyl-1-oxobutan-2-yl)-4-((4-(trifluoromethyl)phenyl)buta-1,3-diynyl)benzamide;
N-(4,4-difluoro-1-(hydroxyamino)-3-methyl-3-(3-methylureido)-1-oxobutan-2-yl)-4-((4-(trifluoromethyl)phenyl)buta-1,3-diynyl)benzamide;
N-(4,4-difluoro-3-hydroxy-1-(hydroxyamino)-3-methyl-1-oxobutan-2-yl)-4-((4-hydroxyphenyl)buta-1,3-diynyl)benzamide;
N-(4,4-difluoro-1-(hydroxyamino)-3-methoxy-3-methyl-1-oxobutan-2-yl)-4-((4-hydroxyphenyl)buta-1,3-diynyl)benzamide;
N-(3-amino-4,4-difluoro-1-(hydroxyamino)-3-methyl-1-oxobutan-2-yl)-4-((4-hydroxyphenyl)buta-1,3-diynyl)benzamide;
N-(3-acetamido-4,4-difluoro-1-(hydroxyamino)-3-methyl-1-oxobutan-2-yl)-4-((4-hydroxyphenyl)buta-1,3-diynyl)benzamide;
N-(4,4-difluoro-1-(hydroxyamino)-3-methyl-3-(3-methylureido)-1-oxobutan-2-yl)-4-((4-hydroxyphenyl)buta-1,3-diynyl)benzamide;

N-(4,4-difluoro-3-hydroxy-1-(hydroxyamino)-3-methyl-1-oxobutan-2-yl)-4-((4-methoxyphenyl)buta-1,3-diynyl)benzamide;
N-(4,4-difluoro-1-(hydroxyamino)-3-methoxy-3-methyl-1-oxobutan-2-yl)-4-((4-methoxyphenyl)buta-1,3-diynyl)benzamide;
N-(3-amino-4,4-difluoro-1-(hydroxyamino)-3-methyl-1-oxobutan-2-yl)-4-((4-methoxyphenyl)buta-1,3-diynyl)benzamide;
N-(3-acetamido-4,4-difluoro-1-(hydroxyamino)-3-methyl-1-oxobutan-2-yl)-4-((4-methoxyphenyl)buta-1,3-diynyl)benzamide;
N-(4,4-difluoro-1-(hydroxyamino)-3-methyl-3-(3-methylureido)-1-oxobutan-2-yl)-4-((4-methoxyphenyl)buta-1,3-diynyl)benzamide;
N-(4,4-difluoro-3-hydroxy-1-(hydroxyamino)-3-methyl-1-oxobutan-2-yl)-4-((4-(dimethylamino)phenyl)buta-1,3-diynyl)benzamide;
N-(4,4-difluoro-1-(hydroxyamino)-3-methoxy-3-methyl-1-oxobutan-2-yl)-4-((4-(dimethylamino)phenyl)buta-1,3-diynyl)benzamide;
N-(3-amino-4,4-difluoro-1-(hydroxyamino)-3-methyl-1-oxobutan-2-yl)-4-((4-(dimethylamino)phenyl)buta-1,3-diynyl)benzamide;
N-(3-acetamido-4,4-difluoro-1-(hydroxyamino)-3-methyl-1-oxobutan-2-yl)-4-((4-(dimethylamino)phenyl)buta-1,3-diynyl)benzamide;
N-(4,4-difluoro-1-(hydroxyamino)-3-methyl-3-(3-methylureido)-1-oxobutan-2-yl)-4-((4-(dimethylamino)phenyl)buta-1,3-diynyl)benzamide;
N-(4,4-difluoro-3-hydroxy-1-(hydroxyamino)-3-methyl-1-oxobutan-2-yl)-4-((4-(3-methylureido)phenyl)buta-1,3-diynyl)benzamide;
N-(4,4-difluoro-1-(hydroxyamino)-3-methoxy-3-methyl-1-oxobutan-2-yl)-4-((4-(3-methylureido)phenyl)buta-1,3-diynyl)benzamide;
N-(3-amino-4,4-difluoro-1-(hydroxyamino)-3-methyl-1-oxobutan-2-yl)-4-((4-(3-methylureido)phenyl)buta-1,3-diynyl)benzamide;
N-(3-acetamido-4,4-difluoro-1-(hydroxyamino)-3-methyl-1-oxobutan-2-yl)-4-((4-(3-methylureido)phenyl)buta-1,3-diynyl)benzamide;
N-(4,4-difluoro-1-(hydroxyamino)-3-methyl-3-(3-methylureido)-1-oxobutan-2-yl)-4-((4-(3-methylureido)phenyl)buta-1,3-diynyl)benzamide;
N-(4,4-difluoro-3-hydroxy-1-(hydroxyamino)-3-methyl-1-oxobutan-2-yl)-4-((4-ureidophenyl)buta-1,3-diynyl)benzamide;
N-(4,4-difluoro-1-(hydroxyamino)-3-methoxy-3-methyl-1-oxobutan-2-yl)-4-((4-ureidophenyl)buta-1,3-diynyl)benzamide;
N-(3-amino-4,4-difluoro-1-(hydroxyamino)-3-methyl-1-oxobutan-2-yl)-4-((4-ureidophenyl)buta-1,3-diynyl)benzamide;
N-(3-acetamido-4,4-difluoro-1-(hydroxyamino)-3-methyl-1-oxobutan-2-yl)-4-((4-ureidophenyl)buta-1,3-diynyl)benzamide;
N-(4,4-difluoro-1-(hydroxyamino)-3-methyl-3-(3-methylureido)-1-oxobutan-2-yl)-4-((4-ureidophenyl)buta-1,3-diynyl)benzamide;
4-((4-acetamidophenyl)buta-1,3-diynyl)-N-(4,4-difluoro-3-hydroxy-1-(hydroxyamino)-3-methyl-1-oxobutan-2-yl)benzamide;
4-((4-acetamidophenyl)buta-1,3-diynyl)-N-(4,4-difluoro-1-(hydroxyamino)-3-methoxy-3-methyl-1-oxobutan-2-yl)benzamide;
4-((4-acetamidophenyl)buta-1,3-diynyl)-N-(3-amino-4,4-difluoro-1-(hydroxyamino)-3-methyl-1-oxobutan-2-yl)benzamide;
N-(3-acetamido-4,4-difluoro-1-(hydroxyamino)-3-methyl-1-oxobutan-2-yl)-4-((4-acetamidophenyl)buta-1,3-diynyl)benzamide;
4-((4-acetamidophenyl)buta-1,3-diynyl)-N-(4,4-difluoro-1-(hydroxyamino)-3-methyl-3-(3-methylureido)-1-oxobutan-2-yl)benzamide;
N-(4,4-difluoro-3-hydroxy-1-(hydroxyamino)-3-methyl-1-oxobutan-2-yl)-4-((4-(methylsulfonamido)phenyl)buta-1,3-diynyl)benzamide;
N-(4,4-difluoro-1-(hydroxyamino)-3-methoxy-3-methyl-1-oxobutan-2-yl)-4-((4-(methylsulfonamido)phenyl)buta-1,3-diynyl)benzamide;
N-(3-amino-4,4-difluoro-1-(hydroxyamino)-3-methyl-1-oxobutan-2-yl)-4-((4-(methylsulfonamido)phenyl)buta-1,3-diynyl)benzamide;
N-(3-acetamido-4,4-difluoro-1-(hydroxyamino)-3-methyl-1-oxobutan-2-yl)-4-((4-(methylsulfonamido)phenyl)buta-1,3-diynyl)benzamide;
N-(4,4-difluoro-1-(hydroxyamino)-3-methyl-3-(3-methylureido)-1-oxobutan-2-yl)-4-((4-(methylsulfonamido)phenyl)buta-1,3-diynyl)benzamide;
N-(4,4-difluoro-3-hydroxy-1-(hydroxyamino)-3-methyl-1-oxobutan-2-yl)-4-((4-(hydroxymethyl)phenyl)buta-1,3-diynyl)benzamide;
N-(4,4-difluoro-1-(hydroxyamino)-3-methoxy-3-methyl-1-oxobutan-2-yl)-4-((4-(hydroxymethyl)phenyl)buta-1,3-diynyl)benzamide;
N-(3-amino-4,4-difluoro-1-(hydroxyamino)-3-methyl-1-oxobutan-2-yl)-4-((4-(hydroxymethyl)phenyl)buta-1,3-diynyl)benzamide;
N-(3-acetamido-4,4-difluoro-1-(hydroxyamino)-3-methyl-1-oxobutan-2-yl)-4-((4-(hydroxymethyl)phenyl)buta-1,3-diynyl)benzamide;
N-(4,4-difluoro-1-(hydroxyamino)-3-methyl-3-(3-methylureido)-1-oxobutan-2-yl)-4-((4-(hydroxymethyl)phenyl)buta-1,3-diynyl)benzamide;
4-((4-(4,4-difluoro-3-hydroxy-1-(hydroxyamino)-3-methyl-1-oxobutan-2-ylcarbamoyl)phenyl)buta-1,3-diynyl)benzoic acid;
4-((4-(4,4-difluoro-1-(hydroxyamino)-3-methoxy-3-methyl-1-oxobutan-2-ylcarbamoyl)phenyl)buta-1,3-diynyl)benzoic acid;
4-((4-(3-amino-4,4-difluoro-1-(hydroxyamino)-3-methyl-1-oxobutan-2-ylcarbamoyl)phenyl)buta-1,3-diynyl)benzoic acid;
4-((4-(3-acetamido-4,4-difluoro-1-(hydroxyamino)-3-methyl-1-oxobutan-2-ylcarbamoyl)phenyl)buta-1,3-diynyl)benzoic acid;
4-((4-(4,4-difluoro-1-(hydroxyamino)-3-methyl-3-(3-methylureido)-1-oxobutan-2-ylcarbamoyl)phenyl)buta-1,3-diynyl)benzoic acid;
N-(4,4-difluoro-3-hydroxy-1-(hydroxyamino)-3-methyl-1-oxobutan-2-yl)-4-((4-formylphenyl)buta-1,3-diynyl)benzamide;
N-(4,4-difluoro-1-(hydroxyamino)-3-methoxy-3-methyl-1-oxobutan-2-yl)-4-((4-formylphenyl)buta-1,3-diynyl)benzamide;
N-(3-amino-4,4-difluoro-1-(hydroxyamino)-3-methyl-1-oxobutan-2-yl)-4-((4-formylphenyl)buta-1,3-diynyl)benzamide;
N-(3-acetamido-4,4-difluoro-1-(hydroxyamino)-3-methyl-1-oxobutan-2-yl)-4-((4-formylphenyl)buta-1,3-diynyl)benzamide;

N-(4,4-difluoro-1-(hydroxyamino)-3-methyl-3-(3-methylureido)-1-oxobutan-2-yl)-4-((4-formylphenyl)buta-1,3-diynyl)benzamide;

4-((4-carbamoylphenyl)buta-1,3-diynyl)-N-(4,4-difluoro-3-hydroxy-1-(hydroxyamino)-3-methyl-1-oxobutan-2-yl)benzamide;

4-((4-carbamoylphenyl)buta-1,3-diynyl)-N-(4,4-difluoro-1-(hydroxyamino)-3-methoxy-3-methyl-1-oxobutan-2-yl)benzamide;

N-(3-amino-4,4-difluoro-1-(hydroxyamino)-3-methyl-1-oxobutan-2-yl)-4-((4-carbamoylphenyl)buta-1,3-diynyl)benzamide;

N-(3-acetamido-4,4-difluoro-1-(hydroxyamino)-3-methyl-1-oxobutan-2-yl)-4-((4-carbamoylphenyl)buta-1,3-diynyl)benzamide;

4-((4-carbamoylphenyl)buta-1,3-diynyl)-N-(4,4-difluoro-1-(hydroxyamino)-3-methyl-3-(3-methylureido)-1-oxobutan-2-yl)benzamide;

4-((4-(aminomethyl)phenyl)buta-1,3-diynyl)-N-(4,4-difluoro-3-hydroxy-1-(hydroxyamino)-3-methyl-1-oxobutan-2-yl)benzamide;

4-((4-(aminomethyl)phenyl)buta-1,3-diynyl)-N-(4,4-difluoro-1-(hydroxyamino)-3-methoxy-3-methyl-1-oxobutan-2-yl)benzamide;

N-(3-amino-4,4-difluoro-1-(hydroxyamino)-3-methyl-1-oxobutan-2-yl)-4-((4-(aminomethyl)phenyl)buta-1,3-diynyl)benzamide;

N-(3-acetamido-4,4-difluoro-1-(hydroxyamino)-3-methyl-1-oxobutan-2-yl)-4-((4-(aminomethyl)phenyl)buta-1,3-diynyl)benzamide;

4-((4-(aminomethyl)phenyl)buta-1,3-diynyl)-N-(4,4-difluoro-1-(hydroxyamino)-3-methyl-3-(3-methylureido)-1-oxobutan-2-yl)benzamide;

4-((4-cyanophenyl)buta-1,3-diynyl)-N-(4,4-difluoro-3-hydroxy-1-(hydroxyamino)-3-methyl-1-oxobutan-2-yl)benzamide;

4-((4-cyanophenyl)buta-1,3-diynyl)-N-(4,4-difluoro-1-(hydroxyamino)-3-methoxy-3-methyl-1-oxobutan-2-yl)benzamide;

N-(3-amino-4,4-difluoro-1-(hydroxyamino)-3-methyl-1-oxobutan-2-yl)-4-((4-cyanophenyl)buta-1,3-diynyl)benzamide;

N-(3-acetamido-4,4-difluoro-1-(hydroxyamino)-3-methyl-1-oxobutan-2-yl)-4-((4-cyanophenyl)buta-1,3-diynyl)benzamide;

4-((4-cyanophenyl)buta-1,3-diynyl)-N-(4,4-difluoro-1-(hydroxyamino)-3-methyl-3-(3-methylureido)-1-oxobutan-2-yl)benzamide;

N-(4,4-difluoro-3-hydroxy-1-(hydroxyamino)-3-methyl-1-oxobutan-2-yl)-4-((4-((dimethylamino)methyl)phenyl)buta-1,3-diynyl)benzamide;

N-(4,4-difluoro-1-(hydroxyamino)-3-methoxy-3-methyl-1-oxobutan-2-yl)-4-((4-((dimethylamino)methyl)phenyl)buta-1,3-diynyl)benzamide;

N-(3-amino-4,4-difluoro-1-(hydroxyamino)-3-methyl-1-oxobutan-2-yl)-4-((4-((dimethylamino)methyl)phenyl)buta-1,3-diynyl)benzamide;

N-(3-acetamido-4,4-difluoro-1-(hydroxyamino)-3-methyl-1-oxobutan-2-yl)-4-((4-((dimethylamino)methyl)phenyl)buta-1,3-diynyl)benzamide;

N-(4,4-difluoro-1-(hydroxyamino)-3-methyl-3-(3-methylureido)-1-oxobutan-2-yl)-4-((4-((dimethylamino)methyl)phenyl)buta-1,3-diynyl)benzamide;

N-(4,4-difluoro-3-hydroxy-1-(hydroxyamino)-3-methyl-1-oxobutan-2-yl)-4-((4-(ureidomethyl)phenyl)buta-1,3-diynyl)benzamide;

N-(4,4-difluoro-1-(hydroxyamino)-3-methoxy-3-methyl-1-oxobutan-2-yl)-4-((4-(ureidomethyl)phenyl)buta-1,3-diynyl)benzamide;

N-(3-amino-4,4-difluoro-1-(hydroxyamino)-3-methyl-1-oxobutan-2-yl)-4-((4-(ureidomethyl)phenyl)buta-1,3-diynyl)benzamide;

N-(3-acetamido-4,4-difluoro-1-(hydroxyamino)-3-methyl-1-oxobutan-2-yl)-4-((4-(ureidomethyl)phenyl)buta-1,3-diynyl)benzamide;

N-(4,4-difluoro-1-(hydroxyamino)-3-methyl-3-(3-methylureido)-1-oxobutan-2-yl)-4-((4-(ureidomethyl)phenyl)buta-1,3-diynyl)benzamide;

N-(4,4-difluoro-3-hydroxy-1-(hydroxyamino)-3-methyl-1-oxobutan-2-yl)-4-((4-(morpholinomethyl)phenyl)buta-1,3-diynyl)benzamide;

N-(4,4-difluoro-1-(hydroxyamino)-3-methoxy-3-methyl-1-oxobutan-2-yl)-4-((4-(morpholinomethyl)phenyl)buta-1,3-diynyl)benzamide;

N-(3-amino-4,4-difluoro-1-(hydroxyamino)-3-methyl-1-oxobutan-2-yl)-4-((4-(morpholinomethyl)phenyl)buta-1,3-diynyl)benzamide;

N-(3-acetamido-4,4-difluoro-1-(hydroxyamino)-3-methyl-1-oxobutan-2-yl)-4-((4-(morpholinomethyl)phenyl)buta-1,3-diynyl)benzamide;

N-(4,4-difluoro-1-(hydroxyamino)-3-methyl-3-(3-methylureido)-1-oxobutan-2-yl)-4-((4-(morpholinomethyl)phenyl)buta-1,3-diynyl)benzamide;

N-(4,4-difluoro-3-hydroxy-1-(hydroxyamino)-3-methyl-1-oxobutan-2-yl)-4-((4-(pyrrolidin-1-ylmethyl)phenyl)buta-1,3-diynyl)benzamide;

N-(4,4-difluoro-1-(hydroxyamino)-3-methoxy-3-methyl-1-oxobutan-2-yl)-4-((4-(pyrrolidin-1-ylmethyl)phenyl)buta-1,3-diynyl)benzamide;

N-(3-amino-4,4-difluoro-1-(hydroxyamino)-3-methyl-1-oxobutan-2-yl)-4-((4-(pyrrolidin-1-ylmethyl)phenyl)buta-1,3-diynyl)benzamide;

N-(3-acetamido-4,4-difluoro-1-(hydroxyamino)-3-methyl-1-oxobutan-2-yl)-4-((4-(pyrrolidin-1-ylmethyl)phenyl)buta-1,3-diynyl)benzamide;

N-(4,4-difluoro-1-(hydroxyamino)-3-methyl-3-(3-methylureido)-1-oxobutan-2-yl)-4-((4-(pyrrolidin-1-ylmethyl)phenyl)buta-1,3-diynyl)benzamide;

4-((4-((1H-imidazol-1-yl)methyl)phenyl)buta-1,3-diynyl)-N-(4,4-difluoro-3-hydroxy-1-(hydroxyamino)-3-methyl-1-oxobutan-2-yl)benzamide;

4-((4-((1H-imidazol-1-yl)methyl)phenyl)buta-1,3-diynyl)-N-(4,4-difluoro-1-(hydroxyamino)-3-methoxy-3-methyl-1-oxobutan-2-yl)benzamide;

4-((4-((1H-imidazol-1-yl)methyl)phenyl)buta-1,3-diynyl)-N-(3-amino-4,4-difluoro-1-(hydroxyamino)-3-methyl-1-oxobutan-2-yl)benzamide;

4-((4-((1H-imidazol-1-yl)methyl)phenyl)buta-1,3-diynyl)-N-(3-acetamido-4,4-difluoro-1-(hydroxyamino)-3-methyl-1-oxobutan-2-yl)benzamide;

4-((4-((1H-imidazol-1-yl)methyl)phenyl)buta-1,3-diynyl)-N-(4,4-difluoro-1-(hydroxyamino)-3-methyl-3-(3-methylureido)-1-oxobutan-2-yl)benzamide;

N-(4,4-difluoro-3-hydroxy-1-(hydroxyamino)-3-methyl-1-oxobutan-2-yl)-4-(thiophen-2-ylbuta-1,3-diynyl)benzamide;

N-(4,4-difluoro-1-(hydroxyamino)-3-methoxy-3-methyl-1-oxobutan-2-yl)-4-(thiophen-2-ylbuta-1,3-diynyl)benzamide;

N-(3-amino-4,4-difluoro-1-(hydroxyamino)-3-methyl-1-oxobutan-2-yl)-4-(thiophen-2-ylbuta-1,3-diynyl)benzamide;

N-(3-acetamido-4,4-difluoro-1-(hydroxyamino)-3-methyl-1-oxobutan-2-yl)-4-(thiophen-2-ylbuta-1,3-diynyl)benzamide;
N-(4,4-difluoro-1-(hydroxyamino)-3-methyl-3-(3-methylureido)-1-oxobutan-2-yl)-4-(thiophen-2-ylbuta-1,3-diynyl)benzamide;
4-((5-aminothiophen-2-yl)buta-1,3-diynyl)-N-(4,4-difluoro-3-hydroxy-1-(hydroxyamino)-3-methyl-1-oxobutan-2-yl)benzamide;
4-((5-aminothiophen-2-yl)buta-1,3-diynyl)-N-(4,4-difluoro-1-(hydroxyamino)-3-methoxy-3-methyl-1-oxobutan-2-yl)benzamide;
N-(3-amino-4,4-difluoro-1-(hydroxyamino)-3-methyl-1-oxobutan-2-yl)-4-((5-aminothiophen-2-yl)buta-1,3-diynyl)benzamide;
N-(3-acetamido-4,4-difluoro-1-(hydroxyamino)-3-methyl-1-oxobutan-2-yl)-4-((5-aminothiophen-2-yl)buta-1,3-diynyl)benzamide;
4-((5-aminothiophen-2-yl)buta-1,3-diynyl)-N-(4,4-difluoro-1-(hydroxyamino)-3-methyl-3-(3-methylureido)-1-oxobutan-2-yl)benzamide;
N-(4,4-difluoro-3-hydroxy-1-(hydroxyamino)-3-methyl-1-oxobutan-2-yl)-4-((1-methyl-1H-imidazol-4-yl)buta-1,3-diynyl)benzamide;
N-(4,4-difluoro-1-(hydroxyamino)-3-methoxy-3-methyl-1-oxobutan-2-yl)-4-((1-methyl-1H-imidazol-4-yl)buta-1,3-diynyl)benzamide;
N-(3-amino-4,4-difluoro-1-(hydroxyamino)-3-methyl-1-oxobutan-2-yl)-4-((1-methyl-1H-imidazol-4-yl)buta-1,3-diynyl)benzamide;
N-(3-acetamido-4,4-difluoro-1-(hydroxyamino)-3-methyl-1-oxobutan-2-yl)-4-((1-methyl-1H-imidazol-4-yl)buta-1,3-diynyl)benzamide;
N-(4,4-difluoro-1-(hydroxyamino)-3-methyl-3-(3-methylureido)-1-oxobutan-2-yl)-4-((1-methyl-1H-imidazol-4-yl)buta-1,3-diynyl)benzamide;
4-((1H-imidazol-4-yl)buta-1,3-diynyl)-N-(4,4-difluoro-3-hydroxy-1-(hydroxyamino)-3-methyl-1-oxobutan-2-yl)benzamide;
4-((1H-imidazol-4-yl)buta-1,3-diynyl)-N-(4,4-difluoro-1-(hydroxyamino)-3-methoxy-3-methyl-1-oxobutan-2-yl)benzamide;
4-((1H-imidazol-4-yl)buta-1,3-diynyl)-N-(3-amino-4,4-difluoro-1-(hydroxyamino)-3-methyl-1-oxobutan-2-yl)benzamide;
4-((1H-imidazol-4-yl)buta-1,3-diynyl)-N-(3-acetamido-4,4-difluoro-1-(hydroxyamino)-3-methyl-1-oxobutan-2-yl)benzamide;
4-((1H-imidazol-4-yl)buta-1,3-diynyl)-N-(4,4-difluoro-1-(hydroxyamino)-3-methyl-3-(3-methylureido)-1-oxobutan-2-yl)benzamide;
4-((1H-1,2,3-triazol-4-yl)buta-1,3-diynyl)-N-(4,4-difluoro-3-hydroxy-1-(hydroxyamino)-3-methyl-1-oxobutan-2-yl)benzamide;
4-((1H-1,2,3-triazol-4-yl)buta-1,3-diynyl)-N-(4,4-difluoro-1-(hydroxyamino)-3-methoxy-3-methyl-1-oxobutan-2-yl)benzamide;
4-((1H-1,2,3-triazol-4-yl)buta-1,3-diynyl)-N-(3-amino-4,4-difluoro-1-(hydroxyamino)-3-methyl-1-oxobutan-2-yl)benzamide;
4-((1H-1,2,3-triazol-4-yl)buta-1,3-diynyl)-N-(3-acetamido-4,4-difluoro-1-(hydroxyamino)-3-methyl-1-oxobutan-2-yl)benzamide;
4-((1H-1,2,3-triazol-4-yl)buta-1,3-diynyl)-N-(4,4-difluoro-1-(hydroxyamino)-3-methyl-3-(3-methylureido)-1-oxobutan-2-yl)benzamide;
4-((2H-tetrazol-5-yl)buta-1,3-diynyl)-N-(4,4-difluoro-3-hydroxy-1-(hydroxyamino)-3-methyl-1-oxobutan-2-yl)benzamide;
4-((2H-tetrazol-5-yl)buta-1,3-diynyl)-N-(4,4-difluoro-1-(hydroxyamino)-3-methoxy-3-methyl-1-oxobutan-2-yl)benzamide;
4-((2H-tetrazol-5-yl)buta-1,3-diynyl)-N-(3-amino-4,4-difluoro-1-(hydroxyamino)-3-methyl-1-oxobutan-2-yl)benzamide;
4-((2H-tetrazol-5-yl)buta-1,3-diynyl)-N-(3-acetamido-4,4-difluoro-1-(hydroxyamino)-3-methyl-1-oxobutan-2-yl)benzamide;
4-((2H-tetrazol-5-yl)buta-1,3-diynyl)-N-(4,4-difluoro-1-(hydroxyamino)-3-methyl-3-(3-methylureido)-1-oxobutan-2-yl)benzamide;
N-(4,4-difluoro-3-hydroxy-1-(hydroxyamino)-3-methyl-1-oxobutan-2-yl)-4-((1-methyl-1H-pyrazol-4-yl)buta-1,3-diynyl)benzamide;
N-(4,4-difluoro-1-(hydroxyamino)-3-methoxy-3-methyl-1-oxobutan-2-yl)-4-((1-methyl-1H-pyrazol-4-yl)buta-1,3-diynyl)benzamide;
N-(3-amino-4,4-difluoro-1-(hydroxyamino)-3-methyl-1-oxobutan-2-yl)-4-((1-methyl-1H-pyrazol-4-yl)buta-1,3-diynyl)benzamide;
N-(3-acetamido-4,4-difluoro-1-(hydroxyamino)-3-methyl-1-oxobutan-2-yl)-4-((1-methyl-1H-pyrazol-4-yl)buta-1,3-diynyl)benzamide;
N-(4,4-difluoro-1-(hydroxyamino)-3-methyl-3-(3-methylureido)-1-oxobutan-2-yl)-4-((1-methyl-1H-pyrazol-4-yl)buta-1,3-diynyl)benzamide;
N-(4,4-difluoro-3-hydroxy-1-(hydroxyamino)-3-methyl-1-oxobutan-2-yl)-4-(isoxazol-5-ylbuta-1,3-diynyl)benzamide;
N-(4,4-difluoro-1-(hydroxyamino)-3-methoxy-3-methyl-1-oxobutan-2-yl)-4-(isoxazol-5-ylbuta-1,3-diynyl)benzamide;
N-(3-amino-4,4-difluoro-1-(hydroxyamino)-3-methyl-1-oxobutan-2-yl)-4-(isoxazol-5-ylbuta-1,3-diynyl)benzamide;
N-(3-acetamido-4,4-difluoro-1-(hydroxyamino)-3-methyl-1-oxobutan-2-yl)-4-(isoxazol-5-ylbuta-1,3-diynyl)benzamide;
N-(4,4-difluoro-1-(hydroxyamino)-3-methyl-3-(3-methylureido)-1-oxobutan-2-yl)-4-(isoxazol-5-ylbuta-1,3-diynyl)benzamide;
N-(4,4-difluoro-3-hydroxy-1-(hydroxyamino)-3-methyl-1-oxobutan-2-yl)-4-(oxazol-5-ylbuta-1,3-diynyl)benzamide;
N-(4,4-difluoro-1-(hydroxyamino)-3-methoxy-3-methyl-1-oxobutan-2-yl)-4-(oxazol-5-ylbuta-1,3-diynyl)benzamide;
N-(3-amino-4,4-difluoro-1-(hydroxyamino)-3-methyl-1-oxobutan-2-yl)-4-(oxazol-5-ylbuta-1,3-diynyl)benzamide;
N-(3-acetamido-4,4-difluoro-1-(hydroxyamino)-3-methyl-1-oxobutan-2-yl)-4-(oxazol-5-ylbuta-1,3-diynyl)benzamide;
N-(4,4-difluoro-1-(hydroxyamino)-3-methyl-3-(3-methylureido)-1-oxobutan-2-yl)-4-(oxazol-5-ylbuta-1,3-diynyl)benzamide;
N-(4,4-difluoro-3-hydroxy-1-(hydroxyamino)-3-methyl-1-oxobutan-2-yl)-4-(isothiazol-5-ylbuta-1,3-diynyl)benzamide;
N-(4,4-difluoro-1-(hydroxyamino)-3-methoxy-3-methyl-1-oxobutan-2-yl)-4-(isothiazol-5-ylbuta-1,3-diynyl)benzamide;

N-(3-amino-4,4-difluoro-1-(hydroxyamino)-3-methyl-1-oxobutan-2-yl)-4-(isothiazol-5-ylbuta-1,3-diynyl)benzamide;
N-(3-acetamido-4,4-difluoro-1-(hydroxyamino)-3-methyl-1-oxobutan-2-yl)-4-(isothiazol-5-ylbuta-1,3-diynyl)benzamide;
N-(4,4-difluoro-1-(hydroxyamino)-3-methyl-3-(3-methylureido)-1-oxobutan-2-yl)-4-(isothiazol-5-ylbuta-1,3-diynyl)benzamide;
N-(4,4-difluoro-3-hydroxy-1-(hydroxyamino)-3-methyl-1-oxobutan-2-yl)-4-(thiazol-5-ylbuta-1,3-diynyl)benzamide;
N-(4,4-difluoro-1-(hydroxyamino)-3-methoxy-3-methyl-1-oxobutan-2-yl)-4-(thiazol-5-ylbuta-1,3-diynyl)benzamide;
N-(3-amino-4,4-difluoro-1-(hydroxyamino)-3-methyl-1-oxobutan-2-yl)-4-(thiazol-5-ylbuta-1,3-diynyl)benzamide;
N-(3-acetamido-4,4-difluoro-1-(hydroxyamino)-3-methyl-1-oxobutan-2-yl)-4-(thiazol-5-ylbuta-1,3-diynyl)benzamide;
N-(4,4-difluoro-1-(hydroxyamino)-3-methyl-3-(3-methylureido)-1-oxobutan-2-yl)-4-(thiazol-5-ylbuta-1,3-diynyl)benzamide;
N-(4,4-difluoro-3-hydroxy-1-(hydroxyamino)-3-methyl-1-oxobutan-2-yl)-4-(thiophen-3-ylbuta-1,3-diynyl)benzamide;
N-(4,4-difluoro-1-(hydroxyamino)-3-methoxy-3-methyl-1-oxobutan-2-yl)-4-(thiophen-3-ylbuta-1,3-diynyl)benzamide;
N-(3-amino-4,4-difluoro-1-(hydroxyamino)-3-methyl-1-oxobutan-2-yl)-4-(thiophen-3-ylbuta-1,3-diynyl)benzamide;
N-(3-acetamido-4,4-difluoro-1-(hydroxyamino)-3-methyl-1-oxobutan-2-yl)-4-(thiophen-3-ylbuta-1,3-diynyl)benzamide;
N-(4,4-difluoro-1-(hydroxyamino)-3-methyl-3-(3-methylureido)-1-oxobutan-2-yl)-4-(thiophen-3-ylbuta-1,3-diynyl)benzamide;
N-(4,4-difluoro-3-hydroxy-1-(hydroxyamino)-3-methyl-1-oxobutan-2-yl)-4-(furan-3-ylbuta-1,3-diynyl)benzamide;
N-(4,4-difluoro-1-(hydroxyamino)-3-methoxy-3-methyl-1-oxobutan-2-yl)-4-(furan-3-ylbuta-1,3-diynyl)benzamide;
N-(3-amino-4,4-difluoro-1-(hydroxyamino)-3-methyl-1-oxobutan-2-yl)-4-(furan-3-ylbuta-1,3-diynyl)benzamide;
N-(3-acetamido-4,4-difluoro-1-(hydroxyamino)-3-methyl-1-oxobutan-2-yl)-4-(furan-3-ylbuta-1,3-diynyl)benzamide;
N-(4,4-difluoro-1-(hydroxyamino)-3-methyl-3-(3-methylureido)-1-oxobutan-2-yl)-4-(furan-3-ylbuta-1,3-diynyl)benzamide;
4-((2-aminothiazol-5-yl)buta-1,3-diynyl)-N-(4,4-difluoro-3-hydroxy-1-(hydroxyamino)-3-methyl-1-oxobutan-2-yl)benzamide;
4-((2-aminothiazol-5-yl)buta-1,3-diynyl)-N-(4,4-difluoro-1-(hydroxyamino)-3-methoxy-3-methyl-1-oxobutan-2-yl)benzamide;
N-(3-amino-4,4-difluoro-1-(hydroxyamino)-3-methyl-1-oxobutan-2-yl)-4-((2-aminothiazol-5-yl)buta-1,3-diynyl)benzamide;
N-(3-acetamido-4,4-difluoro-1-(hydroxyamino)-3-methyl-1-oxobutan-2-yl)-4-((2-aminothiazol-5-yl)buta-1,3-diynyl)benzamide;
4-((2-aminothiazol-5-yl)buta-1, 3-diynyl)-N-(4,4-difluoro-1-(hydroxyamino)-3-methyl-3-(3-methylureido)-1-oxobutan-2-yl)benzamide;
4-((2-aminophenyl)buta-1,3-diynyl)-N-(4,4-difluoro-1-(hydroxyamino)-3-methoxy-3-methyl-1-oxobutan-2-yl)benzamide;
N-(3-amino-4,4-difluoro-1-(hydroxyamino)-3-methyl-1-oxobutan-2-yl)-4-((2-aminophenyl)buta-1,3-diynyl)benzamide;
N-(3-acetamido-4,4-difluoro-1-(hydroxyamino)-3-methyl-1-oxobutan-2-yl)-4-((2-aminophenyl)buta-1,3-diynyl)benzamide;
4-((2-aminophenyl)buta-1,3-diynyl)-N-(4,4-difluoro-1-(hydroxyamino)-3-methyl-3-(3-methylureido)-1-oxobutan-2-yl)benzamide;
N-(4,4-difluoro-3-hydroxy-1-(hydroxyamino)-3-methyl-1-oxobutan-2-yl)-4-((2-hydroxyphenyl)buta-1,3-diynyl)benzamide;
N-(4,4-difluoro-1-(hydroxyamino)-3-methoxy-3-methyl-1-oxobutan-2-yl)-4-((2-hydroxyphenyl)buta-1,3-diynyl)benzamide;
N-(3-amino-4,4-difluoro-1-(hydroxyamino)-3-methyl-1-oxobutan-2-yl)-4-((2-hydroxyphenyl)buta-1,3-diynyl)benzamide;
N-(3-acetamido-4,4-difluoro-1-(hydroxyamino)-3-methyl-1-oxobutan-2-yl)-4-((2-hydroxyphenyl)buta-1, 3-diynyl)benzamide;
N-(4,4-difluoro-1-(hydroxyamino)-3-methyl-3-(3-methylureido)-1-oxobutan-2-yl)-4-((2-hydroxyphenyl)buta-1,3-diynyl)benzamide;
N-(4,4-difluoro-3-hydroxy-1-(hydroxyamino)-3-methyl-1-oxobutan-2-yl)-4-((2-methoxyphenyl)buta-1,3-diynyl)benzamide;
N-(4,4-difluoro-1-(hydroxyamino)-3-methoxy-3-methyl-1-oxobutan-2-yl)-4-((2-methoxyphenyl)buta-1,3-diynyl)benzamide;
N-(3-amino-4,4-difluoro-1-(hydroxyamino)-3-methyl-1-oxobutan-2-yl)-4-((2-methoxyphenyl)buta-1,3-diynyl)benzamide;
N-(3-acetamido-4,4-difluoro-1-(hydroxyamino)-3-methyl-1-oxobutan-2-yl)-4-((2-methoxyphenyl)buta-1, 3-diynyl)benzamide;
N-(4,4-difluoro-1-(hydroxyamino)-3-methyl-3-(3-methylureido)-1-oxobutan-2-yl)-4-((2-methoxyphenyl)buta-1,3-diynyl)benzamide;
or a pharmaceutically acceptable salt thereof.

12. A method according to claim 1 wherein the compound is administered in a pharmaceutical composition comprising the compound and a pharmaceutically acceptable carrier, solvent, adjuvant or diluent.

13. A method according to claim 1 wherein the compound is 4-((4-aminophenyl)buta-1,3-diynyl)-N-((2S,3S)-4,4-difluoro-3-hydroxy-1-(hydroxyamino)-3-methyl-1-oxobutan-2-yl)benzamide.

* * * * *